(12) United States Patent
Glass et al.

(10) Patent No.: US 8,420,088 B2
(45) Date of Patent: Apr. 16, 2013

(54) METHODS AND COMPOSITIONS USING FGF23 FUSION POLYPEPTIDES

(75) Inventors: David Glass, East Hanover, NJ (US); Shou-Ih Hu, East Hanover, NJ (US)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 12/696,693

(22) Filed: Jan. 29, 2010

(65) Prior Publication Data

US 2010/0215657 A1    Aug. 26, 2010

Related U.S. Application Data

(63) Continuation-in-part of application No. 12/360,970, filed on Jan. 28, 2009.

(60) Provisional application No. 61/063,015, filed on Jan. 28, 2008.

(51) Int. Cl.
| | |
|---|---|
| A61K 38/18 | (2006.01) |
| A61K 39/395 | (2006.01) |
| C07K 14/50 | (2006.01) |
| C07K 16/00 | (2006.01) |
| C12N 1/21 | (2006.01) |
| C12N 5/10 | (2006.01) |
| C12N 15/12 | (2006.01) |
| C12N 15/63 | (2006.01) |

(52) U.S. Cl.
USPC ............. 424/134.1; 435/320.1; 435/243; 435/325; 435/69.7; 514/9.1; 514/21.2

(58) Field of Classification Search ............... None
See application file for complete search history.

(56) References Cited

U.S. PATENT DOCUMENTS

| | | | | | |
|---|---|---|---|---|---|
| 5,408,038 | A | * | 4/1995 | Smith et al. | 530/359 |
| 5,541,094 | A | * | 7/1996 | Anton et al. | 435/136 |
| 7,060,479 | B2 | * | 6/2006 | Dumas et al. | 435/196 |
| 7,217,798 | B2 | | 5/2007 | Hinton et al. | |
| 7,223,563 | B2 | | 5/2007 | Econs et al. | |
| 7,259,248 | B2 | | 8/2007 | Itoh et al. | |
| 7,745,406 | B2 | | 6/2010 | Econs et al. | |
| 2006/0160181 | A1 | * | 7/2006 | Luethy et al. | 435/69.1 |
| 2009/0192087 | A1 | | 7/2009 | Glass et al. | |

OTHER PUBLICATIONS

Strewler PNAS 98(11): 5945-5946, 2001.*
Goetz et al, "Molecular Insights into the Klotho-Dependent, Endocrine Mode of Action of Fibroblast Growth Factor 19 Subfamily Members"; Mol. and Cell. Bio.; May 2007; 3417.
Hessell et al, "Fc receptor but not complement binding is important in antibody protection against HIV" Nature (2007); vol. 449 p. 101.
Lode et al, "Gene therapy with a single chain interleukin 12 fusion protein induces T cell-dependent protective immunity in a syngeneic mode of murine neuroblastoma"; Proc. Nat. Acad. Sci. USA (1998) vol. 95 p. 2475.
Ray, L. Bryan; "Klotho Gets Around"; Sci. STKE (2006) vol. 2006(365) p. tw416.
Urakawa, et al; "Klotho converts canonical FGF receptor into a specific receptor for FGF23"; Nature (2006) vol. 444, p. 770.
Razzaue et al., "Therapeutic potential of klotho—FGF23 fusion polypeptides: WO2009095372", Expert Opin. Ther. Patents, 2010 vol. 20 No. 6 pp. 1-5.
The ADHR Consortium; "Autosomal dominant hypophosphataemic rickets is associated with mutations in FGF23"; Nature Genetics; 26:345-348 (2000).
Bai et al.; "The Autosomal Dominant Hypophosphatemic Rickets R176Q Mutation in Fibroblast Growth Factor 23 Resists Proteolytic Cleavage and Enhances in Vivo Biological Potency"; The Journal of Biological Chemistry; 278(11):9843-9849 (2003).
Bai et al.; "Transgenic Mice Overexpressing Human Fibroblast Growth Factor 23 (R176Q) Delineate a Putative Role for Parathyroid Hormone in Renal Phosphate Wasting Disorders"; Endocrinology; 145(11):5269-5279 (2004).
Bai et al.; "Klotho ablation converts the biochemical and skeletal alterations in FGF23 (R176Q) transgenic mice to a Klotho-deficient phenotype"; Am. J. Physiol. Endocrinol. Metab.; 296:E79-E88 (2009).
Ben-Dov et al.; "The parathyroid is a target organ for FGF23 in rats"; The Journal of Clinical Investigation—Research Article; 117(12):4003-4008 (2007).
Berndt et al.; "Biological activity of FGF-23 fragments"; Pflugers Arch—Eur. J. Physiol.; 454:615-623 (2007).
Carpenter et al.; "Circulating Levels of Soluble Klotho and FGF23 in X-Linked Hypophosphatemia: Circadian Variance, Effects of Treatment, and Relationship to Parathyroid Status"; J. Clin. Endocrinol. Metab.; 95:E352-E357 (2010).
Drueke et al.; "Klotho spins the thread of life-what does Klotho do to the receptors of fibroblast growth factor-23 (FGF23)?"; Nephrol Dial. Transplant.; 22:1524-1526 (2007).
KURO-O; "Overview of the FGF23-Klotho axis"; Pediatr. Nephrol.; 25:583-590 (2010).
Kurosu et al.; "Regulation of Fibroblast Growth Factor-23 Signaling by Klotho"; The Journal of Biological Chemistry; 281(10):6120-6123 (2006).
Shimada et al.; "Mutant FGF-23 responsible for autosomal dominant hypophosphatemic rickets is resistant to proteolytic cleavage and causes hypophosphatemia in vivo"; Endocrinology; 143(8):3179-3182 (2002).
Strewler; "FGF23, hypophosphatemia, and rickets: Has phosphatonin been found?"; PNAS—Commentary; 98 (11):5945-5946 (2001).
Tohyama et al.; "Klotho is a Novel Beta-Glucuronidase Capable of Hydrolyzing Steroid Beta-Glucuronides"; The Journal of Biological Chemistry; 279(11):9777-9784 (2004).
Torres et al.; "Klotho: An antiaging protein involved in mineral and vitamin D metabolism"; Kidney International; 71:730-737 (2007).
Urakawa et al; "Klotho converts canonical FGF receptor into a specific receptor for FGF23"; Nature; 444:770-774 (2006)[Supplemental Data List; Supplemental Figures 1-6; Supplemental Discussion; Supplemental Methods and Supplemental Table].
White et al.; "Autosomal-dominant hypophosphatemic rickets (ADHR) mutations stabilize FGF-23"; Kidney International; 60:2079-2086 (2001).
Wu et al.; "Co-receptor Requirements for Fibroblast Growth Factor-19 Signaling"; The Journal of Biological Chemistry; 282(40):29069-29072 (2007).

(Continued)

*Primary Examiner* — Christine J Saoud
(74) *Attorney, Agent, or Firm* — Frank Wu

(57) ABSTRACT

The present invention is directed to fusion polypeptides comprising Klotho protein or an active fragment thereof and FGF23 or an active fragment thereof.

18 Claims, 8 Drawing Sheets

OTHER PUBLICATIONS

Figure 1A:
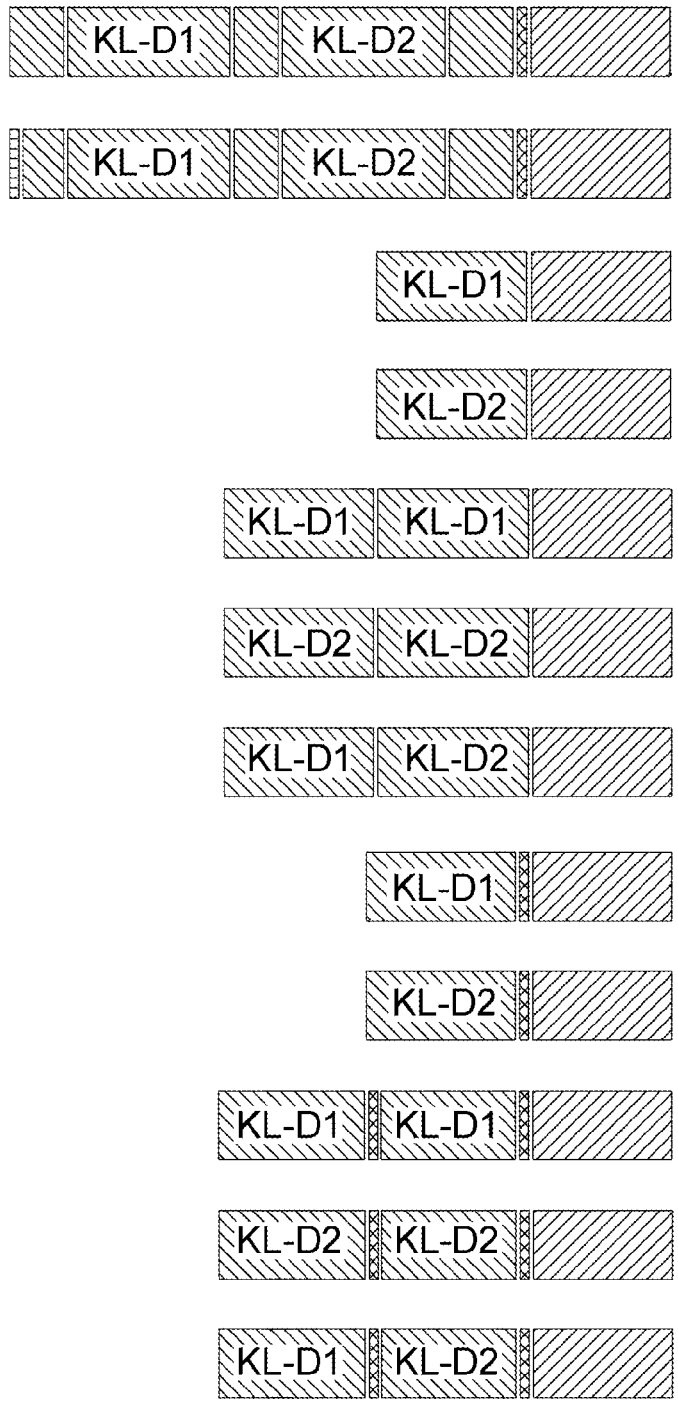

Yu et al.; "FGF23 and disorders of phosphate homeostasis"; Cytokine & Growth Factor Reviews; 16:221-232 (2005).

Ito et al., "Molecular cloning and expression analyses of mouse bklotho, which encodes a novel Klotho family protein", Mech. Dev., 98:115-119 (2000).

Wu et al., "C-terminal Tail of FGF19 Determines Its Specificity toward Klotho Co-receptors", J. Biol. Chem., 283 (48);33304-33309 (2008).

* cited by examiner

▨ : Klotho (extracellular domain) or active fragment of Klotho;

▨ : FGF23 (R179Q), FGF23, FGF 19, FGF21; ▩: linker; ▮ : IgG signal peptide.

▨ : Klotho (extracellular domain) or active fragment of Klotho;

▧ : FGF23 (R179Q), FGF23, FGF 19, FGF21; ▦: linker; ▤: IgG signal peptide.

lane 1, Ctrl; lane 2, FGF23; lane 3, sKlotho; lanes 4-6, sKlotho-FGF23 lane 1, Ctrl; lane 2, FGF23; lane 3, sKlotho; lanes 4-6, sKlotho-FGF23 lane 1, purified sKlotho-FGF23-6xHis;
lane 2, molecular weight marker

SEQUENCE LISTING

<160> NUMBER OF SEQ ID NOS: 53

<210> SEQ ID NO 1
<211> LENGTH: 5003
<212> TYPE: DNA
<213> ORGANISM: Homo sapiens

<400> SEQUENCE: 1
cgcgcagcat gcccgccagc gccccgccgc gccgcccgcg gccgccgccg ccgtcgctgt      60
cgctgctgct ggtgctgctg ggcctgggcg gccgccgcct cgtgcggag ccgggcgacg     120 gcgcgcagac ctgggcccgt ttctcgcggc ctcctgcccc cgaggccgcg ggcctcttcc     180

-continued

```
agggcacctt ccccgacggc ttcctctggg ccgtgggcag cgccgcctac cagaccgagg    240
gcggctggca gcagcacggc aagggtgcgt ccatctggga tacgttcacc caccaccccc    300
tggcaccccc gggagactcc cggaacgcca gtctgccgtt gggcgccccg tcgccgctgc    360
agcccgccac cggggacgta gccagcgaca gctacaacaa cgtcttccgc gacacggagg    420
cgctgcgcga gctcggggtc actcactacc gcttctccat ctcgtgggcg cgagtgctcc    480
ccaatggcag cgcgggcgtc cccaaccgcg aggggctgcg ctactaccgg cgcctgctgg    540
agcggctgcg ggagctgggc gtgcagcccg tggtcaccct gtaccactgg gacctgcccc    600
agcgcctgca ggacgcctac ggcggctggg ccaaccgcgc cctggccgac cacttcaggg    660
attacgcgga gctctgcttc cgccacttcg gcggtcaggt caagtactgg atcaccatcg    720 acaacccta cgtggtggcc tggcacggct acgccaccgg gcgcctggcc cccggcatcc    780
ggggcagccc gcggctcggg tacctggtgg cgcacaacct cctcctggct catgccaaag    840
tctggcatct ctacaatact tctttccgtc ccactcaggg aggtcaggtg tccattgccc    900
taagctctca ctggatcaat cctcgaagaa tgaccgacca cagcatcaaa gaatgtcaaa    960
aatctctgga ctttgtacta ggttggtttg ccaaacccgt atttattgat ggtgactatc   1020
ccgagagcat gaagaataac ctttcatcta ttctgcctga ttttactgaa tctgagaaaa   1080
agttcatcaa aggaactgct gacttttttg ctctttgctt tggacccacc ttgagttttc   1140
aacttttgga ccctcacatg aagttccgcc aattggaatc tcccaacctg aggcaactgc   1200
tttcctggat tgaccttgaa tttaaccatc tcaaatatt tattgtggaa aatggctggt   1260
ttgtctcagg gaccaccaag agagatgatg ccaaatatat gtattacctc aaaaagttca   1320
tcatggaaac cttaaaagcc atcaagctgg atggggtgga tgtcatcggg tataccgcat   1380
ggtccctcat ggatggtttc gagtggcaca gaggttacag catcaggcgt ggactcttct   1440
atgttgactt tctaagccag gacaagatgt tgttgccaaa gtcttcagcc ttgttctacc   1500
aaaagctgat agagaaaaat ggcttccctc ctttacctga aaatcagccc ctagaaggga   1560
catttccctg tgactttgct tggggagttg ttgacaacta cattcaagta gataccactc   1620
tgtctcagtt taccgacctg aatgtttacc tgtgggatgt ccaccacagt aaaaggctta   1680
ttaaagtgga tggggttgtg accaagaaga ggaaatccta ctgtgttgac tttgctgcca   1740
tccagcccca gatcgcttta ctccaggaaa tgcacgttac acattttcgc ttctccctgg   1800
actgggccct gattctccct ctgggtaacc agtcccaggt gaaccacacc atcctgcagt   1860
actatcgctg catggccagc gagcttgtcc gtgtcaacat caccccagtg gtggccctgt   1920
ggcagcctat ggccccgaac caaggactgc gcgcctcct ggccaggcag ggcgcctggg   1980 agaacccta cactgccctg gcctttgcag agtatgcccg actgtgcttt caagagctcg   2040
gccatcacgt caagctttgg ataacgatga atgagccgta tacaaggaat atgacataca   2100
gtgctggcca caaccttctg aaggcccatg ccctggcttg gcatgtgtac aatgaaaagt   2160
ttaggcatgc tcagaatggg aaaatatcca tagccttgca ggctgattgg atagaacctg   2220
cctgcccttt ctcccaaaag gacaaagagg tggccgagag agttttggaa tttgacattg   2280
gctggctggc tgagcccatt ttcggctctg gagattatcc atgggtgatg agggactggc   2340
tgaaccaaag aaacaatttt cttcttcctt atttcactga agatgaaaaa agctaatcc    2400 agggtacctt tgacttttg gctttaagcc attataccac catccttgta gactcagaaa   2460
aagaagatcc aataaaatac aatgattacc tagaagtgca agaaatgacc gacatcacgt   2520
ggctcaactc ccccagtcag gtggcggtag tgccctgggg gttgcgcaaa gtgctgaact   2580
```

-continued

```
ggctgaagtt caagtacgga gacctcccca tgtacataat atccaacgga atcgatgacg   2640
ggctgcatgc tgaggacgac cagctgaggg tgtattatat gcagaattac ataaacgaag   2700
ctctcaaagc ccacatactg gatggtatca atctttgcgg atactttgct tattcgttta   2760
acgaccgcac agctccgagg tttggcctct atcgttatgc tgcagatcag tttgagccca   2820
aggcatccat gaaacattac aggaaaatta ttgacagcaa tggtttcccg ggcccagaaa   2880
ctctggaaag attttgtcca gaagaattca ccgtgtgtac tgagtgcagt ttttttcaca   2940
cccgaaagtc tttactggct ttcatagctt ttctattttt tgcttctatt atttctctct   3000
cccttatatt ttactactcg aagaaaggca gaagaagtta caaatagttc tgaacatttt   3060
tctattcatt cattttgaaa taattatgca gacacatcag ctgttaacca tttgcacctc   3120
taagtgttgt gaaactgtaa atttcataca tttgacttct agaaaacatt tttgtggctt   3180
atgacagagg ttttgaaatg ggcataggtg atcgtaaaat attgaataat gcgaatagtg   3240
cctgaatttg ttctcttttt gggtgattaa aaaactgaca ggcactataa tttctgtaac   3300
acactaacaa aagcatgaaa aataggaacc acaccaatgc aacatttgtg cagaaatttg   3360
aatgacaaga ttaggaatat tttcttctgc acccacttct aaatttaatg ttttttctgga  3420 agtagtaatt gcaagagttc gaatagaaag ttatgtacca agtaaccatt tctcagctgc   3480
cataataatg cctagtggct tcccctctgt caaatctagt ttcctatgga aagaagatg    3540 gcagatacag gagagacgac agagggtcct aggctggaat gttcctttcg aaagcaatgc   3600
ttctatcaaa tactagtatt aatttatgta tctggttaat gacatacttg gagagcaaat   3660
tatggaaatg tgtattttat atgatttttg aggtcctgtc taaaccctgt gtccctgagg   3720
gatctgtctc actggcatct tgttgagggc cttgcacata ggaaactttt gataagtatc   3780
tgcggaaaaa caaacatgaa tcctgtgata ttgggctctt caggaagcat aaagcaattg   3840
tgaaatacag tataccgcag tggctctagg tggaggaaag gaggaaaaag tgcttattat   3900
gtgcaacatt atgattaatc tgattataca ccatttttga gcagatcttg gaatgaatga   3960
catgaccttt ccctagagaa taaggatgaa ataatcactc attctatgaa cagtgacact   4020
actttctatt ctttagctgt actgtaattt ctttgagttg atagttttac aaattcttaa   4080
taggttcaaa agcaatctgg tctgaataac actggatttg tttctgtgat ctctgaggtc   4140
tattttatgt ttttgctgct acttctgtgg aagtagcttt gaactagttt acttttgaac   4200
tttcacgctg aaacatgcta gtgatatcta gaaagggcta attaggtctc atcctttaat   4260
gccccttaaa taagtcttgc tgattttcag acagggaagt ctctctatta cactggagct   4320
gttttataga taagtcaata ttgtatcagg caagataaac caatgtcata acaggcattg   4380
ccaacctcac tgacacaggg tcatagtgta taataatata ctgtactata taatatatca   4440
tctttagagg tatgattttt tcatgaaaga taagcttttg gtaatattca ttttaaagtg   4500
gacttattaa aattggatgc tagagaatca agtttatttt atgtatatat ttttctgatt   4560
ataagagtaa tatatgttca ttgtaaaaat ttttaaaaca cagaaactat atgcaaagaa   4620
aaaataaaaa ttatctataa tctcagaacc cagaaatagc cactattaac atttcctacg   4680
tattttattt tacatagatc atattgtata tagttagtat ctttattaat tttattatg    4740 aaactttcct ttgtcattat tagtcttcaa aagcatgatt tttaatagtt gttgagtatt   4800
ccaccacagg aatgtatcac aacttaaccg ttcccgtttg ttagactagt ttcttattaa   4860
tgttgatgaa tgttgtttaa aaataatttt gttgctacat ttactttaat ttccttgact   4920
gtaaagagaa gtaattttgc tccttgataa agtattatat taataataaa tctgcctgca   4980
```

-continued

```
acttttgcc ttctttcata atc                                           5003
```

<210> SEQ ID NO 2
<211> LENGTH: 1012
<212> TYPE: PRT
<213> ORGANISM: Homo sapiens

<400> SEQUENCE: 2

```
Met Pro Ala Ser Ala Pro Pro Arg Arg Pro Arg Pro Pro Pro Pro Ser
1               5                   10                  15

Leu Ser Leu Leu Leu Val Leu Leu Gly Leu Gly Gly Arg Arg Leu Arg
            20                  25                  30

Ala Glu Pro Gly Asp Gly Ala Gln Thr Trp Ala Arg Phe Ser Arg Pro
        35                  40                  45

Pro Ala Pro Glu Ala Ala Gly Leu Phe Gln Gly Thr Phe Pro Asp Gly
    50                  55                  60

Phe Leu Trp Ala Val Gly Ser Ala Ala Tyr Gln Thr Glu Gly Gly Trp
65                  70                  75                  80

Gln Gln His Gly Lys Gly Ala Ser Ile Trp Asp Thr Phe Thr His His
                85                  90                  95

Pro Leu Ala Pro Pro Gly Asp Ser Arg Asn Ala Ser Leu Pro Leu Gly
            100                 105                 110

Ala Pro Ser Pro Leu Gln Pro Ala Thr Gly Asp Val Ala Ser Asp Ser
        115                 120                 125

Tyr Asn Asn Val Phe Arg Asp Thr Glu Ala Leu Arg Glu Leu Gly Val
    130                 135                 140

Thr His Tyr Arg Phe Ser Ile Ser Trp Ala Arg Val Leu Pro Asn Gly
145                 150                 155                 160

Ser Ala Gly Val Pro Asn Arg Glu Gly Leu Arg Tyr Tyr Arg Arg Leu
                165                 170                 175

Leu Glu Arg Leu Arg Glu Leu Gly Val Gln Pro Val Val Thr Leu Tyr
            180                 185                 190

His Trp Asp Leu Pro Gln Arg Leu Gln Asp Ala Tyr Gly Gly Trp Ala
        195                 200                 205

Asn Arg Ala Leu Ala Asp His Phe Arg Asp Tyr Ala Glu Leu Cys Phe
    210                 215                 220

Arg His Phe Gly Gly Gln Val Lys Tyr Trp Ile Thr Ile Asp Asn Pro
225                 230                 235                 240

Tyr Val Val Ala Trp His Gly Tyr Ala Thr Gly Arg Leu Ala Pro Gly
                245                 250                 255

Ile Arg Gly Ser Pro Arg Leu Gly Tyr Leu Val Ala His Asn Leu Leu
            260                 265                 270

Leu Ala His Ala Lys Val Trp His Leu Tyr Asn Thr Ser Phe Arg Pro
        275                 280                 285

Thr Gln Gly Gly Gln Val Ser Ile Ala Leu Ser Ser His Trp Ile Asn
    290                 295                 300

Pro Arg Arg Met Thr Asp His Ser Ile Lys Glu Cys Gln Lys Ser Leu
305                 310                 315                 320

Asp Phe Val Leu Gly Trp Phe Ala Lys Pro Val Phe Ile Asp Gly Asp
                325                 330                 335

Tyr Pro Glu Ser Met Lys Asn Asn Leu Ser Ser Ile Leu Pro Asp Phe
            340                 345                 350

Thr Glu Ser Glu Lys Lys Phe Ile Lys Gly Thr Ala Asp Phe Phe Ala
        355                 360                 365
```

-continued

```
Leu Cys Phe Gly Pro Thr Leu Ser Phe Gln Leu Leu Asp Pro His Met
        370                 375                 380

Lys Phe Arg Gln Leu Glu Ser Pro Asn Leu Arg Gln Leu Leu Ser Trp
385                 390                 395                 400

Ile Asp Leu Glu Phe Asn His Pro Gln Ile Phe Ile Val Glu Asn Gly
                405                 410                 415

Trp Phe Val Ser Gly Thr Thr Lys Arg Asp Asp Ala Lys Tyr Met Tyr
                420                 425                 430

Tyr Leu Lys Lys Phe Ile Met Glu Thr Leu Lys Ala Ile Lys Leu Asp
            435                 440                 445

Gly Val Asp Val Ile Gly Tyr Thr Ala Trp Ser Leu Met Asp Gly Phe
    450                 455                 460

Glu Trp His Arg Gly Tyr Ser Ile Arg Arg Gly Leu Phe Tyr Val Asp
465                 470                 475                 480

Phe Leu Ser Gln Asp Lys Met Leu Leu Pro Lys Ser Ser Ala Leu Phe
                485                 490                 495

Tyr Gln Lys Leu Ile Glu Lys Asn Gly Phe Pro Pro Leu Pro Glu Asn
            500                 505                 510

Gln Pro Leu Glu Gly Thr Phe Pro Cys Asp Phe Ala Trp Gly Val Val
    515                 520                 525

Asp Asn Tyr Ile Gln Val Asp Thr Thr Leu Ser Gln Phe Thr Asp Leu
    530                 535                 540

Asn Val Tyr Leu Trp Asp Val His His Ser Lys Arg Leu Ile Lys Val
545                 550                 555                 560

Asp Gly Val Val Thr Lys Lys Arg Lys Ser Tyr Cys Val Asp Phe Ala
                565                 570                 575

Ala Ile Gln Pro Gln Ile Ala Leu Leu Gln Glu Met His Val Thr His
            580                 585                 590

Phe Arg Phe Ser Leu Asp Trp Ala Leu Ile Leu Pro Leu Gly Asn Gln
    595                 600                 605

Ser Gln Val Asn His Thr Ile Leu Gln Tyr Tyr Arg Cys Met Ala Ser
    610                 615                 620

Glu Leu Val Arg Val Asn Ile Thr Pro Val Val Ala Leu Trp Gln Pro
625                 630                 635                 640

Met Ala Pro Asn Gln Gly Leu Pro Arg Leu Leu Ala Arg Gln Gly Ala
                645                 650                 655

Trp Glu Asn Pro Tyr Thr Ala Leu Ala Phe Ala Glu Tyr Ala Arg Leu
                660                 665                 670

Cys Phe Gln Glu Leu Gly His His Val Lys Leu Trp Ile Thr Met Asn
            675                 680                 685

Glu Pro Tyr Thr Arg Asn Met Thr Tyr Ser Ala Gly His Asn Leu Leu
    690                 695                 700

Lys Ala His Ala Leu Ala Trp His Val Tyr Asn Glu Lys Phe Arg His
705                 710                 715                 720

Ala Gln Asn Gly Lys Ile Ser Ile Ala Leu Gln Ala Asp Trp Ile Glu
                725                 730                 735

Pro Ala Cys Pro Phe Ser Gln Lys Asp Lys Glu Val Ala Glu Arg Val
            740                 745                 750

Leu Glu Phe Asp Ile Gly Trp Leu Ala Glu Pro Ile Phe Gly Ser Gly
    755                 760                 765

Asp Tyr Pro Trp Val Met Arg Asp Trp Leu Asn Gln Arg Asn Asn Phe
    770                 775                 780

Leu Leu Pro Tyr Phe Thr Glu Asp Glu Lys Lys Leu Ile Gln Gly Thr
785                 790                 795                 800
```

```
Phe Asp Phe Leu Ala Leu Ser His Tyr Thr Thr Ile Leu Val Asp Ser
            805                 810                 815
Glu Lys Glu Asp Pro Ile Lys Tyr Asn Asp Tyr Leu Glu Val Gln Glu
        820                 825                 830
Met Thr Asp Ile Thr Trp Leu Asn Ser Pro Ser Gln Val Ala Val Val
    835                 840                 845
Pro Trp Gly Leu Arg Lys Val Leu Asn Trp Leu Lys Phe Lys Tyr Gly
850                 855                 860
Asp Leu Pro Met Tyr Ile Ile Ser Asn Gly Ile Asp Asp Gly Leu His
865                 870                 875                 880
Ala Glu Asp Asp Gln Leu Arg Val Tyr Tyr Met Gln Asn Tyr Ile Asn
                885                 890                 895
Glu Ala Leu Lys Ala His Ile Leu Asp Gly Ile Asn Leu Cys Gly Tyr
            900                 905                 910
Phe Ala Tyr Ser Phe Asn Asp Arg Thr Ala Pro Arg Phe Gly Leu Tyr
        915                 920                 925
Arg Tyr Ala Ala Asp Gln Phe Glu Pro Lys Ala Ser Met Lys His Tyr
    930                 935                 940
Arg Lys Ile Ile Asp Ser Asn Gly Phe Pro Gly Pro Glu Thr Leu Glu
945                 950                 955                 960
Arg Phe Cys Pro Glu Glu Phe Thr Val Cys Thr Glu Cys Ser Phe Phe
                965                 970                 975
His Thr Arg Lys Ser Leu Leu Ala Phe Ile Ala Phe Leu Phe Phe Ala
            980                 985                 990
Ser Ile Ile Ser Leu Ser Leu Ile  Phe Tyr Tyr Ser Lys  Lys Gly Arg
        995                 1000                1005
Arg Ser  Tyr Lys
    1010

<210> SEQ ID NO 3
<211> LENGTH: 3279
<212> TYPE: DNA
<213> ORGANISM: Homo sapiens

<400> SEQUENCE: 3
atcctcagtc tcccagttca agctaatcat tgacagagct ttacaatcac aagcttttac      60
tgaagctttg ataagacagt ccagcagttg gtggcaaatg aagccaggct gtgcggcagg     120
atctccaggg aatgaatgga tttttcttcag cactgatgaa ataaccacac gctataggaa     180
tacaatgtcc aacgggggat tgcaaagatc tgtcatcctg tcagcactta ttctgctacg     240
agctgttact ggattctctg gagatggaag agctatatgg tctaaaaatc ctaattttac     300
tccggtaaat gaaagtcagc tgtttctcta tgacactttc cctaaaaact ttttctgggg     360
tattgggact ggagcattgc aagtggaagg gagttggaag aaggatggaa aaggaccttc     420
tatatgggat catttcatcc acacacacct taaaaatgtc agcagcacga atggttccag     480
tgacagttat attttctctgg aaaaagactt atcagccctg gatttttatag gagtttcttt     540 ttatcaattt tcaatttcct ggccaaggct ttttccccgat ggaatagtaa cagttgccaa     600
cgcaaaaggt ctgcagtact acagtactct tctggacgct ctagtgctta gaaacattga     660
acctatagtt actttatacc actgggattt gcctttggca ctacaagaaa atatgggggg     720
gtggaaaaat gataccataa tagatatctt caatgactat gccacatact gtttccagat     780
gtttggggac cgtgtcaaat attggattac aattcacaac ccatatctag tggcttggca     840
tgggtatggg acaggtatgc atgcccctgg agagaaggga aatttagcag ctgtctacac     900
```

```
tgtgggacac aacttgatca aggctcactc gaaagtttgg cataactaca acacacattt    960
ccgcccacat cagaagggtt ggttatcgat cacgttggga tctcattgga tcgagccaaa   1020
ccggtcggaa acacgatgg atatattcaa atgtcaacaa tccatggttt ctgtgcttgg    1080
atggtttgcc aaccctatcc atggggatgg cgactatcca gagggatga gaaagaagtt    1140
gttctccgtt ctacccattt tctctgaagc agagaagcat gagatgagag cacagctga    1200
tttctttgcc ttttcttttg gacccaacaa cttcaagccc ctaaacacca tggctaaaat   1260
gggacaaaat gtttcactta atttaagaga agcgctgaac tggattaaac tggaatacaa   1320
caaccctcga atcttgattg ctgagaatgg ctggttcaca gacagtcgtg tgaaaacaga   1380
agacaccacg gccatctaca tgatgaagaa tttcctcagc caggtgcttc aagcaataag   1440
gttagatgaa atacgagtgt tggttatac tgcctggtct ctcctggatg gctttgaatg    1500
gcaggatgct tacaccatcc gccgaggatt attttatgtg gattttaaca gtaaacagaa   1560
agagcggaaa cctaagtctt cagcacacta ctacaaacag atcatacgag aaaatggttt   1620
ttctttaaaa gagtccacgc cagatgtgca gggccagttt ccctgtgact ctcctgggg    1680
tgtcactgaa tctgttctta agcccgagtc tgtggcttcg tccccacagt tcagcgatcc   1740
tcatctgtac gtgtggaacg ccactggcaa cagactgttg caccgagtgg aaggggtgag   1800
gctgaaaaca cgaccgctc aatgcacaga ttttgtaaac atcaaaaaac aacttgagat    1860
gttggcaaga atgaaagtca cccactaccg gtttgctctg gattgggcct cggtccttcc   1920
cactggcaac ctgtccgcgg tgaaccgaca ggccctgagg tactacaggt gcgtggtcag   1980
tgaggggctg aagcttggca tctccgcgat ggtcaccctg tattatccga cccacgccca   2040
cctaggcctc cccgagcctc tgttgcatgc cgacgggtgg ctgaacccat cgacggccga   2100
ggccttccag gcctacgctg ggctgtgctt ccaggagctg ggggacctgg tgaagctctg   2160
gatcaccatc aacgagccta accggctaag tgacatctac aaccgctctg caacgacac    2220
ctacggggcg gcgcacaacc tgctggtggc ccacgccctg gcctggcgcc tctacgaccg   2280
gcagttcagg ccctcacagc gcggggccgt gtcgctgtcg ctgcacgcgg actgggcgga   2340
acccgccaac ccctatgctg actcgcactg gagggcggcc gagcgcttcc tgcagttcga   2400
gatcgcctgg ttcgccgagc cgctcttcaa gaccggggac taccccgcgg ccatgaggga   2460
atacattgcc tccaagcacc gacgggggct ttccagctcg ccctgccgc gcctcaccga    2520
ggccgaaagg aggctgctca agggcacggt cgacttctgc gcgctcaacc acttcaccac   2580
taggttcgtg atgcacgagc agctggccgg cagccgctac gactcggaca gggacatcca   2640
gtttctgcag gacatcaccc gcctgagctc ccccacgcgc ctggctgtga ttccctgggg   2700
ggtgcgcaag ctgctgcggt gggtccggag gaactacggc gacatggaca tttacatcac   2760
cgccagtggc atcgacgacc aggctctgga ggatgaccgg ctccggaagt actacctagg   2820
gaagtacctt caggaggtgc tgaaagcata cctgattgat aaagtcagaa tcaaaggcta   2880
ttatgcattc aaactggctg aagagaaatc taaacccaga tttggattct tcacatctga   2940
ttttaaagct aaatcctcaa tacaatttta caacaaagtg atcagcagca ggggcttccc   3000
ttttgagaac agtagttcta gatgcagtca gacccaagaa aatacagagt gcactgtctg   3060
cttattcctt gtgcagaaga aaccactgat attcctgggt tgttgcttct tctccaccct   3120
ggttctactc ttatcaattg ccatttttca aaggcagaag agaagaaagt tttggaaagc   3180
aaaaaactta caacacatac cattaaagaa aggcaagaga gttgttagct aaactgatct   3240
gtctgcatga tagacagttt aaaaattcat cccagttcc                          3279
```

<210> SEQ ID NO 4
<211> LENGTH: 1044
<212> TYPE: PRT
<213> ORGANISM: Homo sapiens

<400> SEQUENCE: 4

```
Met Lys Pro Gly Cys Ala Ala Gly Ser Pro Gly Asn Glu Trp Ile Phe
1               5                   10                  15

Phe Ser Thr Asp Glu Ile Thr Thr Arg Tyr Arg Asn Thr Met Ser Asn
                20                  25                  30

Gly Gly Leu Gln Arg Ser Val Ile Leu Ser Ala Leu Ile Leu Leu Arg
            35                  40                  45

Ala Val Thr Gly Phe Ser Gly Asp Gly Arg Ala Ile Trp Ser Lys Asn
        50                  55                  60

Pro Asn Phe Thr Pro Val Asn Glu Ser Gln Leu Phe Leu Tyr Asp Thr
65                  70                  75                  80

Phe Pro Lys Asn Phe Phe Trp Gly Ile Gly Thr Gly Ala Leu Gln Val
                85                  90                  95

Glu Gly Ser Trp Lys Lys Asp Gly Lys Gly Pro Ser Ile Trp Asp His
            100                 105                 110

Phe Ile His Thr His Leu Lys Asn Val Ser Ser Thr Asn Gly Ser Ser
        115                 120                 125

Asp Ser Tyr Ile Phe Leu Glu Lys Asp Leu Ser Ala Leu Asp Phe Ile
130                 135                 140

Gly Val Ser Phe Tyr Gln Phe Ser Ile Ser Trp Pro Arg Leu Phe Pro
145                 150                 155                 160

Asp Gly Ile Val Thr Val Ala Asn Ala Lys Gly Leu Gln Tyr Tyr Ser
                165                 170                 175

Thr Leu Leu Asp Ala Leu Val Leu Arg Asn Ile Glu Pro Ile Val Thr
            180                 185                 190

Leu Tyr His Trp Asp Leu Pro Leu Ala Leu Gln Glu Lys Tyr Gly Gly
        195                 200                 205

Trp Lys Asn Asp Thr Ile Ile Asp Ile Phe Asn Asp Tyr Ala Thr Tyr
210                 215                 220

Cys Phe Gln Met Phe Gly Asp Arg Val Lys Tyr Trp Ile Thr Ile His
225                 230                 235                 240

Asn Pro Tyr Leu Val Ala Trp His Gly Tyr Gly Thr Gly Met His Ala
                245                 250                 255

Pro Gly Glu Lys Gly Asn Leu Ala Ala Val Tyr Thr Val Gly His Asn
            260                 265                 270

Leu Ile Lys Ala His Ser Lys Val Trp His Asn Tyr Asn Thr His Phe
        275                 280                 285

Arg Pro His Gln Lys Gly Trp Leu Ser Ile Thr Leu Gly Ser His Trp
290                 295                 300

Ile Glu Pro Asn Arg Ser Glu Asn Thr Met Asp Ile Phe Lys Cys Gln
305                 310                 315                 320

Gln Ser Met Val Ser Val Leu Gly Trp Phe Ala Asn Pro Ile His Gly
                325                 330                 335

Asp Gly Asp Tyr Pro Glu Gly Met Arg Lys Lys Leu Phe Ser Val Leu
            340                 345                 350

Pro Ile Phe Ser Glu Ala Glu Lys His Glu Met Arg Gly Thr Ala Asp
        355                 360                 365

Phe Phe Ala Phe Ser Phe Gly Pro Asn Asn Phe Lys Pro Leu Asn Thr
370                 375                 380
```

```
Met Ala Lys Met Gly Gln Asn Val Ser Leu Asn Leu Arg Glu Ala Leu
385                 390                 395                 400

Asn Trp Ile Lys Leu Glu Tyr Asn Asn Pro Arg Ile Leu Ile Ala Glu
            405                 410                 415

Asn Gly Trp Phe Thr Asp Ser Arg Val Lys Thr Glu Asp Thr Thr Ala
        420                 425                 430

Ile Tyr Met Met Lys Asn Phe Leu Ser Gln Val Leu Gln Ala Ile Arg
            435                 440                 445

Leu Asp Glu Ile Arg Val Phe Gly Tyr Thr Ala Trp Ser Leu Leu Asp
    450                 455                 460

Gly Phe Glu Trp Gln Asp Ala Tyr Thr Ile Arg Arg Gly Leu Phe Tyr
465                 470                 475                 480

Val Asp Phe Asn Ser Lys Gln Lys Glu Arg Lys Pro Lys Ser Ser Ala
                485                 490                 495

His Tyr Tyr Lys Gln Ile Ile Arg Glu Asn Gly Phe Ser Leu Lys Glu
                500                 505                 510

Ser Thr Pro Asp Val Gln Gly Gln Phe Pro Cys Asp Phe Ser Trp Gly
        515                 520                 525

Val Thr Glu Ser Val Leu Lys Pro Glu Ser Val Ala Ser Ser Pro Gln
    530                 535                 540

Phe Ser Asp Pro His Leu Tyr Val Trp Asn Ala Thr Gly Asn Arg Leu
545                 550                 555                 560

Leu His Arg Val Glu Gly Val Arg Leu Lys Thr Arg Pro Ala Gln Cys
                565                 570                 575

Thr Asp Phe Val Asn Ile Lys Lys Gln Leu Glu Met Leu Ala Arg Met
            580                 585                 590

Lys Val Thr His Tyr Arg Phe Ala Leu Asp Trp Ala Ser Val Leu Pro
            595                 600                 605

Thr Gly Asn Leu Ser Ala Val Asn Arg Gln Ala Leu Arg Tyr Tyr Arg
    610                 615                 620

Cys Val Val Ser Glu Gly Leu Lys Leu Gly Ile Ser Ala Met Val Thr
625                 630                 635                 640

Leu Tyr Tyr Pro Thr His Ala His Leu Gly Leu Pro Glu Pro Leu Leu
                645                 650                 655

His Ala Asp Gly Trp Leu Asn Pro Ser Thr Ala Glu Ala Phe Gln Ala
            660                 665                 670

Tyr Ala Gly Leu Cys Phe Gln Glu Leu Gly Asp Leu Val Lys Leu Trp
            675                 680                 685

Ile Thr Ile Asn Glu Pro Asn Arg Leu Ser Asp Ile Tyr Asn Arg Ser
    690                 695                 700

Gly Asn Asp Thr Tyr Gly Ala Ala His Asn Leu Leu Val Ala His Ala
705                 710                 715                 720

Leu Ala Trp Arg Leu Tyr Asp Arg Gln Phe Arg Pro Ser Gln Arg Gly
                725                 730                 735

Ala Val Ser Leu Ser Leu His Ala Asp Trp Ala Glu Pro Ala Asn Pro
            740                 745                 750

Tyr Ala Asp Ser His Trp Arg Ala Ala Glu Arg Phe Leu Gln Phe Glu
            755                 760                 765

Ile Ala Trp Phe Ala Glu Pro Leu Phe Lys Thr Gly Asp Tyr Pro Ala
    770                 775                 780

Ala Met Arg Glu Tyr Ile Ala Ser Lys His Arg Arg Gly Leu Ser Ser
785                 790                 795                 800

Ser Ala Leu Pro Arg Leu Thr Glu Ala Glu Arg Arg Leu Leu Lys Gly
```

```
                805                 810                 815
Thr Val Asp Phe Cys Ala Leu Asn His Phe Thr Thr Arg Phe Val Met
        820                 825                 830

His Glu Gln Leu Ala Gly Ser Arg Tyr Asp Ser Asp Arg Asp Ile Gln
        835                 840                 845

Phe Leu Gln Asp Ile Thr Arg Leu Ser Ser Pro Thr Arg Leu Ala Val
850                 855                 860

Ile Pro Trp Gly Val Arg Lys Leu Leu Arg Trp Val Arg Arg Asn Tyr
865                 870                 875                 880

Gly Asp Met Asp Ile Tyr Ile Thr Ala Ser Gly Ile Asp Asp Gln Ala
                885                 890                 895

Leu Glu Asp Asp Arg Leu Arg Lys Tyr Tyr Leu Gly Lys Tyr Leu Gln
        900                 905                 910

Glu Val Leu Lys Ala Tyr Leu Ile Asp Lys Val Arg Ile Lys Gly Tyr
        915                 920                 925

Tyr Ala Phe Lys Leu Ala Glu Glu Lys Ser Lys Pro Arg Phe Gly Phe
        930                 935                 940

Phe Thr Ser Asp Phe Lys Ala Lys Ser Ser Ile Gln Phe Tyr Asn Lys
945                 950                 955                 960

Val Ile Ser Ser Arg Gly Phe Pro Phe Glu Asn Ser Ser Arg Cys
                965                 970                 975

Ser Gln Thr Gln Glu Asn Thr Glu Cys Thr Val Cys Leu Phe Leu Val
        980                 985                 990

Gln Lys Lys Pro Leu Ile Phe Leu Gly Cys Cys Phe Phe Ser Thr Leu
        995                1000                 1005

Val Leu Leu Leu Ser Ile Ala  Ile Phe Gln Arg Gln  Lys Arg Arg
    1010                1015                 1020

Lys Phe Trp Lys Ala Lys Asn Leu Gln His Ile Pro Leu Lys Lys
    1025                1030                1035

Gly Lys Arg Val Val Ser
    1040

<210> SEQ ID NO 5
<211> LENGTH: 449
<212> TYPE: PRT
<213> ORGANISM: Homo sapiens

<400> SEQUENCE: 5

Gln Gly Thr Phe Pro Asp Gly Phe Leu Trp Ala Val Gly Ser Ala Ala
1               5                  10                  15

Tyr Gln Thr Glu Gly Gly Trp Gln Gln His Gly Lys Gly Ala Ser Ile
            20                  25                  30

Trp Asp Thr Phe Thr His His Pro Leu Ala Pro Pro Gly Asp Ser Arg
        35                  40                  45

Asn Ala Ser Leu Pro Leu Gly Ala Pro Ser Pro Leu Gln Pro Ala Thr
    50                  55                  60

Gly Asp Val Ala Ser Asp Ser Tyr Asn Asn Val Phe Arg Asp Thr Glu
65                  70                  75                  80

Ala Leu Arg Glu Leu Gly Val Thr His Tyr Arg Phe Ser Ile Ser Trp
                85                  90                  95

Ala Arg Val Leu Pro Asn Gly Ser Ala Gly Val Pro Asn Arg Glu Gly
            100                 105                 110

Leu Arg Tyr Tyr Arg Arg Leu Leu Glu Arg Leu Arg Glu Leu Gly Val
        115                 120                 125

Gln Pro Val Val Thr Leu Tyr His Trp Asp Leu Pro Gln Arg Leu Gln
```

```
                130                 135                 140
Asp Ala Tyr Gly Gly Trp Ala Asn Arg Ala Leu Ala Asp His Phe Arg
145                 150                 155                 160

Asp Tyr Ala Glu Leu Cys Phe Arg His Phe Gly Gly Gln Val Lys Tyr
                165                 170                 175

Trp Ile Thr Ile Asp Asn Pro Tyr Val Val Ala Trp His Gly Tyr Ala
                180                 185                 190

Thr Gly Arg Leu Ala Pro Gly Ile Arg Gly Ser Pro Arg Leu Gly Tyr
                195                 200                 205

Leu Val Ala His Asn Leu Leu Leu Ala His Ala Lys Val Trp His Leu
210                 215                 220

Tyr Asn Thr Ser Phe Arg Pro Thr Gln Gly Gly Gln Val Ser Ile Ala
225                 230                 235                 240

Leu Ser Ser His Trp Ile Asn Pro Arg Arg Met Thr Asp His Ser Ile
                245                 250                 255

Lys Glu Cys Gln Lys Ser Leu Asp Phe Val Leu Gly Trp Phe Ala Lys
                260                 265                 270

Pro Val Phe Ile Asp Gly Asp Tyr Pro Glu Ser Met Lys Asn Asn Leu
                275                 280                 285

Ser Ser Ile Leu Pro Asp Phe Thr Glu Ser Glu Lys Lys Phe Ile Lys
290                 295                 300

Gly Thr Ala Asp Phe Phe Ala Leu Cys Phe Gly Pro Thr Leu Ser Phe
305                 310                 315                 320

Gln Leu Leu Asp Pro His Met Lys Phe Arg Gln Leu Glu Ser Pro Asn
                325                 330                 335

Leu Arg Gln Leu Leu Ser Trp Ile Asp Leu Glu Phe Asn His Pro Gln
                340                 345                 350

Ile Phe Ile Val Glu Asn Gly Trp Phe Val Ser Gly Thr Thr Lys Arg
                355                 360                 365

Asp Asp Ala Lys Tyr Met Tyr Tyr Leu Lys Lys Phe Ile Met Glu Thr
370                 375                 380

Leu Lys Ala Ile Lys Leu Asp Gly Val Asp Val Ile Gly Tyr Thr Ala
385                 390                 395                 400

Trp Ser Leu Met Asp Gly Phe Glu Trp His Arg Gly Tyr Ser Ile Arg
                405                 410                 415

Arg Gly Leu Phe Tyr Val Asp Phe Leu Ser Gln Asp Lys Met Leu Leu
                420                 425                 430

Pro Lys Ser Ser Ala Leu Phe Tyr Gln Lys Leu Ile Glu Lys Asn Gly
                435                 440                 445

Phe

<210> SEQ ID NO 6
<211> LENGTH: 437
<212> TYPE: PRT
<213> ORGANISM: Homo sapiens

<400> SEQUENCE: 6

Gly Thr Phe Pro Cys Asp Phe Ala Trp Gly Val Val Asp Asn Tyr Ile
1               5                   10                  15

Gln Val Asp Thr Thr Leu Ser Gln Phe Thr Asp Leu Asn Val Tyr Leu
                20                  25                  30

Trp Asp Val His His Ser Lys Arg Leu Ile Lys Val Asp Gly Val Val
            35                  40                  45

Thr Lys Lys Arg Lys Ser Tyr Cys Val Asp Phe Ala Ala Ile Gln Pro
50                  55                  60
```

-continued

Gln Ile Ala Leu Leu Gln Glu Met His Val Thr His Phe Arg Phe Ser
 65                  70                  75                  80

Leu Asp Trp Ala Leu Ile Leu Pro Leu Gly Asn Gln Ser Gln Val Asn
                 85                  90                  95

His Thr Ile Leu Gln Tyr Tyr Arg Cys Met Ala Ser Glu Leu Val Arg
            100                 105                 110

Val Asn Ile Thr Pro Val Val Ala Leu Trp Gln Pro Met Ala Pro Asn
        115                 120                 125

Gln Gly Leu Pro Arg Leu Leu Ala Arg Gln Gly Ala Trp Glu Asn Pro
130                 135                 140

Tyr Thr Ala Leu Ala Phe Ala Glu Tyr Ala Arg Leu Cys Phe Gln Glu
145                 150                 155                 160

Leu Gly His His Val Lys Leu Trp Ile Thr Met Asn Glu Pro Tyr Thr
                165                 170                 175

Arg Asn Met Thr Tyr Ser Ala Gly His Asn Leu Leu Lys Ala His Ala
            180                 185                 190

Leu Ala Trp His Val Tyr Asn Glu Lys Phe Arg His Ala Gln Asn Gly
        195                 200                 205

Lys Ile Ser Ile Ala Leu Gln Ala Asp Trp Ile Glu Pro Ala Cys Pro
210                 215                 220

Phe Ser Gln Lys Asp Lys Glu Val Ala Glu Arg Val Leu Glu Phe Asp
225                 230                 235                 240

Ile Gly Trp Leu Ala Glu Pro Ile Phe Gly Ser Gly Asp Tyr Pro Trp
                245                 250                 255

Val Met Arg Asp Trp Leu Asn Gln Arg Asn Asn Phe Leu Leu Pro Tyr
            260                 265                 270

Phe Thr Glu Asp Glu Lys Lys Leu Ile Gln Gly Thr Phe Asp Phe Leu
        275                 280                 285

Ala Leu Ser His Tyr Thr Thr Ile Leu Val Asp Ser Glu Lys Glu Asp
290                 295                 300

Pro Ile Lys Tyr Asn Asp Tyr Leu Glu Val Gln Glu Met Thr Asp Ile
305                 310                 315                 320

Thr Trp Leu Asn Ser Pro Ser Gln Val Ala Val Pro Trp Gly Leu
                325                 330                 335

Arg Lys Val Leu Asn Trp Leu Lys Phe Lys Tyr Gly Asp Leu Pro Met
            340                 345                 350

Tyr Ile Ile Ser Asn Gly Ile Asp Asp Gly Leu His Ala Glu Asp Asp
        355                 360                 365

Gln Leu Arg Val Tyr Tyr Met Gln Asn Tyr Ile Asn Glu Ala Leu Lys
370                 375                 380

Ala His Ile Leu Asp Gly Ile Asn Leu Cys Gly Tyr Phe Ala Tyr Ser
385                 390                 395                 400

Phe Asn Asp Arg Thr Ala Pro Arg Phe Gly Leu Tyr Arg Tyr Ala Ala
                405                 410                 415

Asp Gln Phe Glu Pro Lys Ala Ser Met Lys His Tyr Arg Lys Ile Ile
            420                 425                 430

Asp Ser Asn Gly Phe
        435

<210> SEQ ID NO 7
<211> LENGTH: 949
<212> TYPE: PRT
<213> ORGANISM: Homo sapiens

<400> SEQUENCE: 7

```
Glu Pro Gly Asp Gly Ala Gln Thr Trp Ala Arg Phe Ser Arg Pro Pro
1               5                   10                  15

Ala Pro Glu Ala Ala Gly Leu Phe Gln Gly Thr Phe Pro Asp Gly Phe
            20                  25                  30

Leu Trp Ala Val Gly Ser Ala Ala Tyr Gln Thr Glu Gly Gly Trp Gln
        35                  40                  45

Gln His Gly Lys Gly Ala Ser Ile Trp Asp Thr Phe Thr His His Pro
50                  55                  60

Leu Ala Pro Pro Gly Asp Ser Arg Asn Ala Ser Leu Pro Leu Gly Ala
65              70                  75                  80

Pro Ser Pro Leu Gln Pro Ala Thr Gly Asp Val Ala Ser Asp Ser Tyr
                85                  90                  95

Asn Asn Val Phe Arg Asp Thr Glu Ala Leu Arg Glu Leu Gly Val Thr
                100                 105                 110

His Tyr Arg Phe Ser Ile Ser Trp Ala Arg Val Leu Pro Asn Gly Ser
            115                 120                 125

Ala Gly Val Pro Asn Arg Glu Gly Leu Arg Tyr Tyr Arg Arg Leu Leu
        130                 135                 140

Glu Arg Leu Arg Glu Leu Gly Val Gln Pro Val Val Thr Leu Tyr His
145                 150                 155                 160

Trp Asp Leu Pro Gln Arg Leu Gln Asp Ala Tyr Gly Gly Trp Ala Asn
                165                 170                 175

Arg Ala Leu Ala Asp His Phe Arg Asp Tyr Ala Glu Leu Cys Phe Arg
            180                 185                 190

His Phe Gly Gly Gln Val Lys Tyr Trp Ile Thr Ile Asp Asn Pro Tyr
        195                 200                 205

Val Val Ala Trp His Gly Tyr Ala Thr Gly Arg Leu Ala Pro Gly Ile
210                 215                 220

Arg Gly Ser Pro Arg Leu Gly Tyr Leu Val Ala His Asn Leu Leu Leu
225                 230                 235                 240

Ala His Ala Lys Val Trp His Leu Tyr Asn Thr Ser Phe Arg Pro Thr
                245                 250                 255

Gln Gly Gly Gln Val Ser Ile Ala Leu Ser Ser His Trp Ile Asn Pro
            260                 265                 270

Arg Arg Met Thr Asp His Ser Ile Lys Glu Cys Gln Lys Ser Leu Asp
        275                 280                 285

Phe Val Leu Gly Trp Phe Ala Lys Pro Val Phe Ile Asp Gly Asp Tyr
290                 295                 300

Pro Glu Ser Met Lys Asn Asn Leu Ser Ser Ile Leu Pro Asp Phe Thr
305                 310                 315                 320

Glu Ser Glu Lys Lys Phe Ile Lys Gly Thr Ala Asp Phe Phe Ala Leu
                325                 330                 335

Cys Phe Gly Pro Thr Leu Ser Phe Gln Leu Leu Asp Pro His Met Lys
            340                 345                 350

Phe Arg Gln Leu Glu Ser Pro Asn Leu Arg Gln Leu Leu Ser Trp Ile
        355                 360                 365

Asp Leu Glu Phe Asn His Pro Gln Ile Phe Ile Val Glu Asn Gly Trp
370                 375                 380

Phe Val Ser Gly Thr Thr Lys Arg Asp Asp Ala Lys Tyr Met Tyr Tyr
385                 390                 395                 400

Leu Lys Lys Phe Ile Met Glu Thr Leu Lys Ala Ile Lys Leu Asp Gly
                405                 410                 415

Val Asp Val Ile Gly Tyr Thr Ala Trp Ser Leu Met Asp Gly Phe Glu
```

```
                420             425             430
Trp His Arg Gly Tyr Ser Ile Arg Arg Gly Leu Phe Tyr Val Asp Phe
            435             440             445

Leu Ser Gln Asp Lys Met Leu Leu Pro Lys Ser Ser Ala Leu Phe Tyr
450             455             460

Gln Lys Leu Ile Glu Lys Asn Gly Phe Pro Pro Leu Pro Glu Asn Gln
465             470             475             480

Pro Leu Glu Gly Thr Phe Pro Cys Asp Phe Ala Trp Gly Val Val Asp
            485             490             495

Asn Tyr Ile Gln Val Asp Thr Thr Leu Ser Gln Phe Thr Asp Leu Asn
            500             505             510

Val Tyr Leu Trp Asp Val His His Ser Lys Arg Leu Ile Lys Val Asp
            515             520             525

Gly Val Val Thr Lys Lys Arg Lys Ser Tyr Cys Val Asp Phe Ala Ala
            530             535             540

Ile Gln Pro Gln Ile Ala Leu Leu Gln Glu Met His Val Thr His Phe
545             550             555             560

Arg Phe Ser Leu Asp Trp Ala Leu Ile Leu Pro Leu Gly Asn Gln Ser
            565             570             575

Gln Val Asn His Thr Ile Leu Gln Tyr Tyr Arg Cys Met Ala Ser Glu
            580             585             590

Leu Val Arg Val Asn Ile Thr Pro Val Val Ala Leu Trp Gln Pro Met
            595             600             605

Ala Pro Asn Gln Gly Leu Pro Arg Leu Leu Ala Arg Gln Gly Ala Trp
            610             615             620

Glu Asn Pro Tyr Thr Ala Leu Ala Phe Ala Glu Tyr Ala Arg Leu Cys
625             630             635             640

Phe Gln Glu Leu Gly His His Val Lys Leu Trp Ile Thr Met Asn Glu
            645             650             655

Pro Tyr Thr Arg Asn Met Thr Tyr Ser Ala Gly His Asn Leu Leu Lys
            660             665             670

Ala His Ala Leu Ala Trp His Val Tyr Asn Glu Lys Phe Arg His Ala
            675             680             685

Gln Asn Gly Lys Ile Ser Ile Ala Leu Gln Ala Asp Trp Ile Glu Pro
            690             695             700

Ala Cys Pro Phe Ser Gln Lys Asp Lys Glu Val Ala Glu Arg Val Leu
705             710             715             720

Glu Phe Asp Ile Gly Trp Leu Ala Glu Pro Ile Phe Gly Ser Gly Asp
            725             730             735

Tyr Pro Trp Val Met Arg Asp Trp Leu Asn Gln Arg Asn Asn Phe Leu
            740             745             750

Leu Pro Tyr Phe Thr Glu Asp Glu Lys Lys Leu Ile Gln Gly Thr Phe
            755             760             765

Asp Phe Leu Ala Leu Ser His Tyr Thr Thr Ile Leu Val Asp Ser Glu
            770             775             780

Lys Glu Asp Pro Ile Lys Tyr Asn Asp Tyr Leu Glu Val Gln Glu Met
785             790             795             800

Thr Asp Ile Thr Trp Leu Asn Ser Pro Ser Gln Val Ala Val Val Pro
            805             810             815

Trp Gly Leu Arg Lys Val Leu Asn Trp Leu Lys Phe Lys Tyr Gly Asp
            820             825             830

Leu Pro Met Tyr Ile Ile Ser Asn Gly Ile Asp Asp Gly Leu His Ala
            835             840             845
```

```
Glu Asp Asp Gln Leu Arg Val Tyr Tyr Met Gln Asn Tyr Ile Asn Glu
    850                 855                 860

Ala Leu Lys Ala His Ile Leu Asp Gly Ile Asn Leu Cys Gly Tyr Phe
865                 870                 875                 880

Ala Tyr Ser Phe Asn Asp Arg Thr Ala Pro Arg Phe Gly Leu Tyr Arg
                885                 890                 895

Tyr Ala Ala Asp Gln Phe Glu Pro Lys Ala Ser Met Lys His Tyr Arg
            900                 905                 910

Lys Ile Ile Asp Ser Asn Gly Phe Pro Gly Pro Glu Thr Leu Glu Arg
        915                 920                 925

Phe Cys Pro Glu Glu Phe Thr Val Cys Thr Glu Cys Ser Phe Phe His
    930                 935                 940

Thr Arg Lys Ser Leu
945
```

<210> SEQ ID NO 8
<211> LENGTH: 33
<212> TYPE: PRT
<213> ORGANISM: Homo sapiens

<400> SEQUENCE: 8

```
Met Pro Ala Ser Ala Pro Pro Arg Arg Pro Arg Pro Pro Pro Pro Ser
1               5                   10                  15

Leu Ser Leu Leu Leu Val Leu Leu Gly Leu Gly Gly Arg Arg Leu Arg
            20                  25                  30

Ala
```

<210> SEQ ID NO 9
<211> LENGTH: 25
<212> TYPE: PRT
<213> ORGANISM: Homo sapiens

<400> SEQUENCE: 9

```
Met Ser Val Leu Thr Gln Val Leu Ala Leu Leu Leu Leu Trp Leu Thr
1               5                   10                  15

Gly Thr Arg Cys Arg Arg Leu Arg Ala
            20                  25
```

<210> SEQ ID NO 10
<211> LENGTH: 45
<212> TYPE: DNA
<213> ORGANISM: Artificial
<220> FEATURE:
<223> OTHER INFORMATION: linker

<400> SEQUENCE: 10
ggaggtggag gttcaggagg tggaggttca ggaggtggag gttca           45

<210> SEQ ID NO 11
<211> LENGTH: 15
<212> TYPE: PRT
<213> ORGANISM: Artificial
<220> FEATURE:
<223> OTHER INFORMATION: linker

<400> SEQUENCE: 11

```
Gly Gly Gly Gly Ser Gly Gly Gly Ser Gly Gly Gly Gly Ser
1               5                   10                  15
```

<210> SEQ ID NO 12
<211> LENGTH: 5
<212> TYPE: PRT

```
<213> ORGANISM: Artificial
<220> FEATURE:
<223> OTHER INFORMATION: linker

<400> SEQUENCE: 12

Gly Gly Gly Gly Ser
1               5

<210> SEQ ID NO 13
<211> LENGTH: 1
<212> TYPE: PRT
<213> ORGANISM: Artificial
<220> FEATURE:
<223> OTHER INFORMATION: linker

<400> SEQUENCE: 13

Gly
1

<210> SEQ ID NO 14
<211> LENGTH: 2
<212> TYPE: PRT
<213> ORGANISM: Artificial
<220> FEATURE:
<223> OTHER INFORMATION: linker

<400> SEQUENCE: 14

Gly Gly
1

<210> SEQ ID NO 15
<211> LENGTH: 2
<212> TYPE: PRT
<213> ORGANISM: Artificial
<220> FEATURE:
<223> OTHER INFORMATION: linker

<400> SEQUENCE: 15

Gly Ser
1

<210> SEQ ID NO 16
<211> LENGTH: 3
<212> TYPE: PRT
<213> ORGANISM: Artificial
<220> FEATURE:
<223> OTHER INFORMATION: linker

<400> SEQUENCE: 16

Gly Gly Ser
1

<210> SEQ ID NO 17
<211> LENGTH: 1
<212> TYPE: PRT
<213> ORGANISM: Artificial
<220> FEATURE:
<223> OTHER INFORMATION: linker

<400> SEQUENCE: 17

Ala
1

<210> SEQ ID NO 18
<211> LENGTH: 2
<212> TYPE: PRT
<213> ORGANISM: Artificial
<220> FEATURE:
```

<223> OTHER INFORMATION: linker

<400> SEQUENCE: 18

Ala Ala
1

<210> SEQ ID NO 19
<211> LENGTH: 1228
<212> TYPE: PRT
<213> ORGANISM: Artificial
<220> FEATURE:
<223> OTHER INFORMATION: fusion polypeptide

<400> SEQUENCE: 19

```
Met Pro Ala Ser Ala Pro Pro Arg Arg Pro Arg Pro Pro Pro Pro Ser
1               5                   10                  15

Leu Ser Leu Leu Leu Val Leu Leu Gly Leu Gly Gly Arg Arg Leu Arg
            20                  25                  30

Ala Glu Pro Gly Asp Gly Ala Gln Thr Trp Ala Arg Phe Ser Arg Pro
        35                  40                  45

Pro Ala Pro Glu Ala Ala Gly Leu Phe Gln Gly Thr Phe Pro Asp Gly
    50                  55                  60

Phe Leu Trp Ala Val Gly Ser Ala Ala Tyr Gln Thr Glu Gly Gly Trp
65                  70                  75                  80

Gln Gln His Gly Lys Gly Ala Ser Ile Trp Asp Thr Phe Thr His His
                85                  90                  95

Pro Leu Ala Pro Pro Gly Asp Ser Arg Asn Ala Ser Leu Pro Leu Gly
            100                 105                 110

Ala Pro Ser Pro Leu Gln Pro Ala Thr Gly Asp Val Ala Ser Asp Ser
        115                 120                 125

Tyr Asn Asn Val Phe Arg Asp Thr Glu Ala Leu Arg Glu Leu Gly Val
130                 135                 140

Thr His Tyr Arg Phe Ser Ile Ser Trp Ala Arg Val Leu Pro Asn Gly
145                 150                 155                 160

Ser Ala Gly Val Pro Asn Arg Glu Gly Leu Arg Tyr Tyr Arg Arg Leu
                165                 170                 175

Leu Glu Arg Leu Arg Glu Leu Gly Val Gln Pro Val Val Thr Leu Tyr
            180                 185                 190

His Trp Asp Leu Pro Gln Arg Leu Gln Asp Ala Tyr Gly Gly Trp Ala
        195                 200                 205

Asn Arg Ala Leu Ala Asp His Phe Arg Asp Tyr Ala Glu Leu Cys Phe
    210                 215                 220

Arg His Phe Gly Gly Gln Val Lys Tyr Trp Ile Thr Ile Asp Asn Pro
225                 230                 235                 240

Tyr Val Val Ala Trp His Gly Tyr Ala Thr Gly Arg Leu Ala Pro Gly
                245                 250                 255

Ile Arg Gly Ser Pro Arg Leu Gly Tyr Leu Val Ala His Asn Leu Leu
            260                 265                 270

Leu Ala His Ala Lys Val Trp His Leu Tyr Asn Thr Ser Phe Arg Pro
        275                 280                 285

Thr Gln Gly Gly Gln Val Ser Ile Ala Leu Ser Ser His Trp Ile Asn
    290                 295                 300

Pro Arg Arg Met Thr Asp His Ser Ile Lys Glu Cys Gln Lys Ser Leu
305                 310                 315                 320

Asp Phe Val Leu Gly Trp Phe Ala Lys Pro Val Phe Ile Asp Gly Asp
                325                 330                 335
```

-continued

Tyr Pro Glu Ser Met Lys Asn Asn Leu Ser Ser Ile Leu Pro Asp Phe
            340                 345                 350

Thr Glu Ser Glu Lys Lys Phe Ile Lys Gly Thr Ala Asp Phe Phe Ala
        355                 360                 365

Leu Cys Phe Gly Pro Thr Leu Ser Phe Gln Leu Leu Asp Pro His Met
    370                 375                 380

Lys Phe Arg Gln Leu Glu Ser Pro Asn Leu Arg Gln Leu Leu Ser Trp
385                 390                 395                 400

Ile Asp Leu Glu Phe Asn His Pro Gln Ile Phe Ile Val Glu Asn Gly
                405                 410                 415

Trp Phe Val Ser Gly Thr Thr Lys Arg Asp Asp Ala Lys Tyr Met Tyr
            420                 425                 430

Tyr Leu Lys Lys Phe Ile Met Glu Thr Leu Lys Ala Ile Lys Leu Asp
        435                 440                 445

Gly Val Asp Val Ile Gly Tyr Thr Ala Trp Ser Leu Met Asp Gly Phe
    450                 455                 460

Glu Trp His Arg Gly Tyr Ser Ile Arg Arg Gly Leu Phe Tyr Val Asp
465                 470                 475                 480

Phe Leu Ser Gln Asp Lys Met Leu Leu Pro Lys Ser Ala Leu Phe
                485                 490                 495

Tyr Gln Lys Leu Ile Glu Lys Asn Gly Phe Pro Pro Leu Pro Glu Asn
        500                 505                 510

Gln Pro Leu Glu Gly Thr Phe Pro Cys Asp Phe Ala Trp Gly Val Val
    515                 520                 525

Asp Asn Tyr Ile Gln Val Asp Thr Thr Leu Ser Gln Phe Thr Asp Leu
    530                 535                 540

Asn Val Tyr Leu Trp Asp Val His His Ser Lys Arg Leu Ile Lys Val
545                 550                 555                 560

Asp Gly Val Val Thr Lys Lys Arg Lys Ser Tyr Cys Val Asp Phe Ala
            565                 570                 575

Ala Ile Gln Pro Gln Ile Ala Leu Leu Gln Glu Met His Val Thr His
        580                 585                 590

Phe Arg Phe Ser Leu Asp Trp Ala Leu Ile Leu Pro Leu Gly Asn Gln
    595                 600                 605

Ser Gln Val Asn His Thr Ile Leu Gln Tyr Tyr Arg Cys Met Ala Ser
    610                 615                 620

Glu Leu Val Arg Val Asn Ile Thr Pro Val Val Ala Leu Trp Gln Pro
625                 630                 635                 640

Met Ala Pro Asn Gln Gly Leu Pro Arg Leu Leu Ala Arg Gln Gly Ala
            645                 650                 655

Trp Glu Asn Pro Tyr Thr Ala Leu Ala Phe Ala Glu Tyr Ala Arg Leu
        660                 665                 670

Cys Phe Gln Glu Leu Gly His His Val Lys Leu Trp Ile Thr Met Asn
    675                 680                 685

Glu Pro Tyr Thr Arg Asn Met Thr Tyr Ser Ala Gly His Asn Leu Leu
    690                 695                 700

Lys Ala His Ala Leu Ala Trp His Val Tyr Asn Glu Lys Phe Arg His
705                 710                 715                 720

Ala Gln Asn Gly Lys Ile Ser Ile Ala Leu Gln Ala Asp Trp Ile Glu
            725                 730                 735

Pro Ala Cys Pro Phe Ser Gln Lys Asp Lys Glu Val Ala Glu Arg Val
        740                 745                 750

Leu Glu Phe Asp Ile Gly Trp Leu Ala Glu Pro Ile Phe Gly Ser Gly
    755                 760                 765

Asp Tyr Pro Trp Val Met Arg Asp Trp Leu Asn Gln Arg Asn Asn Phe
770                 775                 780

Leu Leu Pro Tyr Phe Thr Glu Asp Glu Lys Lys Leu Ile Gln Gly Thr
785                 790                 795                 800

Phe Asp Phe Leu Ala Leu Ser His Tyr Thr Thr Ile Leu Val Asp Ser
                805                 810                 815

Glu Lys Glu Asp Pro Ile Lys Tyr Asn Asp Tyr Leu Gly Val Gln Glu
            820                 825                 830

Met Thr Asp Ile Thr Trp Leu Asn Ser Pro Ser Gln Val Ala Val Val
                835                 840                 845

Pro Trp Gly Leu Arg Lys Val Leu Asn Trp Leu Lys Phe Lys Tyr Gly
            850                 855                 860

Asp Leu Pro Met Tyr Ile Ile Ser Asn Gly Ile Asp Asp Gly Leu His
865                 870                 875                 880

Ala Glu Asp Asp Gln Leu Arg Val Tyr Met Gln Asn Tyr Ile Asn
                885                 890                 895

Glu Ala Leu Lys Ala His Ile Leu Asp Gly Ile Asn Leu Cys Gly Tyr
                900                 905                 910

Phe Ala Tyr Ser Phe Asn Asp Arg Thr Ala Pro Arg Phe Gly Leu Tyr
                915                 920                 925

Arg Tyr Ala Ala Asp Gln Phe Glu Pro Lys Ala Ser Met Lys His Tyr
930                 935                 940

Arg Lys Ile Ile Asp Ser Asn Gly Phe Pro Gly Pro Glu Thr Leu Glu
945                 950                 955                 960

Arg Phe Cys Pro Glu Glu Phe Thr Val Cys Thr Glu Cys Ser Phe Phe
                965                 970                 975

His Thr Arg Lys Ser Leu Gly Ser Gly Gly Gly Ser Gly Gly Gly
                980                 985                 990

Gly Ser Gly Gly Gly Gly Ser Leu Lys Tyr Pro Asn Ala Ser Pro Leu
        995                 1000                1005

Leu Gly Ser Ser Trp Gly Gly Leu Ile His Leu Tyr Thr Ala Thr
    1010                1015                1020

Ala Arg Asn Ser Tyr His Leu Gln Ile His Lys Asn Gly His Val
    1025                1030                1035

Asp Gly Ala Pro His Gln Thr Ile Tyr Ser Ala Leu Met Ile Arg
    1040                1045                1050

Ser Glu Asp Ala Gly Phe Val Val Ile Thr Gly Val Met Ser Arg
    1055                1060                1065

Arg Tyr Leu Cys Met Asp Phe Arg Gly Asn Ile Phe Gly Ser His
    1070                1075                1080

Tyr Phe Asp Pro Glu Asn Cys Arg Phe Gln His Gln Thr Leu Glu
    1085                1090                1095

Asn Gly Tyr Asp Val Tyr His Ser Pro Gln Tyr His Phe Leu Val
    1100                1105                1110

Ser Leu Gly Arg Ala Lys Arg Ala Phe Leu Pro Gly Met Asn Pro
    1115                1120                1125

Pro Pro Tyr Ser Gln Phe Leu Ser Arg Arg Asn Glu Ile Pro Leu
    1130                1135                1140

Ile His Phe Asn Thr Pro Ile Pro Arg Arg His Thr Gln Ser Ala
    1145                1150                1155

Glu Asp Asp Ser Glu Arg Asp Pro Leu Asn Val Leu Lys Pro Arg
    1160                1165                1170

Ala Arg Met Thr Pro Ala Pro Ala Ser Cys Ser Gln Glu Leu Pro

-continued

```
                1175                1180                1185

Ser Ala Glu Asp Asn Ser Pro Met Ala Ser Asp Pro Leu Gly Val
        1190                1195                1200

Val Arg Gly Gly Arg Val Asn Thr His Ala Gly Thr Gly Pro
        1205                1210                1215

Glu Gly Cys Arg Pro Phe Ala Lys Phe Ile
        1220                1225

<210> SEQ ID NO 20
<211> LENGTH: 1220
<212> TYPE: PRT
<213> ORGANISM: Artificial
<220> FEATURE:
<223> OTHER INFORMATION: fusion polypeptide

<400> SEQUENCE: 20

Met Ser Val Leu Thr Gln Val Leu Ala Leu Leu Leu Trp Leu Thr
1               5                   10                  15

Gly Leu Gly Gly Arg Arg Leu Arg Ala Glu Pro Gly Asp Gly Ala Gln
            20                  25                  30

Thr Trp Ala Arg Phe Ser Arg Pro Pro Ala Pro Glu Ala Ala Gly Leu
        35                  40                  45

Phe Gln Gly Thr Phe Pro Asp Gly Phe Leu Trp Ala Val Gly Ser Ala
    50                  55                  60

Ala Tyr Gln Thr Glu Gly Gly Trp Gln Gln His Gly Lys Gly Ala Ser
65                  70                  75                  80

Ile Trp Asp Thr Phe Thr His His Pro Leu Ala Pro Pro Gly Asp Ser
                85                  90                  95

Arg Asn Ala Ser Leu Pro Leu Gly Ala Pro Ser Pro Leu Gln Pro Ala
            100                 105                 110

Thr Gly Asp Val Ala Ser Asp Ser Tyr Asn Asn Val Phe Arg Asp Thr
        115                 120                 125

Glu Ala Leu Arg Glu Leu Gly Val Thr His Tyr Arg Phe Ser Ile Ser
    130                 135                 140

Trp Ala Arg Val Leu Pro Asn Gly Ser Ala Gly Val Pro Asn Arg Glu
145                 150                 155                 160

Gly Leu Arg Tyr Tyr Arg Arg Leu Leu Glu Arg Leu Arg Glu Leu Gly
                165                 170                 175

Val Gln Pro Val Val Thr Leu Tyr His Trp Asp Leu Pro Gln Arg Leu
            180                 185                 190

Gln Asp Ala Tyr Gly Gly Trp Ala Asn Arg Ala Leu Ala Asp His Phe
        195                 200                 205

Arg Asp Tyr Ala Glu Leu Cys Phe Arg His Phe Gly Gly Gln Val Lys
    210                 215                 220

Tyr Trp Ile Thr Ile Asp Asn Pro Tyr Val Val Ala Trp His Gly Tyr
225                 230                 235                 240

Ala Thr Gly Arg Leu Ala Pro Gly Ile Arg Gly Ser Pro Arg Leu Gly
                245                 250                 255

Tyr Leu Val Ala His Asn Leu Leu Leu Ala His Ala Lys Val Trp His
            260                 265                 270

Leu Tyr Asn Thr Ser Phe Arg Pro Thr Gln Gly Gly Gln Val Ser Ile
        275                 280                 285

Ala Leu Ser Ser His Trp Ile Asn Pro Arg Arg Met Thr Asp His Ser
    290                 295                 300

Ile Lys Glu Cys Gln Lys Ser Leu Asp Phe Val Leu Gly Trp Phe Ala
305                 310                 315                 320
```

```
Lys Pro Val Phe Ile Asp Gly Asp Tyr Pro Glu Ser Met Lys Asn Asn
            325                 330                 335

Leu Ser Ser Ile Leu Pro Asp Phe Thr Glu Ser Lys Lys Phe Ile
        340                 345                 350

Lys Gly Thr Ala Asp Phe Phe Ala Leu Cys Phe Gly Pro Thr Leu Ser
            355                 360                 365

Phe Gln Leu Leu Asp Pro His Met Lys Phe Arg Gln Leu Glu Ser Pro
    370                 375                 380

Asn Leu Arg Gln Leu Leu Ser Trp Ile Asp Leu Glu Phe Asn His Pro
385                 390                 395                 400

Gln Ile Phe Ile Val Glu Asn Gly Trp Phe Val Ser Gly Thr Thr Lys
                405                 410                 415

Arg Asp Asp Ala Lys Tyr Met Tyr Tyr Leu Lys Lys Phe Ile Met Glu
                420                 425                 430

Thr Leu Lys Ala Ile Lys Leu Asp Gly Val Asp Val Ile Gly Tyr Thr
            435                 440                 445

Ala Trp Ser Leu Met Asp Gly Phe Glu Trp His Arg Gly Tyr Ser Ile
    450                 455                 460

Arg Arg Gly Leu Phe Tyr Val Asp Phe Leu Ser Gln Asp Lys Met Leu
465                 470                 475                 480

Leu Pro Lys Ser Ser Ala Leu Phe Tyr Gln Lys Leu Ile Glu Lys Asn
                485                 490                 495

Gly Phe Pro Pro Leu Pro Glu Asn Gln Pro Leu Glu Gly Thr Phe Pro
                500                 505                 510

Cys Asp Phe Ala Trp Gly Val Val Asp Asn Tyr Ile Gln Val Asp Thr
            515                 520                 525

Thr Leu Ser Gln Phe Thr Asp Leu Asn Val Tyr Leu Trp Asp Val His
    530                 535                 540

His Ser Lys Arg Leu Ile Lys Val Asp Gly Val Val Thr Lys Lys Arg
545                 550                 555                 560

Lys Ser Tyr Cys Val Asp Phe Ala Ala Ile Gln Pro Gln Ile Ala Leu
                565                 570                 575

Leu Gln Glu Met His Val Thr His Phe Arg Phe Ser Leu Asp Trp Ala
                580                 585                 590

Leu Ile Leu Pro Leu Gly Asn Gln Ser Gln Val Asn His Thr Ile Leu
            595                 600                 605

Gln Tyr Tyr Arg Cys Met Ala Ser Glu Leu Val Arg Val Asn Ile Thr
    610                 615                 620

Pro Val Val Ala Leu Trp Gln Pro Met Ala Pro Asn Gln Gly Leu Pro
625                 630                 635                 640

Arg Leu Leu Ala Arg Gln Gly Ala Trp Glu Asn Pro Tyr Thr Ala Leu
                645                 650                 655

Ala Phe Ala Glu Tyr Ala Arg Leu Cys Phe Gln Glu Leu Gly His His
                660                 665                 670

Val Lys Leu Trp Ile Thr Met Asn Glu Pro Tyr Thr Arg Asn Met Thr
            675                 680                 685

Tyr Ser Ala Gly His Asn Leu Leu Lys Ala His Ala Leu Ala Trp His
    690                 695                 700

Val Tyr Asn Glu Lys Phe Arg His Ala Gln Asn Gly Lys Ile Ser Ile
705                 710                 715                 720

Ala Leu Gln Ala Asp Trp Ile Glu Pro Ala Cys Pro Phe Ser Gln Lys
                725                 730                 735

Asp Lys Glu Val Ala Glu Arg Val Leu Glu Phe Asp Ile Gly Trp Leu
```

```
                        740                 745                 750
Ala Glu Pro Ile Phe Gly Ser Gly Asp Tyr Pro Trp Val Met Arg Asp
            755                 760                 765
Trp Leu Asn Gln Arg Asn Asn Phe Leu Leu Pro Tyr Phe Thr Glu Asp
        770                 775                 780
Glu Lys Lys Leu Ile Gln Gly Thr Phe Asp Phe Leu Ala Leu Ser His
785                 790                 795                 800
Tyr Thr Thr Ile Leu Val Asp Ser Glu Lys Asp Pro Ile Lys Tyr
                805                 810                 815
Asn Asp Tyr Leu Glu Val Gln Glu Met Thr Asp Ile Thr Trp Leu Asn
            820                 825                 830
Ser Pro Ser Gln Val Ala Val Val Pro Trp Gly Leu Arg Lys Val Leu
        835                 840                 845
Asn Trp Leu Lys Phe Lys Tyr Gly Asp Leu Pro Met Tyr Ile Ile Ser
        850                 855                 860
Asn Gly Ile Asp Asp Gly Leu His Ala Glu Asp Asp Gln Leu Arg Val
865                 870                 875                 880
Tyr Tyr Met Gln Asn Tyr Ile Asn Glu Ala Leu Lys Ala His Ile Leu
                885                 890                 895
Asp Gly Ile Asn Leu Cys Gly Tyr Phe Ala Tyr Ser Phe Asn Asp Arg
            900                 905                 910
Thr Ala Pro Arg Phe Gly Leu Tyr Arg Tyr Ala Ala Asp Gln Phe Glu
        915                 920                 925
Pro Lys Ala Ser Met Lys His Tyr Arg Lys Ile Ile Asp Ser Asn Gly
        930                 935                 940
Phe Pro Gly Pro Glu Thr Leu Glu Arg Phe Cys Pro Glu Glu Phe Thr
945                 950                 955                 960
Val Cys Thr Glu Cys Ser Phe Phe His Thr Arg Lys Ser Leu Gly Ser
                965                 970                 975
Gly Gly Gly Gly Ser Gly Gly Gly Ser Gly Gly Gly Gly Ser Leu
            980                 985                 990
Lys Tyr Pro Asn Ala Ser Pro Leu Leu Gly Ser Ser Trp Gly Gly Leu
        995                 1000                1005
Ile His Leu Tyr Thr Ala Thr Ala Arg Asn Ser Tyr His Leu Gln
    1010                1015                1020
Ile His Lys Asn Gly His Val Asp Gly Ala Pro His Gln Thr Ile
    1025                1030                1035
Tyr Ser Ala Leu Met Ile Arg Ser Glu Asp Ala Gly Phe Val Val
    1040                1045                1050
Ile Thr Gly Val Met Ser Arg Arg Tyr Leu Cys Met Asp Phe Arg
    1055                1060                1065
Gly Asn Ile Phe Gly Ser His Tyr Phe Asp Pro Glu Asn Cys Arg
    1070                1075                1080
Phe Gln His Gln Thr Leu Glu Asn Gly Tyr Asp Val Tyr His Ser
    1085                1090                1095
Pro Gln Tyr His Phe Leu Val Ser Leu Gly Arg Ala Lys Arg Ala
    1100                1105                1110
Phe Leu Pro Gly Met Asn Pro Pro Pro Tyr Ser Gln Phe Leu Ser
    1115                1120                1125
Arg Arg Asn Glu Ile Pro Leu Ile His Phe Asn Thr Pro Ile Pro
    1130                1135                1140
Arg Arg His Thr Gln Ser Ala Glu Asp Asp Ser Glu Arg Asp Pro
    1145                1150                1155
```

```
Leu Asn Val Leu Lys Pro Arg Ala Arg Met Thr Pro Ala Pro Ala
    1160            1165                1170

Ser Cys Ser Gln Glu Leu Pro Ser Ala Glu Asp Asn Ser Pro Met
1175                1180                1185

Ala Ser Asp Pro Leu Gly Val Val Arg Gly Gly Arg Val Asn Thr
    1190            1195                1200

His Ala Gly Gly Thr Gly Pro Glu Gly Cys Arg Pro Phe Ala Lys
    1205            1210                1215

Phe Ile
    1220

<210> SEQ ID NO 21
<211> LENGTH: 762
<212> TYPE: PRT
<213> ORGANISM: Artificial
<220> FEATURE:
<223> OTHER INFORMATION: fusion polypeptide

<400> SEQUENCE: 21

Met Pro Ala Ser Ala Pro Pro Arg Arg Pro Arg Pro Pro Pro Ser
1               5                   10                  15

Leu Ser Leu Leu Leu Val Leu Leu Gly Leu Gly Arg Arg Leu Arg
                20                  25                  30

Ala Glu Pro Gly Asp Gly Ala Gln Thr Trp Ala Arg Phe Ser Arg
                35                  40                  45

Pro Ala Pro Glu Ala Ala Gly Leu Phe Gln Gly Thr Phe Pro Asp
    50                  55                  60

Phe Leu Trp Ala Val Gly Ser Ala Ala Tyr Gln Thr Glu Gly Gly Trp
65                  70                  75                  80

Gln Gln His Gly Lys Gly Ala Ser Ile Trp Asp Thr Phe Thr His His
                85                  90                  95

Pro Leu Ala Pro Pro Gly Asp Ser Arg Asn Ala Ser Leu Pro Leu Gly
            100                 105                 110

Ala Pro Ser Pro Leu Gln Pro Ala Thr Gly Asp Val Ala Ser Asp Ser
            115                 120                 125

Tyr Asn Asn Val Phe Arg Asp Thr Glu Ala Leu Arg Glu Leu Gly Val
    130                 135                 140

Thr His Tyr Arg Phe Ser Ile Ser Trp Ala Arg Val Leu Pro Asn Gly
145                 150                 155                 160

Ser Ala Gly Val Pro Asn Arg Glu Gly Leu Arg Tyr Tyr Arg Arg Leu
                165                 170                 175

Leu Glu Arg Leu Arg Glu Leu Gly Val Gln Pro Val Val Thr Leu Tyr
            180                 185                 190

His Trp Asp Leu Pro Gln Arg Leu Gln Asp Ala Tyr Gly Gly Trp Ala
        195                 200                 205

Asn Arg Ala Leu Ala Asp His Phe Arg Asp Tyr Ala Glu Leu Cys Phe
    210                 215                 220

Arg His Phe Gly Gly Gln Val Lys Tyr Trp Ile Thr Ile Asp Asn Pro
225                 230                 235                 240

Tyr Val Val Ala Trp His Gly Tyr Ala Thr Gly Arg Leu Ala Pro Gly
                245                 250                 255

Ile Arg Gly Ser Pro Arg Leu Gly Tyr Leu Val Ala His Asn Leu Leu
            260                 265                 270

Leu Ala His Ala Lys Val Trp His Leu Tyr Asn Thr Ser Phe Arg Pro
        275                 280                 285

Thr Gln Gly Gly Gln Val Ser Ile Ala Leu Ser Ser His Trp Ile Asn
```

```
              290                 295                 300
Pro Arg Arg Met Thr Asp His Ser Ile Lys Glu Cys Gln Lys Ser Leu
305                 310                 315                 320

Asp Phe Val Leu Gly Trp Phe Ala Lys Pro Val Phe Ile Asp Gly Asp
                    325                 330                 335

Tyr Pro Glu Ser Met Lys Asn Asn Leu Ser Ser Ile Leu Pro Asp Phe
                    340                 345                 350

Thr Glu Ser Glu Lys Lys Phe Ile Lys Gly Thr Ala Asp Phe Phe Ala
                    355                 360                 365

Leu Cys Phe Gly Pro Thr Leu Ser Phe Gln Leu Leu Asp Pro His Met
370                 375                 380

Lys Phe Arg Gln Leu Glu Ser Pro Asn Leu Arg Gln Leu Leu Ser Trp
385                 390                 395                 400

Ile Asp Leu Glu Phe Asn His Pro Gln Ile Phe Ile Val Glu Asn Gly
                    405                 410                 415

Trp Phe Val Ser Gly Thr Thr Lys Arg Asp Asp Ala Lys Tyr Met Tyr
                    420                 425                 430

Tyr Leu Lys Lys Phe Ile Met Glu Thr Leu Lys Ala Ile Lys Leu Asp
                    435                 440                 445

Gly Val Asp Val Ile Gly Tyr Thr Ala Trp Ser Leu Met Asp Gly Phe
450                 455                 460

Glu Trp His Arg Gly Tyr Ser Ile Arg Arg Gly Leu Phe Tyr Val Asp
465                 470                 475                 480

Phe Leu Ser Gln Asp Lys Met Leu Leu Pro Lys Ser Ser Ala Leu Phe
                    485                 490                 495

Tyr Gln Lys Leu Ile Glu Lys Asn Gly Phe Pro Pro Leu Pro Glu Asn
                    500                 505                 510

Gln Pro Leu Glu Gly Ser Gly Gly Gly Ser Gly Gly Gly Gly Ser
                    515                 520                 525

Gly Gly Gly Gly Ser Leu Lys Tyr Pro Asn Ala Ser Pro Leu Leu Gly
                    530                 535                 540

Ser Ser Trp Gly Gly Leu Ile His Leu Tyr Thr Ala Thr Ala Arg Asn
545                 550                 555                 560

Ser Tyr His Leu Gln Ile His Lys Asn Gly His Val Asp Gly Ala Pro
                    565                 570                 575

His Gln Thr Ile Tyr Ser Ala Leu Met Ile Arg Ser Glu Asp Ala Gly
                    580                 585                 590

Phe Val Val Ile Thr Gly Val Met Ser Arg Arg Tyr Leu Cys Met Asp
                    595                 600                 605

Phe Arg Gly Asn Ile Phe Gly Ser His Tyr Phe Asp Pro Glu Asn Cys
610                 615                 620

Arg Phe Gln His Gln Thr Leu Glu Asn Gly Tyr Asp Val Tyr His Ser
625                 630                 635                 640

Pro Gln Tyr His Phe Leu Val Ser Leu Gly Arg Ala Lys Arg Ala Phe
                    645                 650                 655

Leu Pro Gly Met Asn Pro Pro Tyr Ser Gln Phe Leu Ser Arg Arg
                    660                 665                 670

Asn Glu Ile Pro Leu Ile His Phe Asn Thr Pro Ile Pro Arg Arg His
                    675                 680                 685

Thr Gln Ser Ala Glu Asp Asp Ser Glu Arg Asp Pro Leu Asn Val Leu
                    690                 695                 700

Lys Pro Arg Ala Arg Met Thr Pro Ala Pro Ala Ser Cys Ser Gln Glu
705                 710                 715                 720
```

```
Leu Pro Ser Ala Glu Asp Asn Ser Pro Met Ala Ser Asp Pro Leu Gly
                725                 730                 735

Val Val Arg Gly Gly Arg Val Asn Thr His Ala Gly Gly Thr Gly Pro
            740                 745                 750

Glu Gly Cys Arg Pro Phe Ala Lys Phe Ile
        755                 760

<210> SEQ ID NO 22
<211> LENGTH: 752
<212> TYPE: PRT
<213> ORGANISM: Artificial
<220> FEATURE:
<223> OTHER INFORMATION: fusion polypeptide

<400> SEQUENCE: 22

Met Pro Ala Ser Ala Pro Pro Arg Arg Pro Arg Pro Pro Pro Pro Ser
1               5                   10                  15

Leu Ser Leu Leu Leu Val Leu Leu Gly Leu Gly Gly Arg Arg Leu Pro
            20                  25                  30

Leu Pro Glu Asn Gln Pro Leu Glu Gly Thr Phe Pro Cys Asp Phe Ala
        35                  40                  45

Trp Gly Val Val Asp Asn Tyr Ile Gln Val Asp Thr Thr Leu Ser Gln
    50                  55                  60

Phe Thr Asp Leu Asn Val Tyr Leu Trp Asp Val His His Ser Lys Arg
65                  70                  75                  80

Leu Ile Lys Val Asp Gly Val Val Thr Lys Lys Arg Lys Ser Tyr Cys
                85                  90                  95

Val Asp Phe Ala Ala Ile Gln Pro Gln Ile Ala Leu Leu Gln Glu Met
            100                 105                 110

His Val Thr His Phe Arg Phe Ser Leu Asp Trp Ala Leu Ile Leu Pro
        115                 120                 125

Leu Gly Asn Gln Ser Gln Val Asn His Thr Ile Leu Gln Tyr Tyr Arg
    130                 135                 140

Cys Met Ala Ser Glu Leu Val Arg Val Asn Ile Thr Pro Val Val Ala
145                 150                 155                 160

Leu Trp Gln Pro Met Ala Pro Asn Gln Gly Leu Pro Arg Leu Leu Ala
                165                 170                 175

Arg Gln Gly Ala Trp Glu Asn Pro Tyr Thr Ala Leu Ala Phe Ala Glu
            180                 185                 190

Tyr Ala Arg Leu Cys Phe Gln Glu Leu Gly His His Val Lys Leu Trp
        195                 200                 205

Ile Thr Met Asn Glu Pro Tyr Thr Arg Asn Met Thr Tyr Ser Ala Gly
    210                 215                 220

His Asn Leu Leu Lys Ala His Ala Leu Ala Trp His Val Tyr Asn Glu
225                 230                 235                 240

Lys Phe Arg His Ala Gln Asn Gly Lys Ile Ser Ile Ala Leu Gln Ala
                245                 250                 255

Asp Trp Ile Glu Pro Ala Cys Pro Phe Ser Gln Lys Asp Lys Glu Val
            260                 265                 270

Ala Glu Arg Val Leu Glu Phe Asp Ile Gly Trp Leu Ala Glu Pro Ile
        275                 280                 285

Phe Gly Ser Gly Asp Tyr Pro Trp Val Met Arg Asp Trp Leu Asn Gln
    290                 295                 300

Arg Asn Asn Phe Leu Leu Pro Tyr Phe Thr Glu Asp Glu Lys Lys Leu
305                 310                 315                 320

Ile Gln Gly Thr Phe Asp Phe Leu Ala Leu Ser His Tyr Thr Thr Ile
```

```
                    325                 330                 335
Leu Val Asp Ser Glu Lys Glu Asp Pro Ile Lys Tyr Asn Asp Tyr Leu
                340                 345                 350

Glu Val Gln Glu Met Thr Asp Ile Thr Trp Leu Asn Ser Pro Ser Gln
                355                 360                 365

Val Ala Val Val Pro Trp Gly Leu Arg Lys Val Leu Asn Trp Leu Lys
            370                 375                 380

Phe Lys Tyr Gly Asp Leu Pro Met Tyr Ile Ile Ser Asn Gly Ile Asp
385                 390                 395                 400

Asp Gly Leu His Ala Glu Asp Gln Leu Arg Val Tyr Tyr Met Gln
                405                 410                 415

Asn Tyr Ile Asn Glu Ala Leu Lys Ala His Ile Leu Asp Gly Ile Asn
                420                 425                 430

Leu Cys Gly Tyr Phe Ala Tyr Ser Phe Asn Asp Arg Thr Ala Pro Arg
            435                 440                 445

Phe Gly Leu Tyr Arg Tyr Ala Ala Asp Gln Phe Glu Pro Lys Ala Ser
            450                 455                 460

Met Lys His Tyr Arg Lys Ile Ile Asp Ser Asn Gly Phe Pro Gly Pro
465                 470                 475                 480

Glu Thr Leu Glu Arg Phe Cys Pro Glu Glu Phe Thr Val Cys Thr Glu
                485                 490                 495

Cys Ser Phe Phe His Thr Arg Lys Ser Leu Gly Ser Gly Gly Gly Gly
                500                 505                 510

Ser Gly Gly Gly Gly Ser Gly Gly Gly Ser Leu Lys Tyr Pro Asn
            515                 520                 525

Ala Ser Pro Leu Leu Gly Ser Ser Trp Gly Gly Leu Ile His Leu Tyr
            530                 535                 540

Thr Ala Thr Ala Arg Asn Ser Tyr His Leu Gln Ile His Lys Asn Gly
545                 550                 555                 560

His Val Asp Gly Ala Pro His Gln Thr Ile Tyr Ser Ala Leu Met Ile
                565                 570                 575

Arg Ser Glu Asp Ala Gly Phe Val Val Ile Thr Gly Val Met Ser Arg
            580                 585                 590

Arg Tyr Leu Cys Met Asp Phe Arg Gly Asn Ile Phe Gly Ser His Tyr
            595                 600                 605

Phe Asp Pro Glu Asn Cys Arg Phe Gln His Gln Thr Leu Glu Asn Gly
            610                 615                 620

Tyr Asp Val Tyr His Ser Pro Gln Tyr His Phe Leu Val Ser Leu Gly
625                 630                 635                 640

Arg Ala Lys Arg Ala Phe Leu Pro Gly Met Asn Pro Pro Tyr Ser
                645                 650                 655

Gln Phe Leu Ser Arg Arg Asn Glu Ile Pro Leu Ile His Phe Asn Thr
            660                 665                 670

Pro Ile Pro Arg Arg His Thr Gln Ser Ala Glu Asp Asp Ser Glu Arg
            675                 680                 685

Asp Pro Leu Asn Val Leu Lys Pro Arg Ala Arg Met Thr Pro Ala Pro
            690                 695                 700

Ala Ser Cys Ser Gln Glu Leu Pro Ser Ala Glu Asp Asn Ser Pro Met
705                 710                 715                 720

Ala Ser Asp Pro Leu Gly Val Val Arg Gly Gly Arg Val Asn Thr His
                725                 730                 735

Ala Gly Gly Thr Gly Pro Glu Gly Cys Arg Pro Phe Ala Lys Phe Ile
                740                 745                 750
```

```
<210> SEQ ID NO 23
<211> LENGTH: 1215
<212> TYPE: PRT
<213> ORGANISM: Artificial
<220> FEATURE:
<223> OTHER INFORMATION: fusion polypeptide

<400> SEQUENCE: 23

Met Pro Ala Ser Ala Pro Pro Arg Arg Pro Arg Pro Pro Pro Pro Ser
1               5                   10                  15

Leu Ser Leu Leu Leu Val Leu Leu Gly Leu Gly Gly Arg Arg Leu Arg
            20                  25                  30

Ala Glu Pro Gly Asp Gly Ala Gln Thr Trp Ala Arg Phe Ser Arg Pro
        35                  40                  45

Pro Ala Pro Glu Ala Ala Gly Leu Phe Gln Gly Thr Phe Pro Asp Gly
    50                  55                  60

Phe Leu Trp Ala Val Gly Ser Ala Ala Tyr Gln Thr Glu Gly Gly Trp
65                  70                  75                  80

Gln Gln His Gly Lys Gly Ala Ser Ile Trp Asp Thr Phe Thr His His
                85                  90                  95

Pro Leu Ala Pro Pro Gly Asp Ser Arg Asn Ala Ser Leu Pro Leu Gly
            100                 105                 110

Ala Pro Ser Pro Leu Gln Pro Ala Thr Gly Asp Val Ala Ser Asp Ser
        115                 120                 125

Tyr Asn Asn Val Phe Arg Asp Thr Glu Ala Leu Arg Glu Leu Gly Val
    130                 135                 140

Thr His Tyr Arg Phe Ser Ile Ser Trp Ala Arg Val Leu Pro Asn Gly
145                 150                 155                 160

Ser Ala Gly Val Pro Asn Arg Glu Gly Leu Arg Tyr Tyr Arg Arg Leu
                165                 170                 175

Leu Glu Arg Leu Arg Glu Leu Gly Val Gln Pro Val Val Thr Leu Tyr
            180                 185                 190

His Trp Asp Leu Pro Gln Arg Leu Gln Asp Ala Tyr Gly Gly Trp Ala
        195                 200                 205

Asn Arg Ala Leu Ala Asp His Phe Arg Asp Tyr Ala Glu Leu Cys Phe
    210                 215                 220

Arg His Phe Gly Gly Gln Val Lys Tyr Trp Ile Thr Ile Asp Asn Pro
225                 230                 235                 240

Tyr Val Val Ala Trp His Gly Tyr Ala Thr Gly Arg Leu Ala Pro Gly
                245                 250                 255

Ile Arg Gly Ser Pro Arg Leu Gly Tyr Leu Val Ala His Asn Leu Leu
            260                 265                 270

Leu Ala His Ala Lys Val Trp His Leu Tyr Asn Thr Ser Phe Arg Pro
        275                 280                 285

Thr Gln Gly Gly Gln Val Ser Ile Ala Leu Ser Ser His Trp Ile Asn
    290                 295                 300

Pro Arg Arg Met Thr Asp His Ser Ile Lys Glu Cys Gln Lys Ser Leu
305                 310                 315                 320

Asp Phe Val Leu Gly Trp Phe Ala Lys Pro Val Phe Ile Asp Gly Asp
                325                 330                 335

Tyr Pro Glu Ser Met Lys Asn Asn Leu Ser Ser Ile Leu Pro Asp Phe
            340                 345                 350

Thr Glu Ser Glu Lys Lys Phe Ile Lys Gly Thr Ala Asp Phe Phe Ala
        355                 360                 365

Leu Cys Phe Gly Pro Thr Leu Ser Phe Gln Leu Leu Asp Pro His Met
```

```
              370            375            380
Lys Phe Arg Gln Leu Glu Ser Pro Asn Leu Arg Gln Leu Leu Ser Trp
385                390                395                400

Ile Asp Leu Glu Phe Asn His Pro Gln Ile Phe Ile Val Glu Asn Gly
                405                410                415

Trp Phe Val Ser Gly Thr Thr Lys Arg Asp Asp Ala Lys Tyr Met Tyr
                420                425                430

Tyr Leu Lys Lys Phe Ile Met Glu Thr Leu Lys Ala Ile Lys Leu Asp
            435                440                445

Gly Val Asp Val Ile Gly Tyr Thr Ala Trp Ser Leu Met Asp Gly Phe
450                455                460

Glu Trp His Arg Gly Tyr Ser Ile Arg Arg Gly Leu Phe Tyr Val Asp
465                470                475                480

Phe Leu Ser Gln Asp Lys Met Leu Leu Pro Lys Ser Ala Leu Phe
                485                490                495

Tyr Gln Lys Leu Ile Glu Lys Asn Gly Phe Pro Pro Leu Pro Glu Asn
            500                505                510

Gln Pro Leu Glu Gly Ser Gly Thr Phe Pro Asp Gly Phe Leu Trp Ala
            515                520                525

Val Gly Ser Ala Ala Tyr Gln Thr Glu Gly Gly Trp Gln Gln His Gly
530                535                540

Lys Gly Ala Ser Ile Trp Asp Thr Phe Thr His Pro Leu Ala Pro
545                550                555                560

Pro Gly Asp Ser Arg Asn Ala Ser Leu Pro Leu Gly Ala Pro Ser Pro
                565                570                575

Leu Gln Pro Ala Thr Gly Asp Val Ala Ser Asp Ser Tyr Asn Asn Val
            580                585                590

Phe Arg Asp Thr Glu Ala Leu Arg Glu Leu Gly Val Thr His Tyr Arg
            595                600                605

Phe Ser Ile Ser Trp Ala Arg Val Leu Pro Asn Gly Ser Ala Gly Val
            610                615                620

Pro Asn Arg Glu Gly Leu Arg Tyr Tyr Arg Arg Leu Leu Glu Arg Leu
625                630                635                640

Arg Glu Leu Gly Val Gln Pro Val Val Thr Leu Tyr His Trp Asp Leu
                645                650                655

Pro Gln Arg Leu Gln Asp Ala Tyr Gly Gly Trp Ala Asn Arg Ala Leu
                660                665                670

Ala Asp His Phe Arg Asp Tyr Ala Glu Leu Cys Phe Arg His Phe Gly
            675                680                685

Gly Gln Val Lys Tyr Trp Ile Thr Ile Asp Asn Pro Tyr Val Val Ala
690                695                700

Trp His Gly Tyr Ala Thr Gly Arg Leu Ala Pro Gly Ile Arg Gly Ser
705                710                715                720

Pro Arg Leu Gly Tyr Leu Val Ala His Asn Leu Leu Leu Ala His Ala
                725                730                735

Lys Val Trp His Leu Tyr Asn Thr Ser Phe Arg Pro Thr Gln Gly Gly
            740                745                750

Gln Val Ser Ile Ala Leu Ser Ser His Trp Ile Asn Pro Arg Arg Met
            755                760                765

Thr Asp His Ser Ile Lys Glu Cys Gln Lys Ser Leu Asp Phe Val Leu
            770                775                780

Gly Trp Phe Ala Lys Pro Val Phe Ile Asp Gly Asp Tyr Pro Glu Ser
785                790                795                800
```

```
Met Lys Asn Asn Leu Ser Ser Ile Leu Pro Asp Phe Thr Glu Ser Glu
                805                 810                 815
Lys Lys Phe Ile Lys Gly Thr Ala Asp Phe Ala Leu Cys Phe Gly
            820                 825                 830
Pro Thr Leu Ser Phe Gln Leu Leu Asp Pro His Met Lys Phe Arg Gln
            835                 840                 845
Leu Glu Ser Pro Asn Leu Arg Gln Leu Leu Ser Trp Ile Asp Leu Glu
850                 855                 860
Phe Asn His Pro Gln Ile Phe Ile Val Glu Asn Gly Trp Phe Val Ser
865                 870                 875                 880
Gly Thr Thr Lys Arg Asp Asp Ala Lys Tyr Met Tyr Tyr Leu Lys Lys
                885                 890                 895
Phe Ile Met Glu Thr Leu Lys Ala Ile Lys Leu Asp Gly Val Asp Val
                900                 905                 910
Ile Gly Tyr Thr Ala Trp Ser Leu Met Asp Gly Phe Glu Trp His Arg
                915                 920                 925
Gly Tyr Ser Ile Arg Arg Gly Leu Phe Tyr Val Asp Phe Leu Ser Gln
                930                 935                 940
Asp Lys Met Leu Leu Pro Lys Ser Ser Ala Leu Phe Tyr Gln Lys Leu
945                 950                 955                 960
Ile Glu Lys Asn Gly Phe Pro Glu Phe Gly Ser Gly Gly Gly Ser
                965                 970                 975
Gly Gly Gly Gly Ser Gly Gly Gly Ser Leu Lys Tyr Pro Asn Ala
                980                 985                 990
Ser Pro Leu Leu Gly Ser Ser Trp Gly Gly Leu Ile His Leu Tyr Thr
                995                 1000                1005
Ala Thr Ala Arg Asn Ser Tyr His Leu Gln Ile His Lys Asn Gly
    1010                1015                1020
His Val Asp Gly Ala Pro His Gln Thr Ile Tyr Ser Ala Leu Met
    1025                1030                1035
Ile Arg Ser Glu Asp Ala Gly Phe Val Val Ile Thr Gly Val Met
    1040                1045                1050
Ser Arg Arg Tyr Leu Cys Met Asp Phe Arg Gly Asn Ile Phe Gly
    1055                1060                1065
Ser His Tyr Phe Asp Pro Glu Asn Cys Arg Phe Gln His Gln Thr
    1070                1075                1080
Leu Glu Asn Gly Tyr Asp Val Tyr His Ser Pro Gln Tyr His Phe
    1085                1090                1095
Leu Val Ser Leu Gly Arg Ala Lys Arg Ala Phe Leu Pro Gly Met
    1100                1105                1110
Asn Pro Pro Pro Tyr Ser Gln Phe Leu Ser Arg Arg Asn Glu Ile
    1115                1120                1125
Pro Leu Ile His Phe Asn Thr Pro Ile Pro Arg Arg His Thr Gln
    1130                1135                1140
Ser Ala Glu Asp Asp Ser Glu Arg Asp Pro Leu Asn Val Leu Lys
    1145                1150                1155
Pro Arg Ala Arg Met Thr Pro Ala Pro Ala Ser Cys Ser Gln Glu
    1160                1165                1170
Leu Pro Ser Ala Glu Asp Asn Ser Pro Met Ala Ser Asp Pro Leu
    1175                1180                1185
Gly Val Val Arg Gly Gly Arg Val Asn Thr His Ala Gly Gly Thr
    1190                1195                1200
Gly Pro Glu Gly Cys Arg Pro Phe Ala Lys Phe Ile
    1205                1210                1215
```

<210> SEQ ID NO 24
<211> LENGTH: 1189
<212> TYPE: PRT
<213> ORGANISM: Artificial
<220> FEATURE:
<223> OTHER INFORMATION: fusion polypeptide

<400> SEQUENCE: 24

```
Met Pro Ala Ser Ala Pro Pro Arg Arg Pro Arg Pro Pro Pro Pro Ser
1               5                   10                  15

Leu Ser Leu Leu Leu Val Leu Leu Gly Leu Gly Gly Arg Arg Leu Pro
            20                  25                  30

Leu Pro Glu Asn Gln Pro Leu Glu Gly Thr Phe Pro Cys Asp Phe Ala
        35                  40                  45

Trp Gly Val Val Asp Asn Tyr Ile Gln Val Asp Thr Thr Leu Ser Gln
50                  55                  60

Phe Thr Asp Leu Asn Val Tyr Leu Trp Asp Val His His Ser Lys Arg
65                  70                  75                  80

Leu Ile Lys Val Asp Gly Val Val Thr Lys Lys Arg Lys Ser Tyr Cys
                85                  90                  95

Val Asp Phe Ala Ala Ile Gln Pro Gln Ile Ala Leu Leu Gln Glu Met
            100                 105                 110

His Val Thr His Phe Arg Phe Ser Leu Asp Trp Ala Leu Ile Leu Pro
        115                 120                 125

Leu Gly Asn Gln Ser Gln Val Asn His Thr Ile Leu Gln Tyr Tyr Arg
    130                 135                 140

Cys Met Ala Ser Glu Leu Val Arg Val Asn Ile Thr Pro Val Val Ala
145                 150                 155                 160

Leu Trp Gln Pro Met Ala Pro Asn Gln Gly Leu Pro Arg Leu Leu Ala
                165                 170                 175

Arg Gln Gly Ala Trp Glu Asn Pro Tyr Thr Ala Leu Ala Phe Ala Glu
            180                 185                 190

Tyr Ala Arg Leu Cys Phe Gln Glu Leu Gly His His Val Lys Leu Trp
        195                 200                 205

Ile Thr Met Asn Glu Pro Tyr Thr Arg Asn Met Thr Tyr Ser Ala Gly
    210                 215                 220

His Asn Leu Leu Lys Ala His Ala Leu Ala Trp His Val Tyr Asn Glu
225                 230                 235                 240

Lys Phe Arg His Ala Gln Asn Gly Lys Ile Ser Ile Ala Leu Gln Ala
                245                 250                 255

Asp Trp Ile Glu Pro Ala Cys Pro Phe Ser Gln Lys Asp Lys Glu Val
            260                 265                 270

Ala Glu Arg Val Leu Glu Phe Asp Ile Gly Trp Leu Ala Glu Pro Ile
        275                 280                 285

Phe Gly Ser Gly Asp Tyr Pro Trp Val Met Arg Asp Trp Leu Asn Gln
    290                 295                 300

Arg Asn Asn Phe Leu Leu Pro Tyr Phe Thr Glu Asp Glu Lys Lys Leu
305                 310                 315                 320

Ile Gln Gly Thr Phe Asp Phe Leu Ala Leu Ser His Tyr Thr Thr Ile
                325                 330                 335

Leu Val Asp Ser Glu Lys Glu Asp Pro Ile Lys Tyr Asn Asp Tyr Leu
            340                 345                 350

Glu Val Gln Glu Met Thr Asp Ile Thr Trp Leu Asn Ser Pro Ser Gln
        355                 360                 365
```

-continued

```
Val Ala Val Val Pro Trp Gly Leu Arg Lys Val Leu Asn Trp Leu Lys
            370                 375                 380

Phe Lys Tyr Gly Asp Leu Pro Met Tyr Ile Ile Ser Asn Gly Ile Asp
385                 390                 395                 400

Asp Gly Leu His Ala Glu Asp Gln Leu Arg Val Tyr Tyr Met Gln
                405                 410                 415

Asn Tyr Ile Asn Glu Ala Leu Lys Ala His Ile Leu Asp Gly Ile Asn
                420                 425                 430

Leu Cys Gly Tyr Phe Ala Tyr Ser Phe Asn Asp Arg Thr Ala Pro Arg
            435                 440                 445

Phe Gly Leu Tyr Arg Tyr Ala Ala Asp Gln Phe Glu Pro Lys Ala Ser
            450                 455                 460

Met Lys His Tyr Arg Lys Ile Ile Asp Ser Asn Gly Phe Pro Gly Pro
465                 470                 475                 480

Glu Thr Leu Glu Arg Phe Cys Pro Glu Glu Phe Thr Val Cys Thr Glu
                485                 490                 495

Cys Ser Phe Phe His Thr Arg Lys Ser Leu Gly Thr Phe Pro Cys Asp
                500                 505                 510

Phe Ala Trp Gly Val Val Asp Asn Tyr Ile Gln Val Asp Thr Thr Leu
            515                 520                 525

Ser Gln Phe Thr Asp Leu Asn Val Tyr Leu Trp Asp Val His His Ser
            530                 535                 540

Lys Arg Leu Ile Lys Val Asp Gly Val Val Thr Lys Arg Lys Ser
545                 550                 555                 560

Tyr Cys Val Asp Phe Ala Ala Ile Gln Pro Gln Ile Ala Leu Leu Gln
                565                 570                 575

Glu Met His Val Thr His Phe Arg Phe Ser Leu Asp Trp Ala Leu Ile
            580                 585                 590

Leu Pro Leu Gly Asn Gln Ser Gln Val Asn His Thr Ile Leu Gln Tyr
            595                 600                 605

Tyr Arg Cys Met Ala Ser Glu Leu Val Arg Val Asn Ile Thr Pro Val
            610                 615                 620

Val Ala Leu Trp Gln Pro Met Ala Pro Asn Gln Gly Leu Pro Arg Leu
625                 630                 635                 640

Leu Ala Arg Gln Gly Ala Trp Glu Asn Pro Tyr Thr Ala Leu Ala Phe
            645                 650                 655

Ala Glu Tyr Ala Arg Leu Cys Phe Gln Glu Leu Gly His His Val Lys
                660                 665                 670

Leu Trp Ile Thr Met Asn Glu Pro Tyr Thr Arg Asn Met Thr Tyr Ser
            675                 680                 685

Ala Gly His Asn Leu Leu Lys Ala His Ala Leu Ala Trp His Val Tyr
            690                 695                 700

Asn Glu Lys Phe Arg His Ala Gln Asn Gly Lys Ile Ser Ile Ala Leu
705                 710                 715                 720

Gln Ala Asp Trp Ile Glu Pro Ala Cys Pro Phe Ser Gln Lys Asp Lys
                725                 730                 735

Glu Val Ala Glu Arg Val Leu Glu Phe Asp Ile Gly Trp Leu Ala Glu
                740                 745                 750

Pro Ile Phe Gly Ser Gly Asp Tyr Pro Trp Val Met Arg Asp Trp Leu
            755                 760                 765

Asn Gln Arg Asn Asn Phe Leu Leu Pro Tyr Phe Thr Glu Asp Glu Lys
            770                 775                 780

Lys Leu Ile Gln Gly Thr Phe Asp Phe Leu Ala Leu Ser His Tyr Thr
785                 790                 795                 800
```

```
Thr Ile Leu Val Asp Ser Glu Lys Glu Asp Pro Ile Lys Tyr Asn Asp
                805                 810                 815

Tyr Leu Glu Val Gln Glu Met Thr Asp Ile Thr Trp Leu Asn Ser Pro
            820                 825                 830

Ser Gln Val Ala Val Pro Trp Gly Leu Arg Lys Val Leu Asn Trp
        835                 840                 845

Leu Lys Phe Lys Tyr Gly Asp Leu Pro Met Tyr Ile Ile Ser Asn Gly
    850                 855                 860

Ile Asp Asp Gly Leu His Ala Glu Asp Gln Leu Arg Val Tyr Tyr
865                 870                 875                 880

Met Gln Asn Tyr Ile Asn Glu Ala Leu Lys Ala His Ile Leu Asp Gly
            885                 890                 895

Ile Asn Leu Cys Gly Tyr Phe Ala Tyr Ser Phe Asn Asp Arg Thr Ala
        900                 905                 910

Pro Arg Phe Gly Leu Tyr Arg Tyr Ala Ala Asp Gln Phe Glu Pro Lys
            915                 920                 925

Ala Ser Met Lys His Tyr Arg Lys Ile Ile Asp Ser Asn Gly Phe Gly
    930                 935                 940

Ser Gly Gly Gly Gly Ser Gly Gly Gly Gly Ser Gly Gly Gly Gly Ser
945                 950                 955                 960

Leu Lys Tyr Pro Asn Ala Ser Pro Leu Leu Gly Ser Ser Trp Gly Gly
            965                 970                 975

Leu Ile His Leu Tyr Thr Ala Thr Ala Arg Asn Ser Tyr His Leu Gln
        980                 985                 990

Ile His Lys Asn Gly His Val Asp Gly Ala Pro His Gln Thr Ile Tyr
    995                 1000                1005

Ser Ala Leu Met Ile Arg Ser Glu Asp Ala Gly Phe Val Val Ile
    1010                1015                1020

Thr Gly Val Met Ser Arg Arg Tyr Leu Cys Met Asp Phe Arg Gly
    1025                1030                1035

Asn Ile Phe Gly Ser His Tyr Phe Asp Pro Glu Asn Cys Arg Phe
    1040                1045                1050

Gln His Gln Thr Leu Glu Asn Gly Tyr Asp Val Tyr His Ser Pro
    1055                1060                1065

Gln Tyr His Phe Leu Val Ser Leu Gly Arg Ala Lys Arg Ala Phe
    1070                1075                1080

Leu Pro Gly Met Asn Pro Pro Tyr Ser Gln Phe Leu Ser Arg
    1085                1090                1095

Arg Asn Glu Ile Pro Leu Ile His Phe Asn Thr Pro Ile Pro Arg
    1100                1105                1110

Arg His Thr Gln Ser Ala Glu Asp Asp Ser Glu Arg Asp Pro Leu
    1115                1120                1125

Asn Val Leu Lys Pro Arg Ala Arg Met Thr Pro Ala Pro Ala Ser
    1130                1135                1140

Cys Ser Gln Glu Leu Pro Ser Ala Glu Asp Asn Ser Pro Met Ala
    1145                1150                1155

Ser Asp Pro Leu Gly Val Val Arg Gly Gly Arg Val Asn Thr His
    1160                1165                1170

Ala Gly Gly Thr Gly Pro Glu Gly Cys Arg Pro Phe Ala Lys Phe
    1175                1180                1185

Ile

<210> SEQ ID NO 25
```

```
<211> LENGTH: 1219
<212> TYPE: PRT
<213> ORGANISM: Artificial
<220> FEATURE:
<223> OTHER INFORMATION: fusion polypeptide

<400> SEQUENCE: 25
```

| | | | | | | | | | | | | | | |
|---|---|---|---|---|---|---|---|---|---|---|---|---|---|---|
| Met | Leu | Gly | Ala | Arg | Leu | Arg | Leu | Trp | Val | Cys | Ala | Leu | Cys | Ser | Val |
| 1 | | | | 5 | | | | | 10 | | | | | 15 | |
| Cys | Ser | Met | Ser | Val | Leu | Arg | Ala | Tyr | Pro | Asn | Ala | Ser | Pro | Leu | Leu |
| | | | 20 | | | | | 25 | | | | | 30 | | |
| Gly | Ser | Ser | Trp | Gly | Gly | Leu | Ile | His | Leu | Tyr | Thr | Ala | Thr | Ala | Arg |
| | | 35 | | | | | 40 | | | | | 45 | | | |
| Asn | Ser | Tyr | His | Leu | Gln | Ile | His | Lys | Asn | Gly | His | Val | Asp | Gly | Ala |
| | 50 | | | | | 55 | | | | | 60 | | | | |
| Pro | His | Gln | Thr | Ile | Tyr | Ser | Ala | Leu | Met | Ile | Arg | Ser | Glu | Asp | Ala |
| 65 | | | | | 70 | | | | | 75 | | | | | 80 |
| Gly | Phe | Val | Val | Ile | Thr | Gly | Val | Met | Ser | Arg | Arg | Tyr | Leu | Cys | Met |
| | | | | 85 | | | | | 90 | | | | | 95 | |
| Asp | Phe | Arg | Gly | Asn | Ile | Phe | Gly | Ser | His | Tyr | Phe | Asp | Pro | Glu | Asn |
| | | | 100 | | | | | 105 | | | | | 110 | | |
| Cys | Arg | Phe | Gln | His | Gln | Thr | Leu | Glu | Asn | Gly | Tyr | Asp | Val | Tyr | His |
| | | 115 | | | | | 120 | | | | | 125 | | | |
| Ser | Pro | Gln | Tyr | His | Phe | Leu | Val | Ser | Leu | Gly | Arg | Ala | Lys | Arg | Ala |
| | 130 | | | | | 135 | | | | | 140 | | | | |
| Phe | Leu | Pro | Gly | Met | Asn | Pro | Pro | Tyr | Ser | Gln | Phe | Leu | Ser | Arg |
| 145 | | | | | 150 | | | | | 155 | | | | | 160 |
| Arg | Asn | Glu | Ile | Pro | Leu | Ile | His | Phe | Asn | Thr | Pro | Ile | Pro | Arg | Arg |
| | | | | 165 | | | | | 170 | | | | | 175 | |
| His | Thr | Gln | Ser | Ala | Glu | Asp | Asp | Ser | Glu | Arg | Asp | Pro | Leu | Asn | Val |
| | | | 180 | | | | | 185 | | | | | 190 | | |
| Leu | Lys | Pro | Arg | Ala | Arg | Met | Thr | Pro | Ala | Pro | Ala | Ser | Cys | Ser | Gln |
| | | 195 | | | | | 200 | | | | | 205 | | | |
| Glu | Leu | Pro | Ser | Ala | Glu | Asp | Asn | Ser | Pro | Met | Ala | Ser | Asp | Pro | Leu |
| | 210 | | | | | 215 | | | | | 220 | | | | |
| Gly | Val | Val | Arg | Gly | Gly | Arg | Val | Asn | Thr | His | Ala | Gly | Gly | Thr | Gly |
| 225 | | | | | 230 | | | | | 235 | | | | | 240 |
| Pro | Glu | Gly | Cys | Arg | Pro | Phe | Ala | Lys | Phe | Ile | Gly | Ser | Gly | Gly | Gly |
| | | | | 245 | | | | | 250 | | | | | 255 | |
| Gly | Ser | Gly | Gly | Gly | Gly | Ser | Gly | Gly | Gly | Gly | Ser | Leu | Lys | Glu | Pro |
| | | | 260 | | | | | 265 | | | | | 270 | | |
| Gly | Asp | Gly | Ala | Gln | Thr | Trp | Ala | Arg | Phe | Ser | Arg | Pro | Pro | Ala | Pro |
| | | 275 | | | | | 280 | | | | | 285 | | | |
| Glu | Ala | Ala | Gly | Leu | Phe | Gln | Gly | Thr | Phe | Pro | Asp | Gly | Phe | Leu | Trp |
| | 290 | | | | | 295 | | | | | 300 | | | | |
| Ala | Val | Gly | Ser | Ala | Ala | Tyr | Gln | Thr | Glu | Gly | Gly | Trp | Gln | Gln | His |
| 305 | | | | | 310 | | | | | 315 | | | | | 320 |
| Gly | Lys | Gly | Ala | Ser | Ile | Trp | Asp | Thr | Phe | Thr | His | His | Pro | Leu | Ala |
| | | | | 325 | | | | | 330 | | | | | 335 | |
| Pro | Pro | Gly | Asp | Ser | Arg | Asn | Ala | Ser | Leu | Pro | Leu | Gly | Ala | Pro | Ser |
| | | | 340 | | | | | 345 | | | | | 350 | | |
| Pro | Leu | Gln | Pro | Ala | Thr | Gly | Asp | Val | Ala | Ser | Asp | Ser | Tyr | Asn | Asn |
| | | 355 | | | | | 360 | | | | | 365 | | | |
| Val | Phe | Arg | Asp | Thr | Glu | Ala | Leu | Arg | Glu | Leu | Gly | Val | Thr | His | Tyr |
| | 370 | | | | | 375 | | | | | 380 | | | | |

-continued

```
Arg Phe Ser Ile Ser Trp Ala Arg Val Leu Pro Asn Gly Ser Ala Gly
385                 390                 395                 400

Val Pro Asn Arg Glu Gly Leu Arg Tyr Tyr Arg Leu Leu Glu Arg
            405                 410                 415

Leu Arg Glu Leu Gly Val Gln Pro Val Val Thr Leu Tyr His Trp Asp
            420                 425                 430

Leu Pro Gln Arg Leu Gln Asp Ala Tyr Gly Gly Trp Ala Asn Arg Ala
            435                 440                 445

Leu Ala Asp His Phe Arg Asp Tyr Ala Glu Leu Cys Phe Arg His Phe
            450                 455                 460

Gly Gly Gln Val Lys Tyr Trp Ile Thr Ile Asp Asn Pro Tyr Val Val
465                 470                 475                 480

Ala Trp His Gly Tyr Ala Thr Gly Arg Leu Ala Pro Gly Ile Arg Gly
                485                 490                 495

Ser Pro Arg Leu Gly Tyr Leu Val Ala His Asn Leu Leu Ala His
            500                 505                 510

Ala Lys Val Trp His Leu Tyr Asn Thr Ser Phe Arg Pro Thr Gln Gly
            515                 520                 525

Gly Gln Val Ser Ile Ala Leu Ser Ser His Trp Ile Asn Pro Arg Arg
530                 535                 540

Met Thr Asp His Ser Ile Lys Glu Cys Gln Lys Ser Leu Asp Phe Val
545                 550                 555                 560

Leu Gly Trp Phe Ala Lys Pro Val Phe Ile Asp Gly Asp Tyr Pro Glu
                565                 570                 575

Ser Met Lys Asn Asn Leu Ser Ser Ile Leu Pro Asp Phe Thr Glu Ser
            580                 585                 590

Glu Lys Lys Phe Ile Lys Gly Thr Ala Asp Phe Phe Ala Leu Cys Phe
            595                 600                 605

Gly Pro Thr Leu Ser Phe Gln Leu Leu Asp Pro His Met Lys Phe Arg
            610                 615                 620

Gln Leu Glu Ser Pro Asn Leu Arg Gln Leu Leu Ser Trp Ile Asp Leu
625                 630                 635                 640

Glu Phe Asn His Pro Gln Ile Phe Ile Val Glu Asn Gly Trp Phe Val
                645                 650                 655

Ser Gly Thr Thr Lys Arg Asp Asp Ala Lys Tyr Met Tyr Tyr Leu Lys
            660                 665                 670

Lys Phe Ile Met Glu Thr Leu Lys Ala Ile Lys Leu Asp Gly Val Asp
            675                 680                 685

Val Ile Gly Tyr Thr Ala Trp Ser Leu Met Asp Gly Phe Glu Trp His
690                 695                 700

Arg Gly Tyr Ser Ile Arg Arg Gly Leu Phe Tyr Val Asp Phe Leu Ser
705                 710                 715                 720

Gln Asp Lys Met Leu Leu Pro Lys Ser Ala Leu Phe Tyr Gln Lys
            725                 730                 735

Leu Ile Glu Lys Asn Gly Phe Pro Pro Leu Pro Glu Asn Gln Pro Leu
            740                 745                 750

Glu Gly Thr Phe Pro Cys Asp Phe Ala Trp Gly Val Val Asp Asn Tyr
            755                 760                 765

Ile Gln Val Asp Thr Thr Leu Ser Gln Phe Thr Asp Leu Asn Val Tyr
            770                 775                 780

Leu Trp Asp Val His His Ser Lys Arg Leu Ile Lys Val Asp Gly Val
785                 790                 795                 800

Val Thr Lys Lys Arg Lys Ser Tyr Cys Val Asp Phe Ala Ala Ile Gln
            805                 810                 815
```

-continued

Pro Gln Ile Ala Leu Leu Gln Glu Met His Val Thr His Phe Arg Phe
        820                 825                 830

Ser Leu Asp Trp Ala Leu Ile Leu Pro Leu Gly Asn Gln Ser Gln Val
        835                 840                 845

Asn His Thr Ile Leu Gln Tyr Tyr Arg Cys Met Ala Ser Glu Leu Val
        850                 855                 860

Arg Val Asn Ile Thr Pro Val Val Ala Leu Trp Gln Pro Met Ala Pro
865                 870                 875                 880

Asn Gln Gly Leu Pro Arg Leu Leu Ala Arg Gln Gly Ala Trp Glu Asn
                885                 890                 895

Pro Tyr Thr Ala Leu Ala Phe Ala Glu Tyr Ala Arg Leu Cys Phe Gln
                900                 905                 910

Glu Leu Gly His His Val Lys Leu Trp Ile Thr Met Asn Glu Pro Tyr
                915                 920                 925

Thr Arg Asn Met Thr Tyr Ser Ala Gly His Asn Leu Leu Lys Ala His
        930                 935                 940

Ala Leu Ala Trp His Val Tyr Asn Glu Lys Phe Arg His Ala Gln Asn
945                 950                 955                 960

Gly Lys Ile Ser Ile Ala Leu Gln Ala Asp Trp Ile Glu Pro Ala Cys
                965                 970                 975

Pro Phe Ser Gln Lys Asp Lys Glu Val Ala Glu Arg Val Leu Glu Phe
                980                 985                 990

Asp Ile Gly Trp Leu Ala Glu Pro Ile Phe Gly Ser Gly Asp Tyr Pro
                995                 1000                1005

Trp Val Met Arg Asp Trp Leu Asn Gln Arg Asn Asn Phe Leu Leu
        1010                1015                1020

Pro Tyr Phe Thr Glu Asp Glu Lys Lys Leu Ile Gln Gly Thr Phe
        1025                1030                1035

Asp Phe Leu Ala Leu Ser His Tyr Thr Thr Ile Leu Val Asp Ser
        1040                1045                1050

Glu Lys Glu Asp Pro Ile Lys Tyr Asn Asp Tyr Leu Glu Val Gln
        1055                1060                1065

Glu Met Thr Asp Ile Thr Trp Leu Asn Ser Pro Ser Gln Val Ala
        1070                1075                1080

Val Val Pro Trp Gly Leu Arg Lys Val Leu Asn Trp Leu Lys Phe
        1085                1090                1095

Lys Tyr Gly Asp Leu Pro Met Tyr Ile Ile Ser Asn Gly Ile Asp
        1100                1105                1110

Asp Gly Leu His Ala Glu Asp Gln Leu Arg Val Tyr Tyr Met
        1115                1120                1125

Gln Asn Tyr Ile Asn Glu Ala Leu Lys Ala His Ile Leu Asp Gly
        1130                1135                1140

Ile Asn Leu Cys Gly Tyr Phe Ala Tyr Ser Phe Asn Asp Arg Thr
        1145                1150                1155

Ala Pro Arg Phe Gly Leu Tyr Arg Tyr Ala Ala Asp Gln Phe Glu
        1160                1165                1170

Pro Lys Ala Ser Met Lys His Tyr Arg Lys Ile Ile Asp Ser Asn
        1175                1180                1185

Gly Phe Pro Gly Pro Glu Thr Leu Glu Arg Phe Cys Pro Glu Glu
        1190                1195                1200

Phe Thr Val Cys Thr Glu Cys Ser Phe Phe His Thr Arg Lys Ser
        1205                1210                1215

Leu

<210> SEQ ID NO 26
<211> LENGTH: 700
<212> TYPE: PRT
<213> ORGANISM: Artificial
<220> FEATURE:
<223> OTHER INFORMATION: fusion polypeptide

<400> SEQUENCE: 26

```
Met Leu Gly Ala Arg Leu Arg Leu Trp Val Cys Ala Leu Cys Ser Val
1               5                   10                  15

Cys Ser Met Ser Val Leu Arg Ala Tyr Pro Asn Ala Ser Pro Leu Leu
            20                  25                  30

Gly Ser Ser Trp Gly Gly Leu Ile His Leu Tyr Thr Ala Thr Ala Arg
        35                  40                  45

Asn Ser Tyr His Leu Gln Ile His Lys Asn Gly His Val Asp Gly Ala
    50                  55                  60

Pro His Gln Thr Ile Tyr Ser Ala Leu Met Ile Arg Ser Glu Asp Ala
65                  70                  75                  80

Gly Phe Val Val Ile Thr Gly Val Met Ser Arg Arg Tyr Leu Cys Met
                85                  90                  95

Asp Phe Arg Gly Asn Ile Phe Gly Ser His Tyr Phe Asp Pro Glu Asn
            100                 105                 110

Cys Arg Phe Gln His Gln Thr Leu Glu Asn Gly Tyr Asp Val Tyr His
        115                 120                 125

Ser Pro Gln Tyr His Phe Leu Val Ser Leu Gly Arg Ala Lys Arg Ala
    130                 135                 140

Phe Leu Pro Gly Met Asn Pro Pro Tyr Ser Gln Phe Leu Ser Arg
145                 150                 155                 160

Arg Asn Glu Ile Pro Leu Ile His Phe Asn Thr Pro Ile Pro Arg Arg
                165                 170                 175

His Thr Gln Ser Ala Glu Asp Asp Ser Glu Arg Asp Pro Leu Asn Val
            180                 185                 190

Leu Lys Pro Arg Ala Arg Met Thr Pro Ala Pro Ala Ser Cys Ser Gln
        195                 200                 205

Glu Leu Pro Ser Ala Glu Asp Asn Ser Pro Met Ala Ser Asp Pro Leu
    210                 215                 220

Gly Val Val Arg Gly Gly Arg Val Asn Thr His Ala Gly Gly Thr Gly
225                 230                 235                 240

Pro Glu Gly Cys Arg Pro Phe Ala Lys Phe Ile Gln Gly Thr Phe Pro
                245                 250                 255

Asp Gly Phe Leu Trp Ala Val Gly Ser Ala Ala Tyr Gln Thr Glu Gly
            260                 265                 270

Gly Trp Gln Gln His Gly Lys Gly Ala Ser Ile Trp Asp Thr Phe Thr
        275                 280                 285

His His Pro Leu Ala Pro Pro Gly Asp Ser Arg Asn Ala Ser Leu Pro
    290                 295                 300

Leu Gly Ala Pro Ser Pro Leu Gln Pro Ala Thr Gly Asp Val Ala Ser
305                 310                 315                 320

Asp Ser Tyr Asn Asn Val Phe Arg Asp Thr Glu Ala Leu Arg Glu Leu
                325                 330                 335

Gly Val Thr His Tyr Arg Phe Ser Ile Ser Trp Ala Arg Val Leu Pro
            340                 345                 350

Asn Gly Ser Ala Gly Val Pro Asn Arg Glu Gly Leu Arg Tyr Tyr Arg
        355                 360                 365
```

```
Arg Leu Leu Glu Arg Leu Arg Glu Leu Gly Val Gln Pro Val Val Thr
        370                 375                 380

Leu Tyr His Trp Asp Leu Pro Gln Arg Leu Gln Asp Ala Tyr Gly Gly
385                 390                 395                 400

Trp Ala Asn Arg Ala Leu Ala Asp His Phe Arg Asp Tyr Ala Glu Leu
                405                 410                 415

Cys Phe Arg His Phe Gly Gly Gln Val Lys Tyr Trp Ile Thr Ile Asp
                420                 425                 430

Asn Pro Tyr Val Val Ala Trp His Gly Tyr Ala Thr Gly Arg Leu Ala
                435                 440                 445

Pro Gly Ile Arg Gly Ser Pro Arg Leu Gly Tyr Leu Val Ala His Asn
        450                 455                 460

Leu Leu Ala His Ala Lys Val Trp His Leu Tyr Asn Thr Ser Phe
465                 470                 475                 480

Arg Pro Thr Gln Gly Gly Gln Val Ser Ile Ala Leu Ser Ser His Trp
                485                 490                 495

Ile Asn Pro Arg Arg Met Thr Asp His Ser Ile Lys Glu Cys Gln Lys
                500                 505                 510

Ser Leu Asp Phe Val Leu Gly Trp Phe Ala Lys Pro Val Phe Ile Asp
        515                 520                 525

Gly Asp Tyr Pro Glu Ser Met Lys Asn Asn Leu Ser Ser Ile Leu Pro
530                 535                 540

Asp Phe Thr Glu Ser Glu Lys Lys Phe Ile Lys Gly Thr Ala Asp Phe
545                 550                 555                 560

Phe Ala Leu Cys Phe Gly Pro Thr Leu Ser Gln Leu Leu Asp Pro
                565                 570                 575

His Met Lys Phe Arg Gln Leu Glu Ser Pro Asn Leu Arg Gln Leu Leu
                580                 585                 590

Ser Trp Ile Asp Leu Glu Phe Asn His Pro Gln Ile Phe Ile Val Glu
        595                 600                 605

Asn Gly Trp Phe Val Ser Gly Thr Thr Lys Arg Asp Asp Ala Lys Tyr
610                 615                 620

Met Tyr Tyr Leu Lys Lys Phe Ile Met Glu Thr Leu Lys Ala Ile Lys
625                 630                 635                 640

Leu Asp Gly Val Asp Val Ile Gly Tyr Thr Ala Trp Ser Leu Met Asp
                645                 650                 655

Gly Phe Glu Trp His Arg Gly Tyr Ser Ile Arg Arg Gly Leu Phe Tyr
                660                 665                 670

Val Asp Phe Leu Ser Gln Asp Lys Met Leu Leu Pro Lys Ser Ser Ala
                675                 680                 685

Leu Phe Tyr Gln Lys Leu Ile Glu Lys Asn Gly Phe
        690                 695                 700

<210> SEQ ID NO 27
<211> LENGTH: 688
<212> TYPE: PRT
<213> ORGANISM: Artificial
<220> FEATURE:
<223> OTHER INFORMATION: fusion polypeptide

<400> SEQUENCE: 27

Met Leu Gly Ala Arg Leu Arg Leu Trp Val Cys Ala Leu Cys Ser Val
1               5                   10                  15

Cys Ser Met Ser Val Leu Arg Ala Tyr Pro Asn Ala Ser Pro Leu Leu
                20                  25                  30

Gly Ser Ser Trp Gly Gly Leu Ile His Leu Tyr Thr Ala Thr Ala Arg
```

```
                35                  40                  45
Asn Ser Tyr His Leu Gln Ile His Lys Asn Gly His Val Asp Gly Ala
            50                  55                  60
Pro His Gln Thr Ile Tyr Ser Ala Leu Met Ile Arg Ser Glu Asp Ala
65                  70                  75                  80
Gly Phe Val Val Ile Thr Gly Val Met Ser Arg Arg Tyr Leu Cys Met
                85                  90                  95
Asp Phe Arg Gly Asn Ile Phe Gly Ser His Tyr Phe Asp Pro Glu Asn
            100                 105                 110
Cys Arg Phe Gln His Gln Thr Leu Glu Asn Gly Tyr Asp Val Tyr His
            115                 120                 125
Ser Pro Gln Tyr His Phe Leu Val Ser Leu Gly Arg Ala Lys Arg Ala
            130                 135                 140
Phe Leu Pro Gly Met Asn Pro Pro Tyr Ser Gln Phe Leu Ser Arg
145                 150                 155                 160
Arg Asn Glu Ile Pro Leu Ile His Phe Asn Thr Pro Ile Pro Arg Arg
                165                 170                 175
His Thr Gln Ser Ala Glu Asp Ser Glu Arg Asp Pro Leu Asn Val
            180                 185                 190
Leu Lys Pro Arg Ala Arg Met Thr Pro Ala Pro Ala Ser Cys Ser Gln
            195                 200                 205
Glu Leu Pro Ser Ala Glu Asp Asn Ser Pro Met Ala Ser Asp Pro Leu
            210                 215                 220
Gly Val Val Arg Gly Gly Arg Val Asn Thr His Ala Gly Gly Thr Gly
225                 230                 235                 240
Pro Glu Gly Cys Arg Pro Phe Ala Lys Phe Ile Gly Thr Phe Pro Cys
                245                 250                 255
Asp Phe Ala Trp Gly Val Val Asp Asn Tyr Ile Gln Val Asp Thr Thr
            260                 265                 270
Leu Ser Gln Phe Thr Asp Leu Asn Val Tyr Leu Trp Asp Val His His
            275                 280                 285
Ser Lys Arg Leu Ile Lys Val Asp Gly Val Val Thr Lys Lys Arg Lys
            290                 295                 300
Ser Tyr Cys Val Asp Phe Ala Ala Ile Gln Pro Gln Ile Ala Leu Leu
305                 310                 315                 320
Gln Glu Met His Val Thr His Phe Arg Phe Ser Leu Asp Trp Ala Leu
                325                 330                 335
Ile Leu Pro Leu Gly Asn Gln Ser Gln Val Asn His Thr Ile Leu Gln
            340                 345                 350
Tyr Tyr Arg Cys Met Ala Ser Glu Leu Val Arg Val Asn Ile Thr Pro
            355                 360                 365
Val Val Ala Leu Trp Gln Pro Met Ala Pro Asn Gln Gly Leu Pro Arg
            370                 375                 380
Leu Leu Ala Arg Gln Gly Ala Trp Glu Asn Pro Tyr Thr Ala Leu Ala
385                 390                 395                 400
Phe Ala Glu Tyr Ala Arg Leu Cys Phe Gln Glu Leu Gly His Val
                405                 410                 415
Lys Leu Trp Ile Thr Met Asn Glu Pro Tyr Thr Arg Asn Met Thr Tyr
            420                 425                 430
Ser Ala Gly His Asn Leu Leu Lys Ala His Ala Leu Ala Trp His Val
            435                 440                 445
Tyr Asn Glu Lys Phe Arg His Ala Gln Asn Gly Lys Ile Ser Ile Ala
            450                 455                 460
```

```
Leu Gln Ala Asp Trp Ile Glu Pro Ala Cys Pro Phe Ser Gln Lys Asp
465                 470                 475                 480

Lys Glu Val Ala Glu Arg Val Leu Glu Phe Asp Ile Gly Trp Leu Ala
                485                 490                 495

Glu Pro Ile Phe Gly Ser Gly Asp Tyr Pro Trp Val Met Arg Asp Trp
                500                 505                 510

Leu Asn Gln Arg Asn Asn Phe Leu Leu Pro Tyr Phe Thr Glu Asp Glu
                515                 520                 525

Lys Lys Leu Ile Gln Gly Thr Phe Asp Phe Leu Ala Leu Ser His Tyr
530                 535                 540

Thr Thr Ile Leu Val Asp Ser Glu Lys Glu Asp Pro Ile Lys Tyr Asn
545                 550                 555                 560

Asp Tyr Leu Glu Val Gln Glu Met Thr Asp Ile Thr Trp Leu Asn Ser
                565                 570                 575

Pro Ser Gln Val Ala Val Pro Trp Gly Leu Arg Lys Val Leu Asn
                580                 585                 590

Trp Leu Lys Phe Lys Tyr Gly Asp Leu Pro Met Tyr Ile Ile Ser Asn
                595                 600                 605

Gly Ile Asp Asp Gly Leu His Ala Glu Asp Gln Leu Arg Val Tyr
610                 615                 620

Tyr Met Gln Asn Tyr Ile Asn Glu Ala Leu Lys Ala His Ile Leu Asp
625                 630                 635                 640

Gly Ile Asn Leu Cys Gly Tyr Phe Ala Tyr Ser Phe Asn Asp Arg Thr
                645                 650                 655

Ala Pro Arg Phe Gly Leu Tyr Arg Tyr Ala Ala Asp Gln Phe Glu Pro
                660                 665                 670

Lys Ala Ser Met Lys His Tyr Arg Lys Ile Ile Asp Ser Asn Gly Phe
                675                 680                 685

<210> SEQ ID NO 28
<211> LENGTH: 1149
<212> TYPE: PRT
<213> ORGANISM: Artificial
<220> FEATURE:
<223> OTHER INFORMATION: fusion polypeptide

<400> SEQUENCE: 28

Met Leu Gly Ala Arg Leu Arg Leu Trp Val Cys Ala Leu Cys Ser Val
1               5                   10                  15

Cys Ser Met Ser Val Leu Arg Ala Tyr Pro Asn Ala Ser Pro Leu Leu
                20                  25                  30

Gly Ser Ser Trp Gly Gly Leu Ile His Leu Tyr Thr Ala Thr Ala Arg
                35                  40                  45

Asn Ser Tyr His Leu Gln Ile His Lys Asn Gly His Val Asp Gly Ala
                50                  55                  60

Pro His Gln Thr Ile Tyr Ser Ala Leu Met Ile Arg Ser Glu Asp Ala
65                  70                  75                  80

Gly Phe Val Val Ile Thr Gly Val Met Ser Arg Arg Tyr Leu Cys Met
                85                  90                  95

Asp Phe Arg Gly Asn Ile Phe Gly Ser His Tyr Phe Asp Pro Glu Asn
                100                 105                 110

Cys Arg Phe Gln His Gln Thr Leu Glu Asn Gly Tyr Asp Val Tyr His
                115                 120                 125

Ser Pro Gln Tyr His Phe Leu Val Ser Leu Gly Arg Ala Lys Arg Ala
                130                 135                 140

Phe Leu Pro Gly Met Asn Pro Pro Tyr Ser Gln Phe Leu Ser Arg
```

```
                145                 150                 155                 160
Arg Asn Glu Ile Pro Leu Ile His Phe Asn Thr Pro Ile Pro Arg Arg
                    165                 170                 175

His Thr Gln Ser Ala Glu Asp Ser Glu Arg Asp Pro Leu Asn Val
            180                 185                 190

Leu Lys Pro Arg Ala Arg Met Thr Pro Ala Pro Ala Ser Cys Ser Gln
            195                 200                 205

Glu Leu Pro Ser Ala Glu Asp Asn Ser Pro Met Ala Ser Asp Pro Leu
        210                 215                 220

Gly Val Val Arg Gly Arg Val Asn Thr His Ala Gly Gly Thr Gly
225                 230                 235                 240

Pro Glu Gly Cys Arg Pro Phe Ala Lys Phe Ile Gln Gly Thr Phe Pro
                245                 250                 255

Asp Gly Phe Leu Trp Ala Val Gly Ser Ala Ala Tyr Gln Thr Glu Gly
            260                 265                 270

Gly Trp Gln Gln His Gly Lys Gly Ala Ser Ile Trp Asp Thr Phe Thr
        275                 280                 285

His His Pro Leu Ala Pro Pro Gly Asp Ser Arg Asn Ala Ser Leu Pro
        290                 295                 300

Leu Gly Ala Pro Ser Pro Leu Gln Pro Ala Thr Gly Asp Val Ala Ser
305                 310                 315                 320

Asp Ser Tyr Asn Asn Val Phe Arg Asp Thr Glu Ala Leu Arg Glu Leu
                325                 330                 335

Gly Val Thr His Tyr Arg Phe Ser Ile Ser Trp Ala Arg Val Leu Pro
            340                 345                 350

Asn Gly Ser Ala Gly Val Pro Asn Arg Glu Gly Leu Arg Tyr Tyr Arg
            355                 360                 365

Arg Leu Leu Glu Arg Leu Arg Glu Leu Gly Val Gln Pro Val Val Thr
        370                 375                 380

Leu Tyr His Trp Asp Leu Pro Gln Arg Leu Gln Asp Ala Tyr Gly Gly
385                 390                 395                 400

Trp Ala Asn Arg Ala Leu Ala Asp His Phe Arg Asp Tyr Ala Glu Leu
                405                 410                 415

Cys Phe Arg His Phe Gly Gly Gln Val Lys Tyr Trp Ile Thr Ile Asp
            420                 425                 430

Asn Pro Tyr Val Val Ala Trp His Gly Tyr Ala Thr Gly Arg Leu Ala
            435                 440                 445

Pro Gly Ile Arg Gly Ser Pro Arg Leu Gly Tyr Leu Val Ala His Asn
        450                 455                 460

Leu Leu Leu Ala His Ala Lys Val Trp His Leu Tyr Asn Thr Ser Phe
465                 470                 475                 480

Arg Pro Thr Gln Gly Gly Gln Val Ser Ile Ala Leu Ser Ser His Trp
                485                 490                 495

Ile Asn Pro Arg Arg Met Thr Asp His Ser Ile Lys Glu Cys Gln Lys
            500                 505                 510

Ser Leu Asp Phe Val Leu Gly Trp Phe Ala Lys Pro Val Phe Ile Asp
            515                 520                 525

Gly Asp Tyr Pro Glu Ser Met Lys Asn Asn Leu Ser Ser Ile Leu Pro
        530                 535                 540

Asp Phe Thr Glu Ser Glu Lys Lys Phe Ile Lys Gly Thr Ala Asp Phe
545                 550                 555                 560

Phe Ala Leu Cys Phe Gly Pro Thr Leu Ser Phe Gln Leu Leu Asp Pro
                565                 570                 575
```

-continued

His Met Lys Phe Arg Gln Leu Glu Ser Pro Asn Leu Arg Gln Leu Leu
            580                 585                 590

Ser Trp Ile Asp Leu Glu Phe Asn His Pro Gln Ile Phe Ile Val Glu
        595                 600                 605

Asn Gly Trp Phe Val Ser Gly Thr Thr Lys Arg Asp Asp Ala Lys Tyr
    610                 615                 620

Met Tyr Tyr Leu Lys Lys Phe Ile Met Glu Thr Leu Lys Ala Ile Lys
625                 630                 635                 640

Leu Asp Gly Val Asp Val Ile Gly Tyr Thr Ala Trp Ser Leu Met Asp
                645                 650                 655

Gly Phe Glu Trp His Arg Gly Tyr Ser Ile Arg Arg Gly Leu Phe Tyr
            660                 665                 670

Val Asp Phe Leu Ser Gln Asp Lys Met Leu Pro Lys Ser Ser Ala
        675                 680                 685

Leu Phe Tyr Gln Lys Leu Ile Glu Lys Asn Gly Phe Gln Gly Thr Phe
    690                 695                 700

Pro Asp Gly Phe Leu Trp Ala Val Gly Ser Ala Ala Tyr Gln Thr Glu
705                 710                 715                 720

Gly Gly Trp Gln Gln His Gly Lys Gly Ala Ser Ile Trp Asp Thr Phe
                725                 730                 735

Thr His His Pro Leu Ala Pro Pro Gly Asp Ser Arg Asn Ala Ser Leu
            740                 745                 750

Pro Leu Gly Ala Pro Ser Pro Leu Gln Pro Ala Thr Gly Asp Val Ala
        755                 760                 765

Ser Asp Ser Tyr Asn Asn Val Phe Arg Asp Thr Glu Ala Leu Arg Glu
    770                 775                 780

Leu Gly Val Thr His Tyr Arg Phe Ser Ile Ser Trp Ala Arg Val Leu
785                 790                 795                 800

Pro Asn Gly Ser Ala Gly Val Pro Asn Arg Glu Gly Leu Arg Tyr Tyr
                805                 810                 815

Arg Arg Leu Leu Glu Arg Leu Arg Glu Leu Gly Val Gln Pro Val Val
            820                 825                 830

Thr Leu Tyr His Trp Asp Leu Pro Gln Arg Leu Gln Asp Ala Tyr Gly
        835                 840                 845

Gly Trp Ala Asn Arg Ala Leu Ala Asp His Phe Arg Asp Tyr Ala Glu
    850                 855                 860

Leu Cys Phe Arg His Phe Gly Gly Gln Val Lys Tyr Trp Ile Thr Ile
865                 870                 875                 880

Asp Asn Pro Tyr Val Val Ala Trp His Gly Tyr Ala Thr Gly Arg Leu
                885                 890                 895

Ala Pro Gly Ile Arg Gly Ser Pro Arg Leu Gly Tyr Leu Val Ala His
            900                 905                 910

Asn Leu Leu Leu Ala His Ala Lys Val Trp His Leu Tyr Asn Thr Ser
        915                 920                 925

Phe Arg Pro Thr Gln Gly Gly Gln Val Ser Ile Ala Leu Ser Ser His
    930                 935                 940

Trp Ile Asn Pro Arg Arg Met Thr Asp His Ser Ile Lys Glu Cys Gln
945                 950                 955                 960

Lys Ser Leu Asp Phe Val Leu Gly Trp Phe Ala Lys Pro Val Phe Ile
                965                 970                 975

Asp Gly Asp Tyr Pro Glu Ser Met Lys Asn Asn Leu Ser Ser Ile Leu
            980                 985                 990

Pro Asp Phe Thr Glu Ser Glu Lys Lys Phe Ile Lys Gly Thr Ala Asp
        995                 1000                1005

```
Phe Phe Ala Leu Cys Phe Gly Pro Thr Leu Ser Phe Gln Leu Leu
    1010                1015                    1020

Asp Pro His Met Lys Phe Arg Gln Leu Glu Ser Pro Asn Leu Arg
    1025                1030                    1035

Gln Leu Leu Ser Trp Ile Asp Leu Glu Phe Asn His Pro Gln Ile
    1040                1045                    1050

Phe Ile Val Glu Asn Gly Trp Phe Val Ser Gly Thr Thr Lys Arg
    1055                1060                    1065

Asp Asp Ala Lys Tyr Met Tyr Tyr Leu Lys Lys Phe Ile Met Glu
    1070                1075                    1080

Thr Leu Lys Ala Ile Lys Leu Asp Gly Val Asp Val Ile Gly Tyr
    1085                1090                    1095

Thr Ala Trp Ser Leu Met Asp Gly Phe Glu Trp His Arg Gly Tyr
    1100                1105                    1110

Ser Ile Arg Arg Gly Leu Phe Tyr Val Asp Phe Leu Ser Gln Asp
    1115                1120                    1125

Lys Met Leu Leu Pro Lys Ser Ser Ala Leu Phe Tyr Gln Lys Leu
    1130                1135                    1140

Ile Glu Lys Asn Gly Phe
    1145

<210> SEQ ID NO 29
<211> LENGTH: 1125
<212> TYPE: PRT
<213> ORGANISM: Artificial
<220> FEATURE:
<223> OTHER INFORMATION: fusion polypeptide

<400> SEQUENCE: 29

Met Leu Gly Ala Arg Leu Arg Leu Trp Val Cys Ala Leu Cys Ser Val
1               5                   10                  15

Cys Ser Met Ser Val Leu Arg Ala Tyr Pro Asn Ala Ser Pro Leu Leu
            20                  25                  30

Gly Ser Ser Trp Gly Gly Leu Ile His Leu Tyr Thr Ala Thr Ala Arg
        35                  40                  45

Asn Ser Tyr His Leu Gln Ile His Lys Asn Gly His Val Asp Gly Ala
    50                  55                  60

Pro His Gln Thr Ile Tyr Ser Ala Leu Met Ile Arg Ser Glu Asp Ala
65                  70                  75                  80

Gly Phe Val Val Ile Thr Gly Val Met Ser Arg Arg Tyr Leu Cys Met
                85                  90                  95

Asp Phe Arg Gly Asn Ile Phe Gly Ser His Tyr Phe Asp Pro Glu Asn
            100                 105                 110

Cys Arg Phe Gln His Gln Thr Leu Glu Asn Gly Tyr Asp Val Tyr His
        115                 120                 125

Ser Pro Gln Tyr His Phe Leu Val Ser Leu Gly Arg Ala Lys Arg Ala
    130                 135                 140

Phe Leu Pro Gly Met Asn Pro Pro Tyr Ser Gln Phe Leu Ser Arg
145                 150                 155                 160

Arg Asn Glu Ile Pro Leu Ile His Phe Asn Thr Pro Ile Pro Arg Arg
                165                 170                 175

His Thr Gln Ser Ala Glu Asp Asp Ser Glu Arg Asp Pro Leu Asn Val
            180                 185                 190

Leu Lys Pro Arg Ala Arg Met Thr Pro Ala Pro Ala Ser Cys Ser Gln
        195                 200                 205
```

```
Glu Leu Pro Ser Ala Glu Asp Asn Ser Pro Met Ala Ser Asp Pro Leu
    210                 215                 220

Gly Val Val Arg Gly Arg Val Asn Thr His Ala Gly Gly Thr Gly
225                 230                 235                 240

Pro Glu Gly Cys Arg Pro Phe Ala Lys Phe Ile Gly Thr Phe Pro Cys
                    245                 250                 255

Asp Phe Ala Trp Gly Val Val Asp Asn Tyr Ile Gln Val Asp Thr Thr
                260                 265                 270

Leu Ser Gln Phe Thr Asp Leu Asn Val Tyr Leu Trp Asp Val His His
        275                 280                 285

Ser Lys Arg Leu Ile Lys Val Asp Gly Val Val Thr Lys Lys Arg Lys
    290                 295                 300

Ser Tyr Cys Val Asp Phe Ala Ala Ile Gln Pro Gln Ile Ala Leu Leu
305                 310                 315                 320

Gln Glu Met His Val Thr His Phe Arg Phe Ser Leu Asp Trp Ala Leu
                325                 330                 335

Ile Leu Pro Leu Gly Asn Gln Ser Gln Val Asn His Thr Ile Leu Gln
                340                 345                 350

Tyr Tyr Arg Cys Met Ala Ser Glu Leu Val Arg Val Asn Ile Thr Pro
        355                 360                 365

Val Val Ala Leu Trp Gln Pro Met Ala Pro Asn Gln Gly Leu Pro Arg
370                 375                 380

Leu Leu Ala Arg Gln Gly Ala Trp Glu Asn Pro Tyr Thr Ala Leu Ala
385                 390                 395                 400

Phe Ala Glu Tyr Ala Arg Leu Cys Phe Gln Glu Leu Gly His His Val
                405                 410                 415

Lys Leu Trp Ile Thr Met Asn Glu Pro Tyr Thr Arg Asn Met Thr Tyr
                420                 425                 430

Ser Ala Gly His Asn Leu Leu Lys Ala His Ala Leu Ala Trp His Val
                435                 440                 445

Tyr Asn Glu Lys Phe Arg His Ala Gln Asn Gly Lys Ile Ser Ile Ala
        450                 455                 460

Leu Gln Ala Asp Trp Ile Glu Pro Ala Cys Pro Phe Ser Gln Lys Asp
465                 470                 475                 480

Lys Glu Val Ala Glu Arg Val Leu Glu Phe Asp Ile Gly Trp Leu Ala
                485                 490                 495

Glu Pro Ile Phe Gly Ser Gly Asp Tyr Pro Trp Val Met Arg Asp Trp
                500                 505                 510

Leu Asn Gln Arg Asn Asn Phe Leu Leu Pro Tyr Phe Thr Glu Asp Glu
        515                 520                 525

Lys Lys Leu Ile Gln Gly Thr Phe Asp Phe Leu Ala Leu Ser His Tyr
    530                 535                 540

Thr Thr Ile Leu Val Asp Ser Glu Lys Glu Asp Pro Ile Lys Tyr Asn
545                 550                 555                 560

Asp Tyr Leu Glu Val Gln Glu Met Thr Asp Ile Thr Trp Leu Asn Ser
                565                 570                 575

Pro Ser Gln Val Ala Val Val Pro Trp Gly Leu Arg Lys Val Leu Asn
            580                 585                 590

Trp Leu Lys Phe Lys Tyr Gly Asp Leu Pro Met Tyr Ile Ile Ser Asn
        595                 600                 605

Gly Ile Asp Asp Gly Leu His Ala Glu Asp Asp Gln Leu Arg Val Tyr
    610                 615                 620

Tyr Met Gln Asn Tyr Ile Asn Glu Ala Leu Lys Ala His Ile Leu Asp
625                 630                 635                 640
```

Gly Ile Asn Leu Cys Gly Tyr Phe Ala Tyr Ser Phe Asn Asp Arg Thr
            645                 650                 655

Ala Pro Arg Phe Gly Leu Tyr Arg Tyr Ala Ala Asp Gln Phe Glu Pro
            660                 665                 670

Lys Ala Ser Met Lys His Tyr Arg Lys Ile Ile Asp Ser Asn Gly Phe
            675                 680                 685

Gly Thr Phe Pro Cys Asp Phe Ala Trp Gly Val Val Asp Asn Tyr Ile
            690                 695                 700

Gln Val Asp Thr Thr Leu Ser Gln Phe Thr Asp Leu Asn Val Tyr Leu
705                 710                 715                 720

Trp Asp Val His His Ser Lys Arg Leu Ile Lys Val Asp Gly Val Val
                    725                 730                 735

Thr Lys Lys Arg Lys Ser Tyr Cys Val Asp Phe Ala Ala Ile Gln Pro
            740                 745                 750

Gln Ile Ala Leu Leu Gln Glu Met His Val Thr His Phe Arg Phe Ser
            755                 760                 765

Leu Asp Trp Ala Leu Ile Leu Pro Leu Gly Asn Gln Ser Gln Val Asn
            770                 775                 780

His Thr Ile Leu Gln Tyr Tyr Arg Cys Met Ala Ser Glu Leu Val Arg
785                 790                 795                 800

Val Asn Ile Thr Pro Val Val Ala Leu Trp Gln Pro Met Ala Pro Asn
                    805                 810                 815

Gln Gly Leu Pro Arg Leu Leu Ala Arg Gln Gly Ala Trp Glu Asn Pro
            820                 825                 830

Tyr Thr Ala Leu Ala Phe Ala Glu Tyr Ala Arg Leu Cys Phe Gln Glu
            835                 840                 845

Leu Gly His His Val Lys Leu Trp Ile Thr Met Asn Glu Pro Tyr Thr
            850                 855                 860

Arg Asn Met Thr Tyr Ser Ala Gly His Asn Leu Leu Lys Ala His Ala
865                 870                 875                 880

Leu Ala Trp His Val Tyr Asn Glu Lys Phe Arg His Ala Gln Asn Gly
                    885                 890                 895

Lys Ile Ser Ile Ala Leu Gln Ala Asp Trp Ile Glu Pro Ala Cys Pro
            900                 905                 910

Phe Ser Gln Lys Asp Lys Glu Val Ala Glu Arg Val Leu Glu Phe Asp
            915                 920                 925

Ile Gly Trp Leu Ala Glu Pro Ile Phe Gly Ser Gly Asp Tyr Pro Trp
            930                 935                 940

Val Met Arg Asp Trp Leu Asn Gln Arg Asn Asn Phe Leu Leu Pro Tyr
945                 950                 955                 960

Phe Thr Glu Asp Glu Lys Lys Leu Ile Gln Gly Thr Phe Asp Phe Leu
                    965                 970                 975

Ala Leu Ser His Tyr Thr Thr Ile Leu Val Asp Ser Glu Lys Glu Asp
            980                 985                 990

Pro Ile Lys Tyr Asn Asp Tyr Leu Glu Val Gln Glu Met Thr Asp Ile
            995                 1000                1005

Thr Trp Leu Asn Ser Pro Ser Gln Val Ala Val Pro Trp Gly
            1010                1015                1020

Leu Arg Lys Val Leu Asn Trp Leu Lys Phe Lys Tyr Gly Asp Leu
            1025                1030                1035

Pro Met Tyr Ile Ile Ser Asn Gly Ile Asp Asp Gly Leu His Ala
            1040                1045                1050

Glu Asp Asp Gln Leu Arg Val Tyr Tyr Met Gln Asn Tyr Ile Asn

| | | | | |
|---|---|---|---|---|
| | 1055 | | 1060 | 1065 |

Glu Ala Leu Lys Ala His Ile Leu Asp Gly Ile Asn Leu Cys Gly
    1070                       1075                   1080

Tyr Phe Ala Tyr Ser Phe Asn Asp Arg Thr Ala Pro Arg Phe Gly
    1085                       1090                   1095

Leu Tyr Arg Tyr Ala Ala Asp Gln Phe Glu Pro Lys Ala Ser Met
    1100                       1105                   1110

Lys His Tyr Arg Lys Ile Ile Asp Ser Asn Gly Phe
    1115                       1120

<210> SEQ ID NO 30
<211> LENGTH: 2157
<212> TYPE: DNA
<213> ORGANISM: Homo sapiens

<400> SEQUENCE: 30

```
gctcccagcc aagaacctcg gggccgctgc gcggtgggga ggagttcccc gaaacccggc    60
cgctaagcga ggcctcctcc tcccgcagat ccgaacggcc tgggcggggt caccccggct   120
gggacaagaa gccgccgcct gcctgccgg gcccggggag ggggctgggg ctggggccgg    180
aggcggggtg tgagtgggtg tgtgcggggg gcggaggctt gatgcaatcc cgataagaaa   240
tgctcgggtc tcttgggcac ctaccgtgg ggcccgtaag gcgctactat ataaggctgc    300
cggcccggag ccgccgcgcc gtcagagcag gagcgctgcg tccaggatct agggccacga   360
ccatcccaac ccggcactca cagccccgca gcgcatcccg gtcgccgccc agcctcccgc   420
acccccatcg ccggagctgc gccgagagcc ccagggaggt gccatgcgga gcgggtgtgt   480
ggtggtccac gtatggatcc tggccggcct ctggctggcc gtggccgggc gcccctcgc    540
cttctcggac gcggggcccc acgtgcacta cggctggggc gaccccatcc gctgcggca    600
cctgtacacc tccggccccc acgggctctc cagctgcttc ctgcgcatcc gtgccgacgg   660
cgtcgtggac tgcgcgcggg gccagagcgc gcacagtttg ctggagatca aggcagtcgc   720
tctgcggacc gtggccatca agggcgtgca cagcgtgcgg tacctctgca tgggcgccga   780
cggcaagatg caggggctgc ttcagtactc ggaggaagac tgtgctttcg aggaggagat   840
ccgcccagat ggctacaatg tgtaccgatc cgagaagcac cgcctcccgg tctccctgag   900
cagtgccaaa cagcggcagc tgtacaagaa cagaggcttt cttccactct ctcatttcct   960
gcccatgctg cccatggtcc cagaggagcc tgaggacctc aggggccact tggaatctga  1020
catgttctct tcgcccctgg agaccgacag catggaccca tttgggcttg tcaccggact  1080
ggaggccgtg aggagtccca gctttgagaa gtaactgaga ccatgcccgg gcctcttcac  1140
tgctgccagg ggctgtggta cctgcagcgt gggggacgtg cttctacaag aacagtcctg  1200
agtccacgtt ctgtttagct ttaggaagaa acatctagaa gttgtacata ttcagagttt  1260
tccattggca gtgccagttt ctagccaata gacttgtctg atcataacat tgtaagcctg  1320
tagcttgccc agctgctgcc tgggccccca ttctgctccc tcgaggttgc tggacaagct  1380
gctgcactgt ctcagttctg cttgaatacc tccatcgatg gggaactcac ttcctttgga  1440
aaaattctta tgtcaagctg aaattctcta attttttctc atcacttccc caggagcagc  1500
cagaagacag gcagtagttt taatttcagg aacaggtgat ccactctgta aaacagcagg  1560
taaatttcac tcaaccccat gtgggaattg atctatatct ctacttccag ggaccatttg  1620
cccttcccaa atccctccag gccagaactg actggagcag gcatggccca ccaggcttca  1680
ggagtagggg aagcctggag ccccactcca gccctgggac aacttgagaa ttccccctga  1740
```

```
ggccagttct gtcatggatg ctgtcctgag aataacttgc tgtcccggtg tcacctgctt    1800
ccatctccca gcccaccagc cctctgccca cctcacatgc ctccccatgg attggggcct    1860
cccaggcccc ccaccttatg tcaacctgca cttcttgttc aaaaatcagg aaaagaaaag    1920
atttgaagac cccaagtctt gtcaataact tgctgtgtgg aagcagcggg ggaagaccta    1980
gaaccctttc cccagcactt ggttttccaa catgatattt atgagtaatt tattttgata    2040
tgtacatctc ttattttctt acattattta tgcccccaaa ttatatttat gtatgtaagt    2100
gaggtttgtt ttgtatatta aatggagtt tgtttgtaaa aaaaaaaaaa aaaaaa         2157
```

<210> SEQ ID NO 31
<211> LENGTH: 216
<212> TYPE: PRT
<213> ORGANISM: Homo sapiens

<400> SEQUENCE: 31

```
Met Arg Ser Gly Cys Val Val His Val Trp Ile Leu Ala Gly Leu
1               5                   10                  15

Trp Leu Ala Val Ala Gly Arg Pro Leu Ala Phe Ser Asp Ala Gly Pro
                20                  25                  30

His Val His Tyr Gly Trp Gly Asp Pro Ile Arg Leu Arg His Leu Tyr
            35                  40                  45

Thr Ser Gly Pro His Gly Leu Ser Ser Cys Phe Leu Arg Ile Arg Ala
        50                  55                  60

Asp Gly Val Val Asp Cys Ala Arg Gly Gln Ser Ala His Ser Leu Leu
65                  70                  75                  80

Glu Ile Lys Ala Val Ala Leu Arg Thr Val Ala Ile Lys Gly Val His
                85                  90                  95

Ser Val Arg Tyr Leu Cys Met Gly Ala Asp Gly Lys Met Gln Gly Leu
            100                 105                 110

Leu Gln Tyr Ser Glu Glu Asp Cys Ala Phe Glu Glu Glu Ile Arg Pro
        115                 120                 125

Asp Gly Tyr Asn Val Tyr Arg Ser Glu Lys His Arg Leu Pro Val Ser
    130                 135                 140

Leu Ser Ser Ala Lys Gln Arg Gln Leu Tyr Lys Asn Arg Gly Phe Leu
145                 150                 155                 160

Pro Leu Ser His Phe Leu Pro Met Leu Pro Met Val Pro Glu Glu Pro
                165                 170                 175

Glu Asp Leu Arg Gly His Leu Glu Ser Asp Met Phe Ser Ser Pro Leu
            180                 185                 190

Glu Thr Asp Ser Met Asp Pro Phe Gly Leu Val Thr Gly Leu Glu Ala
        195                 200                 205

Val Arg Ser Pro Ser Phe Glu Lys
    210                 215
```

<210> SEQ ID NO 32
<211> LENGTH: 940
<212> TYPE: DNA
<213> ORGANISM: Homo sapiens

<400> SEQUENCE: 32

```
ctgtcagctg aggatccagc cgaaagagga gccaggcact caggccacct gagtctactc      60
acctggacaa ctggaatctg gcaccaattc taaaccactc agcttctccg agctcacacc     120
ccggagatca cctgaggacc cgagccattg atggactcgg acgagaccgg gttcgagcac     180
tcaggactgt gggtttctgt gctggctggt cttctgctgg gagcctgcca ggcacacccc     240
```

```
atccctgact ccagtcctct cctgcaattc gggggccaag tccggcagcg gtacctctac    300
acagatgatg cccagcagac agaagcccac ctggagatca ggaggatgg  gacggtgggg    360
ggcgctgctg accagagccc cgaaagtctc ctgcagctga aagccttgaa gccgggagtt    420
attcaaatct tgggagtcaa gacatccagg ttcctgtgcc agcggccaga tggggccctg    480
tatggatcgc tccactttga ccctgaggcc tgcagcttcc gggagctgct tcttgaggac    540
ggatacaatg tttaccagtc cgaagcccac ggcctcccgc tgcacctgcc agggaacaag    600
tccccacacc gggaccctgc acccgagga  ccagctcgct tcctgccact accaggcctg    660
ccccccgcac tcccggagcc acccggaatc ctggcccccc agcccccccga tgtgggctcc   720
tcggacccctc tgagcatggt gggaccttcc cagggccgaa gccccagcta cgcttcctga   780
agccagaggc tgtttactat gacatctcct ctttatttat taggttattt atcttattta    840
ttttttatt  tttcttactt gagataataa agagttccag aggagaaaaa aaaaaaaaaa    900
aaaaaaaaaa aaaaaaaaaa aaaaaaaaaa aaaaaaaaaa                          940
```

```
<210> SEQ ID NO 33
<211> LENGTH: 209
<212> TYPE: PRT
<213> ORGANISM: Homo sapiens

<400> SEQUENCE: 33

Met Asp Ser Asp Glu Thr Gly Phe Glu His Ser Gly Leu Trp Val Ser
1               5                   10                  15

Val Leu Ala Gly Leu Leu Leu Gly Ala Cys Gln Ala His Pro Ile Pro
            20                  25                  30

Asp Ser Ser Pro Leu Leu Gln Phe Gly Gly Gln Val Arg Gln Arg Tyr
        35                  40                  45

Leu Tyr Thr Asp Asp Ala Gln Gln Thr Glu Ala His Leu Glu Ile Arg
    50                  55                  60

Glu Asp Gly Thr Val Gly Gly Ala Ala Asp Gln Ser Pro Glu Ser Leu
65                  70                  75                  80

Leu Gln Leu Lys Ala Leu Lys Pro Gly Val Ile Gln Ile Leu Gly Val
                85                  90                  95

Lys Thr Ser Arg Phe Leu Cys Gln Arg Pro Asp Gly Ala Leu Tyr Gly
            100                 105                 110

Ser Leu His Phe Asp Pro Glu Ala Cys Ser Phe Arg Glu Leu Leu Leu
        115                 120                 125

Glu Asp Gly Tyr Asn Val Tyr Gln Ser Glu Ala His Gly Leu Pro Leu
    130                 135                 140

His Leu Pro Gly Asn Lys Ser Pro His Arg Asp Pro Ala Pro Arg Gly
145                 150                 155                 160

Pro Ala Arg Phe Leu Pro Leu Pro Gly Leu Pro Ala Leu Pro Glu
                165                 170                 175

Pro Pro Gly Ile Leu Ala Pro Gln Pro Pro Asp Val Ser Ser Asp
            180                 185                 190

Pro Leu Ser Met Val Gly Pro Ser Gln Gly Arg Ser Pro Ser Tyr Ala
        195                 200                 205

Ser

<210> SEQ ID NO 34
<211> LENGTH: 3018
<212> TYPE: DNA
<213> ORGANISM: Homo sapiens

<400> SEQUENCE: 34
```

```
cggcaaaaag gagggaatcc agtctaggat cctcacacca gctacttgca agggagaagg      60
aaaaggccag taaggcctgg gccaggagag tcccgacagg agtgtcaggt ttcaatctca     120
gcaccagcca ctcagagcag ggcacgatgt tgggggcccg cctcaggctc tgggtctgtg     180
ccttgtgcag cgtctgcagc atgagcgtcc tcagagccta tcccaatgcc tccccactgc     240
tcggctccag ctggggtggc ctgatccacc tgtacacagc cacagccagg aacagctacc     300
acctgcagat ccacaagaat ggccatgtgg atggcgcacc ccatcagacc atctacagtg     360
ccctgatgat cagatcagag gatgctggct tgtggtgat acaggtgtg atgagcagaa       420 gatacctctg catggatttc agaggcaaca tttttggatc acactatttc gacccggaga     480
actgcaggtt ccaacaccag acgctggaaa acgggtacga cgtctaccac tctcctcagt     540
atcacttcct ggtcagtctg ggccgggcga agagagcctt cctgccaggc atgaacccac     600
ccccgtactc ccagttcctg tcccggagga acgagatccc cctaattcac ttcaacaccc     660
ccataccacg gcggcacacc cggagcgccg aggacgactg ggagcgggac cccctgaacg     720
tgctgaagcc ccgggcccgg atgacccegg ccccggcctc ctgttcacag gagctcccga     780
gcgccgagga caacagcccg atggccagtg acccattagg ggtggtcagg ggcggtcgag     840
tgaacacgca cgctggggga acgggcccgg aaggctgccg ccccttcgcc aagttcatct     900
agggtcgctg gaagggcacc ctctttaacc catccctcag caaacgcagc tcttcccaag     960
gaccaggtcc cttgacgttc cgaggatggg aaaggtgaca ggggcatgta tggaatttgc    1020
tgcttctctg gggtcccttc cacaggaggt cctgtgagaa ccaacctttg aggcccaagt    1080
catggggttt caccgccttc ctcactccat atagaacacc tttcccaata ggaaacccca    1140
acaggtaaac tagaaatttc cccttcatga aggtagagag aaggggtctc tcccaacata    1200
tttctcttcc ttgtgcctct cctctttatc acttttaagc ataaaaaaaa aaaaaaaaa     1260 aaaaaaaaaa aaaagcagtg ggttcctgag ctcaagactt tgaaggtgta gggaagagga    1320
aatcggagat cccagaagct tctccactgc cctatgcatt tatgttagat gccccgatcc    1380
cactggcatt tgagtgtgca aaccttgaca ttaacagctg aatggggcaa gttgatgaaa    1440
acactacttt caagccttcg ttcttccttg agcatctctg gggaagagct gtcaaaagac    1500
tggtggtagg ctggtgaaaa cttgacagct agacttgatg cttgctgaaa tgaggcagga    1560
atcataatag aaaactcagc ctccctacag ggtgagcacc ttctgtctcg ctgtctccct    1620
ctgtgcagcc acagccagag ggcccagaat ggccccactc tgttcccaag cagttcatga    1680
tacagcctca ccttttggcc ccatctctgg ttttttgaaaa tttggtctaa ggaataaata   1740
gcttttacac tggctcacga aaatctgccc tgctagaatt tgcttttcaa aatgaaata    1800 aattccaact ctcctaagag gcatttaatt aaggctctac ttccaggttg agtaggaatc    1860
cattctgaac aaaactacaaa aatgtgactg gaagggggc tttgagagac tgggactgct    1920
ctgggttagg ttttctgtgg actgaaaaat cgtgtccttt tctctaaatg aagtggcatc    1980
aaggactcag ggggaaagaa atcagggac atgttataga agttatgaaa agacaaccac     2040
atggtcaggc tcttgtctgt ggtctctagg gctctgcagc agcagtggct cttcgattag    2100
ttaaaactct cctaggctga cacatctggg tctcaatccc cttggaaatt cttggtgcat    2160
taaatgaagc cttaccccat tactgcggtt cttcctgtaa gggggctcca ttttcctccc    2220
tctctttaaa tgaccaccta aaggacagta tattaacaag caaagtcgat tcaacaacag    2280
cttcttccca gtcacttttt tttttctcac tgccatcaca tactaacctt atactttgat    2340
ctattctttt tggttatgag agaaatgttg ggcaactgtt tttacctgat ggttttaagc    2400
```

-continued

```
tgaacttgaa ggactggttc ctattctgaa acagtaaaac tatgtataat agtatatagc    2460
catgcatggc aaatatttta atatttctgt tttcatttcc tgttggaaat attatcctgc    2520
ataatagcta ttggaggctc ctcagtgaaa gatcccaaaa ggattttggt ggaaaactag    2580
ttgtaatctc acaaactcaa cactaccatc aggggttttc tttatggcaa agccaaaata    2640
gctcctacaa tttcttatat ccctcgtcat gtggcagtat ttatttattt atttggaagt    2700
ttgcctatcc ttctatattt atagatattt ataaaaatgt aaccccttttt tcctttcttc    2760 tgtttaaaat aaaaataaaa tttatctcag cttctgttag cttatcctct ttgtagtact    2820
acttaaaagc atgtcggaat ataagaataa aaaggattat gggaggggaa cattagggaa    2880
atccagagaa ggcaaaattg aaaaaaagat tttagaattt taaaattttc aaagattttct   2940 tccattcata aggagactca atgattttaa ttgatctaga cagaattatt taagttttat    3000
caatattgga tttctggt                                                   3018
```

<210> SEQ ID NO 35
<211> LENGTH: 251
<212> TYPE: PRT
<213> ORGANISM: Homo sapiens

<400> SEQUENCE: 35

```
Met Leu Gly Ala Arg Leu Arg Leu Trp Val Cys Ala Leu Cys Ser Val
 1               5                   10                  15

Cys Ser Met Ser Val Leu Arg Ala Tyr Pro Asn Ala Ser Pro Leu Leu
                20                  25                  30

Gly Ser Ser Trp Gly Gly Leu Ile His Leu Tyr Thr Ala Thr Ala Arg
            35                  40                  45

Asn Ser Tyr His Leu Gln Ile His Lys Asn Gly His Val Asp Gly Ala
        50                  55                  60

Pro His Gln Thr Ile Tyr Ser Ala Leu Met Ile Arg Ser Glu Asp Ala
65                  70                  75                  80

Gly Phe Val Val Ile Thr Gly Val Met Ser Arg Arg Tyr Leu Cys Met
                85                  90                  95

Asp Phe Arg Gly Asn Ile Phe Gly Ser His Tyr Phe Asp Pro Glu Asn
            100                 105                 110

Cys Arg Phe Gln His Gln Thr Leu Glu Asn Gly Tyr Asp Val Tyr His
        115                 120                 125

Ser Pro Gln Tyr His Phe Leu Val Ser Leu Gly Arg Ala Lys Arg Ala
    130                 135                 140

Phe Leu Pro Gly Met Asn Pro Pro Tyr Ser Gln Phe Leu Ser Arg
145                 150                 155                 160

Arg Asn Glu Ile Pro Leu Ile His Phe Asn Thr Pro Ile Pro Arg Arg
                165                 170                 175

His Thr Arg Ser Ala Glu Asp Asp Ser Glu Arg Asp Pro Leu Asn Val
            180                 185                 190

Leu Lys Pro Arg Ala Arg Met Thr Pro Ala Pro Ala Ser Cys Ser Gln
        195                 200                 205

Glu Leu Pro Ser Ala Glu Asp Asn Ser Pro Met Ala Ser Asp Pro Leu
    210                 215                 220

Gly Val Val Arg Gly Gly Arg Val Asn Thr His Ala Gly Gly Thr Gly
225                 230                 235                 240

Pro Glu Gly Cys Arg Pro Phe Ala Lys Phe Ile
                245                 250
```

<210> SEQ ID NO 36
<211> LENGTH: 251
<212> TYPE: PRT
<213> ORGANISM: Artificial
<220> FEATURE:
<223> OTHER INFORMATION: fusion polypeptide

<400> SEQUENCE: 36

```
Met Leu Gly Ala Arg Leu Arg Leu Trp Val Cys Ala Leu Cys Ser Val
1               5                   10                  15

Cys Ser Met Ser Val Leu Arg Ala Tyr Pro Asn Ala Ser Pro Leu Leu
            20                  25                  30

Gly Ser Ser Trp Gly Gly Leu Ile His Leu Tyr Thr Ala Thr Ala Arg
        35                  40                  45

Asn Ser Tyr His Leu Gln Ile His Lys Asn Gly His Val Asp Gly Ala
    50                  55                  60

Pro His Gln Thr Ile Tyr Ser Ala Leu Met Ile Arg Ser Glu Asp Ala
65                  70                  75                  80

Gly Phe Val Val Ile Thr Gly Val Met Ser Arg Arg Tyr Leu Cys Met
                85                  90                  95

Asp Phe Arg Gly Asn Ile Phe Gly Ser His Tyr Phe Asp Pro Glu Asn
            100                 105                 110

Cys Arg Phe Gln His Gln Thr Leu Glu Asn Gly Tyr Asp Val Tyr His
        115                 120                 125

Ser Pro Gln Tyr His Phe Leu Val Ser Leu Gly Arg Ala Lys Arg Ala
    130                 135                 140

Phe Leu Pro Gly Met Asn Pro Pro Tyr Ser Gln Phe Leu Ser Arg
145                 150                 155                 160

Arg Asn Glu Ile Pro Leu Ile His Phe Asn Thr Pro Ile Pro Arg Arg
                165                 170                 175

His Thr Gln Ser Ala Glu Asp Ser Glu Arg Asp Pro Leu Asn Val
            180                 185                 190

Leu Lys Pro Arg Ala Arg Met Thr Pro Ala Pro Ala Ser Cys Ser Gln
        195                 200                 205

Glu Leu Pro Ser Ala Glu Asp Asn Ser Pro Met Ala Ser Asp Pro Leu
    210                 215                 220

Gly Val Val Arg Gly Gly Arg Val Asn Thr His Ala Gly Gly Thr Gly
225                 230                 235                 240

Pro Glu Gly Cys Arg Pro Phe Ala Lys Phe Ile
                245                 250
```

<210> SEQ ID NO 37
<211> LENGTH: 431
<212> TYPE: PRT
<213> ORGANISM: Homo sapiens

<400> SEQUENCE: 37

```
Tyr Asp Thr Phe Pro Lys Asn Phe Phe Trp Gly Ile Gly Thr Gly Ala
1               5                   10                  15

Leu Gln Val Glu Gly Ser Trp Lys Lys Asp Gly Lys Gly Pro Ser Ile
            20                  25                  30

Trp Asp His Phe Ile His Thr His Leu Lys Asn Val Ser Ser Thr Asn
        35                  40                  45

Gly Ser Ser Asp Ser Tyr Ile Phe Leu Glu Lys Asp Leu Ser Ala Leu
    50                  55                  60

Asp Phe Ile Gly Val Ser Phe Tyr Gln Phe Ser Ile Ser Trp Pro Arg
65                  70                  75                  80
```

```
Leu Phe Pro Asp Gly Ile Val Thr Val Ala Asn Ala Lys Gly Leu Gln
                85                  90                  95

Tyr Tyr Ser Thr Leu Leu Asp Ala Leu Val Leu Arg Asn Ile Glu Pro
            100                 105                 110

Ile Val Thr Leu Tyr His Trp Asp Leu Pro Leu Ala Leu Gln Glu Lys
        115                 120                 125

Tyr Gly Gly Trp Lys Asn Asp Thr Ile Ile Asp Ile Phe Asn Asp Tyr
    130                 135                 140

Ala Thr Tyr Cys Phe Gln Met Phe Gly Asp Arg Val Lys Tyr Trp Ile
145                 150                 155                 160

Thr Ile His Asn Pro Tyr Leu Val Ala Trp His Gly Tyr Gly Thr Gly
                165                 170                 175

Met His Ala Pro Gly Glu Lys Gly Asn Leu Ala Ala Val Tyr Thr Val
            180                 185                 190

Gly His Asn Leu Ile Lys Ala His Ser Lys Val Trp His Asn Tyr Asn
        195                 200                 205

Thr His Phe Arg Pro His Gln Lys Gly Trp Leu Ser Ile Thr Leu Gly
    210                 215                 220

Ser His Trp Ile Glu Pro Asn Arg Ser Glu Asn Thr Met Asp Ile Phe
225                 230                 235                 240

Lys Cys Gln Gln Ser Met Val Ser Val Leu Gly Trp Phe Ala Asn Pro
                245                 250                 255

Ile His Gly Asp Gly Asp Tyr Pro Glu Gly Met Arg Lys Lys Leu Phe
            260                 265                 270

Ser Val Leu Pro Ile Phe Ser Glu Ala Glu Lys His Glu Met Arg Gly
        275                 280                 285

Thr Ala Asp Phe Phe Ala Phe Ser Phe Gly Pro Asn Asn Phe Lys Pro
    290                 295                 300

Leu Asn Thr Met Ala Lys Met Gly Gln Asn Val Ser Leu Asn Leu Arg
305                 310                 315                 320

Glu Ala Leu Asn Trp Ile Lys Leu Glu Tyr Asn Asn Pro Arg Ile Leu
                325                 330                 335

Ile Ala Glu Asn Gly Trp Phe Thr Asp Ser Arg Val Lys Thr Glu Asp
            340                 345                 350

Thr Thr Ala Ile Tyr Met Met Lys Asn Phe Leu Ser Gln Val Leu Gln
        355                 360                 365

Ala Ile Arg Leu Asp Glu Ile Arg Val Phe Gly Tyr Thr Ala Trp Ser
    370                 375                 380

Leu Leu Asp Gly Phe Glu Trp Gln Asp Ala Tyr Thr Ile Arg Arg Gly
385                 390                 395                 400

Leu Phe Tyr Val Asp Phe Asn Ser Lys Gln Lys Glu Arg Lys Pro Lys
                405                 410                 415

Ser Ser Ala His Tyr Tyr Lys Gln Ile Ile Arg Glu Asn Gly Phe
            420                 425                 430

<210> SEQ ID NO 38
<211> LENGTH: 397
<212> TYPE: PRT
<213> ORGANISM: Homo sapiens

<400> SEQUENCE: 38

Thr Arg Pro Ala Gln Cys Thr Asp Phe Val Asn Ile Lys Lys Gln Leu
1               5                   10                  15

Glu Met Leu Ala Arg Met Lys Val Thr His Tyr Arg Phe Ala Leu Asp
            20                  25                  30
```

-continued

```
Trp Ala Ser Val Leu Pro Thr Gly Asn Leu Ser Ala Val Asn Arg Gln
             35                  40                  45

Ala Leu Arg Tyr Tyr Arg Cys Val Val Ser Glu Gly Leu Lys Leu Gly
 50                  55                  60

Ile Ser Ala Met Val Thr Leu Tyr Tyr Pro Thr His Ala His Leu Gly
 65                  70                  75                  80

Leu Pro Glu Pro Leu Leu His Ala Asp Gly Trp Leu Asn Pro Ser Thr
                 85                  90                  95

Ala Glu Ala Phe Gln Ala Tyr Ala Gly Leu Cys Phe Gln Glu Leu Gly
            100                 105                 110

Asp Leu Val Lys Leu Trp Ile Thr Ile Asn Glu Pro Asn Arg Leu Ser
        115                 120                 125

Asp Ile Tyr Asn Arg Ser Gly Asn Asp Thr Tyr Gly Ala Ala His Asn
130                 135                 140

Leu Leu Val Ala His Ala Leu Ala Trp Arg Leu Tyr Asp Arg Gln Phe
145                 150                 155                 160

Arg Pro Ser Gln Arg Gly Ala Val Ser Leu Ser Leu His Ala Asp Trp
                165                 170                 175

Ala Glu Pro Ala Asn Pro Tyr Ala Asp Ser His Trp Arg Ala Ala Glu
            180                 185                 190

Arg Phe Leu Gln Phe Glu Ile Ala Trp Phe Ala Glu Pro Leu Phe Lys
        195                 200                 205

Thr Gly Asp Tyr Pro Ala Ala Met Arg Glu Tyr Ile Ala Ser Lys His
210                 215                 220

Arg Arg Gly Leu Ser Ser Ser Ala Leu Pro Arg Leu Thr Glu Ala Glu
225                 230                 235                 240

Arg Arg Leu Leu Lys Gly Thr Val Asp Phe Cys Ala Leu Asn His Phe
                245                 250                 255

Thr Thr Arg Phe Val Met His Glu Gln Leu Ala Gly Ser Arg Tyr Asp
            260                 265                 270

Ser Asp Arg Asp Ile Gln Phe Leu Gln Asp Ile Thr Arg Leu Ser Ser
        275                 280                 285

Pro Thr Arg Leu Ala Val Ile Pro Trp Gly Val Arg Lys Leu Leu Arg
290                 295                 300

Trp Val Arg Arg Asn Tyr Gly Asp Met Asp Ile Tyr Ile Thr Ala Ser
305                 310                 315                 320

Gly Ile Asp Asp Gln Ala Leu Glu Asp Asp Arg Leu Arg Lys Tyr Tyr
                325                 330                 335

Leu Gly Lys Tyr Leu Gln Glu Val Leu Lys Ala Tyr Leu Ile Asp Lys
            340                 345                 350

Val Arg Ile Lys Gly Tyr Tyr Ala Phe Lys Leu Ala Glu Glu Lys Ser
        355                 360                 365

Lys Pro Arg Phe Gly Phe Phe Thr Ser Asp Phe Lys Ala Lys Ser Ser
370                 375                 380

Ile Gln Phe Tyr Asn Lys Val Ile Ser Ser Arg Gly Phe
385                 390                 395
```

<210> SEQ ID NO 39
<211> LENGTH: 946
<212> TYPE: PRT
<213> ORGANISM: Homo sapiens

<400> SEQUENCE: 39

```
Gly Phe Ser Gly Asp Gly Arg Ala Ile Trp Ser Lys Asn Pro Asn Phe
  1               5                  10                  15
```

```
Thr Pro Val Asn Glu Ser Gln Leu Phe Leu Tyr Asp Thr Phe Pro Lys
         20                  25                  30

Asn Phe Phe Trp Gly Ile Gly Thr Gly Ala Leu Gln Val Glu Gly Ser
             35                  40                  45

Trp Lys Lys Asp Gly Lys Gly Pro Ser Ile Trp Asp His Phe Ile His
 50                  55                  60

Thr His Leu Lys Asn Val Ser Ser Thr Asn Gly Ser Ser Asp Ser Tyr
 65                  70                  75                  80

Ile Phe Leu Glu Lys Asp Leu Ser Ala Leu Asp Phe Ile Gly Val Ser
                 85                  90                  95

Phe Tyr Gln Phe Ser Ile Ser Trp Pro Arg Leu Phe Pro Asp Gly Ile
            100                 105                 110

Val Thr Val Ala Asn Ala Lys Gly Leu Gln Tyr Tyr Ser Thr Leu Leu
        115                 120                 125

Asp Ala Leu Val Leu Arg Asn Ile Glu Pro Ile Val Thr Leu Tyr His
    130                 135                 140

Trp Asp Leu Pro Leu Ala Leu Gln Glu Lys Tyr Gly Gly Trp Lys Asn
145                 150                 155                 160

Asp Thr Ile Ile Asp Ile Phe Asn Asp Tyr Ala Thr Tyr Cys Phe Gln
                165                 170                 175

Met Phe Gly Asp Arg Val Lys Tyr Trp Ile Thr Ile His Asn Pro Tyr
            180                 185                 190

Leu Val Ala Trp His Gly Tyr Gly Thr Gly Met His Ala Pro Gly Glu
        195                 200                 205

Lys Gly Asn Leu Ala Ala Val Tyr Thr Val Gly His Asn Leu Ile Lys
    210                 215                 220

Ala His Ser Lys Val Trp His Asn Tyr Asn Thr His Phe Arg Pro His
225                 230                 235                 240

Gln Lys Gly Trp Leu Ser Ile Thr Leu Gly Ser His Trp Ile Glu Pro
                245                 250                 255

Asn Arg Ser Glu Asn Thr Met Asp Ile Phe Lys Cys Gln Gln Ser Met
            260                 265                 270

Val Ser Val Leu Gly Trp Phe Ala Asn Pro Ile His Gly Asp Gly Asp
        275                 280                 285

Tyr Pro Glu Gly Met Arg Lys Lys Leu Phe Ser Val Leu Pro Ile Phe
    290                 295                 300

Ser Glu Ala Glu Lys His Glu Met Arg Gly Thr Ala Asp Phe Phe Ala
305                 310                 315                 320

Phe Ser Phe Gly Pro Asn Asn Phe Lys Pro Leu Asn Thr Met Ala Lys
                325                 330                 335

Met Gly Gln Asn Val Ser Leu Asn Leu Arg Glu Ala Leu Asn Trp Ile
            340                 345                 350

Lys Leu Glu Tyr Asn Asn Pro Arg Ile Leu Ile Ala Glu Asn Gly Trp
        355                 360                 365

Phe Thr Asp Ser Arg Val Lys Thr Glu Asp Thr Thr Ala Ile Tyr Met
    370                 375                 380

Met Lys Asn Phe Leu Ser Gln Val Leu Gln Ala Ile Arg Leu Asp Glu
385                 390                 395                 400

Ile Arg Val Phe Gly Tyr Thr Ala Trp Ser Leu Leu Asp Gly Phe Glu
                405                 410                 415

Trp Gln Asp Ala Tyr Thr Ile Arg Arg Gly Leu Phe Tyr Val Asp Phe
            420                 425                 430

Asn Ser Lys Gln Lys Glu Arg Lys Pro Lys Ser Ser Ala His Tyr Tyr
        435                 440                 445
```

```
Lys Gln Ile Ile Arg Glu Asn Gly Phe Ser Leu Lys Glu Ser Thr Pro
    450                 455                 460
Asp Val Gln Gly Gln Phe Pro Cys Asp Phe Ser Trp Gly Val Thr Glu
465                 470                 475                 480
Ser Val Leu Lys Pro Glu Ser Val Ala Ser Ser Pro Gln Phe Ser Asp
                485                 490                 495
Pro His Leu Tyr Val Trp Asn Ala Thr Gly Asn Arg Leu Leu His Arg
            500                 505                 510
Val Glu Gly Val Arg Leu Lys Thr Arg Pro Ala Gln Cys Thr Asp Phe
        515                 520                 525
Val Asn Ile Lys Lys Gln Leu Glu Met Leu Ala Arg Met Lys Val Thr
    530                 535                 540
His Tyr Arg Phe Ala Leu Asp Trp Ala Ser Val Leu Pro Thr Gly Asn
545                 550                 555                 560
Leu Ser Ala Val Asn Arg Gln Ala Leu Arg Tyr Tyr Arg Cys Val Val
                565                 570                 575
Ser Glu Gly Leu Lys Leu Gly Ile Ser Ala Met Val Thr Leu Tyr Tyr
            580                 585                 590
Pro Thr His Ala His Leu Gly Leu Pro Glu Pro Leu Leu His Ala Asp
        595                 600                 605
Gly Trp Leu Asn Pro Ser Thr Ala Glu Ala Phe Gln Ala Tyr Ala Gly
610                 615                 620
Leu Cys Phe Gln Glu Leu Gly Asp Leu Val Lys Leu Trp Ile Thr Ile
625                 630                 635                 640
Asn Glu Pro Asn Arg Leu Ser Asp Ile Tyr Asn Arg Ser Gly Asn Asp
                645                 650                 655
Thr Tyr Gly Ala Ala His Asn Leu Leu Val Ala His Ala Leu Ala Trp
            660                 665                 670
Arg Leu Tyr Asp Arg Gln Phe Arg Pro Ser Gln Arg Gly Ala Val Ser
        675                 680                 685
Leu Ser Leu His Ala Asp Trp Ala Glu Pro Ala Asn Pro Tyr Ala Asp
690                 695                 700
Ser His Trp Arg Ala Ala Glu Arg Phe Leu Gln Phe Glu Ile Ala Trp
705                 710                 715                 720
Phe Ala Glu Pro Leu Phe Lys Thr Gly Asp Tyr Pro Ala Ala Met Arg
                725                 730                 735
Glu Tyr Ile Ala Ser Lys His Arg Arg Gly Leu Ser Ser Ser Ala Leu
            740                 745                 750
Pro Arg Leu Thr Glu Ala Glu Arg Arg Leu Leu Lys Gly Thr Val Asp
        755                 760                 765
Phe Cys Ala Leu Asn His Phe Thr Thr Arg Phe Val Met His Glu Gln
770                 775                 780
Leu Ala Gly Ser Arg Tyr Asp Ser Asp Arg Asp Ile Gln Phe Leu Gln
785                 790                 795                 800
Asp Ile Thr Arg Leu Ser Ser Pro Thr Arg Leu Ala Val Ile Pro Trp
                805                 810                 815
Gly Val Arg Lys Leu Leu Arg Trp Val Arg Arg Asn Tyr Gly Asp Met
            820                 825                 830
Asp Ile Tyr Ile Thr Ala Ser Gly Ile Asp Asp Gln Ala Leu Glu Asp
        835                 840                 845
Asp Arg Leu Arg Lys Tyr Tyr Leu Gly Lys Tyr Leu Gln Glu Val Leu
850                 855                 860
Lys Ala Tyr Leu Ile Asp Lys Val Arg Ile Lys Gly Tyr Tyr Ala Phe
```

```
                865                 870                 875                 880
Lys Leu Ala Glu Glu Lys Ser Lys Pro Arg Phe Gly Phe Phe Thr Ser
                    885                 890                 895
Asp Phe Lys Ala Lys Ser Ser Ile Gln Phe Tyr Asn Lys Val Ile Ser
                900                 905                 910
Ser Arg Gly Phe Pro Phe Glu Asn Ser Ser Ser Arg Cys Ser Gln Thr
            915                 920                 925
Gln Glu Asn Thr Glu Cys Thr Val Cys Leu Phe Leu Val Gln Lys Lys
        930                 935                 940
Pro Leu
945

<210> SEQ ID NO 40
<211> LENGTH: 1195
<212> TYPE: PRT
<213> ORGANISM: Artificial
<220> FEATURE:
<223> OTHER INFORMATION: fusion polypeptide

<400> SEQUENCE: 40

Glu Pro Gly Asp Gly Ala Gln Thr Trp Ala Arg Phe Ser Arg Pro Pro
1               5                   10                  15
Ala Pro Glu Ala Ala Gly Leu Phe Gln Gly Thr Phe Pro Asp Gly Phe
            20                  25                  30
Leu Trp Ala Val Gly Ser Ala Ala Tyr Gln Thr Glu Gly Gly Trp Gln
        35                  40                  45
Gln His Gly Lys Gly Ala Ser Ile Trp Asp Thr Phe Thr His His Pro
    50                  55                  60
Leu Ala Pro Pro Gly Asp Ser Arg Asn Ala Ser Leu Pro Leu Gly Ala
65                  70                  75                  80
Pro Ser Pro Leu Gln Pro Ala Thr Gly Asp Val Ala Ser Asp Ser Tyr
                85                  90                  95
Asn Asn Val Phe Arg Asp Thr Glu Ala Leu Arg Glu Leu Gly Val Thr
            100                 105                 110
His Tyr Arg Phe Ser Ile Ser Trp Ala Arg Val Leu Pro Asn Gly Ser
        115                 120                 125
Ala Gly Val Pro Asn Arg Glu Gly Leu Arg Tyr Tyr Arg Arg Leu Leu
    130                 135                 140
Glu Arg Leu Arg Glu Leu Gly Val Gln Pro Val Val Thr Leu Tyr His
145                 150                 155                 160
Trp Asp Leu Pro Gln Arg Leu Gln Asp Ala Tyr Gly Gly Trp Ala Asn
                165                 170                 175
Arg Ala Leu Ala Asp His Phe Arg Asp Tyr Ala Glu Leu Cys Phe Arg
            180                 185                 190
His Phe Gly Gly Gln Val Lys Tyr Trp Ile Thr Ile Asp Asn Pro Tyr
        195                 200                 205
Val Val Ala Trp His Gly Tyr Ala Thr Gly Arg Leu Ala Pro Gly Ile
    210                 215                 220
Arg Gly Ser Pro Arg Leu Gly Tyr Leu Val Ala His Asn Leu Leu Leu
225                 230                 235                 240
Ala His Ala Lys Val Trp His Leu Tyr Asn Thr Ser Phe Arg Pro Thr
                245                 250                 255
Gln Gly Gly Gln Val Ser Ile Ala Leu Ser Ser His Trp Ile Asn Pro
            260                 265                 270
Arg Arg Met Thr Asp His Ser Ile Lys Glu Cys Gln Lys Ser Leu Asp
        275                 280                 285
```

```
Phe Val Leu Gly Trp Phe Ala Lys Pro Val Phe Ile Asp Gly Asp Tyr
    290                 295                 300

Pro Glu Ser Met Lys Asn Asn Leu Ser Ser Ile Leu Pro Asp Phe Thr
305                 310                 315                 320

Glu Ser Glu Lys Lys Phe Ile Lys Gly Thr Ala Asp Phe Phe Ala Leu
                325                 330                 335

Cys Phe Gly Pro Thr Leu Ser Phe Gln Leu Leu Asp Pro His Met Lys
            340                 345                 350

Phe Arg Gln Leu Glu Ser Pro Asn Leu Arg Gln Leu Leu Ser Trp Ile
        355                 360                 365

Asp Leu Glu Phe Asn His Pro Gln Ile Phe Ile Val Glu Asn Gly Trp
    370                 375                 380

Phe Val Ser Gly Thr Thr Lys Arg Asp Asp Ala Lys Tyr Met Tyr Tyr
385                 390                 395                 400

Leu Lys Lys Phe Ile Met Glu Thr Leu Lys Ala Ile Lys Leu Asp Gly
                405                 410                 415

Val Asp Val Ile Gly Tyr Thr Ala Trp Ser Leu Met Asp Gly Phe Glu
            420                 425                 430

Trp His Arg Gly Tyr Ser Ile Arg Arg Gly Leu Phe Tyr Val Asp Phe
        435                 440                 445

Leu Ser Gln Asp Lys Met Leu Leu Pro Lys Ser Ser Ala Leu Phe Tyr
    450                 455                 460

Gln Lys Leu Ile Glu Lys Asn Gly Phe Pro Pro Leu Pro Glu Asn Gln
465                 470                 475                 480

Pro Leu Glu Gly Thr Phe Pro Cys Asp Phe Ala Trp Gly Val Val Asp
                485                 490                 495

Asn Tyr Ile Gln Val Asp Thr Thr Leu Ser Gln Phe Thr Asp Leu Asn
            500                 505                 510

Val Tyr Leu Trp Asp Val His His Ser Lys Arg Leu Ile Lys Val Asp
        515                 520                 525

Gly Val Val Thr Lys Lys Arg Lys Ser Tyr Cys Val Asp Phe Ala Ala
    530                 535                 540

Ile Gln Pro Gln Ile Ala Leu Leu Gln Glu Met His Val Thr His Phe
545                 550                 555                 560

Arg Phe Ser Leu Asp Trp Ala Leu Ile Leu Pro Leu Gly Asn Gln Ser
                565                 570                 575

Gln Val Asn His Thr Ile Leu Gln Tyr Tyr Arg Cys Met Ala Ser Glu
            580                 585                 590

Leu Val Arg Val Asn Ile Thr Pro Val Val Ala Leu Trp Gln Pro Met
        595                 600                 605

Ala Pro Asn Gln Gly Leu Pro Arg Leu Leu Ala Arg Gln Gly Ala Trp
    610                 615                 620

Glu Asn Pro Tyr Thr Ala Leu Ala Phe Ala Glu Tyr Ala Arg Leu Cys
625                 630                 635                 640

Phe Gln Glu Leu Gly His His Val Lys Leu Trp Ile Thr Met Asn Glu
                645                 650                 655

Pro Tyr Thr Arg Asn Met Thr Tyr Ser Ala Gly His Asn Leu Leu Lys
            660                 665                 670

Ala His Ala Leu Ala Trp His Val Tyr Asn Glu Lys Phe Arg His Ala
        675                 680                 685

Gln Asn Gly Lys Ile Ser Ile Ala Leu Gln Ala Asp Trp Ile Glu Pro
    690                 695                 700

Ala Cys Pro Phe Ser Gln Lys Asp Lys Glu Val Ala Glu Arg Val Leu
```

```
                705                 710                 715                 720
Glu Phe Asp Ile Gly Trp Leu Ala Pro Ile Phe Gly Ser Gly Asp
                        725                 730                 735
Tyr Pro Trp Val Met Arg Asp Trp Leu Asn Gln Arg Asn Asn Phe Leu
                740                 745                 750
Leu Pro Tyr Phe Thr Glu Asp Glu Lys Lys Leu Ile Gln Gly Thr Phe
                755                 760                 765
Asp Phe Leu Ala Leu Ser His Tyr Thr Thr Ile Leu Val Asp Ser Glu
                770                 775                 780
Lys Glu Asp Pro Ile Lys Tyr Asn Asp Tyr Leu Glu Val Gln Glu Met
785                 790                 795                 800
Thr Asp Ile Thr Trp Leu Asn Ser Pro Ser Gln Val Ala Val Val Pro
                    805                 810                 815
Trp Gly Leu Arg Lys Val Leu Asn Trp Leu Lys Phe Lys Tyr Gly Asp
                    820                 825                 830
Leu Pro Met Tyr Ile Ile Ser Asn Gly Ile Asp Asp Gly Leu His Ala
                    835                 840                 845
Glu Asp Asp Gln Leu Arg Val Tyr Tyr Met Gln Asn Tyr Ile Asn Glu
                850                 855                 860
Ala Leu Lys Ala His Ile Leu Asp Gly Ile Asn Leu Cys Gly Tyr Phe
865                 870                 875                 880
Ala Tyr Ser Phe Asn Asp Arg Thr Ala Pro Arg Phe Gly Leu Tyr Arg
                    885                 890                 895
Tyr Ala Ala Asp Gln Phe Glu Pro Lys Ala Ser Met Lys His Tyr Arg
                    900                 905                 910
Lys Ile Ile Asp Ser Asn Gly Phe Pro Gly Pro Glu Thr Leu Glu Arg
                    915                 920                 925
Phe Cys Pro Glu Glu Phe Thr Val Cys Thr Glu Cys Ser Phe Phe His
                930                 935                 940
Thr Arg Lys Ser Leu Gly Ser Gly Gly Gly Ser Gly Gly Gly Gly
945                 950                 955                 960
Ser Gly Gly Gly Gly Ser Leu Lys Tyr Pro Asn Ala Ser Pro Leu Leu
                    965                 970                 975
Gly Ser Ser Trp Gly Gly Leu Ile His Leu Tyr Thr Ala Thr Ala Arg
                    980                 985                 990
Asn Ser Tyr His Leu Gln Ile His  Lys Asn Gly His Val  Asp Gly Ala
                    995                 1000                1005
Pro His Gln Thr Ile Tyr Ser  Ala Leu Met Ile Arg  Ser Glu Asp
                1010                1015                1020
Ala Gly Phe Val Val Ile Thr  Gly Val Met Ser Arg  Arg Tyr Leu
                1025                1030                1035
Cys Met Asp Phe Arg Gly Asn  Ile Phe Gly Ser His  Tyr Phe Asp
                1040                1045                1050
Pro Glu Asn Cys Arg Phe Gln  His Gln Thr Leu Glu  Asn Gly Tyr
                1055                1060                1065
Asp Val Tyr His Ser Pro Gln  Tyr His Phe Leu Val  Ser Leu Gly
                1070                1075                1080
Arg Ala Lys Arg Ala Phe Leu  Pro Gly Met Asn Pro  Pro Pro Tyr
                1085                1090                1095
Ser Gln Phe Leu Ser Arg Arg  Asn Glu Ile Pro Leu  Ile His Phe
                1100                1105                1110
Asn Thr Pro Ile Pro Arg Arg  His Thr Arg Ser Ala  Glu Asp Asp
                1115                1120                1125
```

Ser Glu Arg Asp Pro Leu Asn Val Leu Lys Pro Arg Ala Arg Met
    1130                1135                1140

Thr Pro Ala Pro Ala Ser Cys Ser Gln Glu Leu Pro Ser Ala Glu
    1145                1150                1155

Asp Asn Ser Pro Met Ala Ser Asp Pro Leu Gly Val Val Arg Gly
    1160                1165                1170

Gly Arg Val Asn Thr His Ala Gly Gly Thr Gly Pro Glu Gly Cys
    1175                1180                1185

Arg Pro Phe Ala Lys Phe Ile
    1190                1195

<210> SEQ ID NO 41
<211> LENGTH: 1195
<212> TYPE: PRT
<213> ORGANISM: Artificial
<220> FEATURE:
<223> OTHER INFORMATION: fusion polypeptide

<400> SEQUENCE: 41

Glu Pro Gly Asp Gly Ala Gln Thr Trp Ala Arg Phe Ser Arg Pro
1               5                   10                  15

Ala Pro Glu Ala Ala Gly Leu Phe Gln Gly Thr Phe Pro Asp Gly Phe
            20                  25                  30

Leu Trp Ala Val Gly Ser Ala Ala Tyr Gln Thr Glu Gly Gly Trp Gln
        35                  40                  45

Gln His Gly Lys Gly Ala Ser Ile Trp Asp Thr Phe Thr His His Pro
    50                  55                  60

Leu Ala Pro Pro Gly Asp Ser Arg Asn Ala Ser Leu Pro Leu Gly Ala
65                  70                  75                  80

Pro Ser Pro Leu Gln Pro Ala Thr Gly Asp Val Ala Ser Asp Ser Tyr
                85                  90                  95

Asn Asn Val Phe Arg Asp Thr Glu Ala Leu Arg Glu Leu Gly Val Thr
            100                 105                 110

His Tyr Arg Phe Ser Ile Ser Trp Ala Arg Val Leu Pro Asn Gly Ser
        115                 120                 125

Ala Gly Val Pro Asn Arg Glu Gly Leu Arg Tyr Tyr Arg Arg Leu Leu
    130                 135                 140

Glu Arg Leu Arg Glu Leu Gly Val Gln Pro Val Val Thr Leu Tyr His
145                 150                 155                 160

Trp Asp Leu Pro Gln Arg Leu Gln Asp Ala Tyr Gly Gly Trp Ala Asn
                165                 170                 175

Arg Ala Leu Ala Asp His Phe Arg Asp Tyr Ala Glu Leu Cys Phe Arg
            180                 185                 190

His Phe Gly Gly Gln Val Lys Tyr Trp Ile Thr Ile Asp Asn Pro Tyr
        195                 200                 205

Val Val Ala Trp His Gly Tyr Ala Thr Gly Arg Leu Ala Pro Gly Ile
    210                 215                 220

Arg Gly Ser Pro Arg Leu Gly Tyr Leu Val Ala His Asn Leu Leu Leu
225                 230                 235                 240

Ala His Ala Lys Val Trp His Leu Tyr Asn Thr Ser Phe Arg Pro Thr
                245                 250                 255

Gln Gly Gly Gln Val Ser Ile Ala Leu Ser Ser His Trp Ile Asn Pro
            260                 265                 270

Arg Arg Met Thr Asp His Ser Ile Lys Glu Cys Gln Lys Ser Leu Asp
        275                 280                 285

Phe Val Leu Gly Trp Phe Ala Lys Pro Val Phe Ile Asp Gly Asp Tyr

-continued

```
            290                 295                 300
Pro Glu Ser Met Lys Asn Asn Leu Ser Ser Ile Leu Pro Asp Phe Thr
305                 310                 315                 320
Glu Ser Glu Lys Lys Phe Ile Lys Gly Thr Ala Asp Phe Phe Ala Leu
                    325                 330                 335
Cys Phe Gly Pro Thr Leu Ser Phe Gln Leu Leu Asp Pro His Met Lys
                    340                 345                 350
Phe Arg Gln Leu Glu Ser Pro Asn Leu Arg Gln Leu Leu Ser Trp Ile
                    355                 360                 365
Asp Leu Glu Phe Asn His Pro Gln Ile Phe Ile Val Glu Asn Gly Trp
370                 375                 380
Phe Val Ser Gly Thr Thr Lys Arg Asp Asp Ala Lys Tyr Met Tyr Tyr
385                 390                 395                 400
Leu Lys Lys Phe Ile Met Glu Thr Leu Lys Ala Ile Lys Leu Asp Gly
                    405                 410                 415
Val Asp Val Ile Gly Tyr Thr Ala Trp Ser Leu Met Asp Gly Phe Glu
                    420                 425                 430
Trp His Arg Gly Tyr Ser Ile Arg Arg Gly Leu Phe Tyr Val Asp Phe
                    435                 440                 445
Leu Ser Gln Asp Lys Met Leu Leu Pro Lys Ser Ser Ala Leu Phe Tyr
450                 455                 460
Gln Lys Leu Ile Glu Lys Asn Gly Phe Pro Pro Leu Pro Glu Asn Gln
465                 470                 475                 480
Pro Leu Glu Gly Thr Phe Pro Cys Asp Phe Ala Trp Gly Val Val Asp
                    485                 490                 495
Asn Tyr Ile Gln Val Asp Thr Thr Leu Ser Gln Phe Thr Asp Leu Asn
                    500                 505                 510
Val Tyr Leu Trp Asp Val His His Ser Lys Arg Leu Ile Lys Val Asp
                    515                 520                 525
Gly Val Val Thr Lys Lys Arg Lys Ser Tyr Cys Val Asp Phe Ala Ala
530                 535                 540
Ile Gln Pro Gln Ile Ala Leu Leu Gln Glu Met His Val Thr His Phe
545                 550                 555                 560
Arg Phe Ser Leu Asp Trp Ala Leu Ile Leu Pro Leu Gly Asn Gln Ser
                    565                 570                 575
Gln Val Asn His Thr Ile Leu Gln Tyr Tyr Arg Cys Met Ala Ser Glu
                    580                 585                 590
Leu Val Arg Val Asn Ile Thr Pro Val Val Ala Leu Trp Gln Pro Met
                    595                 600                 605
Ala Pro Asn Gln Gly Leu Pro Arg Leu Leu Ala Arg Gln Gly Ala Trp
610                 615                 620
Glu Asn Pro Tyr Thr Ala Leu Ala Phe Ala Glu Tyr Ala Arg Leu Cys
625                 630                 635                 640
Phe Gln Glu Leu Gly His His Val Lys Leu Trp Ile Thr Met Asn Glu
                    645                 650                 655
Pro Tyr Thr Arg Asn Met Thr Tyr Ser Ala Gly His Asn Leu Leu Lys
                    660                 665                 670
Ala His Ala Leu Ala Trp His Val Tyr Asn Glu Lys Phe Arg His Ala
                    675                 680                 685
Gln Asn Gly Lys Ile Ser Ile Ala Leu Gln Ala Asp Trp Ile Glu Pro
690                 695                 700
Ala Cys Pro Phe Ser Gln Lys Asp Lys Glu Val Ala Glu Arg Val Leu
705                 710                 715                 720
```

```
Glu Phe Asp Ile Gly Trp Leu Ala Glu Pro Ile Phe Gly Ser Gly Asp
                725                 730                 735

Tyr Pro Trp Val Met Arg Asp Trp Leu Asn Gln Arg Asn Asn Phe Leu
            740                 745                 750

Leu Pro Tyr Phe Thr Glu Asp Glu Lys Lys Leu Ile Gln Gly Thr Phe
        755                 760                 765

Asp Phe Leu Ala Leu Ser His Tyr Thr Thr Ile Leu Val Asp Ser Glu
    770                 775                 780

Lys Glu Asp Pro Ile Lys Tyr Asn Asp Tyr Leu Glu Val Gln Glu Met
785                 790                 795                 800

Thr Asp Ile Thr Trp Leu Asn Ser Pro Ser Gln Val Ala Val Val Pro
                805                 810                 815

Trp Gly Leu Arg Lys Val Leu Asn Trp Leu Lys Phe Lys Tyr Gly Asp
            820                 825                 830

Leu Pro Met Tyr Ile Ile Ser Asn Gly Ile Asp Asp Gly Leu His Ala
        835                 840                 845

Glu Asp Asp Gln Leu Arg Val Tyr Tyr Met Gln Asn Tyr Ile Asn Glu
    850                 855                 860

Ala Leu Lys Ala His Ile Leu Asp Gly Ile Asn Leu Cys Gly Tyr Phe
865                 870                 875                 880

Ala Tyr Ser Phe Asn Asp Arg Thr Ala Pro Arg Phe Gly Leu Tyr Arg
                885                 890                 895

Tyr Ala Ala Asp Gln Phe Glu Pro Lys Ala Ser Met Lys His Tyr Arg
            900                 905                 910

Lys Ile Ile Asp Ser Asn Gly Phe Pro Gly Pro Glu Thr Leu Glu Arg
        915                 920                 925

Phe Cys Pro Glu Glu Phe Thr Val Cys Thr Glu Cys Ser Phe Phe His
    930                 935                 940

Thr Arg Lys Ser Leu Gly Ser Gly Gly Gly Ser Gly Gly Gly Gly
945                 950                 955                 960

Ser Gly Gly Gly Gly Ser Leu Lys Tyr Pro Asn Ala Ser Pro Leu Leu
                965                 970                 975

Gly Ser Ser Trp Gly Gly Leu Ile His Leu Tyr Thr Ala Thr Ala Arg
            980                 985                 990

Asn Ser Tyr His Leu Gln Ile His  Lys Asn Gly His Val  Asp Gly Ala
        995                 1000                1005

Pro His  Gln Thr Ile Tyr Ser  Ala Leu Met Ile Arg  Ser Glu Asp
    1010                1015                1020

Ala Gly  Phe Val Val Ile Thr  Gly Val Met Ser Arg  Arg Tyr Leu
    1025                1030                1035

Cys Met  Asp Phe Arg Gly Asn  Ile Phe Gly Ser His  Tyr Phe Asp
    1040                1045                1050

Pro Glu  Asn Cys Arg Phe Gln  His Gln Thr Leu Glu  Asn Gly Tyr
    1055                1060                1065

Asp Val  Tyr His Ser Pro Gln  Tyr His Phe Leu Val  Ser Leu Gly
    1070                1075                1080

Arg Ala  Lys Arg Ala Phe Leu  Pro Gly Met Asn Pro  Pro Pro Tyr
    1085                1090                1095

Ser Gln  Phe Leu Ser Arg Arg  Asn Glu Ile Pro Leu  Ile His Phe
    1100                1105                1110

Asn Thr  Pro Ile Pro Arg Arg  His Thr Gln Ser Ala  Glu Asp Asp
    1115                1120                1125

Ser Glu  Arg Asp Pro Leu Asn  Val Leu Lys Pro Arg  Ala Arg Met
    1130                1135                1140
```

```
Thr Pro Ala Pro Ala Ser Cys Ser Gln Glu Leu Pro Ser Ala Glu
        1145                1150                1155

Asp Asn Ser Pro Met Ala Ser Asp Pro Leu Gly Val Val Arg Gly
        1160                1165                1170

Gly Arg Val Asn Thr His Ala Gly Gly Thr Gly Pro Glu Gly Cys
        1175                1180                1185

Arg Pro Phe Ala Lys Phe Ile
        1190            1195

<210> SEQ ID NO 42
<211> LENGTH: 227
<212> TYPE: PRT
<213> ORGANISM: Artificial
<220> FEATURE:
<223> OTHER INFORMATION: fusion polypeptide

<400> SEQUENCE: 42

Tyr Pro Asn Ala Ser Pro Leu Leu Gly Ser Ser Trp Gly Gly Leu Ile
1               5                   10                  15

His Leu Tyr Thr Ala Thr Ala Arg Asn Ser Tyr His Leu Gln Ile His
            20                  25                  30

Lys Asn Gly His Val Asp Gly Ala Pro His Gln Thr Ile Tyr Ser Ala
        35                  40                  45

Leu Met Ile Arg Ser Glu Asp Ala Gly Phe Val Val Ile Thr Gly Val
    50                  55                  60

Met Ser Arg Arg Tyr Leu Cys Met Asp Phe Arg Gly Asn Ile Phe Gly
65                  70                  75                  80

Ser His Tyr Phe Asp Pro Glu Asn Cys Arg Phe Gln His Gln Thr Leu
                85                  90                  95

Glu Asn Gly Tyr Asp Val Tyr His Ser Pro Gln Tyr His Phe Leu Val
            100                 105                 110

Ser Leu Gly Arg Ala Lys Arg Ala Phe Leu Pro Gly Met Asn Pro Pro
        115                 120                 125

Pro Tyr Ser Gln Phe Leu Ser Arg Arg Asn Glu Ile Pro Leu Ile His
    130                 135                 140

Phe Asn Thr Pro Ile Pro Arg Arg His Thr Arg Ser Ala Glu Asp Asp
145                 150                 155                 160

Ser Glu Arg Asp Pro Leu Asn Val Leu Lys Pro Arg Ala Arg Met Thr
                165                 170                 175

Pro Ala Pro Ala Ser Cys Ser Gln Glu Leu Pro Ser Ala Glu Asp Asn
            180                 185                 190

Ser Pro Met Ala Ser Asp Pro Leu Gly Val Val Arg Gly Gly Arg Val
        195                 200                 205

Asn Thr His Ala Gly Gly Thr Gly Pro Glu Gly Cys Arg Pro Phe Ala
    210                 215                 220

Lys Phe Ile
225

<210> SEQ ID NO 43
<211> LENGTH: 227
<212> TYPE: PRT
<213> ORGANISM: Artificial
<220> FEATURE:
<223> OTHER INFORMATION: fusion polypeptide

<400> SEQUENCE: 43

Tyr Pro Asn Ala Ser Pro Leu Leu Gly Ser Ser Trp Gly Gly Leu Ile
1               5                   10                  15
```

```
His Leu Tyr Thr Ala Thr Ala Arg Asn Ser Tyr His Leu Gln Ile His
            20                  25                  30

Lys Asn Gly His Val Asp Gly Ala Pro His Gln Thr Ile Tyr Ser Ala
        35                  40                  45

Leu Met Ile Arg Ser Glu Asp Ala Gly Phe Val Val Ile Thr Gly Val
    50                  55                  60

Met Ser Arg Arg Tyr Leu Cys Met Asp Phe Arg Gly Asn Ile Phe Gly
65                  70                  75                  80

Ser His Tyr Phe Asp Pro Glu Asn Cys Arg Phe Gln His Gln Thr Leu
                85                  90                  95

Glu Asn Gly Tyr Asp Val Tyr His Ser Pro Gln Tyr His Phe Leu Val
            100                 105                 110

Ser Leu Gly Arg Ala Lys Arg Ala Phe Leu Pro Gly Met Asn Pro Pro
        115                 120                 125

Pro Tyr Ser Gln Phe Leu Ser Arg Arg Asn Glu Ile Pro Leu Ile His
    130                 135                 140

Phe Asn Thr Pro Ile Pro Arg Arg His Thr Gln Ser Ala Glu Asp Asp
145                 150                 155                 160

Ser Glu Arg Asp Pro Leu Asn Val Leu Lys Pro Arg Ala Arg Met Thr
                165                 170                 175

Pro Ala Pro Ala Ser Cys Ser Gln Glu Leu Pro Ser Ala Glu Asp Asn
            180                 185                 190

Ser Pro Met Ala Ser Asp Pro Leu Gly Val Val Arg Gly Gly Arg Val
        195                 200                 205

Asn Thr His Ala Gly Gly Thr Gly Pro Glu Gly Cys Arg Pro Phe Ala
    210                 215                 220

Lys Phe Ile
225

<210> SEQ ID NO 44
<211> LENGTH: 982
<212> TYPE: PRT
<213> ORGANISM: Artificial
<220> FEATURE:
<223> OTHER INFORMATION: fusion polypeptide

<400> SEQUENCE: 44

Met Pro Ala Ser Ala Pro Pro Arg Arg Pro Arg Pro Pro Pro Pro Ser
1               5                   10                  15

Leu Ser Leu Leu Leu Val Leu Leu Gly Leu Gly Gly Arg Arg Leu Arg
            20                  25                  30

Ala Glu Pro Gly Asp Gly Ala Gln Thr Trp Ala Arg Phe Ser Arg Pro
        35                  40                  45

Pro Ala Pro Glu Ala Ala Gly Leu Phe Gln Gly Thr Phe Pro Asp Gly
    50                  55                  60

Phe Leu Trp Ala Val Gly Ser Ala Ala Tyr Gln Thr Glu Gly Gly Trp
65                  70                  75                  80

Gln Gln His Gly Lys Gly Ala Ser Ile Trp Asp Thr Phe Thr His His
                85                  90                  95

Pro Leu Ala Pro Pro Gly Asp Ser Arg Asn Ala Ser Leu Pro Leu Gly
            100                 105                 110

Ala Pro Ser Pro Leu Gln Pro Ala Thr Gly Asp Val Ala Ser Asp Ser
        115                 120                 125

Tyr Asn Asn Val Phe Arg Asp Thr Glu Ala Leu Arg Glu Leu Gly Val
    130                 135                 140
```

```
Thr His Tyr Arg Phe Ser Ile Ser Trp Ala Arg Val Leu Pro Asn Gly
145                 150                 155                 160

Ser Ala Gly Val Pro Asn Arg Glu Gly Leu Arg Tyr Tyr Arg Arg Leu
            165                 170                 175

Leu Glu Arg Leu Arg Glu Leu Gly Val Gln Pro Val Val Thr Leu Tyr
        180                 185                 190

His Trp Asp Leu Pro Gln Arg Leu Gln Asp Ala Tyr Gly Gly Trp Ala
    195                 200                 205

Asn Arg Ala Leu Ala Asp His Phe Arg Asp Tyr Ala Glu Leu Cys Phe
210                 215                 220

Arg His Phe Gly Gly Gln Val Lys Tyr Trp Ile Thr Ile Asp Asn Pro
225                 230                 235                 240

Tyr Val Val Ala Trp His Gly Tyr Ala Thr Gly Arg Leu Ala Pro Gly
                245                 250                 255

Ile Arg Gly Ser Pro Arg Leu Gly Tyr Leu Val Ala His Asn Leu Leu
            260                 265                 270

Leu Ala His Ala Lys Val Trp His Leu Tyr Asn Thr Ser Phe Arg Pro
        275                 280                 285

Thr Gln Gly Gly Gln Val Ser Ile Ala Leu Ser Ser His Trp Ile Asn
290                 295                 300

Pro Arg Arg Met Thr Asp His Ser Ile Lys Glu Cys Gln Lys Ser Leu
305                 310                 315                 320

Asp Phe Val Leu Gly Trp Phe Ala Lys Pro Val Phe Ile Asp Gly Asp
                325                 330                 335

Tyr Pro Glu Ser Met Lys Asn Asn Leu Ser Ser Ile Leu Pro Asp Phe
            340                 345                 350

Thr Glu Ser Glu Lys Lys Phe Ile Lys Gly Thr Ala Asp Phe Phe Ala
        355                 360                 365

Leu Cys Phe Gly Pro Thr Leu Ser Phe Gln Leu Leu Asp Pro His Met
    370                 375                 380

Lys Phe Arg Gln Leu Glu Ser Pro Asn Leu Arg Gln Leu Leu Ser Trp
385                 390                 395                 400

Ile Asp Leu Glu Phe Asn His Pro Gln Ile Phe Ile Val Glu Asn Gly
                405                 410                 415

Trp Phe Val Ser Gly Thr Thr Lys Arg Asp Asp Ala Lys Tyr Met Tyr
            420                 425                 430

Tyr Leu Lys Lys Phe Ile Met Glu Thr Leu Lys Ala Ile Lys Leu Asp
        435                 440                 445

Gly Val Asp Val Ile Gly Tyr Thr Ala Trp Ser Leu Met Asp Gly Phe
    450                 455                 460

Glu Trp His Arg Gly Tyr Ser Ile Arg Arg Gly Leu Phe Tyr Val Asp
465                 470                 475                 480

Phe Leu Ser Gln Asp Lys Met Leu Leu Pro Lys Ser Ser Ala Leu Phe
                485                 490                 495

Tyr Gln Lys Leu Ile Glu Lys Asn Gly Phe Pro Leu Pro Glu Asn
            500                 505                 510

Gln Pro Leu Glu Gly Thr Phe Pro Cys Asp Phe Ala Trp Gly Val Val
        515                 520                 525

Asp Asn Tyr Ile Gln Val Asp Thr Thr Leu Ser Gln Phe Thr Asp Leu
    530                 535                 540

Asn Val Tyr Leu Trp Asp Val His His Ser Lys Arg Leu Ile Lys Val
545                 550                 555                 560

Asp Gly Val Val Thr Lys Lys Arg Lys Ser Tyr Cys Val Asp Phe Ala
                565                 570                 575
```

```
Ala Ile Gln Pro Gln Ile Ala Leu Leu Gln Glu Met His Val Thr His
            580                 585                 590

Phe Arg Phe Ser Leu Asp Trp Ala Leu Ile Leu Pro Leu Gly Asn Gln
        595                 600                 605

Ser Gln Val Asn His Thr Ile Leu Gln Tyr Tyr Arg Cys Met Ala Ser
    610                 615                 620

Glu Leu Val Arg Val Asn Ile Thr Pro Val Val Ala Leu Trp Gln Pro
625                 630                 635                 640

Met Ala Pro Asn Gln Gly Leu Pro Arg Leu Leu Ala Arg Gln Gly Ala
                645                 650                 655

Trp Glu Asn Pro Tyr Thr Ala Leu Ala Phe Ala Glu Tyr Ala Arg Leu
            660                 665                 670

Cys Phe Gln Glu Leu Gly His His Val Lys Leu Trp Ile Thr Met Asn
        675                 680                 685

Glu Pro Tyr Thr Arg Asn Met Thr Tyr Ser Ala Gly His Asn Leu Leu
    690                 695                 700

Lys Ala His Ala Leu Ala Trp His Val Tyr Asn Glu Lys Phe Arg His
705                 710                 715                 720

Ala Gln Asn Gly Lys Ile Ser Ile Ala Leu Gln Ala Asp Trp Ile Glu
                725                 730                 735

Pro Ala Cys Pro Phe Ser Gln Lys Asp Lys Glu Val Ala Glu Arg Val
            740                 745                 750

Leu Glu Phe Asp Ile Gly Trp Leu Ala Glu Pro Ile Phe Gly Ser Gly
        755                 760                 765

Asp Tyr Pro Trp Val Met Arg Asp Trp Leu Asn Gln Arg Asn Asn Phe
    770                 775                 780

Leu Leu Pro Tyr Phe Thr Glu Asp Glu Lys Lys Leu Ile Gln Gly Thr
785                 790                 795                 800

Phe Asp Phe Leu Ala Leu Ser His Tyr Thr Thr Ile Leu Val Asp Ser
                805                 810                 815

Glu Lys Glu Asp Pro Ile Lys Tyr Asn Asp Tyr Leu Glu Val Gln Glu
            820                 825                 830

Met Thr Asp Ile Thr Trp Leu Asn Ser Pro Ser Gln Val Ala Val Val
        835                 840                 845

Pro Trp Gly Leu Arg Lys Val Leu Asn Trp Leu Lys Phe Lys Tyr Gly
    850                 855                 860

Asp Leu Pro Met Tyr Ile Ile Ser Asn Gly Ile Asp Asp Gly Leu His
865                 870                 875                 880

Ala Glu Asp Asp Gln Leu Arg Val Tyr Tyr Met Gln Asn Tyr Ile Asn
                885                 890                 895

Glu Ala Leu Lys Ala His Ile Leu Asp Gly Ile Asn Leu Cys Gly Tyr
            900                 905                 910

Phe Ala Tyr Ser Phe Asn Asp Arg Thr Ala Pro Arg Phe Gly Leu Tyr
        915                 920                 925

Arg Tyr Ala Ala Asp Gln Phe Glu Pro Lys Ala Ser Met Lys His Tyr
    930                 935                 940

Arg Lys Ile Ile Asp Ser Asn Gly Phe Pro Gly Pro Glu Thr Leu Glu
945                 950                 955                 960

Arg Phe Cys Pro Glu Glu Phe Thr Val Cys Thr Glu Cys Ser Phe Phe
                965                 970                 975

His Thr Arg Lys Ser Leu
            980
```

-continued

```
<210> SEQ ID NO 45
<211> LENGTH: 974
<212> TYPE: PRT
<213> ORGANISM: Artificial
<220> FEATURE:
<223> OTHER INFORMATION: fusion polypeptide

<400> SEQUENCE: 45
```

| | | | | | | | | | | | | | | | |
|---|---|---|---|---|---|---|---|---|---|---|---|---|---|---|---|
| Met | Ser | Val | Leu | Thr | Gln | Val | Leu | Ala | Leu | Leu | Leu | Trp | Leu | Thr | |
| 1 | | | | 5 | | | | | 10 | | | | | 15 | |
| Gly | Leu | Gly | Gly | Arg | Arg | Leu | Arg | Ala | Glu | Pro | Gly | Asp | Gly | Ala | Gln |
| | | | 20 | | | | | 25 | | | | | 30 | | |
| Thr | Trp | Ala | Arg | Phe | Ser | Arg | Pro | Pro | Ala | Pro | Glu | Ala | Ala | Gly | Leu |
| | | | 35 | | | | | 40 | | | | | 45 | | |
| Phe | Gln | Gly | Thr | Phe | Pro | Asp | Gly | Phe | Leu | Trp | Ala | Val | Gly | Ser | Ala |
| | 50 | | | | | 55 | | | | | 60 | | | | |
| Ala | Tyr | Gln | Thr | Glu | Gly | Gly | Trp | Gln | Gln | His | Gly | Lys | Gly | Ala | Ser |
| 65 | | | | | 70 | | | | | 75 | | | | | 80 |
| Ile | Trp | Asp | Thr | Phe | Thr | His | His | Pro | Leu | Ala | Pro | Pro | Gly | Asp | Ser |
| | | | | 85 | | | | | 90 | | | | | 95 | |
| Arg | Asn | Ala | Ser | Leu | Pro | Leu | Gly | Ala | Pro | Ser | Pro | Leu | Gln | Pro | Ala |
| | | | 100 | | | | | 105 | | | | | 110 | | |
| Thr | Gly | Asp | Val | Ala | Ser | Asp | Ser | Tyr | Asn | Asn | Val | Phe | Arg | Asp | Thr |
| | | | 115 | | | | | 120 | | | | | 125 | | |
| Glu | Ala | Leu | Arg | Glu | Leu | Gly | Val | Thr | His | Tyr | Arg | Phe | Ser | Ile | Ser |
| | 130 | | | | | 135 | | | | | 140 | | | | |
| Trp | Ala | Arg | Val | Leu | Pro | Asn | Gly | Ser | Ala | Gly | Val | Pro | Asn | Arg | Glu |
| 145 | | | | | 150 | | | | | 155 | | | | | 160 |
| Gly | Leu | Arg | Tyr | Tyr | Arg | Arg | Leu | Leu | Glu | Arg | Leu | Arg | Glu | Leu | Gly |
| | | | | 165 | | | | | 170 | | | | | 175 | |
| Val | Gln | Pro | Val | Val | Thr | Leu | Tyr | His | Trp | Asp | Leu | Pro | Gln | Arg | Leu |
| | | | 180 | | | | | 185 | | | | | 190 | | |
| Gln | Asp | Ala | Tyr | Gly | Gly | Trp | Ala | Asn | Arg | Ala | Leu | Ala | Asp | His | Phe |
| | | | 195 | | | | | 200 | | | | | 205 | | |
| Arg | Asp | Tyr | Ala | Glu | Leu | Cys | Phe | Arg | His | Phe | Gly | Gly | Gln | Val | Lys |
| | 210 | | | | | 215 | | | | | 220 | | | | |
| Tyr | Trp | Ile | Thr | Ile | Asp | Asn | Pro | Tyr | Val | Val | Ala | Trp | His | Gly | Tyr |
| 225 | | | | | 230 | | | | | 235 | | | | | 240 |
| Ala | Thr | Gly | Arg | Leu | Ala | Pro | Gly | Ile | Arg | Gly | Ser | Pro | Arg | Leu | Gly |
| | | | | 245 | | | | | 250 | | | | | 255 | |
| Tyr | Leu | Val | Ala | His | Asn | Leu | Leu | Leu | Ala | His | Ala | Lys | Val | Trp | His |
| | | | 260 | | | | | 265 | | | | | 270 | | |
| Leu | Tyr | Asn | Thr | Ser | Phe | Arg | Pro | Thr | Gln | Gly | Gly | Gln | Val | Ser | Ile |
| | | | 275 | | | | | 280 | | | | | 285 | | |
| Ala | Leu | Ser | Ser | His | Trp | Ile | Asn | Pro | Arg | Arg | Met | Thr | Asp | His | Ser |
| | 290 | | | | | 295 | | | | | 300 | | | | |
| Ile | Lys | Glu | Cys | Gln | Lys | Ser | Leu | Asp | Phe | Val | Leu | Gly | Trp | Phe | Ala |
| 305 | | | | | 310 | | | | | 315 | | | | | 320 |
| Lys | Pro | Val | Phe | Ile | Asp | Gly | Asp | Tyr | Pro | Glu | Ser | Met | Lys | Asn | Asn |
| | | | | 325 | | | | | 330 | | | | | 335 | |
| Leu | Ser | Ser | Ile | Leu | Pro | Asp | Phe | Thr | Glu | Ser | Glu | Lys | Lys | Phe | Ile |
| | | | 340 | | | | | 345 | | | | | 350 | | |
| Lys | Gly | Thr | Ala | Asp | Phe | Phe | Ala | Leu | Cys | Phe | Gly | Pro | Thr | Leu | Ser |
| | | | 355 | | | | | 360 | | | | | 365 | | |
| Phe | Gln | Leu | Leu | Asp | Pro | His | Met | Lys | Phe | Arg | Gln | Leu | Glu | Ser | Pro |
| | 370 | | | | | 375 | | | | | 380 | | | | |

```
Asn Leu Arg Gln Leu Leu Ser Trp Ile Asp Leu Glu Phe Asn His Pro
385                 390                 395                 400

Gln Ile Phe Ile Val Glu Asn Gly Trp Phe Val Ser Gly Thr Thr Lys
            405                 410                 415

Arg Asp Asp Ala Lys Tyr Met Tyr Tyr Leu Lys Lys Phe Ile Met Glu
                420                 425                 430

Thr Leu Lys Ala Ile Lys Leu Asp Gly Val Asp Val Ile Gly Tyr Thr
            435                 440                 445

Ala Trp Ser Leu Met Asp Gly Phe Glu Trp His Arg Gly Tyr Ser Ile
        450                 455                 460

Arg Arg Gly Leu Phe Tyr Val Asp Phe Leu Ser Gln Asp Lys Met Leu
465                 470                 475                 480

Leu Pro Lys Ser Ser Ala Leu Phe Tyr Gln Lys Leu Ile Glu Lys Asn
                485                 490                 495

Gly Phe Pro Pro Leu Pro Glu Asn Gln Pro Leu Glu Gly Thr Phe Pro
                500                 505                 510

Cys Asp Phe Ala Trp Gly Val Val Asp Asn Tyr Ile Gln Val Asp Thr
            515                 520                 525

Thr Leu Ser Gln Phe Thr Asp Leu Asn Val Tyr Leu Trp Asp Val His
        530                 535                 540

His Ser Lys Arg Leu Ile Lys Val Asp Gly Val Val Thr Lys Lys Arg
545                 550                 555                 560

Lys Ser Tyr Cys Val Asp Phe Ala Ala Ile Gln Pro Gln Ile Ala Leu
                565                 570                 575

Leu Gln Glu Met His Val Thr His Phe Arg Phe Ser Leu Asp Trp Ala
            580                 585                 590

Leu Ile Leu Pro Leu Gly Asn Gln Ser Gln Val Asn His Thr Ile Leu
        595                 600                 605

Gln Tyr Tyr Arg Cys Met Ala Ser Glu Leu Val Arg Val Asn Ile Thr
        610                 615                 620

Pro Val Val Ala Leu Trp Gln Pro Met Ala Pro Asn Gln Gly Leu Pro
625                 630                 635                 640

Arg Leu Leu Ala Arg Gln Gly Ala Trp Glu Asn Pro Tyr Thr Ala Leu
                645                 650                 655

Ala Phe Ala Glu Tyr Ala Arg Leu Cys Phe Gln Glu Leu Gly His His
                660                 665                 670

Val Lys Leu Trp Ile Thr Met Asn Glu Pro Tyr Thr Arg Asn Met Thr
            675                 680                 685

Tyr Ser Ala Gly His Asn Leu Leu Lys Ala His Ala Leu Ala Trp His
        690                 695                 700

Val Tyr Asn Glu Lys Phe Arg His Ala Gln Asn Gly Lys Ile Ser Ile
705                 710                 715                 720

Ala Leu Gln Ala Asp Trp Ile Glu Pro Ala Cys Pro Phe Ser Gln Lys
                725                 730                 735

Asp Lys Glu Val Ala Glu Arg Val Leu Glu Phe Asp Ile Gly Trp Leu
            740                 745                 750

Ala Glu Pro Ile Phe Gly Ser Gly Asp Tyr Pro Trp Val Met Arg Asp
        755                 760                 765

Trp Leu Asn Gln Arg Asn Asn Phe Leu Leu Pro Tyr Phe Thr Glu Asp
            770                 775                 780

Glu Lys Lys Leu Ile Gln Gly Thr Phe Asp Phe Leu Ala Leu Ser His
785                 790                 795                 800

Tyr Thr Thr Ile Leu Val Asp Ser Glu Lys Glu Asp Pro Ile Lys Tyr
```

```
                       805                 810                 815
Asn Asp Tyr Leu Glu Val Gln Glu Met Thr Asp Ile Thr Trp Leu Asn
                820                 825                 830

Ser Pro Ser Gln Val Ala Val Val Pro Trp Gly Leu Arg Lys Val Leu
            835                 840                 845

Asn Trp Leu Lys Phe Lys Tyr Gly Asp Leu Pro Met Tyr Ile Ile Ser
        850                 855                 860

Asn Gly Ile Asp Asp Gly Leu His Ala Glu Asp Gln Leu Arg Val
865                 870                 875                 880

Tyr Tyr Met Gln Asn Tyr Ile Asn Glu Ala Leu Lys Ala His Ile Leu
                885                 890                 895

Asp Gly Ile Asn Leu Cys Gly Tyr Phe Ala Tyr Ser Phe Asn Asp Arg
            900                 905                 910

Thr Ala Pro Arg Phe Gly Leu Tyr Arg Tyr Ala Ala Asp Gln Phe Glu
        915                 920                 925

Pro Lys Ala Ser Met Lys His Tyr Arg Lys Ile Ile Asp Ser Asn Gly
    930                 935                 940

Phe Pro Gly Pro Glu Thr Leu Glu Arg Phe Cys Pro Glu Glu Phe Thr
945                 950                 955                 960

Val Cys Thr Glu Cys Ser Phe Phe His Thr Arg Lys Ser Leu
                965                 970

<210> SEQ ID NO 46
<211> LENGTH: 4380
<212> TYPE: PRT
<213> ORGANISM: Artificial
<220> FEATURE:
<223> OTHER INFORMATION: fusion peptide derived from human

<400> SEQUENCE: 46

Ala Thr Gly Cys Cys Gly Cys Cys Ala Gly Cys Gly Cys Cys Cys Cys
1               5                   10                  15

Cys Gly Cys Cys Gly Cys Gly Cys Cys Gly Cys Cys Gly Cys Cys Gly
                20                  25                  30

Gly Cys Cys Gly Cys Cys Gly Cys Cys Gly Cys Cys Gly Thr Cys Gly
            35                  40                  45

Cys Thr Gly Thr Cys Gly Cys Thr Gly Cys Thr Gly Cys Thr Gly Gly
        50                  55                  60

Thr Gly Cys Thr Gly Cys Thr Gly Gly Cys Cys Thr Gly Gly Gly Gly
65                  70                  75                  80

Cys Gly Gly Cys Cys Gly Cys Cys Gly Cys Cys Thr Gly Cys Gly Thr
                85                  90                  95

Gly Cys Gly Gly Ala Gly Cys Cys Gly Gly Gly Cys Gly Ala Cys Gly
            100                 105                 110

Gly Cys Gly Cys Gly Cys Ala Gly Ala Cys Cys Thr Gly Gly Gly Cys
        115                 120                 125

Cys Cys Gly Thr Thr Thr Cys Thr Gly Cys Gly Gly Cys Cys Cys Thr
    130                 135                 140

Cys Cys Thr Gly Cys Cys Cys Cys Gly Ala Gly Gly Cys Cys Gly
145                 150                 155                 160

Cys Gly Gly Gly Cys Cys Thr Cys Thr Thr Cys Cys Ala Gly Gly Gly
                165                 170                 175

Cys Ala Cys Cys Thr Cys Cys Cys Gly Ala Cys Gly Gly Cys
            180                 185                 190

Thr Thr Cys Cys Thr Cys Thr Gly Gly Gly Cys Cys Gly Thr Gly Gly
        195                 200                 205
```

-continued

```
Gly Cys Ala Gly Cys Gly Cys Gly Cys Cys Thr Ala Cys Cys Ala
    210                 215                 220
Gly Ala Cys Cys Gly Ala Gly Gly Cys Gly Gly Cys Thr Gly Gly
225                 230                 235                 240
Cys Ala Gly Cys Ala Gly Cys Ala Cys Gly Gly Cys Ala Ala Gly Gly
                245                 250                 255
Gly Thr Gly Cys Gly Thr Cys Cys Ala Thr Cys Thr Gly Gly Gly Ala
            260                 265                 270
Thr Ala Cys Gly Thr Thr Cys Ala Cys Cys Ala Cys Cys Ala Cys
275                 280                 285
Cys Cys Cys Cys Thr Gly Gly Cys Ala Cys Cys Cys Cys Gly Gly
    290                 295                 300
Gly Ala Gly Ala Cys Thr Cys Cys Gly Gly Ala Ala Cys Gly Cys
305                 310                 315                 320
Cys Ala Gly Thr Cys Thr Gly Cys Cys Gly Thr Thr Gly Gly Gly Cys
                325                 330                 335
Gly Cys Cys Cys Gly Thr Cys Gly Cys Cys Gly Cys Thr Gly Cys
            340                 345                 350
Ala Gly Cys Cys Cys Gly Cys Cys Ala Cys Cys Gly Gly Gly Ala
    355                 360                 365
Cys Gly Thr Ala Gly Cys Cys Ala Gly Cys Gly Ala Cys Ala Gly Cys
                370                 375                 380
Thr Ala Cys Ala Ala Cys Ala Ala Cys Gly Thr Cys Thr Thr Cys Cys
385                 390                 395                 400
Gly Cys Gly Ala Cys Ala Cys Gly Gly Ala Gly Gly Cys Gly Cys Thr
                405                 410                 415
Gly Cys Gly Cys Gly Ala Gly Cys Thr Cys Gly Gly Gly Thr Cys
            420                 425                 430
Ala Cys Thr Cys Ala Cys Thr Ala Cys Cys Gly Cys Thr Thr Cys Thr
    435                 440                 445
Cys Cys Ala Thr Cys Thr Cys Gly Thr Gly Gly Gly Cys Gly Cys Gly
450                 455                 460
Ala Gly Thr Gly Cys Thr Cys Cys Cys Cys Ala Ala Thr Gly Gly Cys
465                 470                 475                 480
Ala Gly Cys Gly Cys Gly Gly Gly Cys Gly Thr Cys Cys Cys Ala
                485                 490                 495
Ala Cys Cys Gly Cys Gly Ala Gly Gly Gly Cys Thr Gly Cys Gly
    500                 505                 510
Cys Thr Ala Cys Thr Ala Cys Cys Gly Gly Cys Gly Cys Cys Thr Gly
            515                 520                 525
Cys Thr Gly Gly Ala Gly Cys Gly Gly Cys Thr Gly Cys Gly Gly Gly
    530                 535                 540
Ala Gly Cys Thr Gly Gly Cys Gly Thr Gly Cys Ala Gly Cys Cys
545                 550                 555                 560
Cys Gly Thr Gly Gly Thr Cys Ala Cys Cys Thr Gly Thr Ala Cys
                565                 570                 575
Cys Ala Cys Thr Gly Gly Ala Cys Cys Thr Gly Cys Cys Cys
    580                 585                 590
Ala Gly Cys Gly Cys Cys Thr Gly Cys Ala Gly Ala Cys Gly Cys
                595                 600                 605
Cys Thr Ala Cys Gly Gly Cys Gly Gly Cys Thr Gly Gly Cys Cys
    610                 615                 620
Ala Ala Cys Cys Gly Cys Gly Cys Cys Cys Thr Gly Gly Cys Cys Gly
```

-continued

```
            625                 630                 635                 640
Ala Cys Cys Ala Cys Thr Thr Cys Ala Gly Gly Ala Thr Thr Ala
                645                 650                 655
Cys Gly Cys Gly Gly Ala Gly Cys Thr Cys Thr Gly Cys Thr Thr Cys
                660                 665                 670
Cys Gly Cys Cys Ala Cys Thr Thr Cys Gly Gly Cys Gly Gly Thr Cys
                675                 680                 685
Ala Gly Gly Thr Cys Ala Ala Gly Thr Ala Cys Thr Gly Gly Ala Thr
                690                 695                 700
Cys Ala Cys Cys Ala Thr Cys Gly Ala Cys Ala Cys Cys Cys
705                 710                 715                 720
Thr Ala Cys Gly Thr Gly Gly Thr Gly Gly Cys Cys Thr Gly Cys
                725                 730                 735
Ala Cys Gly Gly Cys Thr Ala Cys Gly Cys Cys Ala Cys Gly Gly
                740                 745                 750
Gly Cys Gly Cys Gly Cys Thr Gly Gly Cys Cys Cys Cys Gly Gly Cys
                755                 760                 765
Ala Thr Cys Cys Gly Gly Gly Cys Ala Gly Cys Cys Cys Gly Cys
                770                 775                 780
Gly Gly Cys Thr Cys Gly Gly Gly Thr Ala Cys Cys Thr Gly Gly Thr
785                 790                 795                 800
Gly Gly Cys Gly Cys Ala Cys Ala Ala Cys Cys Thr Cys Thr Cys
                805                 810                 815
Cys Thr Gly Gly Cys Thr Cys Ala Thr Gly Cys Cys Ala Ala Ala Gly
                820                 825                 830
Thr Cys Thr Gly Gly Cys Ala Thr Cys Thr Cys Thr Ala Cys Ala Ala
                835                 840                 845
Thr Ala Cys Thr Thr Cys Thr Thr Cys Cys Gly Thr Cys Cys Cys
850                 855                 860
Ala Cys Thr Cys Ala Gly Gly Ala Gly Gly Thr Cys Ala Gly Gly
865                 870                 875                 880
Thr Gly Thr Cys Cys Ala Thr Thr Gly Cys Cys Thr Ala Ala Gly
                885                 890                 895
Cys Thr Cys Thr Cys Ala Cys Thr Gly Gly Ala Thr Cys Ala Ala Thr
                900                 905                 910
Cys Cys Thr Cys Gly Ala Ala Gly Ala Ala Thr Gly Ala Cys Cys Gly
                915                 920                 925
Ala Cys Cys Ala Cys Ala Gly Cys Ala Thr Cys Ala Ala Ala Gly Ala
                930                 935                 940
Ala Thr Gly Thr Cys Ala Ala Ala Ala Thr Cys Thr Cys Thr Gly
945                 950                 955                 960
Gly Ala Cys Thr Thr Thr Gly Thr Ala Cys Thr Ala Gly Gly Thr Thr
                965                 970                 975
Gly Gly Thr Thr Thr Gly Cys Cys Ala Ala Ala Cys Cys Cys Gly Thr
                980                 985                 990
Ala Thr Thr Thr Ala Thr Thr Gly  Ala Thr Gly Gly Thr  Gly Ala Cys
                995                 1000                 1005
Thr Ala  Thr Cys Cys Cys Gly  Ala Gly Ala Gly Cys  Ala Thr Gly
                1010                 1015                 1020
Ala Ala  Gly Ala Ala Thr Ala  Ala Cys Cys Thr Thr  Thr Cys Ala
                1025                 1030                 1035
Thr Cys  Thr Ala Thr Thr Cys  Thr Gly Cys Cys Thr  Gly Ala Thr
                1040                 1045                 1050
```

-continued

```
Thr Thr Thr Ala Cys Thr Gly Ala Ala Thr Cys Thr Gly Ala Gly
    1055                1060                1065

Ala Ala Ala Ala Ala Gly Thr Thr Cys Ala Thr Cys Ala Ala Ala
    1070                1075                1080

Gly Gly Ala Ala Cys Thr Gly Cys Thr Gly Ala Cys Thr Thr Thr
    1085                1090                1095

Thr Thr Thr Gly Cys Thr Cys Thr Thr Thr Gly Cys Thr Thr Thr
    1100                1105                1110

Gly Gly Ala Cys Cys Cys Ala Cys Cys Thr Thr Gly Ala Gly Thr
    1115                1120                1125

Thr Thr Thr Cys Ala Ala Cys Thr Thr Thr Thr Gly Gly Ala Cys
    1130                1135                1140

Cys Cys Thr Cys Ala Cys Ala Thr Gly Ala Ala Gly Thr Thr Cys
    1145                1150                1155

Cys Gly Cys Cys Ala Ala Thr Thr Gly Gly Ala Ala Thr Cys Thr
    1160                1165                1170

Cys Cys Cys Ala Ala Cys Cys Thr Gly Ala Gly Gly Cys Ala Ala
    1175                1180                1185

Cys Thr Gly Cys Thr Thr Thr Cys Cys Thr Gly Gly Ala Thr Thr
    1190                1195                1200

Gly Ala Cys Cys Thr Thr Gly Ala Ala Thr Thr Thr Ala Ala Cys
    1205                1210                1215

Cys Ala Thr Cys Cys Thr Cys Ala Ala Ala Thr Ala Thr Thr Thr
    1220                1225                1230

Ala Thr Thr Gly Thr Gly Gly Ala Ala Ala Ala Thr Gly Gly Cys
    1235                1240                1245

Thr Gly Gly Thr Thr Thr Gly Thr Cys Thr Cys Ala Gly Gly Gly
    1250                1255                1260

Ala Cys Cys Ala Cys Cys Ala Ala Gly Ala Gly Ala Gly Ala Thr
    1265                1270                1275

Gly Ala Thr Gly Cys Cys Ala Ala Thr Ala Thr Ala Thr Gly
    1280                1285                1290

Thr Ala Thr Thr Ala Cys Cys Thr Cys Ala Ala Ala Ala Ala Gly
    1295                1300                1305

Thr Thr Cys Ala Thr Cys Ala Thr Gly Gly Ala Ala Ala Cys Cys
    1310                1315                1320

Thr Thr Ala Ala Ala Ala Gly Cys Cys Ala Thr Cys Ala Ala Gly
    1325                1330                1335

Cys Thr Gly Gly Ala Thr Gly Gly Gly Gly Thr Gly Gly Ala Thr
    1340                1345                1350

Gly Thr Cys Ala Thr Cys Gly Gly Gly Thr Ala Thr Ala Cys Cys
    1355                1360                1365

Gly Cys Ala Thr Gly Gly Thr Cys Cys Cys Thr Cys Ala Thr Gly
    1370                1375                1380

Gly Ala Thr Gly Gly Thr Thr Thr Cys Gly Ala Gly Thr Gly Gly
    1385                1390                1395

Cys Ala Cys Ala Gly Ala Gly Gly Thr Thr Ala Cys Ala Gly Cys
    1400                1405                1410

Ala Thr Cys Ala Gly Gly Cys Gly Thr Gly Gly Ala Cys Thr Cys
    1415                1420                1425

Thr Thr Cys Thr Ala Thr Gly Thr Thr Gly Ala Cys Thr Thr Thr
    1430                1435                1440

Cys Thr Ala Ala Gly Cys Cys Ala Gly Gly Ala Cys Ala Ala Gly
    1445                1450                1455
```

-continued

Ala Thr Gly Thr Thr Gly Thr Thr Gly Cys Cys Ala Ala Ala Gly
1460 1465 1470

Thr Cys Thr Thr Cys Ala Gly Cys Cys Thr Thr Gly Thr Thr Cys
1475 1480 1485

Thr Ala Cys Cys Ala Ala Ala Ala Gly Cys Thr Gly Ala Thr Ala
1490 1495 1500

Gly Ala Gly Ala Ala Ala Ala Ala Thr Gly Gly Cys Thr Thr Cys
1505 1510 1515

Cys Cys Thr Cys Cys Thr Thr Thr Ala Cys Cys Thr Gly Ala Ala
1520 1525 1530

Ala Ala Thr Cys Ala Gly Cys Cys Cys Cys Thr Ala Gly Ala Ala
1535 1540 1545

Gly Gly Gly Ala Cys Ala Thr Thr Thr Cys Cys Cys Thr Gly Thr
1550 1555 1560

Gly Ala Cys Thr Thr Thr Gly Cys Thr Thr Gly Gly Gly Gly Ala
1565 1570 1575

Gly Thr Thr Gly Thr Thr Gly Ala Cys Ala Ala Cys Thr Ala Cys
1580 1585 1590

Ala Thr Thr Cys Ala Ala Gly Thr Ala Gly Ala Thr Ala Cys Cys
1595 1600 1605

Ala Cys Thr Cys Thr Gly Thr Cys Thr Cys Ala Gly Thr Thr Thr
1610 1615 1620

Ala Cys Cys Gly Ala Cys Cys Thr Gly Ala Ala Thr Gly Thr Thr
1625 1630 1635

Thr Ala Cys Cys Thr Gly Thr Gly Gly Gly Ala Thr Gly Thr Cys
1640 1645 1650

Cys Ala Cys Cys Ala Cys Ala Gly Thr Ala Ala Ala Ala Gly Gly
1655 1660 1665

Cys Thr Thr Ala Thr Thr Ala Ala Ala Gly Thr Gly Gly Ala Thr
1670 1675 1680

Gly Gly Gly Gly Thr Thr Gly Thr Gly Ala Cys Cys Ala Ala Gly
1685 1690 1695

Ala Ala Gly Ala Gly Gly Ala Ala Ala Thr Cys Cys Thr Ala Cys
1700 1705 1710

Thr Gly Thr Gly Thr Thr Gly Ala Cys Thr Thr Thr Gly Cys Thr
1715 1720 1725

Gly Cys Cys Ala Thr Cys Cys Ala Gly Cys Cys Cys Cys Ala Gly
1730 1735 1740

Ala Thr Cys Gly Cys Thr Thr Thr Ala Cys Thr Cys Cys Ala Gly
1745 1750 1755

Gly Ala Ala Ala Thr Gly Cys Ala Cys Gly Thr Thr Ala Cys Ala
1760 1765 1770

Cys Ala Thr Thr Thr Thr Cys Gly Cys Thr Thr Cys Thr Cys Cys
1775 1780 1785

Cys Thr Gly Gly Ala Cys Thr Gly Gly Gly Cys Cys Cys Thr Gly
1790 1795 1800

Ala Thr Thr Cys Thr Cys Cys Cys Thr Cys Thr Gly Gly Gly Thr
1805 1810 1815

Ala Ala Cys Cys Ala Gly Thr Cys Cys Cys Ala Gly Gly Thr Gly
1820 1825 1830

Ala Ala Cys Cys Ala Cys Ala Cys Cys Ala Thr Cys Cys Thr Gly
1835 1840 1845

Cys Ala Gly Thr Ala Cys Thr Ala Thr Cys Gly Cys Thr Gly Cys 1850                1855                1860

Ala  Thr  Gly  Gly  Cys  Cys  Ala  Gly  Cys  Gly  Ala  Gly  Cys  Thr  Thr
         1865                1870                1875

Gly  Thr  Cys  Cys  Gly  Thr  Gly  Thr  Cys  Ala  Ala  Cys  Ala  Thr  Cys
         1880                1885                1890

Ala  Cys  Cys  Cys  Ala  Gly  Thr  Gly  Thr  Gly  Gly  Cys  Cys
         1895                1900                1905

Cys  Thr  Gly  Thr  Gly  Gly  Cys  Ala  Gly  Cys  Cys  Thr  Ala  Thr  Gly
         1910                1915                1920

Gly  Cys  Cys  Cys  Cys  Gly  Ala  Ala  Cys  Cys  Ala  Ala  Gly  Gly  Ala
         1925                1930                1935

Cys  Thr  Gly  Cys  Cys  Gly  Cys  Gly  Cys  Cys  Thr  Cys  Cys  Thr  Gly
         1940                1945                1950

Gly  Cys  Cys  Ala  Gly  Gly  Cys  Ala  Gly  Gly  Gly  Cys  Gly  Cys  Cys
         1955                1960                1965

Thr  Gly  Gly  Gly  Ala  Gly  Ala  Ala  Cys  Cys  Cys  Thr  Ala  Cys
         1970                1975                1980

Ala  Cys  Thr  Gly  Cys  Cys  Thr  Gly  Gly  Cys  Cys  Thr  Thr  Thr
         1985                1990                1995

Gly  Cys  Ala  Gly  Ala  Gly  Thr  Ala  Thr  Gly  Cys  Cys  Cys  Gly  Ala
         2000                2005                2010

Cys  Thr  Gly  Thr  Gly  Cys  Thr  Thr  Thr  Cys  Ala  Ala  Gly  Ala  Gly
         2015                2020                2025

Cys  Thr  Cys  Gly  Gly  Cys  Cys  Ala  Thr  Cys  Ala  Cys  Gly  Thr  Cys
         2030                2035                2040

Ala  Ala  Gly  Cys  Thr  Thr  Thr  Gly  Gly  Ala  Thr  Ala  Ala  Cys  Gly
         2045                2050                2055

Ala  Thr  Gly  Ala  Ala  Thr  Gly  Ala  Gly  Cys  Cys  Gly  Thr  Ala  Thr
         2060                2065                2070

Ala  Cys  Ala  Ala  Gly  Gly  Ala  Ala  Thr  Ala  Thr  Gly  Ala  Cys  Ala
         2075                2080                2085

Thr  Ala  Cys  Ala  Gly  Thr  Gly  Cys  Thr  Gly  Gly  Cys  Cys  Ala  Cys
         2090                2095                2100

Ala  Ala  Cys  Cys  Thr  Thr  Cys  Thr  Gly  Ala  Ala  Gly  Gly  Cys  Cys
         2105                2110                2115

Cys  Ala  Thr  Gly  Cys  Cys  Cys  Thr  Gly  Gly  Cys  Thr  Thr  Gly  Gly
         2120                2125                2130

Cys  Ala  Thr  Gly  Thr  Gly  Thr  Ala  Cys  Ala  Ala  Thr  Gly  Ala  Ala
         2135                2140                2145

Ala  Ala  Gly  Thr  Thr  Thr  Ala  Gly  Gly  Cys  Ala  Thr  Gly  Cys  Thr
         2150                2155                2160

Cys  Ala  Gly  Ala  Ala  Thr  Gly  Gly  Gly  Ala  Ala  Ala  Ala  Thr  Ala
         2165                2170                2175

Thr  Cys  Cys  Ala  Thr  Ala  Gly  Cys  Cys  Thr  Thr  Gly  Cys  Ala  Gly
         2180                2185                2190

Gly  Cys  Thr  Gly  Ala  Thr  Thr  Gly  Gly  Ala  Thr  Ala  Gly  Ala  Ala
         2195                2200                2205

Cys  Cys  Thr  Gly  Cys  Cys  Thr  Gly  Cys  Cys  Thr  Thr  Thr  Thr  Cys
         2210                2215                2220

Thr  Cys  Cys  Cys  Ala  Ala  Ala  Ala  Gly  Gly  Ala  Cys  Ala  Ala  Ala
         2225                2230                2235

Gly  Ala  Gly  Gly  Thr  Gly  Gly  Cys  Cys  Gly  Ala  Gly  Ala  Gly  Ala
         2240                2245                2250

-continued

Gly Thr Thr Thr Thr Gly Gly Ala Ala Thr Thr Gly Ala Cys
2255                2260            2265

Ala Thr Thr Gly Gly Cys Thr Gly Gly Cys Thr Gly Cys Thr
2270            2275            2280

Gly Ala Gly Cys Cys Cys Ala Thr Thr Thr Thr Cys Gly Gly Cys
2285            2290            2295

Thr Cys Thr Gly Gly Ala Gly Ala Thr Thr Ala Thr Cys Cys Ala
2300            2305            2310

Thr Gly Gly Gly Thr Gly Ala Thr Gly Ala Gly Gly Gly Ala Cys
2315            2320            2325

Thr Gly Gly Cys Thr Gly Ala Ala Cys Cys Ala Ala Ala Gly Ala
2330            2335            2340

Ala Ala Cys Ala Ala Thr Thr Thr Thr Cys Thr Thr Cys Thr Thr
2345            2350            2355

Cys Cys Thr Thr Ala Thr Thr Thr Cys Ala Cys Thr Gly Ala Ala
2360            2365            2370

Gly Ala Thr Gly Ala Ala Ala Ala Ala Ala Gly Cys Thr Ala
2375            2380            2385

Ala Thr Cys Cys Ala Gly Gly Gly Thr Ala Cys Cys Thr Thr Thr
2390            2395            2400

Gly Ala Cys Thr Thr Thr Thr Gly Gly Cys Thr Thr Thr Ala
2405            2410            2415

Ala Gly Cys Cys Ala Thr Thr Ala Thr Ala Cys Cys Ala Cys Cys
2420            2425            2430

Ala Thr Cys Cys Thr Thr Gly Thr Ala Gly Ala Cys Thr Cys Ala
2435            2440            2445

Gly Ala Ala Ala Ala Ala Gly Ala Ala Gly Ala Thr Cys Cys Ala
2450            2455            2460

Ala Thr Ala Ala Ala Ala Thr Ala Cys Ala Ala Thr Gly Ala Thr
2465            2470            2475

Thr Ala Cys Cys Thr Ala Gly Ala Ala Gly Thr Gly Cys Ala Ala
2480            2485            2490

Gly Ala Ala Ala Thr Gly Ala Cys Cys Gly Ala Cys Ala Thr Cys
2495            2500            2505

Ala Cys Gly Thr Gly Gly Cys Thr Cys Ala Ala Cys Thr Cys Cys
2510            2515            2520

Cys Cys Cys Ala Gly Thr Cys Ala Gly Gly Thr Gly Gly Cys Gly
2525            2530            2535

Gly Thr Ala Gly Thr Gly Cys Cys Cys Thr Gly Gly Gly Gly Gly
2540            2545            2550

Thr Thr Gly Cys Gly Cys Ala Ala Ala Gly Thr Gly Cys Thr Gly
2555            2560            2565

Ala Ala Cys Thr Gly Gly Cys Thr Gly Ala Ala Gly Thr Thr Cys
2570            2575            2580

Ala Ala Gly Thr Ala Cys Gly Gly Ala Gly Ala Cys Cys Thr Cys
2585            2590            2595

Cys Cys Cys Ala Thr Gly Thr Ala Cys Ala Thr Ala Ala Thr Ala
2600            2605            2610

Thr Cys Cys Ala Ala Cys Gly Gly Ala Ala Thr Cys Gly Ala Thr
2615            2620            2625

Gly Ala Cys Gly Gly Gly Cys Thr Gly Cys Ala Thr Gly Cys Thr
2630            2635            2640

Gly Ala Gly Gly Ala Cys Gly Ala Cys Cys Ala Gly Cys Thr Gly
2645            2650            2655

```
Ala Gly Gly Gly Thr Gly Thr Ala Thr Thr Ala Thr Gly
    2660            2665            2670

Cys Ala Gly Ala Ala Thr Thr Ala Cys Ala Thr Ala Ala Cys
    2675            2680            2685

Gly Ala Ala Gly Cys Thr Cys Thr Cys Ala Ala Gly Cys Cys
    2690            2695            2700

Cys Ala Cys Ala Thr Ala Cys Thr Gly Gly Ala Thr Gly Gly Thr
    2705            2710            2715

Ala Thr Cys Ala Ala Thr Cys Thr Thr Thr Gly Cys Gly Gly Ala
    2720            2725            2730

Thr Ala Cys Thr Thr Thr Gly Cys Thr Ala Thr Thr Cys Gly
    2735            2740            2745

Thr Thr Thr Ala Ala Cys Gly Ala Cys Cys Gly Cys Ala Cys Ala
    2750            2755            2760

Gly Cys Thr Cys Cys Gly Ala Gly Gly Thr Thr Gly Gly Cys
    2765            2770            2775

Cys Thr Cys Thr Ala Thr Cys Gly Thr Ala Thr Gly Cys Thr
    2780            2785            2790

Gly Cys Ala Gly Ala Thr Cys Ala Gly Thr Thr Thr Gly Ala Gly
    2795            2800            2805

Cys Cys Cys Ala Ala Gly Gly Cys Ala Thr Cys Cys Ala Thr Gly
    2810            2815            2820

Ala Ala Ala Cys Ala Thr Thr Ala Cys Ala Gly Gly Ala Ala Ala
    2825            2830            2835

Ala Thr Thr Ala Thr Thr Gly Ala Cys Ala Gly Cys Ala Ala Thr
    2840            2845            2850

Gly Gly Thr Thr Thr Cys Cys Cys Gly Gly Gly Cys Cys Cys Ala
    2855            2860            2865

Gly Ala Ala Ala Cys Thr Cys Thr Gly Gly Ala Ala Ala Gly Ala
    2870            2875            2880

Thr Thr Thr Thr Gly Thr Cys Cys Ala Gly Ala Ala Gly Ala Ala
    2885            2890            2895

Thr Thr Cys Ala Cys Cys Gly Thr Gly Thr Gly Thr Ala Cys Thr
    2900            2905            2910

Gly Ala Gly Thr Gly Cys Ala Gly Thr Thr Thr Thr Thr Thr Thr
    2915            2920            2925

Cys Ala Cys Ala Cys Cys Cys Gly Ala Ala Ala Gly Thr Cys Thr
    2930            2935            2940

Thr Thr Ala Gly Gly Ala Thr Cys Cys Gly Gly Ala Gly Gly Thr
    2945            2950            2955

Gly Gly Ala Gly Gly Thr Thr Cys Ala Gly Gly Ala Gly Gly Thr
    2960            2965            2970

Gly Gly Ala Gly Gly Thr Thr Cys Ala Gly Gly Ala Gly Gly Thr
    2975            2980            2985

Gly Gly Ala Gly Gly Thr Thr Cys Ala Cys Thr Thr Ala Ala Gly
    2990            2995            3000

Thr Ala Thr Cys Cys Cys Ala Ala Thr Gly Cys Cys Thr Cys Cys
    3005            3010            3015

Cys Cys Ala Cys Thr Gly Cys Thr Cys Gly Gly Cys Thr Cys Cys
    3020            3025            3030

Ala Gly Cys Thr Gly Gly Gly Thr Gly Gly Cys Cys Thr Gly
    3035            3040            3045

Ala Thr Cys Cys Ala Cys Cys Thr Gly Thr Ala Cys Ala Cys Ala
```

```
                3050                3055                3060
Gly Cys Cys Ala Cys Ala Gly Cys Cys Ala Gly Gly Ala Ala Cys
    3065                3070                3075
Ala Gly Cys Thr Ala Cys Cys Ala Cys Cys Thr Gly Cys Ala Gly
    3080                3085                3090
Ala Thr Cys Cys Ala Cys Ala Ala Gly Ala Ala Thr Gly Gly Cys
    3095                3100                3105
Cys Ala Thr Gly Thr Gly Gly Ala Thr Gly Gly Cys Gly Cys Ala
    3110                3115                3120
Cys Cys Cys Ala Thr Cys Ala Gly Ala Cys Cys Ala Thr Cys
    3125                3130                3135
Thr Ala Cys Ala Gly Thr Gly Cys Cys Thr Gly Ala Thr Gly
    3140                3145                3150
Ala Thr Cys Ala Gly Ala Thr Cys Ala Gly Ala Gly Gly Ala Thr
    3155                3160                3165
Gly Cys Thr Gly Gly Cys Thr Thr Thr Gly Thr Gly Gly Thr Gly
    3170                3175                3180
Ala Thr Thr Ala Cys Ala Gly Gly Thr Gly Thr Gly Ala Thr Gly
    3185                3190                3195
Ala Gly Cys Ala Gly Ala Ala Gly Ala Thr Ala Cys Cys Thr Cys
    3200                3205                3210
Thr Gly Cys Ala Thr Gly Gly Ala Thr Thr Thr Cys Ala Gly Ala
    3215                3220                3225
Gly Gly Cys Ala Ala Cys Ala Thr Thr Thr Thr Thr Gly Gly Ala
    3230                3235                3240
Thr Cys Ala Cys Ala Cys Thr Ala Thr Thr Thr Cys Gly Ala Cys
    3245                3250                3255
Cys Cys Gly Gly Ala Gly Ala Ala Cys Thr Gly Cys Ala Gly Gly
    3260                3265                3270
Thr Thr Cys Cys Ala Ala Cys Ala Cys Cys Ala Gly Ala Cys Gly
    3275                3280                3285
Cys Thr Gly Gly Ala Ala Ala Ala Cys Gly Gly Gly Thr Ala Cys
    3290                3295                3300
Gly Ala Cys Gly Thr Cys Thr Ala Cys Cys Ala Cys Thr Cys Thr
    3305                3310                3315
Cys Cys Thr Cys Ala Gly Thr Ala Thr Cys Ala Cys Thr Thr Cys
    3320                3325                3330
Cys Thr Gly Gly Thr Cys Ala Gly Thr Cys Thr Gly Gly Gly Cys
    3335                3340                3345
Cys Gly Gly Gly Cys Gly Ala Ala Gly Ala Gly Ala Gly Cys Cys
    3350                3355                3360
Thr Thr Cys Cys Thr Gly Cys Cys Ala Gly Gly Cys Ala Thr Gly
    3365                3370                3375
Ala Ala Cys Cys Cys Ala Cys Cys Cys Cys Gly Thr Ala Cys
    3380                3385                3390
Thr Cys Cys Cys Ala Gly Thr Thr Cys Cys Thr Gly Thr Cys Cys
    3395                3400                3405
Cys Gly Gly Ala Gly Gly Ala Ala Cys Gly Ala Gly Ala Thr Cys
    3410                3415                3420
Cys Cys Cys Cys Thr Ala Ala Thr Thr Cys Ala Cys Thr Thr Cys
    3425                3430                3435
Ala Ala Cys Ala Cys Cys Cys Cys Ala Thr Ala Cys Cys Ala
    3440                3445                3450
```

```
Cys Gly Gly Cys Gly Gly Cys Ala Cys Ala Cys Cys Ala Gly
3455                3460                3465

Ala Gly Cys Gly Cys Cys Gly Ala Gly Ala Cys Gly Ala Cys
3470                3475                3480

Thr Cys Gly Gly Ala Gly Cys Gly Gly Gly Ala Cys Cys Cys
3485                3490                3495

Cys Thr Gly Ala Ala Cys Gly Thr Gly Cys Thr Gly Ala Ala Gly
3500                3505                3510

Cys Cys Cys Cys Gly Gly Gly Cys Cys Cys Gly Gly Ala Thr Gly
3515                3520                3525

Ala Cys Cys Cys Cys Gly Gly Cys Cys Cys Cys Gly Gly Cys Cys
3530                3535                3540

Thr Cys Cys Thr Gly Thr Thr Cys Ala Cys Ala Gly Gly Ala Gly
3545                3550                3555

Cys Thr Cys Cys Cys Gly Ala Gly Cys Gly Cys Cys Gly Ala Gly
3560                3565                3570

Gly Ala Cys Ala Ala Cys Ala Gly Cys Cys Cys Gly Ala Thr Gly
3575                3580                3585

Gly Cys Cys Ala Gly Thr Gly Ala Cys Cys Cys Ala Thr Thr Ala
3590                3595                3600

Gly Gly Gly Gly Thr Gly Gly Thr Cys Ala Gly Gly Gly Gly Cys
3605                3610                3615

Gly Gly Thr Cys Gly Ala Gly Thr Gly Ala Ala Cys Ala Cys Gly
3620                3625                3630

Cys Ala Cys Gly Cys Thr Gly Gly Gly Gly Ala Ala Cys Gly
3635                3640                3645

Gly Gly Cys Cys Cys Gly Gly Ala Ala Gly Gly Cys Thr Gly Cys
3650                3655                3660

Cys Gly Cys Cys Cys Cys Thr Thr Cys Gly Cys Cys Ala Ala Gly
3665                3670                3675

Thr Thr Cys Ala Thr Cys Gly Gly Ala Gly Gly Thr Gly Gly Ala
3680                3685                3690

Gly Gly Thr Thr Cys Ala Ala Ala Ala Ala Cys Cys Cys Ala Cys
3695                3700                3705

Ala Cys Gly Thr Gly Thr Cys Thr Cys Cys Thr Thr Gly Thr
3710                3715                3720

Cys Cys Thr Gly Cys Cys Cys Ala Gly Ala Ala Gly Cys Ala
3725                3730                3735

Gly Cys Ala Gly Gly Thr Gly Gly Thr Cys Ala Thr Cys Ala
3740                3745                3750

Gly Thr Thr Thr Thr Thr Cys Thr Thr Thr Thr Cys Cys Cys Thr
3755                3760                3765

Cys Cys Cys Ala Ala Ala Cys Cys Cys Ala Ala Gly Gly Ala Thr
3770                3775                3780

Ala Cys Gly Cys Thr Gly Ala Thr Gly Ala Thr Cys Thr Cys Thr
3785                3790                3795

Cys Gly Cys Ala Cys Gly Cys Cys Thr Gly Ala Gly Gly Thr Gly
3800                3805                3810

Ala Cys Ala Thr Gly Cys Gly Thr Cys Gly Thr Ala Gly Thr Ala
3815                3820                3825

Gly Ala Cys Gly Thr Gly Ala Gly Cys Cys Ala Cys Gly Ala Ala
3830                3835                3840

Gly Ala Thr Cys Cys Cys Gly Ala Gly Gly Thr Gly Ala Ala Gly
3845                3850                3855
```

-continued

```
Thr Thr Cys Ala Ala Thr Gly Gly Thr Ala Thr Gly Thr Gly
    3860              3865              3870

Gly Ala Cys Gly Gly Ala Gly Thr Ala Gly Ala Ala Gly Thr Gly
    3875              3880              3885

Cys Ala Thr Ala Ala Cys Gly Cys Gly Ala Ala Ala Ala Cys Thr
    3890              3895              3900

Ala Ala Gly Cys Cys Gly Cys Gly Cys Gly Ala Gly Gly Ala Ala
    3905              3910              3915

Cys Ala Ala Thr Ala Thr Ala Ala Cys Ala Gly Thr Ala Cys Thr
    3920              3925              3930

Thr Ala Cys Ala Gly Gly Gly Thr Gly Gly Thr Ala Thr Cys Cys
    3935              3940              3945

Gly Thr Gly Cys Thr Cys Ala Cys Ala Gly Thr Cys Cys Thr Gly
    3950              3955              3960

Cys Ala Cys Cys Ala Gly Gly Ala Cys Thr Gly Gly Cys Thr Gly
    3965              3970              3975

Ala Ala Cys Gly Gly Thr Ala Ala Gly Gly Ala Ala Thr Ala Cys
    3980              3985              3990

Ala Ala Gly Thr Gly Cys Ala Ala Ala Gly Thr Ala Ala Gly Cys
    3995              4000              4005

Ala Ala Cys Ala Ala Gly Gly Cys Ala Cys Thr Cys Cys Cys
    4010              4015              4020

Gly Cys Gly Cys Cys Thr Ala Thr Thr Gly Ala Gly Ala Ala Ala
    4025              4030              4035

Ala Cys Ala Ala Thr Cys Thr Cys Cys Ala Ala Gly Gly Cys Gly
    4040              4045              4050

Ala Ala Gly Gly Gly Ala Cys Ala Ala Cys Cys Ala Ala Gly Ala
    4055              4060              4065

Gly Ala Ala Cys Cys Thr Cys Ala Gly Gly Thr Thr Thr Ala Cys
    4070              4075              4080

Ala Cys Thr Cys Thr Cys Cys Gly Cys Cys Thr Thr Cys Cys
    4085              4090              4095

Ala Gly Gly Gly Ala Ala Gly Ala Gly Ala Thr Gly Ala Cys Cys
    4100              4105              4110

Ala Ala Ala Ala Ala Thr Cys Ala Ala Gly Thr Thr Thr Cys Cys
    4115              4120              4125

Cys Thr Gly Ala Cys Thr Thr Gly Cys Cys Thr Cys Gly Thr Cys
    4130              4135              4140

Ala Ala Ala Gly Gly Ala Thr Thr Cys Thr Ala Cys Cys Cys Thr
    4145              4150              4155

Thr Cys Cys Gly Ala Cys Ala Thr Thr Gly Cys Thr Gly Thr Thr
    4160              4165              4170

Gly Ala Ala Thr Gly Gly Gly Ala Ala Ala Gly Cys Ala Ala Thr
    4175              4180              4185

Gly Gly Ala Cys Ala Ala Cys Cys Ala Gly Ala Gly Ala Ala Cys
    4190              4195              4200

Ala Ala Cys Thr Ala Cys Ala Ala Gly Ala Cys Ala Ala Cys Ala
    4205              4210              4215

Cys Cys Cys Cys Cys Gly Gly Thr Gly Cys Thr Gly Gly Ala Thr
    4220              4225              4230

Ala Gly Thr Gly Ala Cys Gly Gly Ala Thr Cys Thr Thr Thr Cys
    4235              4240              4245

Thr Thr Thr Cys Thr Cys Thr Ala Cys Thr Cys Ala Ala Ala Gly
```

```
              4250               4255                4260

Cys  Thr  Gly  Ala  Cys  Cys  Gly  Thr  Gly  Gly  Ala  Thr  Ala  Ala  Gly
          4265               4270                4275

Thr  Cys  Cys  Ala  Gly  Gly  Thr  Gly  Gly  Cys  Ala  Gly  Cys  Ala  Gly
          4280               4285                4290

Gly  Gly  Ala  Ala  Ala  Cys  Gly  Thr  Gly  Thr  Thr  Thr  Cys  Cys
          4295               4300                4305

Thr  Gly  Cys  Thr  Cys  Thr  Gly  Thr  Cys  Ala  Thr  Gly  Cys  Ala  Thr
          4310               4315                4320

Gly  Ala  Ala  Gly  Cys  Gly  Cys  Thr  Gly  Cys  Ala  Thr  Ala  Ala  Thr
          4325               4330                4335

Cys  Ala  Cys  Thr  Ala  Thr  Ala  Cys  Cys  Ala  Gly  Ala  Ala  Gly
          4340               4345                4350

Thr  Cys  Thr  Cys  Thr  Gly  Ala  Gly  Cys  Thr  Thr  Gly  Ala  Gly  Cys
          4355               4360                4365

Cys  Cys  Ala  Gly  Gly  Cys  Ala  Ala  Gly  Thr  Ala  Ala
          4370               4375                4380

<210> SEQ ID NO 47
<211> LENGTH: 1459
<212> TYPE: PRT
<213> ORGANISM: Artificial
<220> FEATURE:
<223> OTHER INFORMATION: fusion peptide derived from human

<400> SEQUENCE: 47

Met  Pro  Ala  Ser  Ala  Pro  Pro  Arg  Arg  Pro  Arg  Pro  Pro  Pro  Ser
1                 5                  10                  15

Leu  Ser  Leu  Leu  Leu  Val  Leu  Leu  Gly  Leu  Gly  Gly  Arg  Arg  Leu  Arg
            20                  25                  30

Ala  Glu  Pro  Gly  Asp  Gly  Ala  Gln  Thr  Trp  Ala  Arg  Phe  Ser  Arg  Pro
            35                  40                  45

Pro  Ala  Pro  Glu  Ala  Ala  Gly  Leu  Phe  Gln  Gly  Thr  Phe  Pro  Asp  Gly
            50                  55                  60

Phe  Leu  Trp  Ala  Val  Gly  Ser  Ala  Ala  Tyr  Gln  Thr  Glu  Gly  Gly  Trp
65                  70                  75                  80

Gln  Gln  His  Gly  Lys  Gly  Ala  Ser  Ile  Trp  Asp  Thr  Phe  Thr  His  His
                85                  90                  95

Pro  Leu  Ala  Pro  Pro  Gly  Asp  Ser  Arg  Asn  Ala  Ser  Leu  Pro  Leu  Gly
            100                 105                 110

Ala  Pro  Ser  Pro  Leu  Gln  Pro  Ala  Thr  Gly  Asp  Val  Ala  Ser  Asp  Ser
            115                 120                 125

Tyr  Asn  Asn  Val  Phe  Arg  Asp  Thr  Glu  Ala  Leu  Arg  Glu  Leu  Gly  Val
            130                 135                 140

Thr  His  Tyr  Arg  Phe  Ser  Ile  Ser  Trp  Ala  Arg  Val  Leu  Pro  Asn  Gly
145                 150                 155                 160

Ser  Ala  Gly  Val  Pro  Asn  Arg  Glu  Gly  Leu  Arg  Tyr  Tyr  Arg  Arg  Leu
                165                 170                 175

Leu  Glu  Arg  Leu  Arg  Glu  Leu  Gly  Val  Gln  Pro  Val  Val  Thr  Leu  Tyr
            180                 185                 190

His  Trp  Asp  Leu  Pro  Gln  Arg  Leu  Gln  Asp  Ala  Tyr  Gly  Gly  Trp  Ala
            195                 200                 205

Asn  Arg  Ala  Leu  Ala  Asp  His  Phe  Arg  Asp  Tyr  Ala  Glu  Leu  Cys  Phe
            210                 215                 220

Arg  His  Phe  Gly  Gly  Gln  Val  Lys  Tyr  Trp  Ile  Thr  Ile  Asp  Asn  Pro
225                 230                 235                 240
```

```
Tyr Val Val Ala Trp His Gly Tyr Ala Thr Gly Arg Leu Ala Pro Gly
                245                 250                 255

Ile Arg Gly Ser Pro Arg Leu Gly Tyr Leu Val Ala His Asn Leu Leu
                260                 265                 270

Leu Ala His Ala Lys Val Trp His Leu Tyr Asn Thr Ser Phe Arg Pro
                275                 280                 285

Thr Gln Gly Gly Gln Val Ser Ile Ala Leu Ser Ser His Trp Ile Asn
                290                 295                 300

Pro Arg Arg Met Thr Asp His Ser Ile Lys Glu Cys Gln Lys Ser Leu
305                 310                 315                 320

Asp Phe Val Leu Gly Trp Phe Ala Lys Pro Val Phe Ile Asp Gly Asp
                325                 330                 335

Tyr Pro Glu Ser Met Lys Asn Asn Leu Ser Ser Ile Leu Pro Asp Phe
                340                 345                 350

Thr Glu Ser Glu Lys Lys Phe Ile Lys Gly Thr Ala Asp Phe Phe Ala
                355                 360                 365

Leu Cys Phe Gly Pro Thr Leu Ser Phe Gln Leu Leu Asp Pro His Met
                370                 375                 380

Lys Phe Arg Gln Leu Glu Ser Pro Asn Leu Arg Gln Leu Leu Ser Trp
385                 390                 395                 400

Ile Asp Leu Glu Phe Asn His Pro Gln Ile Phe Ile Val Glu Asn Gly
                405                 410                 415

Trp Phe Val Ser Gly Thr Thr Lys Arg Asp Asp Ala Lys Tyr Met Tyr
                420                 425                 430

Tyr Leu Lys Lys Phe Ile Met Glu Thr Leu Lys Ala Ile Lys Leu Asp
                435                 440                 445

Gly Val Asp Val Ile Gly Tyr Thr Ala Trp Ser Leu Met Asp Gly Phe
                450                 455                 460

Glu Trp His Arg Gly Tyr Ser Ile Arg Arg Gly Leu Phe Tyr Val Asp
465                 470                 475                 480

Phe Leu Ser Gln Asp Lys Met Leu Leu Pro Lys Ser Ser Ala Leu Phe
                485                 490                 495

Tyr Gln Lys Leu Ile Glu Lys Asn Gly Phe Pro Pro Leu Pro Glu Asn
                500                 505                 510

Gln Pro Leu Glu Gly Thr Phe Pro Cys Asp Phe Ala Trp Gly Val Val
                515                 520                 525

Asp Asn Tyr Ile Gln Val Asp Thr Thr Leu Ser Gln Phe Thr Asp Leu
                530                 535                 540

Asn Val Tyr Leu Trp Asp Val His His Ser Lys Arg Leu Ile Lys Val
545                 550                 555                 560

Asp Gly Val Val Thr Lys Lys Arg Lys Ser Tyr Cys Val Asp Phe Ala
                565                 570                 575

Ala Ile Gln Pro Gln Ile Ala Leu Leu Gln Glu Met His Val Thr His
                580                 585                 590

Phe Arg Phe Ser Leu Asp Trp Ala Leu Ile Leu Pro Leu Gly Asn Gln
                595                 600                 605

Ser Gln Val Asn His Thr Ile Leu Gln Tyr Tyr Arg Cys Met Ala Ser
                610                 615                 620

Glu Leu Val Arg Val Asn Ile Thr Pro Val Val Ala Leu Trp Gln Pro
625                 630                 635                 640

Met Ala Pro Asn Gln Gly Leu Pro Arg Leu Leu Ala Arg Gln Gly Ala
                645                 650                 655

Trp Glu Asn Pro Tyr Thr Ala Leu Ala Phe Ala Glu Tyr Ala Arg Leu
```

-continued

```
                660                 665                 670
Cys Phe Gln Glu Leu Gly His His Val Lys Leu Trp Ile Thr Met Asn
            675                 680                 685
Glu Pro Tyr Thr Arg Asn Met Thr Tyr Ser Ala Gly His Asn Leu Leu
        690                 695                 700
Lys Ala His Ala Leu Ala Trp His Val Tyr Asn Glu Lys Phe Arg His
705                 710                 715                 720
Ala Gln Asn Gly Lys Ile Ser Ile Ala Leu Gln Ala Asp Trp Ile Glu
                725                 730                 735
Pro Ala Cys Pro Phe Ser Gln Lys Asp Lys Glu Val Ala Glu Arg Val
            740                 745                 750
Leu Glu Phe Asp Ile Gly Trp Leu Ala Glu Pro Ile Phe Gly Ser Gly
        755                 760                 765
Asp Tyr Pro Trp Val Met Arg Asp Trp Leu Asn Gln Arg Asn Asn Phe
    770                 775                 780
Leu Leu Pro Tyr Phe Thr Glu Asp Glu Lys Lys Leu Ile Gln Gly Thr
785                 790                 795                 800
Phe Asp Phe Leu Ala Leu Ser His Tyr Thr Thr Ile Leu Val Asp Ser
                805                 810                 815
Glu Lys Glu Asp Pro Ile Lys Tyr Asn Asp Tyr Leu Glu Val Gln Glu
            820                 825                 830
Met Thr Asp Ile Thr Trp Leu Asn Ser Pro Ser Gln Val Ala Val Val
        835                 840                 845
Pro Trp Gly Leu Arg Lys Val Leu Asn Trp Leu Lys Phe Lys Tyr Gly
    850                 855                 860
Asp Leu Pro Met Tyr Ile Ile Ser Asn Gly Ile Asp Asp Gly Leu His
865                 870                 875                 880
Ala Glu Asp Asp Gln Leu Arg Val Tyr Tyr Met Gln Asn Tyr Ile Asn
                885                 890                 895
Glu Ala Leu Lys Ala His Ile Leu Asp Gly Ile Asn Leu Cys Gly Tyr
            900                 905                 910
Phe Ala Tyr Ser Phe Asn Asp Arg Thr Ala Pro Arg Phe Gly Leu Tyr
        915                 920                 925
Arg Tyr Ala Ala Asp Gln Phe Glu Pro Lys Ala Ser Met Lys His Tyr
    930                 935                 940
Arg Lys Ile Ile Asp Ser Asn Gly Phe Pro Gly Pro Glu Thr Leu Glu
945                 950                 955                 960
Arg Phe Cys Pro Glu Glu Phe Thr Val Cys Thr Glu Cys Ser Phe Phe
                965                 970                 975
His Thr Arg Lys Ser Leu Gly Ser Gly Gly Gly Ser Gly Gly Gly
            980                 985                 990
Gly Ser Gly Gly Gly Ser Leu Lys Tyr Pro Asn Ala Ser Pro Leu
        995                 1000                1005
Leu Gly Ser Ser Trp Gly Gly Leu Ile His Leu Tyr Thr Ala Thr
        1010                1015                1020
Ala Arg Asn Ser Tyr His Leu Gln Ile His Lys Asn Gly His Val
        1025                1030                1035
Asp Gly Ala Pro His Gln Thr Ile Tyr Ser Ala Leu Met Ile Arg
        1040                1045                1050
Ser Glu Asp Ala Gly Phe Val Val Ile Thr Gly Val Met Ser Arg
        1055                1060                1065
Arg Tyr Leu Cys Met Asp Phe Arg Gly Asn Ile Phe Gly Ser His
        1070                1075                1080
```

-continued

Tyr Phe Asp Pro Glu Asn Cys Arg Phe Gln His Gln Thr Leu Glu
1085                1090                1095

Asn Gly Tyr Asp Val Tyr His Ser Pro Gln Tyr His Phe Leu Val
1100                1105                1110

Ser Leu Gly Arg Ala Lys Arg Ala Phe Leu Pro Gly Met Asn Pro
1115                1120                1125

Pro Pro Tyr Ser Gln Phe Leu Ser Arg Arg Asn Glu Ile Pro Leu
1130                1135                1140

Ile His Phe Asn Thr Pro Ile Pro Arg Arg His Thr Gln Ser Ala
1145                1150                1155

Glu Asp Asp Ser Glu Arg Asp Pro Leu Asn Val Leu Lys Pro Arg
1160                1165                1170

Ala Arg Met Thr Pro Ala Pro Ala Ser Cys Ser Gln Glu Leu Pro
1175                1180                1185

Ser Ala Glu Asp Asn Ser Pro Met Ala Ser Asp Pro Leu Gly Val
1190                1195                1200

Val Arg Gly Gly Arg Val Asn Thr His Ala Gly Gly Thr Gly Pro
1205                1210                1215

Glu Gly Cys Arg Pro Phe Ala Lys Phe Ile Gly Gly Gly Ser
1220                1225                1230

Lys Thr His Thr Cys Pro Pro Cys Pro Ala Pro Glu Ala Ala Gly
1235                1240                1245

Gly Pro Ser Val Phe Leu Phe Pro Pro Lys Pro Lys Asp Thr Leu
1250                1255                1260

Met Ile Ser Arg Thr Pro Glu Val Thr Cys Val Val Val Asp Val
1265                1270                1275

Ser His Glu Asp Pro Glu Val Lys Phe Asn Trp Tyr Val Asp Gly
1280                1285                1290

Val Glu Val His Asn Ala Lys Thr Lys Pro Arg Glu Glu Gln Tyr
1295                1300                1305

Asn Ser Thr Tyr Arg Val Val Ser Val Leu Thr Val Leu His Gln
1310                1315                1320

Asp Trp Leu Asn Gly Lys Glu Tyr Lys Cys Lys Val Ser Asn Lys
1325                1330                1335

Ala Leu Pro Ala Pro Ile Glu Lys Thr Ile Ser Lys Ala Lys Gly
1340                1345                1350

Gln Pro Arg Glu Pro Gln Val Tyr Thr Leu Pro Pro Ser Arg Glu
1355                1360                1365

Glu Met Thr Lys Asn Gln Val Ser Leu Thr Cys Leu Val Lys Gly
1370                1375                1380

Phe Tyr Pro Ser Asp Ile Ala Val Glu Trp Glu Ser Asn Gly Gln
1385                1390                1395

Pro Glu Asn Asn Tyr Lys Thr Thr Pro Pro Val Leu Asp Ser Asp
1400                1405                1410

Gly Ser Phe Phe Leu Tyr Ser Lys Leu Thr Val Asp Lys Ser Arg
1415                1420                1425

Trp Gln Gln Gly Asn Val Phe Ser Cys Ser Val Met His Glu Ala
1430                1435                1440

Leu His Asn His Tyr Thr Gln Lys Ser Leu Ser Leu Ser Pro Gly
1445                1450                1455

Lys

<210> SEQ ID NO 48
<211> LENGTH: 4353

```
<212> TYPE: PRT
<213> ORGANISM: Artificial
<220> FEATURE:
<223> OTHER INFORMATION: fusion peptide derived from human

<400> SEQUENCE: 48

Ala Thr Gly Cys Cys Gly Cys Cys Ala Gly Cys Gly Cys Cys Cys
 1               5                  10                  15

Cys Gly Cys Cys Gly Cys Gly Cys Cys Gly Cys Cys Cys Gly Cys Gly
            20                  25                  30

Gly Cys Cys Gly Cys Cys Gly Cys Cys Gly Cys Cys Gly Thr Cys Gly
            35                  40                  45

Cys Thr Gly Thr Cys Gly Cys Thr Gly Cys Thr Gly Cys Thr Gly Gly
50                  55                  60

Thr Gly Cys Thr Gly Cys Thr Gly Gly Gly Cys Cys Thr Gly Gly Gly
65                  70                  75                  80

Cys Gly Gly Cys Cys Gly Cys Cys Gly Cys Cys Thr Gly Cys Gly Thr
                85                  90                  95

Gly Cys Gly Gly Ala Gly Cys Cys Gly Gly Cys Gly Ala Cys Gly
            100                 105                 110

Gly Cys Gly Cys Gly Cys Ala Gly Ala Cys Cys Thr Gly Gly Gly Cys
            115                 120                 125

Cys Cys Gly Thr Thr Thr Cys Thr Cys Gly Cys Gly Gly Cys Cys Thr
130                 135                 140

Cys Cys Thr Gly Cys Cys Cys Cys Gly Ala Gly Gly Cys Cys Gly
145                 150                 155                 160

Cys Gly Gly Gly Cys Cys Thr Cys Thr Thr Cys Cys Ala Gly Gly
                165                 170                 175

Cys Ala Cys Cys Thr Thr Cys Cys Cys Gly Ala Cys Gly Gly Cys
            180                 185                 190

Thr Thr Cys Cys Thr Cys Thr Gly Gly Gly Cys Cys Gly Thr Gly Gly
            195                 200                 205

Gly Cys Ala Gly Cys Gly Cys Gly Cys Cys Thr Ala Cys Cys Ala
            210                 215                 220

Gly Ala Cys Cys Gly Ala Gly Gly Cys Gly Gly Cys Thr Gly Gly
225                 230                 235                 240

Cys Ala Gly Cys Ala Gly Cys Ala Cys Gly Gly Cys Ala Ala Gly Gly
                245                 250                 255

Gly Thr Gly Cys Gly Thr Cys Cys Ala Thr Cys Thr Gly Gly Gly Ala
            260                 265                 270

Thr Ala Cys Gly Thr Thr Cys Ala Cys Cys Ala Cys Cys Ala Cys
            275                 280                 285

Cys Cys Cys Cys Thr Gly Gly Cys Ala Cys Cys Cys Cys Gly Gly
290                 295                 300

Gly Ala Gly Ala Cys Thr Cys Cys Cys Gly Gly Ala Ala Cys Gly Cys
305                 310                 315                 320

Cys Ala Gly Thr Cys Thr Gly Cys Cys Gly Thr Gly Gly Gly Cys
            325                 330                 335

Gly Cys Cys Cys Cys Gly Thr Cys Gly Cys Cys Gly Cys Thr Gly Cys
            340                 345                 350

Ala Gly Cys Cys Cys Gly Cys Cys Ala Cys Cys Gly Gly Gly Ala
                355                 360                 365

Cys Gly Thr Ala Gly Cys Cys Ala Gly Cys Gly Ala Cys Ala Gly Cys
            370                 375                 380

Thr Ala Cys Ala Ala Cys Ala Ala Cys Gly Thr Cys Thr Thr Cys Cys
```

385 390 395 400

Gly Cys Gly Ala Cys Ala Cys Gly Gly Ala Gly Gly Cys Gly Cys Thr
405 410 415

Gly Cys Gly Cys Gly Ala Gly Cys Thr Cys Gly Gly Gly Gly Thr Cys
420 425 430

Ala Cys Thr Cys Ala Cys Thr Ala Cys Cys Gly Cys Thr Thr Cys Thr
435 440 445

Cys Cys Ala Thr Cys Thr Cys Gly Thr Gly Gly Gly Cys Gly Cys Gly
450 455 460

Ala Gly Thr Gly Cys Thr Cys Cys Cys Cys Ala Ala Thr Gly Gly Cys
465 470 475 480

Ala Gly Cys Gly Cys Gly Gly Gly Cys Gly Thr Cys Cys Cys Cys Ala
485 490 495

Ala Cys Cys Gly Cys Gly Ala Gly Gly Gly Gly Cys Thr Gly Cys Gly
500 505 510

Cys Thr Ala Cys Thr Ala Cys Cys Gly Gly Cys Gly Cys Cys Thr Gly
515 520 525

Cys Thr Gly Gly Ala Gly Cys Gly Gly Cys Thr Gly Cys Gly Gly Gly
530 535 540

Ala Gly Cys Thr Gly Gly Gly Cys Gly Thr Gly Cys Ala Gly Cys Cys
545 550 555 560

Cys Gly Thr Gly Gly Thr Cys Ala Cys Cys Cys Thr Gly Thr Ala Cys
565 570 575

Cys Ala Cys Thr Gly Gly Gly Ala Cys Cys Thr Gly Cys Cys Cys Cys
580 585 590

Ala Gly Cys Gly Cys Cys Thr Gly Cys Ala Gly Gly Ala Cys Gly Cys
595 600 605

Cys Thr Ala Cys Gly Gly Cys Gly Gly Cys Thr Gly Gly Gly Cys Cys
610 615 620

Ala Ala Cys Cys Gly Cys Gly Cys Cys Cys Thr Gly Gly Cys Cys Gly
625 630 635 640

Ala Cys Cys Ala Cys Thr Thr Cys Ala Gly Gly Gly Ala Thr Thr Ala
645 650 655

Cys Gly Cys Gly Gly Ala Gly Cys Thr Cys Thr Gly Cys Thr Thr Cys
660 665 670

Cys Gly Cys Cys Ala Cys Thr Thr Cys Gly Gly Cys Gly Gly Thr Cys
675 680 685

Ala Gly Gly Thr Cys Ala Ala Gly Thr Ala Cys Thr Gly Gly Ala Thr
690 695 700

Cys Ala Cys Cys Ala Thr Cys Gly Ala Cys Ala Ala Cys Cys Cys Cys
705 710 715 720

Thr Ala Cys Gly Thr Gly Gly Thr Gly Gly Cys Cys Thr Gly Gly Cys
725 730 735

Ala Cys Gly Gly Cys Thr Ala Cys Gly Cys Cys Ala Cys Cys Gly Gly
740 745 750

Gly Cys Gly Cys Cys Thr Gly Gly Cys Cys Cys Cys Cys Gly Gly Cys
755 760 765

Ala Thr Cys Cys Gly Gly Gly Gly Cys Ala Gly Cys Cys Cys Gly Cys
770 775 780

Gly Gly Cys Thr Cys Gly Gly Gly Thr Ala Cys Cys Thr Gly Gly Thr
785 790 795 800

Gly Gly Cys Gly Cys Ala Cys Ala Ala Cys Cys Thr Cys Cys Thr Cys
805 810 815

-continued

```
Cys Thr Gly Gly Cys Thr Cys Ala Thr Gly Cys Cys Ala Ala Ala Gly
                820                 825                 830
Thr Cys Thr Gly Gly Cys Ala Thr Thr Cys Thr Cys Thr Ala Cys Ala Ala
                835                 840                 845
Thr Ala Cys Thr Thr Cys Thr Thr Thr Cys Cys Gly Thr Cys Cys Cys
        850                 855                 860
Ala Cys Thr Cys Ala Gly Gly Ala Gly Gly Thr Cys Ala Gly Gly
865                 870                 875                 880
Thr Gly Thr Cys Ala Thr Thr Gly Cys Cys Thr Ala Ala Gly
            885                 890                 895
Cys Thr Cys Thr Cys Ala Cys Thr Gly Gly Ala Thr Cys Ala Ala Thr
                900                 905                 910
Cys Cys Thr Cys Gly Ala Ala Gly Ala Ala Thr Gly Ala Cys Cys Gly
            915                 920                 925
Ala Cys Cys Ala Cys Ala Gly Cys Ala Thr Cys Ala Ala Ala Gly Ala
        930                 935                 940
Ala Thr Gly Thr Cys Ala Ala Ala Ala Thr Cys Thr Cys Thr Gly
945                 950                 955                 960
Gly Ala Cys Thr Thr Thr Gly Thr Ala Cys Thr Ala Gly Gly Thr Thr
            965                 970                 975
Gly Gly Thr Thr Thr Gly Cys Cys Ala Ala Cys Cys Cys Gly Thr
                980                 985                 990
Ala Thr Thr Thr Ala Thr Thr Gly  Ala Thr Gly Gly Thr  Gly Ala Cys
        995                1000                1005
Thr Ala  Thr Cys Cys Cys Gly  Ala Gly Ala Gly Cys  Ala Thr Gly
    1010                1015                1020
Ala Ala  Gly Ala Ala Thr Ala  Ala Cys Cys Thr Thr  Thr Cys Ala
    1025                1030                1035
Thr Cys  Thr Ala Thr Thr Cys  Thr Gly Cys Cys Thr  Gly Ala Thr
    1040                1045                1050
Thr Thr  Thr Ala Cys Thr Gly  Ala Ala Thr Cys Thr  Gly Ala Gly
    1055                1060                1065
Ala Ala  Ala Ala Ala Gly Thr  Thr Cys Ala Thr Cys  Ala Ala Ala
    1070                1075                1080
Gly Gly  Ala Ala Cys Thr Gly  Cys Thr Gly Ala Cys  Thr Thr Thr
    1085                1090                1095
Thr Thr  Thr Gly Cys Thr Cys  Thr Thr Thr Gly Cys  Thr Thr Thr
    1100                1105                1110
Gly Gly  Ala Cys Cys Cys Ala  Cys Cys Thr Thr Gly  Ala Gly Thr
    1115                1120                1125
Thr Thr  Thr Cys Ala Ala Cys  Thr Thr Thr Thr Gly  Gly Ala Cys
    1130                1135                1140
Cys Cys  Thr Cys Ala Cys Ala  Thr Gly Ala Ala Gly  Thr Thr Cys
    1145                1150                1155
Cys Gly  Cys Cys Ala Ala Thr  Thr Gly Gly Ala Ala  Thr Cys Thr
    1160                1165                1170
Cys Cys  Cys Ala Ala Cys Cys  Thr Gly Ala Gly Gly  Cys Ala Ala
    1175                1180                1185
Cys Thr  Gly Cys Thr Thr Thr  Cys Cys Thr Gly Gly  Ala Thr Thr
    1190                1195                1200
Gly Ala  Cys Cys Thr Thr Gly  Ala Ala Thr Thr Thr  Ala Ala Cys
    1205                1210                1215
Cys Ala  Thr Cys Cys Thr Cys  Ala Ala Ala Thr Ala  Thr Thr Thr
    1220                1225                1230
```

Ala Thr Thr Gly Thr Gly Gly Ala Ala Ala Thr Gly Gly Cys
1235            1240                1245

Thr Gly Gly Thr Thr Thr Gly Thr Cys Thr Cys Ala Gly Gly Gly
1250            1255                1260

Ala Cys Cys Ala Cys Cys Ala Ala Gly Ala Gly Ala Gly Ala Thr
1265            1270                1275

Gly Ala Thr Gly Cys Cys Ala Ala Ala Thr Ala Thr Ala Thr Gly
1280            1285                1290

Thr Ala Thr Thr Ala Cys Cys Thr Cys Ala Ala Ala Ala Ala Gly
1295            1300                1305

Thr Thr Cys Ala Thr Cys Ala Thr Gly Gly Ala Ala Ala Cys Cys
1310            1315                1320

Thr Thr Ala Ala Ala Ala Gly Cys Cys Ala Thr Cys Ala Ala Gly
1325            1330                1335

Cys Thr Gly Gly Ala Thr Gly Gly Gly Thr Gly Gly Ala Thr
1340            1345                1350

Gly Thr Cys Ala Thr Cys Gly Gly Gly Thr Ala Thr Ala Cys Cys
1355            1360                1365

Gly Cys Ala Thr Gly Gly Thr Cys Cys Cys Thr Cys Ala Thr Gly
1370            1375                1380

Gly Ala Thr Gly Gly Thr Thr Thr Cys Gly Ala Gly Thr Gly Gly
1385            1390                1395

Cys Ala Cys Ala Gly Ala Gly Gly Thr Thr Ala Cys Ala Gly Cys
1400            1405                1410

Ala Thr Cys Ala Gly Gly Cys Gly Thr Gly Gly Ala Cys Thr Cys
1415            1420                1425

Thr Thr Cys Thr Ala Thr Gly Thr Thr Gly Ala Cys Thr Thr Thr
1430            1435                1440

Cys Thr Ala Ala Gly Cys Cys Ala Gly Gly Ala Cys Ala Ala Gly
1445            1450                1455

Ala Thr Gly Thr Thr Gly Thr Gly Cys Cys Ala Ala Ala Gly
1460            1465                1470

Thr Cys Thr Thr Cys Ala Gly Cys Cys Thr Thr Gly Thr Thr Cys
1475            1480                1485

Thr Ala Cys Cys Ala Ala Ala Ala Gly Cys Thr Gly Ala Thr Ala
1490            1495                1500

Gly Ala Gly Ala Ala Ala Ala Thr Gly Gly Cys Thr Thr Cys
1505            1510                1515

Cys Cys Thr Cys Cys Thr Thr Thr Ala Cys Cys Thr Gly Ala Ala
1520            1525                1530

Ala Ala Thr Cys Ala Gly Cys Cys Cys Cys Thr Ala Gly Ala Ala
1535            1540                1545

Gly Gly Gly Ala Cys Ala Thr Thr Thr Cys Cys Cys Thr Gly Thr
1550            1555                1560

Gly Ala Cys Thr Thr Thr Gly Cys Thr Cys Thr Gly Gly Gly Ala
1565            1570                1575

Gly Thr Thr Gly Thr Thr Gly Ala Cys Ala Ala Cys Thr Ala Cys
1580            1585                1590

Ala Thr Thr Cys Ala Ala Gly Thr Ala Gly Ala Thr Ala Cys Cys
1595            1600                1605

Ala Cys Thr Cys Thr Gly Cys Thr Cys Ala Gly Thr Thr Thr
1610            1615                1620

Ala Cys Cys Gly Ala Cys Cys Thr Gly Ala Ala Thr Gly Thr Thr

-continued

```
        1625                1630                1635

Thr Ala Cys Cys Thr Gly Thr Gly Gly Ala Thr Gly Thr Cys
        1640                1645                1650

Cys Ala Cys Cys Ala Cys Ala Gly Thr Ala Ala Ala Gly Gly
        1655                1660                1665

Cys Thr Thr Ala Thr Thr Ala Ala Ala Gly Thr Gly Gly Ala Thr
        1670                1675                1680

Gly Gly Gly Gly Thr Thr Gly Thr Gly Ala Cys Cys Ala Ala Gly
        1685                1690                1695

Ala Ala Gly Ala Gly Gly Ala Ala Ala Thr Cys Cys Thr Ala Cys
        1700                1705                1710

Thr Gly Thr Gly Thr Thr Gly Ala Cys Thr Thr Gly Cys Thr
        1715                1720                1725

Gly Cys Cys Ala Thr Cys Cys Ala Gly Cys Cys Cys Cys Ala Gly
        1730                1735                1740

Ala Thr Cys Gly Cys Thr Thr Thr Ala Cys Thr Cys Cys Ala Gly
        1745                1750                1755

Gly Ala Ala Ala Thr Gly Cys Ala Cys Gly Thr Ala Cys Ala
        1760                1765                1770

Cys Ala Thr Thr Thr Thr Cys Gly Cys Thr Thr Cys Thr Cys Cys
        1775                1780                1785

Cys Thr Gly Gly Ala Cys Thr Gly Gly Gly Cys Cys Cys Thr Gly
        1790                1795                1800

Ala Thr Thr Cys Thr Cys Cys Cys Thr Cys Thr Gly Gly Gly Thr
        1805                1810                1815

Ala Ala Cys Cys Ala Gly Thr Cys Cys Ala Gly Gly Thr Gly
        1820                1825                1830

Ala Ala Cys Cys Ala Cys Ala Cys Cys Ala Thr Cys Cys Thr Gly
        1835                1840                1845

Cys Ala Gly Thr Ala Cys Thr Ala Thr Cys Gly Cys Thr Gly Cys
        1850                1855                1860

Ala Thr Gly Gly Cys Cys Ala Gly Cys Gly Ala Gly Cys Thr Thr
        1865                1870                1875

Gly Thr Cys Cys Gly Thr Gly Thr Cys Ala Ala Cys Ala Thr Cys
        1880                1885                1890

Ala Cys Cys Cys Ala Gly Thr Gly Gly Thr Gly Gly Cys Cys
        1895                1900                1905

Cys Thr Gly Thr Gly Gly Cys Ala Gly Cys Cys Thr Ala Thr Gly
        1910                1915                1920

Gly Cys Cys Cys Cys Gly Ala Ala Cys Cys Ala Ala Gly Gly Ala
        1925                1930                1935

Cys Thr Gly Cys Cys Gly Cys Gly Cys Cys Thr Cys Cys Thr Gly
        1940                1945                1950

Gly Cys Cys Ala Gly Gly Cys Ala Gly Gly Cys Gly Cys Cys
        1955                1960                1965

Thr Gly Gly Gly Ala Gly Ala Ala Cys Cys Cys Thr Ala Cys
        1970                1975                1980

Ala Cys Thr Gly Cys Cys Thr Gly Gly Cys Cys Thr Thr Thr
        1985                1990                1995

Gly Cys Ala Gly Ala Gly Thr Ala Thr Gly Cys Cys Gly Ala
        2000                2005                2010

Cys Thr Gly Thr Gly Cys Thr Thr Cys Ala Ala Gly Ala Gly
        2015                2020                2025
```

```
Cys Thr Cys Gly Gly Cys Cys Ala Thr Cys Ala Cys Gly Thr Cys
    2030                2035                2040

Ala Ala Gly Cys Thr Thr Thr Gly Gly Ala Thr Ala Ala Cys Gly
    2045                2050                2055

Ala Thr Gly Ala Ala Thr Gly Ala Gly Cys Cys Gly Thr Ala Thr
    2060                2065                2070

Ala Cys Ala Ala Gly Gly Ala Ala Thr Ala Thr Gly Ala Cys Ala
    2075                2080                2085

Thr Ala Cys Ala Gly Thr Gly Cys Thr Gly Gly Cys Cys Ala Cys
    2090                2095                2100

Ala Ala Cys Cys Thr Thr Cys Thr Gly Ala Ala Gly Gly Cys Cys
    2105                2110                2115

Cys Ala Thr Gly Cys Cys Cys Thr Gly Gly Cys Thr Thr Gly Gly
    2120                2125                2130

Cys Ala Thr Gly Thr Gly Thr Ala Cys Ala Ala Thr Gly Ala Ala
    2135                2140                2145

Ala Ala Gly Thr Thr Thr Ala Gly Gly Cys Ala Thr Gly Cys Thr
    2150                2155                2160

Cys Ala Gly Ala Ala Thr Gly Gly Ala Ala Ala Ala Thr Ala
    2165                2170                2175

Thr Cys Cys Ala Thr Ala Gly Cys Cys Thr Thr Gly Cys Ala Gly
    2180                2185                2190

Gly Cys Thr Gly Ala Thr Thr Gly Gly Ala Thr Ala Gly Ala Ala
    2195                2200                2205

Cys Cys Thr Gly Cys Cys Thr Gly Cys Cys Cys Thr Thr Thr Cys
    2210                2215                2220

Thr Cys Cys Cys Ala Ala Ala Ala Gly Gly Ala Cys Ala Ala Ala
    2225                2230                2235

Gly Ala Gly Gly Thr Gly Gly Cys Cys Gly Ala Gly Ala Gly Ala
    2240                2245                2250

Gly Thr Thr Thr Thr Gly Gly Ala Ala Thr Thr Thr Gly Ala Cys
    2255                2260                2265

Ala Thr Thr Gly Gly Cys Thr Gly Gly Cys Thr Gly Gly Cys Thr
    2270                2275                2280

Gly Ala Gly Cys Cys Cys Ala Thr Thr Thr Thr Cys Gly Gly Cys
    2285                2290                2295

Thr Cys Thr Gly Gly Ala Gly Ala Thr Thr Ala Thr Cys Cys Ala
    2300                2305                2310

Thr Gly Gly Gly Thr Gly Ala Thr Gly Ala Gly Gly Gly Ala Cys
    2315                2320                2325

Thr Gly Gly Cys Thr Gly Ala Ala Cys Cys Ala Ala Ala Gly Ala
    2330                2335                2340

Ala Ala Cys Ala Ala Thr Thr Thr Cys Thr Thr Cys Thr Thr Thr
    2345                2350                2355

Cys Cys Thr Thr Ala Thr Thr Thr Cys Ala Cys Thr Gly Ala Ala
    2360                2365                2370

Gly Ala Thr Gly Ala Ala Ala Ala Ala Ala Gly Cys Thr Ala
    2375                2380                2385

Ala Thr Cys Cys Ala Gly Gly Gly Thr Ala Cys Cys Thr Thr Thr
    2390                2395                2400

Gly Ala Cys Thr Thr Thr Thr Gly Gly Cys Thr Thr Thr Ala
    2405                2410                2415

Ala Gly Cys Cys Ala Thr Thr Ala Thr Ala Cys Cys Ala Cys Cys
    2420                2425                2430
```

```
Ala Thr Cys Cys Thr Thr Gly Thr Ala Gly Ala Cys Thr Cys Ala
    2435                2440                2445
Gly Ala Ala Ala Ala Ala Gly Ala Ala Gly Ala Thr Cys Cys Ala
    2450                2455                2460
Ala Thr Ala Ala Ala Ala Thr Ala Cys Ala Ala Thr Gly Ala Thr
    2465                2470                2475
Thr Ala Cys Cys Thr Ala Gly Ala Ala Gly Thr Gly Cys Ala Ala
    2480                2485                2490
Gly Ala Ala Ala Thr Gly Ala Cys Cys Gly Ala Cys Ala Thr Cys
    2495                2500                2505
Ala Cys Gly Thr Gly Gly Cys Thr Cys Ala Ala Cys Thr Cys Cys
    2510                2515                2520
Cys Cys Cys Ala Gly Thr Cys Ala Gly Gly Thr Gly Gly Cys Gly
    2525                2530                2535
Gly Thr Ala Gly Thr Gly Cys Cys Cys Thr Gly Gly Gly Gly Gly
    2540                2545                2550
Thr Thr Gly Cys Gly Cys Ala Ala Ala Gly Thr Gly Cys Thr Gly
    2555                2560                2565
Ala Ala Cys Thr Gly Gly Cys Thr Gly Ala Ala Gly Thr Thr Cys
    2570                2575                2580
Ala Ala Gly Thr Ala Cys Gly Gly Ala Gly Ala Cys Cys Thr Cys
    2585                2590                2595
Cys Cys Cys Ala Thr Gly Thr Ala Cys Ala Thr Ala Ala Thr Ala
    2600                2605                2610
Thr Cys Cys Ala Ala Cys Gly Gly Ala Ala Thr Cys Gly Ala Thr
    2615                2620                2625
Gly Ala Cys Gly Gly Gly Cys Thr Gly Cys Ala Thr Gly Cys Thr
    2630                2635                2640
Gly Ala Gly Gly Ala Cys Gly Ala Cys Cys Ala Gly Cys Thr Gly
    2645                2650                2655
Ala Gly Gly Gly Thr Gly Thr Ala Thr Thr Ala Thr Ala Thr Gly
    2660                2665                2670
Cys Ala Gly Ala Ala Thr Thr Ala Cys Ala Thr Ala Ala Ala Cys
    2675                2680                2685
Gly Ala Ala Gly Cys Thr Cys Thr Cys Ala Ala Ala Gly Cys Cys
    2690                2695                2700
Cys Ala Cys Ala Thr Ala Cys Thr Gly Gly Ala Thr Gly Gly Thr
    2705                2710                2715
Ala Thr Cys Ala Ala Thr Cys Thr Thr Thr Gly Cys Gly Gly Ala
    2720                2725                2730
Thr Ala Cys Thr Thr Thr Gly Cys Thr Thr Ala Thr Thr Cys Gly
    2735                2740                2745
Thr Thr Thr Ala Ala Cys Gly Ala Cys Cys Gly Cys Ala Cys Ala
    2750                2755                2760
Gly Cys Thr Cys Cys Gly Ala Gly Gly Thr Thr Gly Gly Cys
    2765                2770                2775
Cys Thr Cys Thr Ala Thr Cys Gly Thr Thr Ala Thr Gly Cys Thr
    2780                2785                2790
Gly Cys Ala Gly Ala Thr Cys Ala Gly Thr Thr Thr Gly Ala Gly
    2795                2800                2805
Cys Cys Cys Ala Ala Gly Gly Cys Ala Thr Cys Cys Ala Thr Gly
    2810                2815                2820
Ala Ala Ala Cys Ala Thr Thr Ala Cys Ala Gly Gly Ala Ala Ala
```

-continued

```
                    2825                2830                2835

Ala Thr Thr Ala Thr Thr Gly Ala Cys Ala Gly Cys  Ala Ala Thr
    2840                2845                2850

Gly Gly Thr Thr Thr Cys Cys Cys Gly Gly Cys  Cys Cys Ala
    2855                2860                2865

Gly Ala Ala Ala Cys Thr Cys  Thr Gly Gly Ala Ala  Ala Gly Ala
    2870                2875                2880

Thr Thr Thr Thr Gly Thr Cys  Cys Ala Gly Ala Ala  Gly Ala Ala
    2885                2890                2895

Thr Thr Cys Ala Cys Cys Gly  Thr Gly Thr Gly Thr  Ala Cys Thr
    2900                2905                2910

Gly Ala Gly Thr Gly Cys Ala  Gly Thr Thr Thr  Thr Thr Thr
    2915                2920                2925

Cys Ala Cys Ala Cys Cys  Gly Ala Ala Ala Gly  Thr Cys Thr
    2930                2935                2940

Thr Thr Ala Gly Gly Ala Thr  Cys Cys Gly Gly Ala  Gly Gly Thr
    2945                2950                2955

Gly Gly Ala Gly Gly Thr Thr  Cys Ala Gly Gly Ala  Gly Gly Thr
    2960                2965                2970

Gly Gly Ala Gly Gly Thr Thr  Cys Ala Gly Gly Ala  Gly Gly Thr
    2975                2980                2985

Gly Gly Ala Gly Gly Thr Thr  Cys Ala Cys Thr Thr  Ala Ala Gly
    2990                2995                3000

Thr Ala Thr Cys Cys Cys Ala  Ala Thr Gly Cys Cys  Thr Cys Cys
    3005                3010                3015

Cys Cys Ala Cys Thr Gly Cys  Thr Cys Gly Gly Cys  Thr Cys Cys
    3020                3025                3030

Ala Gly Cys Thr Gly Gly Gly  Gly Thr Gly Gly Cys  Cys Thr Gly
    3035                3040                3045

Ala Thr Cys Cys Ala Cys Cys  Thr Gly Thr Ala Cys  Ala Cys Ala
    3050                3055                3060

Gly Cys Cys Ala Cys Ala Gly  Cys Cys Ala Gly Ala  Ala Ala Cys
    3065                3070                3075

Ala Gly Cys Thr Ala Cys Cys  Ala Cys Cys Thr Gly  Cys Ala Gly
    3080                3085                3090

Ala Thr Cys Cys Ala Cys Ala  Ala Gly Ala Ala Thr  Gly Gly Cys
    3095                3100                3105

Cys Ala Thr Gly Thr Gly Gly  Ala Thr Gly Gly Cys  Gly Cys Ala
    3110                3115                3120

Cys Cys Cys Cys Ala Thr Cys  Ala Gly Ala Cys Cys  Ala Thr Cys
    3125                3130                3135

Thr Ala Cys Ala Gly Thr Gly  Cys Cys Cys Thr Gly  Ala Thr Gly
    3140                3145                3150

Ala Thr Cys Ala Gly Ala Thr  Cys Ala Gly Ala Gly  Gly Ala Thr
    3155                3160                3165

Gly Cys Thr Gly Gly Cys Thr  Thr Thr Gly Thr Gly  Gly Thr Gly
    3170                3175                3180

Ala Thr Thr Ala Cys Ala Gly  Gly Thr Gly Thr Gly  Ala Thr Gly
    3185                3190                3195

Ala Gly Cys Ala Gly Ala Ala  Gly Ala Thr Ala Cys  Cys Thr Cys
    3200                3205                3210

Thr Gly Cys Ala Thr Gly Gly  Ala Thr Thr Thr Cys  Ala Gly Ala
    3215                3220                3225
```

```
Gly Gly Cys Ala Ala Cys Ala Thr Thr Thr Thr Gly Gly Ala
    3230             3235             3240

Thr Cys Ala Cys Ala Cys Thr Ala Thr Thr Cys Gly Ala Cys
    3245             3250             3255

Cys Cys Gly Gly Ala Gly Ala Ala Cys Thr Gly Cys Ala Gly Gly
    3260             3265             3270

Thr Thr Cys Cys Ala Ala Cys Ala Cys Ala Gly Ala Cys Gly
    3275             3280             3285

Cys Thr Gly Gly Ala Ala Ala Cys Gly Gly Gly Thr Ala Cys
    3290             3295             3300

Gly Ala Cys Gly Thr Cys Thr Ala Cys Cys Ala Cys Thr Cys Thr
    3305             3310             3315

Cys Cys Thr Cys Ala Gly Thr Ala Thr Cys Ala Cys Thr Thr Cys
    3320             3325             3330

Cys Thr Gly Gly Thr Cys Ala Gly Thr Cys Thr Gly Gly Gly Cys
    3335             3340             3345

Cys Gly Gly Gly Cys Gly Ala Ala Gly Ala Gly Ala Gly Cys Cys
    3350             3355             3360

Thr Thr Cys Cys Thr Gly Cys Cys Ala Gly Gly Cys Ala Thr Gly
    3365             3370             3375

Ala Ala Cys Cys Cys Ala Cys Cys Cys Cys Gly Thr Ala Cys
    3380             3385             3390

Thr Cys Cys Cys Ala Gly Thr Thr Cys Cys Thr Gly Thr Cys Cys
    3395             3400             3405

Cys Gly Gly Ala Gly Gly Ala Ala Cys Gly Ala Gly Ala Thr Cys
    3410             3415             3420

Cys Cys Cys Cys Thr Ala Ala Thr Thr Cys Ala Cys Thr Thr Cys
    3425             3430             3435

Ala Ala Cys Ala Cys Cys Cys Cys Ala Thr Ala Cys Cys Ala
    3440             3445             3450

Cys Gly Gly Cys Gly Gly Cys Ala Cys Ala Cys Cys Cys Ala Gly
    3455             3460             3465

Ala Gly Cys Gly Cys Cys Gly Ala Gly Gly Ala Cys Gly Ala Cys
    3470             3475             3480

Thr Cys Gly Gly Ala Gly Cys Gly Gly Gly Ala Cys Cys Cys Cys
    3485             3490             3495

Cys Thr Gly Ala Ala Cys Gly Thr Gly Cys Thr Gly Ala Ala Gly
    3500             3505             3510

Cys Cys Cys Cys Gly Gly Gly Cys Cys Cys Gly Gly Ala Thr Gly
    3515             3520             3525

Ala Cys Cys Cys Cys Gly Gly Cys Cys Cys Cys Gly Gly Cys Cys
    3530             3535             3540

Thr Cys Cys Thr Gly Thr Cys Ala Cys Ala Gly Gly Ala Gly
    3545             3550             3555

Cys Thr Cys Cys Cys Gly Ala Gly Cys Gly Cys Cys Gly Ala Gly
    3560             3565             3570

Gly Ala Cys Ala Ala Cys Ala Gly Cys Cys Cys Gly Ala Thr Gly
    3575             3580             3585

Gly Cys Cys Ala Gly Thr Gly Ala Cys Cys Cys Ala Thr Thr Ala
    3590             3595             3600

Gly Gly Gly Gly Thr Gly Gly Thr Cys Ala Gly Gly Gly Gly Cys
    3605             3610             3615

Gly Gly Thr Cys Gly Ala Gly Thr Gly Ala Ala Cys Ala Cys Gly
    3620             3625             3630
```

```
Cys Ala  Cys Gly Cys Thr Gly  Gly Gly Gly Ala  Ala Cys Gly
    3635             3640              3645

Gly Gly  Cys Cys Cys Gly Gly  Ala Ala Gly Cys  Thr Gly Cys
    3650             3655              3660

Cys Gly  Cys Cys Cys Cys Thr  Thr Cys Gly Cys  Cys Ala Ala Gly
    3665             3670              3675

Thr Thr  Cys Ala Thr Cys Gly  Gly Ala Gly Gly  Thr Gly Gly Ala
    3680             3685              3690

Gly Gly  Thr Thr Cys Ala Gly  Cys Cys Cys Cys  Ala Gly Ala Ala
    3695             3700              3705

Gly Cys  Ala Gly Cys Ala Gly  Gly Thr Gly Gly  Thr Cys Cys Ala
    3710             3715              3720

Thr Cys  Ala Gly Thr Thr Thr  Thr Thr Cys Thr  Thr Thr Thr Cys
    3725             3730              3735

Cys Cys  Thr Cys Cys Ala Ala  Ala Cys Cys Cys  Ala Ala Gly
    3740             3745              3750

Gly Ala  Thr Ala Cys Gly Cys  Thr Gly Ala Thr  Gly Ala Thr Cys
    3755             3760              3765

Thr Cys  Thr Cys Gly Cys Ala  Cys Gly Cys Cys  Thr Gly Ala Gly
    3770             3775              3780

Gly Thr  Gly Ala Cys Ala Thr  Gly Cys Gly Thr  Cys Gly Thr Ala
    3785             3790              3795

Gly Thr  Ala Gly Ala Cys Gly  Thr Gly Ala Gly  Cys Cys Ala Cys
    3800             3805              3810

Gly Ala  Ala Gly Ala Thr Cys  Cys Cys Gly Ala Gly  Gly Thr Gly
    3815             3820              3825

Ala Ala  Gly Thr Thr Cys Ala  Ala Thr Thr Gly Gly  Thr Ala Thr
    3830             3835              3840

Gly Thr  Gly Gly Ala Cys Gly  Gly Ala Gly Thr Ala  Gly Ala Ala
    3845             3850              3855

Gly Thr  Gly Cys Ala Thr Ala  Ala Cys Gly Cys Gly  Ala Ala Ala
    3860             3865              3870

Ala Cys  Thr Ala Ala Gly Cys  Cys Gly Cys Gly  Cys Gly Ala Gly
    3875             3880              3885

Gly Ala  Ala Cys Ala Ala Thr  Ala Thr Ala Cys  Ala Gly Thr
    3890             3895              3900

Ala Cys  Thr Thr Ala Cys Ala  Gly Gly Gly Thr Gly  Gly Thr Ala
    3905             3910              3915

Thr Cys  Cys Gly Thr Gly Cys  Thr Cys Ala Cys  Ala Gly Thr Cys
    3920             3925              3930

Cys Thr  Gly Cys Ala Cys Cys  Ala Gly Gly Ala Cys  Thr Gly Gly
    3935             3940              3945

Cys Thr  Gly Ala Ala Cys Gly  Gly Thr Ala Ala Gly  Gly Ala Ala
    3950             3955              3960

Thr Ala  Cys Ala Ala Gly Thr  Gly Cys Ala Ala Ala  Gly Thr Ala
    3965             3970              3975

Ala Gly  Cys Ala Ala Cys Ala  Ala Gly Gly Cys Ala  Cys Thr Thr
    3980             3985              3990

Cys Cys  Cys Gly Cys Gly Cys  Cys Thr Ala Thr Thr  Gly Ala Gly
    3995             4000              4005

Ala Ala  Ala Ala Cys Ala Ala  Thr Cys Thr Cys  Ala Ala Gly
    4010             4015              4020

Gly Cys  Gly Ala Ala Gly Gly  Gly Ala Cys Ala Ala  Cys Cys Ala
```

-continued

```
                4025                4030                4035

Ala Gly Ala Gly Ala Ala Cys Cys Thr Cys Ala Gly Gly Thr Thr
        4040                4045                4050

Thr Ala Cys Ala Cys Thr Cys Thr Cys Cys Gly Cys Cys Thr
        4055                4060                4065

Thr Cys Cys Ala Gly Gly Gly Ala Ala Gly Ala Gly Ala Thr Gly
        4070                4075                4080

Ala Cys Cys Ala Ala Ala Ala Thr Cys Ala Ala Gly Thr Thr
        4085                4090                4095

Thr Cys Cys Cys Thr Gly Ala Cys Thr Thr Gly Cys Cys Thr Cys
        4100                4105                4110

Gly Thr Cys Ala Ala Ala Gly Gly Ala Thr Thr Cys Thr Ala Cys
        4115                4120                4125

Cys Cys Thr Thr Cys Cys Gly Ala Cys Ala Thr Thr Gly Cys Thr
        4130                4135                4140

Gly Thr Thr Gly Ala Ala Thr Gly Gly Gly Ala Ala Ala Gly Cys
        4145                4150                4155

Ala Ala Thr Gly Gly Ala Cys Ala Ala Cys Cys Ala Gly Ala Gly
        4160                4165                4170

Ala Ala Cys Ala Ala Cys Thr Ala Cys Ala Ala Gly Ala Cys Ala
        4175                4180                4185

Ala Cys Ala Cys Cys Cys Cys Cys Gly Gly Thr Gly Cys Thr Gly
        4190                4195                4200

Gly Ala Thr Ala Gly Thr Gly Ala Cys Gly Gly Ala Thr Cys Thr
        4205                4210                4215

Thr Thr Cys Thr Thr Thr Cys Thr Cys Thr Ala Cys Thr Cys Ala
        4220                4225                4230

Ala Ala Gly Cys Thr Gly Ala Cys Cys Gly Thr Gly Gly Ala Thr
        4235                4240                4245

Ala Ala Gly Thr Cys Cys Ala Gly Gly Thr Gly Gly Cys Ala Gly
        4250                4255                4260

Cys Ala Gly Gly Gly Ala Ala Ala Cys Gly Thr Gly Thr Thr Thr
        4265                4270                4275

Thr Cys Cys Thr Gly Cys Thr Cys Thr Gly Thr Cys Ala Thr Gly
        4280                4285                4290

Cys Ala Thr Gly Ala Ala Gly Cys Gly Cys Thr Gly Cys Ala Thr
        4295                4300                4305

Ala Ala Thr Cys Ala Cys Thr Ala Thr Ala Cys Cys Ala Gly
        4310                4315                4320

Ala Ala Gly Thr Cys Thr Cys Thr Gly Ala Gly Cys Thr Thr Gly
        4325                4330                4335

Ala Gly Cys Cys Cys Ala Gly Gly Cys Ala Ala Gly Thr Ala Ala
        4340                4345                4350

<210> SEQ ID NO 49
<211> LENGTH: 1450
<212> TYPE: PRT
<213> ORGANISM: Artificial
<220> FEATURE:
<223> OTHER INFORMATION: fusion peptide derived from human

<400> SEQUENCE: 49

Met Pro Ala Ser Ala Pro Pro Arg Arg Pro Arg Pro Pro Pro Ser
1               5                   10                  15

Leu Ser Leu Leu Leu Val Leu Leu Gly Leu Gly Gly Arg Arg Leu Arg
                20                  25                  30
```

```
Ala Glu Pro Gly Asp Gly Ala Gln Thr Trp Ala Arg Phe Ser Arg Pro
         35                  40                  45

Pro Ala Pro Glu Ala Ala Gly Leu Phe Gln Gly Thr Phe Pro Asp Gly
     50                  55                  60

Phe Leu Trp Ala Val Gly Ser Ala Ala Tyr Gln Thr Glu Gly Gly Trp
 65                  70                  75                  80

Gln Gln His Gly Lys Gly Ala Ser Ile Trp Asp Thr Phe Thr His His
                 85                  90                  95

Pro Leu Ala Pro Pro Gly Asp Ser Arg Asn Ala Ser Leu Pro Leu Gly
             100                 105                 110

Ala Pro Ser Pro Leu Gln Pro Ala Thr Gly Asp Val Ala Ser Asp Ser
         115                 120                 125

Tyr Asn Asn Val Phe Arg Asp Thr Glu Ala Leu Arg Glu Leu Gly Val
     130                 135                 140

Thr His Tyr Arg Phe Ser Ile Ser Trp Ala Arg Val Leu Pro Asn Gly
145                 150                 155                 160

Ser Ala Gly Val Pro Asn Arg Glu Gly Leu Arg Tyr Tyr Arg Arg Leu
                 165                 170                 175

Leu Glu Arg Leu Arg Glu Leu Gly Val Gln Pro Val Val Thr Leu Tyr
             180                 185                 190

His Trp Asp Leu Pro Gln Arg Leu Gln Asp Ala Tyr Gly Gly Trp Ala
         195                 200                 205

Asn Arg Ala Leu Ala Asp His Phe Arg Asp Tyr Ala Glu Leu Cys Phe
     210                 215                 220

Arg His Phe Gly Gly Gln Val Lys Tyr Trp Ile Thr Ile Asp Asn Pro
225                 230                 235                 240

Tyr Val Val Ala Trp His Gly Tyr Ala Thr Gly Arg Leu Ala Pro Gly
                 245                 250                 255

Ile Arg Gly Ser Pro Arg Leu Gly Tyr Leu Val Ala His Asn Leu Leu
             260                 265                 270

Leu Ala His Ala Lys Val Trp His Leu Tyr Asn Thr Ser Phe Arg Pro
         275                 280                 285

Thr Gln Gly Gly Gln Val Ser Ile Ala Leu Ser Ser His Trp Ile Asn
     290                 295                 300

Pro Arg Arg Met Thr Asp His Ser Ile Lys Glu Cys Gln Lys Ser Leu
305                 310                 315                 320

Asp Phe Val Leu Gly Trp Phe Ala Lys Pro Val Phe Ile Asp Gly Asp
                 325                 330                 335

Tyr Pro Glu Ser Met Lys Asn Asn Leu Ser Ser Ile Leu Pro Asp Phe
             340                 345                 350

Thr Glu Ser Glu Lys Lys Phe Ile Lys Gly Thr Ala Asp Phe Phe Ala
         355                 360                 365

Leu Cys Phe Gly Pro Thr Leu Ser Phe Gln Leu Leu Asp Pro His Met
     370                 375                 380

Lys Phe Arg Gln Leu Glu Ser Pro Asn Leu Arg Gln Leu Leu Ser Trp
385                 390                 395                 400

Ile Asp Leu Glu Phe Asn His Pro Gln Ile Phe Ile Val Glu Asn Gly
                 405                 410                 415

Trp Phe Val Ser Gly Thr Thr Lys Arg Asp Asp Ala Lys Tyr Met Tyr
             420                 425                 430

Tyr Leu Lys Lys Phe Ile Met Glu Thr Leu Lys Ala Ile Lys Leu Asp
         435                 440                 445

Gly Val Asp Val Ile Gly Tyr Thr Ala Trp Ser Leu Met Asp Gly Phe
```

```
                450                 455                 460
Glu Trp His Arg Gly Tyr Ser Ile Arg Arg Gly Leu Phe Tyr Val Asp
465                 470                 475                 480

Phe Leu Ser Gln Asp Lys Met Leu Leu Pro Lys Ser Ser Ala Leu Phe
                485                 490                 495

Tyr Gln Lys Leu Ile Glu Lys Asn Gly Phe Pro Pro Leu Pro Glu Asn
                500                 505                 510

Gln Pro Leu Glu Gly Thr Phe Pro Cys Asp Phe Ala Trp Gly Val Val
                515                 520                 525

Asp Asn Tyr Ile Gln Val Asp Thr Thr Leu Ser Gln Phe Thr Asp Leu
530                 535                 540

Asn Val Tyr Leu Trp Asp Val His His Ser Lys Arg Leu Ile Lys Val
545                 550                 555                 560

Asp Gly Val Val Thr Lys Lys Arg Lys Ser Tyr Cys Val Asp Phe Ala
                565                 570                 575

Ala Ile Gln Pro Gln Ile Ala Leu Leu Gln Glu Met His Val Thr His
                580                 585                 590

Phe Arg Phe Ser Leu Asp Trp Ala Leu Ile Leu Pro Leu Gly Asn Gln
                595                 600                 605

Ser Gln Val Asn His Thr Ile Leu Gln Tyr Tyr Arg Cys Met Ala Ser
610                 615                 620

Glu Leu Val Arg Val Asn Ile Thr Pro Val Val Ala Leu Trp Gln Pro
625                 630                 635                 640

Met Ala Pro Asn Gln Gly Leu Pro Arg Leu Leu Ala Arg Gln Gly Ala
                645                 650                 655

Trp Glu Asn Pro Tyr Thr Ala Leu Ala Phe Ala Glu Tyr Ala Arg Leu
                660                 665                 670

Cys Phe Gln Glu Leu Gly His His Val Lys Leu Trp Ile Thr Met Asn
                675                 680                 685

Glu Pro Tyr Thr Arg Asn Met Thr Tyr Ser Ala Gly His Asn Leu Leu
                690                 695                 700

Lys Ala His Ala Leu Ala Trp His Val Tyr Asn Glu Lys Phe Arg His
705                 710                 715                 720

Ala Gln Asn Gly Lys Ile Ser Ile Ala Leu Gln Ala Asp Trp Ile Glu
                725                 730                 735

Pro Ala Cys Pro Phe Ser Gln Lys Lys Glu Val Ala Glu Arg Val
                740                 745                 750

Leu Glu Phe Asp Ile Gly Trp Leu Ala Glu Pro Ile Phe Gly Ser Gly
                755                 760                 765

Asp Tyr Pro Trp Val Met Arg Asp Trp Leu Asn Gln Arg Asn Asn Phe
770                 775                 780

Leu Leu Pro Tyr Phe Thr Glu Asp Glu Lys Lys Leu Ile Gln Gly Thr
785                 790                 795                 800

Phe Asp Phe Leu Ala Leu Ser His Tyr Thr Thr Ile Leu Val Asp Ser
                805                 810                 815

Glu Lys Glu Asp Pro Ile Lys Tyr Asn Asp Tyr Leu Glu Val Gln Glu
                820                 825                 830

Met Thr Asp Ile Thr Trp Leu Asn Ser Pro Ser Gln Val Ala Val Val
                835                 840                 845

Pro Trp Gly Leu Arg Lys Val Leu Asn Trp Leu Lys Phe Lys Tyr Gly
                850                 855                 860

Asp Leu Pro Met Tyr Ile Ile Ser Asn Gly Ile Asp Asp Gly Leu His
865                 870                 875                 880
```

```
Ala Glu Asp Asp Gln Leu Arg Val Tyr Tyr Met Gln Asn Tyr Ile Asn
            885                 890                 895

Glu Ala Leu Lys Ala His Ile Leu Asp Gly Ile Asn Leu Cys Gly Tyr
        900                 905                 910

Phe Ala Tyr Ser Phe Asn Asp Arg Thr Ala Pro Arg Phe Gly Leu Tyr
        915                 920                 925

Arg Tyr Ala Ala Asp Gln Phe Glu Pro Lys Ala Ser Met Lys His Tyr
        930                 935                 940

Arg Lys Ile Ile Asp Ser Asn Gly Phe Pro Gly Pro Glu Thr Leu Glu
945                 950                 955                 960

Arg Phe Cys Pro Glu Glu Phe Thr Val Cys Thr Glu Cys Ser Phe Phe
                965                 970                 975

His Thr Arg Lys Ser Leu Gly Ser Gly Gly Gly Ser Gly Gly Gly
            980                 985                 990

Gly Ser Gly Gly Gly Gly Ser Leu Lys Tyr Pro Asn Ala Ser Pro Leu
        995                 1000                1005

Leu Gly Ser Ser Trp Gly Gly Leu Ile His Leu Tyr Thr Ala Thr
    1010                1015                1020

Ala Arg Asn Ser Tyr His Leu Gln Ile His Lys Asn Gly His Val
    1025                1030                1035

Asp Gly Ala Pro His Gln Thr Ile Tyr Ser Ala Leu Met Ile Arg
    1040                1045                1050

Ser Glu Asp Ala Gly Phe Val Val Ile Thr Gly Val Met Ser Arg
    1055                1060                1065

Arg Tyr Leu Cys Met Asp Phe Arg Gly Asn Ile Phe Gly Ser His
    1070                1075                1080

Tyr Phe Asp Pro Glu Asn Cys Arg Phe Gln His Gln Thr Leu Glu
    1085                1090                1095

Asn Gly Tyr Asp Val Tyr His Ser Pro Gln Tyr His Phe Leu Val
    1100                1105                1110

Ser Leu Gly Arg Ala Lys Arg Ala Phe Leu Pro Gly Met Asn Pro
    1115                1120                1125

Pro Pro Tyr Ser Gln Phe Leu Ser Arg Arg Asn Glu Ile Pro Leu
    1130                1135                1140

Ile His Phe Asn Thr Pro Ile Pro Arg Arg His Thr Gln Ser Ala
    1145                1150                1155

Glu Asp Asp Ser Glu Arg Asp Pro Leu Asn Val Leu Lys Pro Arg
    1160                1165                1170

Ala Arg Met Thr Pro Ala Pro Ala Ser Cys Ser Gln Glu Leu Pro
    1175                1180                1185

Ser Ala Glu Asp Asn Ser Pro Met Ala Ser Asp Pro Leu Gly Val
    1190                1195                1200

Val Arg Gly Gly Arg Val Asn Thr His Ala Gly Gly Thr Gly Pro
    1205                1210                1215

Glu Gly Cys Arg Pro Phe Ala Lys Phe Ile Gly Gly Gly Gly Ser
    1220                1225                1230

Ala Pro Glu Ala Ala Gly Gly Pro Ser Val Phe Leu Phe Pro Pro
    1235                1240                1245

Lys Pro Lys Asp Thr Leu Met Ile Ser Arg Thr Pro Glu Val Thr
    1250                1255                1260

Cys Val Val Val Asp Val Ser His Glu Asp Pro Glu Val Lys Phe
    1265                1270                1275

Asn Trp Tyr Val Asp Gly Val Glu Val His Asn Ala Lys Thr Lys
    1280                1285                1290
```

```
Pro Arg Glu Glu Gln Tyr Asn Ser Thr Tyr Arg Val Val Ser Val
    1295                1300                1305

Leu Thr Val Leu His Gln Asp Trp Leu Asn Gly Lys Glu Tyr Lys
    1310                1315                1320

Cys Lys Val Ser Asn Lys Ala Leu Pro Ala Pro Ile Glu Lys Thr
    1325                1330                1335

Ile Ser Lys Ala Lys Gly Gln Pro Arg Glu Pro Gln Val Tyr Thr
    1340                1345                1350

Leu Pro Pro Ser Arg Glu Glu Met Thr Lys Asn Gln Val Ser Leu
    1355                1360                1365

Thr Cys Leu Val Lys Gly Phe Tyr Pro Ser Asp Ile Ala Val Glu
    1370                1375                1380

Trp Glu Ser Asn Gly Gln Pro Glu Asn Asn Tyr Lys Thr Thr Pro
    1385                1390                1395

Pro Val Leu Asp Ser Asp Gly Ser Phe Phe Leu Tyr Ser Lys Leu
    1400                1405                1410

Thr Val Asp Lys Ser Arg Trp Gln Gln Gly Asn Val Phe Ser Cys
    1415                1420                1425

Ser Val Met His Glu Ala Leu His Asn His Tyr Thr Gln Lys Ser
    1430                1435                1440

Leu Ser Leu Ser Pro Gly Lys
    1445                1450

<210> SEQ ID NO 50
<211> LENGTH: 1449
<212> TYPE: PRT
<213> ORGANISM: Artificial
<220> FEATURE:
<223> OTHER INFORMATION: fusion peptide derived from human

<400> SEQUENCE: 50

Ala Thr Gly Thr Thr Gly Gly Gly Gly Cys Cys Gly Cys Cys
1               5                   10                  15

Thr Cys Ala Gly Gly Cys Thr Cys Thr Gly Gly Thr Cys Thr Gly
                20                  25                  30

Thr Gly Cys Cys Thr Thr Gly Thr Gly Cys Ala Gly Cys Gly Thr Cys
        35                  40                  45

Thr Gly Cys Ala Gly Cys Ala Thr Gly Ala Gly Cys Gly Thr Cys Cys
    50                  55                  60

Thr Cys Ala Gly Ala Gly Cys Cys Thr Ala Thr Cys Cys Ala Ala
65                  70                  75                  80

Thr Gly Cys Cys Thr Cys Cys Cys Ala Cys Thr Gly Cys Thr Cys
                85                  90                  95

Gly Gly Cys Thr Cys Cys Ala Gly Cys Thr Gly Gly Gly Thr Gly
                100                 105                 110

Gly Cys Cys Thr Gly Ala Thr Cys Cys Ala Cys Thr Gly Thr Ala
        115                 120                 125

Cys Ala Cys Ala Gly Cys Cys Ala Cys Ala Gly Cys Cys Ala Gly Gly
130                 135                 140

Ala Ala Cys Ala Gly Cys Thr Ala Cys Cys Ala Cys Cys Thr Gly Cys
145                 150                 155                 160

Ala Gly Ala Thr Cys Cys Ala Cys Ala Ala Gly Ala Ala Thr Gly Gly
                165                 170                 175

Cys Cys Ala Thr Gly Thr Gly Gly Ala Thr Gly Cys Gly Cys Ala
        180                 185                 190
```

-continued

```
Cys Cys Cys Cys Ala Thr Cys Ala Gly Ala Cys Cys Ala Thr Cys Thr
        195                 200                 205

Ala Cys Ala Gly Thr Gly Cys Cys Thr Gly Ala Thr Gly Ala Thr
    210                 215                 220

Cys Ala Gly Ala Thr Cys Ala Gly Ala Gly Gly Ala Thr Gly Cys Thr
225                 230                 235                 240

Gly Gly Cys Thr Thr Gly Thr Gly Thr Gly Ala Thr Thr Ala
            245                 250                 255

Cys Ala Gly Gly Thr Gly Thr Gly Ala Thr Gly Ala Gly Cys Ala Gly
                260                 265                 270

Ala Ala Gly Ala Thr Ala Cys Cys Thr Cys Thr Gly Cys Ala Thr Gly
    275                 280                 285

Gly Ala Thr Thr Thr Cys Ala Gly Ala Gly Gly Cys Ala Ala Cys Ala
    290                 295                 300

Thr Thr Thr Thr Thr Gly Gly Ala Thr Cys Ala Cys Ala Cys Thr Ala
305                 310                 315                 320

Thr Thr Thr Cys Gly Ala Cys Cys Cys Gly Ala Gly Ala Ala Cys
                325                 330                 335

Thr Gly Cys Ala Gly Gly Thr Thr Cys Cys Ala Ala Cys Ala Cys Cys
        340                 345                 350

Ala Gly Ala Cys Gly Cys Thr Gly Gly Ala Ala Ala Cys Gly Gly
    355                 360                 365

Gly Thr Ala Cys Gly Ala Cys Gly Thr Cys Thr Ala Cys Ala Cys
    370                 375                 380

Thr Cys Thr Cys Cys Thr Cys Ala Gly Thr Ala Thr Cys Ala Cys Thr
385                 390                 395                 400

Thr Cys Cys Thr Gly Gly Thr Cys Ala Gly Thr Cys Thr Gly Gly Gly
        405                 410                 415

Cys Cys Gly Gly Gly Cys Gly Ala Ala Gly Ala Gly Ala Gly Cys Cys
                420                 425                 430

Thr Thr Cys Cys Thr Gly Cys Cys Ala Gly Gly Cys Ala Thr Gly Ala
        435                 440                 445

Ala Cys Cys Cys Ala Cys Cys Cys Cys Gly Thr Ala Cys Thr Cys
    450                 455                 460

Cys Cys Ala Gly Thr Thr Cys Cys Thr Gly Thr Cys Cys Cys Gly Gly
465                 470                 475                 480

Ala Gly Gly Ala Ala Cys Gly Ala Gly Thr Cys Cys Cys Cys
        485                 490                 495

Thr Ala Ala Thr Thr Cys Ala Cys Thr Thr Cys Ala Ala Cys Ala Cys
            500                 505                 510

Cys Cys Cys Cys Ala Thr Ala Cys Cys Ala Cys Gly Gly Cys Gly Gly
        515                 520                 525

Cys Ala Cys Ala Cys Cys Cys Ala Gly Ala Gly Cys Gly Cys Cys Gly
        530                 535                 540

Ala Gly Gly Ala Cys Gly Ala Cys Thr Cys Gly Gly Ala Gly Cys Gly
545                 550                 555                 560

Gly Gly Ala Cys Cys Cys Cys Thr Gly Ala Ala Cys Gly Thr Gly
            565                 570                 575

Cys Thr Gly Ala Ala Gly Cys Cys Cys Gly Gly Gly Cys Cys Cys
    580                 585                 590

Gly Gly Ala Thr Gly Ala Cys Cys Cys Gly Gly Cys Cys Cys Cys
    595                 600                 605

Gly Gly Cys Cys Thr Cys Cys Thr Gly Thr Thr Cys Ala Cys Ala Gly
610                 615                 620
```

```
Gly Ala Gly Cys Thr Cys Cys Gly Ala Cys Gly Cys Gly
625                 630                 635             640

Ala Gly Gly Ala Cys Ala Cys Ala Gly Cys Cys Gly Thr
                645                 650             655

Gly Gly Cys Cys Ala Gly Thr Gly Ala Cys Cys Ala Thr Ala
            660                 665             670

Gly Gly Gly Gly Thr Gly Thr Cys Ala Gly Gly Gly Cys Gly
            675                 680             685

Gly Thr Cys Gly Ala Gly Thr Gly Ala Ala Cys Ala Cys Ala
        690             695             700

Cys Gly Cys Thr Gly Gly Gly Gly Ala Ala Cys Gly Gly Cys
705             710             715                 720

Cys Cys Gly Gly Ala Ala Gly Gly Cys Thr Gly Cys Gly Cys
            725                 730             735

Cys Cys Thr Thr Cys Gly Cys Cys Ala Ala Gly Thr Thr Cys Ala Thr
        740             745             750

Cys Gly Gly Ala Gly Gly Thr Gly Gly Ala Gly Gly Thr Thr Cys Ala
        755             760             765

Ala Ala Ala Cys Cys Cys Ala Cys Ala Cys Gly Thr Gly Thr Cys
770             775             780

Cys Thr Cys Cys Thr Thr Gly Thr Cys Thr Gly Cys Cys Cys
785             790             795                 800

Ala Gly Ala Ala Gly Cys Ala Gly Cys Ala Gly Gly Thr Gly Gly Thr
            805             810             815

Cys Cys Ala Thr Cys Ala Gly Thr Thr Thr Thr Cys Thr Thr Thr
        820             825             830

Thr Cys Cys Cys Thr Cys Cys Ala Ala Ala Cys Cys Cys Ala Ala
        835             840             845

Gly Gly Ala Thr Ala Cys Gly Cys Thr Gly Ala Thr Gly Ala Thr Cys
850                 855             860

Thr Cys Thr Cys Gly Cys Ala Cys Gly Cys Cys Thr Gly Ala Gly Gly
865                 870             875             880

Thr Gly Ala Cys Ala Thr Gly Cys Gly Thr Cys Gly Thr Ala Gly Thr
                885             890             895

Ala Gly Ala Cys Gly Thr Gly Ala Gly Cys Cys Cys Gly Ala Ala
            900             905             910

Gly Ala Thr Cys Cys Cys Gly Ala Gly Gly Thr Gly Ala Ala Gly Thr
            915             920             925

Thr Cys Ala Ala Thr Thr Gly Gly Thr Ala Cys Gly Thr Gly Gly Ala
            930             935             940

Cys Gly Gly Ala Gly Thr Ala Gly Ala Ala Gly Thr Cys Ala Thr
945             950             955             960

Ala Ala Cys Gly Cys Gly Ala Ala Ala Cys Thr Ala Ala Gly Cys
            965             970             975

Cys Gly Cys Gly Cys Gly Ala Gly Gly Ala Cys Ala Ala Thr Ala
            980             985             990

Thr Ala Ala Cys Ala Gly Thr Ala Cys Thr Thr Ala Cys Ala Gly Gly
            995             1000            1005

Gly Thr Gly Gly Thr Ala Thr Cys Cys Gly Thr Gly Cys Thr Cys
    1010            1015            1020

Ala Cys Ala Gly Thr Cys Thr Gly Cys Ala Cys Cys Ala Gly
    1025            1030            1035

Gly Ala Cys Thr Gly Gly Cys Thr Gly Ala Ala Cys Gly Gly Thr
```

-continued

```
    1040                1045                1050

Ala Ala  Gly Gly Ala Ala Thr  Ala Cys Ala Ala Gly  Thr Gly Cys
    1055                1060                1065

Ala Ala  Ala Gly Thr Ala Ala  Gly Cys Ala Ala Cys  Ala Ala Gly
    1070                1075                1080

Gly Cys  Ala Cys Thr Thr Cys  Cys Cys Gly Cys Gly  Cys Cys Thr
    1085                1090                1095

Ala Thr  Thr Gly Ala Gly Ala  Ala Ala Ala Cys Ala  Ala Thr Cys
    1100                1105                1110

Thr Cys  Cys Ala Ala Gly Gly  Cys Gly Ala Ala Gly  Gly Gly Ala
    1115                1120                1125

Cys Ala  Ala Cys Cys Ala Ala  Gly Ala Gly Ala Ala  Cys Cys Thr
    1130                1135                1140

Cys Ala  Gly Gly Thr Thr Thr  Ala Cys Ala Cys Thr  Cys Thr Cys
    1145                1150                1155

Cys Cys  Gly Cys Cys Thr Thr  Cys Cys Ala Gly Gly  Gly Ala Ala
    1160                1165                1170

Gly Ala  Gly Ala Thr Gly Ala  Cys Cys Ala Ala Ala  Ala Ala Thr
    1175                1180                1185

Cys Ala  Ala Gly Thr Thr Thr  Cys Cys Cys Thr Gly  Ala Cys Thr
    1190                1195                1200

Thr Gly  Cys Cys Thr Cys Gly  Thr Cys Ala Ala Ala  Gly Gly Ala
    1205                1210                1215

Thr Thr  Cys Thr Ala Cys Cys  Cys Thr Thr Cys Cys  Gly Ala Cys
    1220                1225                1230

Ala Thr  Thr Gly Cys Thr Gly  Thr Thr Gly Ala Ala  Thr Gly Gly
    1235                1240                1245

Gly Ala  Ala Ala Gly Cys Ala  Ala Thr Gly Gly Ala  Cys Ala Ala
    1250                1255                1260

Cys Cys  Ala Gly Ala Gly Ala  Ala Cys Ala Ala Cys  Thr Ala Cys
    1265                1270                1275

Ala Ala  Gly Ala Cys Ala Ala  Cys Ala Cys Cys Cys  Cys Cys Gly
    1280                1285                1290

Gly Thr  Gly Cys Thr Gly Gly  Ala Thr Ala Gly Thr  Gly Ala Cys
    1295                1300                1305

Gly Gly  Ala Thr Cys Thr Thr  Thr Cys Thr Thr Thr  Cys Thr Cys
    1310                1315                1320

Thr Ala  Cys Thr Cys Ala Ala  Ala Gly Cys Thr Gly  Ala Cys Cys
    1325                1330                1335

Gly Thr  Gly Gly Ala Thr Ala  Ala Gly Thr Cys Cys  Ala Gly Gly
    1340                1345                1350

Thr Gly  Gly Cys Ala Gly Cys  Ala Gly Gly Gly Ala  Ala Ala Cys
    1355                1360                1365

Gly Thr  Gly Thr Thr Thr Thr  Cys Cys Thr Gly Cys  Thr Cys Thr
    1370                1375                1380

Gly Thr  Cys Ala Thr Gly Cys  Ala Thr Gly Ala Ala  Gly Cys Gly
    1385                1390                1395

Cys Thr  Gly Cys Ala Thr Ala  Ala Thr Cys Ala Cys  Thr Ala Thr
    1400                1405                1410

Ala Cys  Cys Cys Ala Gly Ala  Ala Gly Thr Cys Thr  Cys Thr Gly
    1415                1420                1425

Ala Gly  Cys Thr Thr Gly Ala  Gly Cys Cys Cys Ala  Gly Gly Cys
    1430                1435                1440
```

```
Ala Ala  Gly Thr Ala Ala
    1445
```

<210> SEQ ID NO 51
<211> LENGTH: 482
<212> TYPE: PRT
<213> ORGANISM: Artificial
<220> FEATURE:
<223> OTHER INFORMATION: fusion peptide derived from human

<400> SEQUENCE: 51

```
Met Leu Gly Ala Arg Leu Arg Leu Trp Val Cys Ala Leu Cys Ser Val
1               5                   10                  15

Cys Ser Met Ser Val Leu Arg Ala Tyr Pro Asn Ala Ser Pro Leu Leu
            20                  25                  30

Gly Ser Ser Trp Gly Gly Leu Ile His Leu Tyr Thr Ala Thr Ala Arg
        35                  40                  45

Asn Ser Tyr His Leu Gln Ile His Lys Asn Gly His Val Asp Gly Ala
    50                  55                  60

Pro His Gln Thr Ile Tyr Ser Ala Leu Met Ile Arg Ser Glu Asp Ala
65                  70                  75                  80

Gly Phe Val Val Ile Thr Gly Val Met Ser Arg Arg Tyr Leu Cys Met
                85                  90                  95

Asp Phe Arg Gly Asn Ile Phe Gly Ser His Tyr Phe Asp Pro Glu Asn
            100                 105                 110

Cys Arg Phe Gln His Gln Thr Leu Glu Asn Gly Tyr Asp Val Tyr His
        115                 120                 125

Ser Pro Gln Tyr His Phe Leu Val Ser Leu Gly Arg Ala Lys Arg Ala
    130                 135                 140

Phe Leu Pro Gly Met Asn Pro Pro Tyr Ser Gln Phe Leu Ser Arg Arg
145                 150                 155                 160

Arg Asn Glu Ile Pro Leu Ile His Phe Asn Thr Pro Ile Pro Arg Arg
                165                 170                 175

His Thr Gln Ser Ala Glu Asp Ser Glu Arg Asp Pro Leu Asn Val
            180                 185                 190

Leu Lys Pro Arg Ala Arg Met Thr Pro Ala Pro Ala Ser Cys Ser Gln
        195                 200                 205

Glu Leu Pro Ser Ala Glu Asp Asn Ser Pro Met Ala Ser Asp Pro Leu
    210                 215                 220

Gly Val Val Arg Gly Gly Arg Val Asn Thr His Ala Gly Gly Thr Gly
225                 230                 235                 240

Pro Glu Gly Cys Arg Pro Phe Ala Lys Phe Ile Gly Gly Gly Ser
                245                 250                 255

Lys Thr His Thr Cys Pro Pro Cys Pro Ala Pro Glu Ala Ala Gly Gly
            260                 265                 270

Pro Ser Val Phe Leu Phe Pro Pro Lys Pro Lys Asp Thr Leu Met Ile
        275                 280                 285

Ser Arg Thr Pro Glu Val Thr Cys Val Val Asp Val Ser His Glu
    290                 295                 300

Asp Pro Glu Val Lys Phe Asn Trp Tyr Val Asp Gly Val Glu Val His
305                 310                 315                 320

Asn Ala Lys Thr Lys Pro Arg Glu Glu Gln Tyr Asn Ser Thr Tyr Arg
                325                 330                 335

Val Val Ser Val Leu Thr Val Leu His Gln Asp Trp Leu Asn Gly Lys
            340                 345                 350

Glu Tyr Lys Cys Lys Val Ser Asn Lys Ala Leu Pro Ala Pro Ile Glu
```

```
                 355                 360                 365
Lys Thr Ile Ser Lys Ala Lys Gly Gln Pro Arg Glu Pro Gln Val Tyr
            370                 375                 380

Thr Leu Pro Pro Ser Arg Glu Glu Met Thr Lys Asn Gln Val Ser Leu
385                 390                 395                 400

Thr Cys Leu Val Lys Gly Phe Tyr Pro Ser Asp Ile Ala Val Glu Trp
                405                 410                 415

Glu Ser Asn Gly Gln Pro Glu Asn Asn Tyr Lys Thr Thr Pro Pro Val
            420                 425                 430

Leu Asp Ser Asp Gly Ser Phe Phe Leu Tyr Ser Lys Leu Thr Val Asp
                435                 440                 445

Lys Ser Arg Trp Gln Gln Gly Asn Val Phe Ser Cys Ser Val Met His
        450                 455                 460

Glu Ala Leu His Asn His Tyr Thr Gln Lys Ser Leu Ser Leu Ser Pro
465                 470                 475                 480

Gly Lys

<210> SEQ ID NO 52
<211> LENGTH: 1422
<212> TYPE: PRT
<213> ORGANISM: Artificial
<220> FEATURE:
<223> OTHER INFORMATION: fusion peptide derived from human

<400> SEQUENCE: 52

Ala Thr Gly Thr Thr Gly Gly Gly Gly Cys Cys Cys Gly Cys Cys
1               5                   10                  15

Thr Cys Ala Gly Gly Cys Thr Cys Thr Gly Gly Thr Cys Thr Gly
                20                  25                  30

Thr Gly Cys Cys Thr Cys Thr Gly Thr Gly Cys Ala Gly Cys Gly Thr Cys
            35                  40                  45

Thr Gly Cys Ala Gly Cys Ala Thr Gly Ala Gly Cys Gly Thr Cys Cys
        50                  55                  60

Thr Cys Ala Gly Ala Gly Cys Cys Thr Ala Thr Cys Cys Cys Ala Ala
65                  70                  75                  80

Thr Gly Cys Cys Thr Cys Cys Cys Ala Cys Thr Gly Cys Thr Cys
                85                  90                  95

Gly Gly Cys Thr Cys Cys Ala Gly Cys Thr Gly Gly Gly Thr Gly
                100                 105                 110

Gly Cys Cys Thr Gly Ala Thr Cys Cys Ala Cys Thr Gly Thr Ala
            115                 120                 125

Cys Ala Cys Ala Gly Cys Cys Ala Cys Ala Gly Cys Ala Gly Gly
        130                 135                 140

Ala Ala Cys Ala Gly Cys Thr Ala Cys Cys Ala Cys Cys Thr Gly Cys
145                 150                 155                 160

Ala Gly Ala Thr Cys Cys Ala Cys Ala Ala Gly Ala Thr Gly Gly
                165                 170                 175

Cys Cys Ala Thr Gly Thr Gly Gly Ala Thr Gly Cys Gly Cys Ala
            180                 185                 190

Cys Cys Cys Cys Ala Thr Cys Ala Gly Ala Cys Ala Thr Cys Thr
        195                 200                 205

Ala Cys Ala Gly Thr Gly Cys Cys Thr Gly Ala Thr Gly Ala Thr
    210                 215                 220

Cys Ala Gly Ala Thr Cys Ala Gly Ala Gly Gly Ala Thr Gly Cys Thr
225                 230                 235                 240
```

-continued

```
Gly Gly Cys Thr Thr Thr Gly Thr Gly Thr Ala Thr Ala
            245                 250                 255

Cys Ala Gly Gly Thr Gly Thr Gly Ala Thr Gly Ala Gly Cys Ala Gly
            260                 265                 270

Ala Ala Gly Ala Thr Ala Cys Thr Cys Thr Gly Cys Ala Thr Gly
            275                 280                 285

Gly Ala Thr Thr Thr Cys Ala Gly Ala Gly Gly Cys Ala Ala Cys Ala
            290                 295                 300

Thr Thr Thr Thr Thr Gly Gly Ala Thr Cys Ala Cys Ala Cys Thr Ala
305                 310                 315                 320

Thr Thr Thr Cys Gly Ala Cys Cys Cys Gly Gly Ala Gly Ala Ala Cys
            325                 330                 335

Thr Gly Cys Ala Gly Gly Thr Thr Cys Cys Ala Ala Cys Ala Cys Cys
            340                 345                 350

Ala Gly Ala Cys Gly Cys Thr Gly Gly Ala Ala Ala Cys Gly Gly
            355                 360                 365

Gly Thr Ala Cys Gly Ala Cys Gly Thr Cys Thr Ala Cys Ala Cys
            370                 375                 380

Thr Cys Thr Cys Thr Cys Ala Gly Thr Ala Thr Cys Ala Cys Thr
385                 390                 395                 400

Thr Cys Cys Thr Gly Gly Thr Cys Ala Gly Thr Cys Thr Gly Gly Gly
            405                 410                 415

Cys Cys Gly Gly Gly Cys Gly Ala Ala Gly Ala Gly Ala Gly Cys Cys
            420                 425                 430

Thr Thr Cys Cys Thr Gly Cys Cys Ala Gly Gly Cys Ala Thr Gly Ala
            435                 440                 445

Ala Cys Cys Cys Ala Cys Cys Cys Cys Gly Thr Ala Cys Thr Cys
450                 455                 460

Cys Cys Ala Gly Thr Thr Cys Cys Thr Gly Thr Cys Cys Gly Gly
465                 470                 475                 480

Ala Gly Gly Ala Ala Cys Gly Ala Gly Ala Thr Cys Cys Cys Cys
            485                 490                 495

Thr Ala Ala Thr Thr Cys Ala Cys Thr Thr Cys Ala Ala Cys Ala Cys
            500                 505                 510

Cys Cys Cys Cys Ala Thr Ala Cys Cys Ala Cys Gly Gly Cys Gly Gly
            515                 520                 525

Cys Ala Cys Ala Cys Cys Ala Gly Ala Gly Cys Gly Cys Cys Gly
            530                 535                 540

Ala Gly Gly Ala Cys Gly Ala Cys Thr Cys Gly Gly Ala Gly Cys Gly
545                 550                 555                 560

Gly Gly Ala Cys Cys Cys Cys Thr Gly Ala Ala Cys Gly Thr Gly
            565                 570                 575

Cys Thr Gly Ala Ala Gly Cys Cys Cys Gly Gly Gly Cys Cys Cys
            580                 585                 590

Gly Gly Ala Thr Gly Ala Cys Cys Cys Gly Gly Cys Cys Cys
            595                 600                 605

Gly Gly Cys Cys Thr Cys Cys Thr Gly Thr Thr Cys Ala Cys Ala Gly
            610                 615                 620

Gly Ala Gly Cys Thr Cys Cys Cys Gly Ala Gly Cys Gly Cys Cys Gly
625                 630                 635                 640

Ala Gly Gly Ala Cys Ala Ala Cys Ala Gly Cys Cys Cys Gly Ala Thr
            645                 650                 655

Gly Gly Cys Cys Ala Gly Thr Gly Ala Cys Cys Cys Ala Thr Thr Ala
            660                 665                 670
```

```
Gly Gly Gly Gly Thr Gly Gly Thr Cys Ala Gly Gly Cys Gly
            675                 680                 685
Gly Thr Cys Gly Ala Gly Thr Gly Ala Ala Cys Ala Cys Gly Cys Ala
            690                 695                 700
Cys Gly Cys Thr Gly Gly Gly Gly Ala Ala Cys Gly Gly Gly Cys
705                 710                 715                 720
Cys Cys Gly Gly Ala Ala Gly Gly Cys Thr Gly Cys Cys Gly Cys Cys
                725                 730                 735
Cys Cys Thr Thr Cys Gly Cys Cys Ala Ala Gly Thr Thr Cys Ala Thr
                740                 745                 750
Cys Gly Gly Ala Gly Gly Thr Gly Gly Ala Gly Gly Thr Thr Cys Ala
            755                 760                 765
Gly Cys Cys Cys Cys Ala Gly Ala Ala Gly Cys Ala Gly Cys Ala Gly
        770                 775                 780
Gly Thr Gly Gly Thr Cys Cys Ala Thr Cys Ala Gly Thr Thr Thr Thr
785                 790                 795                 800
Thr Cys Thr Thr Thr Thr Cys Cys Thr Cys Cys Ala Ala Ala
                805                 810                 815
Cys Cys Cys Ala Ala Gly Gly Ala Thr Ala Cys Gly Cys Thr Gly Ala
                820                 825                 830
Thr Gly Ala Thr Cys Thr Cys Thr Cys Gly Cys Ala Cys Gly Cys Cys
            835                 840                 845
Thr Gly Ala Gly Gly Thr Gly Ala Cys Ala Thr Gly Cys Gly Thr Cys
        850                 855                 860
Gly Thr Ala Gly Thr Ala Gly Ala Cys Gly Thr Gly Ala Gly Cys Cys
865                 870                 875                 880
Ala Cys Gly Ala Ala Gly Ala Thr Cys Cys Gly Ala Gly Gly Thr
            885                 890                 895
Gly Ala Ala Gly Thr Thr Cys Ala Ala Thr Thr Gly Gly Thr Ala Thr
        900                 905                 910
Gly Thr Gly Gly Ala Cys Gly Gly Ala Gly Thr Ala Gly Ala Ala Gly
        915                 920                 925
Thr Gly Cys Ala Thr Ala Ala Cys Gly Cys Gly Ala Ala Ala Ala Cys
        930                 935                 940
Thr Ala Ala Gly Cys Cys Gly Cys Gly Cys Gly Ala Gly Gly Ala Ala
945                 950                 955                 960
Cys Ala Ala Thr Ala Thr Ala Ala Cys Ala Gly Thr Ala Cys Thr Thr
            965                 970                 975
Ala Cys Ala Gly Gly Gly Thr Gly Thr Ala Thr Cys Cys Gly Thr
        980                 985                 990
Gly Cys Thr Cys Ala Cys Ala Gly  Thr Cys Cys Thr Gly Cys Ala Cys
            995                  1000                 1005
Cys Ala  Gly Gly Ala Cys Thr  Gly Gly Cys Thr Gly  Ala Ala Cys
        1010                 1015                 1020
Gly Gly  Thr Ala Ala Gly Gly  Ala Ala Thr Ala Cys  Ala Ala Gly
        1025                 1030                 1035
Thr Gly  Cys Ala Ala Ala Gly  Thr Ala Ala Gly Cys  Ala Ala Cys
        1040                 1045                 1050
Ala Ala  Gly Gly Cys Ala Cys  Thr Thr Cys Cys  Gly Cys Gly
        1055                 1060                 1065
Cys Cys  Thr Ala Thr Thr Gly  Ala Gly Ala Ala Ala  Ala Cys Ala
        1070                 1075                 1080
Ala Thr  Cys Thr Cys Cys Ala  Ala Gly Gly Cys Gly  Ala Ala Gly
```

```
                    1085              1090              1095

Gly Gly Ala Cys Ala Ala Cys Cys Ala Ala Gly Ala Gly Ala Ala
    1100              1105              1110

Cys Cys Thr Cys Ala Gly Gly Thr Thr Thr Ala Cys Ala Cys Thr
    1115              1120              1125

Cys Thr Cys Cys Cys Gly Cys Cys Thr Cys Cys Ala Gly Gly
    1130              1135              1140

Gly Ala Ala Gly Ala Gly Ala Thr Gly Ala Cys Cys Ala Ala Ala
    1145              1150              1155

Ala Ala Thr Cys Ala Ala Gly Thr Thr Thr Cys Cys Cys Thr Gly
    1160              1165              1170

Ala Cys Thr Thr Gly Cys Cys Thr Cys Gly Thr Cys Ala Ala Ala
    1175              1180              1185

Gly Gly Ala Thr Thr Cys Thr Ala Cys Cys Cys Thr Cys Cys
    1190              1195              1200

Gly Ala Cys Ala Thr Thr Gly Cys Thr Gly Thr Thr Gly Ala Ala
    1205              1210              1215

Thr Gly Gly Gly Ala Ala Ala Gly Cys Ala Ala Thr Gly Gly Ala
    1220              1225              1230

Cys Ala Ala Cys Cys Ala Gly Ala Gly Ala Ala Cys Ala Ala Cys
    1235              1240              1245

Thr Ala Cys Ala Ala Gly Ala Cys Ala Ala Cys Ala Cys Cys Cys
    1250              1255              1260

Cys Cys Gly Gly Thr Gly Cys Thr Gly Gly Ala Thr Ala Gly Thr
    1265              1270              1275

Gly Ala Cys Gly Gly Ala Thr Cys Thr Thr Thr Cys Thr Thr Thr
    1280              1285              1290

Cys Thr Cys Thr Ala Cys Thr Cys Ala Ala Ala Gly Cys Thr Gly
    1295              1300              1305

Ala Cys Cys Gly Thr Gly Gly Ala Thr Ala Ala Gly Thr Cys Cys
    1310              1315              1320

Ala Gly Gly Thr Gly Gly Cys Ala Gly Cys Ala Gly Gly Gly Ala
    1325              1330              1335

Ala Ala Cys Gly Thr Gly Thr Thr Thr Cys Cys Thr Gly Cys
    1340              1345              1350

Thr Cys Thr Gly Thr Cys Ala Thr Gly Cys Ala Thr Gly Ala Ala
    1355              1360              1365

Gly Cys Gly Cys Thr Gly Cys Ala Thr Ala Ala Thr Cys Ala Cys
    1370              1375              1380

Thr Ala Thr Ala Cys Cys Cys Ala Gly Ala Ala Gly Thr Cys Thr
    1385              1390              1395

Cys Thr Gly Ala Gly Cys Thr Thr Gly Ala Gly Cys Cys Cys Ala
    1400              1405              1410

Gly Gly Cys Ala Ala Gly Thr Ala Ala
    1415              1420

<210> SEQ ID NO 53
<211> LENGTH: 473
<212> TYPE: PRT
<213> ORGANISM: Artificial
<220> FEATURE:
<223> OTHER INFORMATION: fusion peptide derived from human

<400> SEQUENCE: 53

Met Leu Gly Ala Arg Leu Arg Leu Trp Val Cys Ala Leu Cys Ser Val
1               5                   10                  15
```

Cys Ser Met Ser Val Leu Arg Ala Tyr Pro Asn Ala Ser Pro Leu Leu
            20                  25                  30

Gly Ser Ser Trp Gly Gly Leu Ile His Leu Tyr Thr Ala Thr Ala Arg
         35                  40                  45

Asn Ser Tyr His Leu Gln Ile His Lys Asn Gly His Val Asp Gly Ala
     50                  55                  60

Pro His Gln Thr Ile Tyr Ser Ala Leu Met Ile Arg Ser Glu Asp Ala
 65                  70                  75                  80

Gly Phe Val Val Ile Thr Gly Val Met Ser Arg Arg Tyr Leu Cys Met
                 85                  90                  95

Asp Phe Arg Gly Asn Ile Phe Gly Ser His Tyr Phe Asp Pro Glu Asn
            100                 105                 110

Cys Arg Phe Gln His Gln Thr Leu Glu Asn Gly Tyr Asp Val Tyr His
            115                 120                 125

Ser Pro Gln Tyr His Phe Leu Val Ser Leu Gly Arg Ala Lys Arg Ala
        130                 135                 140

Phe Leu Pro Gly Met Asn Pro Pro Tyr Ser Gln Phe Leu Ser Arg
145                 150                 155                 160

Arg Asn Glu Ile Pro Leu Ile His Phe Asn Thr Pro Ile Pro Arg Arg
                165                 170                 175

His Thr Gln Ser Ala Glu Asp Ser Glu Arg Asp Pro Leu Asn Val
            180                 185                 190

Leu Lys Pro Arg Ala Arg Met Thr Pro Ala Pro Ala Ser Cys Ser Gln
        195                 200                 205

Glu Leu Pro Ser Ala Glu Asp Asn Ser Pro Met Ala Ser Asp Pro Leu
210                 215                 220

Gly Val Val Arg Gly Gly Arg Val Asn Thr His Ala Gly Gly Thr Gly
225                 230                 235                 240

Pro Glu Gly Cys Arg Pro Phe Ala Lys Phe Ile Gly Gly Gly Ser
            245                 250                 255

Ala Pro Glu Ala Ala Gly Gly Pro Ser Val Phe Leu Phe Pro Pro Lys
        260                 265                 270

Pro Lys Asp Thr Leu Met Ile Ser Arg Thr Pro Glu Val Thr Cys Val
        275                 280                 285

Val Val Asp Val Ser His Glu Asp Pro Glu Val Lys Phe Asn Trp Tyr
        290                 295                 300

Val Asp Gly Val Glu Val His Asn Ala Lys Thr Lys Pro Arg Glu Glu
305                 310                 315                 320

Gln Tyr Asn Ser Thr Tyr Arg Val Val Ser Val Leu Thr Val Leu His
                325                 330                 335

Gln Asp Trp Leu Asn Gly Lys Glu Tyr Lys Cys Lys Val Ser Asn Lys
            340                 345                 350

Ala Leu Pro Ala Pro Ile Glu Lys Thr Ile Ser Lys Ala Lys Gly Gln
        355                 360                 365

Pro Arg Glu Pro Gln Val Tyr Thr Leu Pro Pro Ser Arg Glu Glu Met
        370                 375                 380

Thr Lys Asn Gln Val Ser Leu Thr Cys Leu Val Lys Gly Phe Tyr Pro
385                 390                 395                 400

Ser Asp Ile Ala Val Glu Trp Glu Ser Asn Gly Gln Pro Glu Asn Asn
                405                 410                 415

Tyr Lys Thr Thr Pro Pro Val Leu Asp Ser Asp Gly Ser Phe Phe Leu
            420                 425                 430

Tyr Ser Lys Leu Thr Val Asp Lys Ser Arg Trp Gln Gln Gly Asn Val

-continued

```
            435                 440                 445
Phe Ser Cys Ser Val Met His Glu Ala Leu His Asn His Tyr Thr Gln
    450                 455                 460

Lys Ser Leu Ser Leu Ser Pro Gly Lys
465                 470
```

METHODS AND COMPOSITIONS USING FGF23 FUSION POLYPEPTIDES

This application claims priority to U.S. Provisional Application Ser. No. 61/063,015, filed 28 Jan. 2008, and to U.S. application Ser. No. 12/360,970, filed 28 Jan. 2009, the contents of which are incorporated herein by reference in their entirety.

1. BACKGROUND

The alpha-Klotho gene encodes a 130 kDa single pass type I transmembrane protein with an extracellular domain and a short cytoplasmic domain. The extracellular domain of alpha-Klotho protein comprises two subdomains termed, KL-D1 and KL-D2. These two subdomains share sequence homology to β-glucosidase of bacteria and plants. The extracellular domain of the alpha-Klotho protein may be bound to the cell surface by the transmembrane domain or may be cleaved and released into the extracellular milieu. Cleavage of the extracellular domain appears to be facilitated by local low extracellular $Ca^{2+}$ concentrations.

In addition to alpha-Klotho, a homolog of alpha-Klotho, beta-Klotho, has been identified (Ito et al., Mech. Dev. 98:115-9 (2000)). Beta-Klotho is also a single pass type I transmembrane protein with extracellular KL-D1 and KL-D2 subdomains.

Modulation of alpha-Klotho expression has been demonstrated to produce aging related characteristics in mammals. Mice homozygous for a loss of function mutation in the alpha-Klotho gene develop characteristics resembling human aging, including shortened lifespan, skin atrophy, muscle wasting, arteriosclerosis, pulmonary emphysema and osteoporosis (Kuro-o et al., Nature, 390:45-51 (1997)). In contrast, overexpression of the alpha-Klotho gene in mice extends lifespan and increases resistance to oxidative stress relative to wild-type mice (Kurosu et al., Science 309:1829-1833 (2005); Yamamoto et al., J. Biol. Chem. 280:38029-38034 (2005)).

Fibroblast growth factors (FGFs) constitute a family of homologous polypeptide growth factors expressed in many organisms (Ornitz and Itoh, Genome Biol. 2: reviews, 3005.1-3005.12 (2001)). Among vertebrate species, FGFs are highly conserved in both gene structure and amino-acid sequence, having between 13-71% amino acid identity with one another. In humans, there are 22 known members of the FGF family (FGF15 is the mouse ortholog of human FGF19, hence there is no human FGF15). During early development, FGFs regulate cell proliferation, migration, and differentiation, but in the adult organism, FGFs maintain homeostasis, function in tissue repair, and respond to injury.

FGFs function as growth factors by binding and thereby activating cell-surface FGF receptors. FGF receptors (FGFRs) are tyrosine kinase receptors that activate signal transduction through autophosphorylation of FGFR, phosphorylation of FRS2 (FGF receptor substrate 2) and ERK1/2 (extracellular signal-regulated protein kinase 1/2), and activating Egr-1 (early growth response-1). FGFs also have a high affinity for heparin sulfate proteoglycans. When bound to FGFs, heparin sulfate enhances the activation of FGFRs.

Recent studies have demonstrated strikingly similar biological characteristics between FGF23-deficient mice and alpha-Klotho-deficient mice (Shimada et al., J. Clin. Invest. 113:561-568 (2004); Yoshida et al. Endocrinology 143:683-689 (2002)), indicating functional crosstalk between FGF23 and alpha-Klotho. These studies led to the identification of alpha-Klotho as an obligatory partner of FGF23, in terms of both binding and signaling through its cognate FGF receptors (Urakawa et al., Nature 22:1524-6 (2007)). The alpha-Klotho gene is mainly expressed in kidney, parathyroid gland and choroid plexus. It is hypothesized that the tissue-specific expression of alpha-Klotho restricts activation of FGF23 signaling to those tissues.

Similar to FGF23/alpha-Klotho, beta-Klotho is an obligatory partner of FGF19 and FGF21, both in binding and in signaling though their respective cognate FGF receptors (Ogawa et al., Proc. Natl. Acad. Sci. USA 104:7432-7 (2007); Lin et al., J. Biol. Chem. 282:27227-84 (2007); and Wu et al., J. Biol. Chem. 282:29069-72 (2007)). Such studies have also demonstrated the involvement of beta-Klotho in regulating tissue-specific metabolic activity. Beta-Klotho was initially shown to act with FGF21 as a cofactor for regulating carbohydrate and lipid metabolism in adipose tissue. Beta-Klotho in conjunction with FGF19 regulates bile acid metabolism in liver, thus explaining elevated bile synthesis in beta-Klotho deficient mice (Ito et al., J Clin Invest. 2005 August; 115(8): 2202-8).

U.S. Pat. No. 6,579,850 describes polypeptides and compositions comprising an alpha-Klotho polypeptide. Human and mouse alpha-Klotho polypeptides are disclosed. The patent also disclosed that compositions comprising the polypeptides are useful in treating a syndrome resembling premature aging, treating adult diseases, and suppressing aging.

U.S. Pat. No. 7,223,563 describes isolated nucleic acids encoding the FGF23 polypeptide sequence or recombinant cells comprising such an isolated nucleic acid. The patent further relates to methods of diagnosing and treating hypophosphatemic and hyperphosphatemic disorders, osteoporosis, dermatomyositis, and coronary artery disease.

U.S. Pat. No. 7,259,248 describes isolated nucleic acids encoding the FGF21 polypeptide sequence. The patent further relates to methods of diagnosing and treating liver disease, conditions related to thymic function, and methods of treating conditions of the testis.

2. SUMMARY OF THE INVENTION

The present invention is directed to methods, kits and compositions for preventing or treating age-related conditions or metabolic disorders with Klotho fusion polypeptides or soluble Klotho polypeptides. The Klotho fusion polypeptides of the present invention are formed of a Klotho protein or an active fragment thereof (e.g., sKlotho). In some embodiments, the present invention provides a Klotho fusion polypeptide comprising a Klotho protein or an active fragment thereof and a fibroblast growth factor or an active fragment thereof. In some embodiments, the fusion polypeptide comprises a Klotho polypeptide, a FGF (such as FGF23) and a modified Fc fragment. The Fc fragment can, for example, have decreased binding to Fc-gamma-receptor and increased serum half-life. Fusion proteins comprising sKlotho, FGF23 and FcLALA (a modified Fc fragment having decreased affinity for Fc-gamma-receptor and/or increased serum half-life) are described in SEQ ID NOs. 46, 47, 48, and 49. In some embodiments, the fusion polypeptide or protein comprises a FGF (e.g., FGF23) and a modified Fc fragment. Fusion proteins comprising FGF23 and FcLALA are described in SEQ ID NOs. 50, 51, 52 and 53.

In a first aspect, the invention provides a fusion polypeptide having at least one extracellular subdomain of a Klotho protein and a fibroblast growth factor or an active fragment thereof. In some embodiments, the fusion further comprises a modified Fc fragment having decreased affinity (e.g., decreased Ka or increased Kd) for Fc-gamma-receptor and/or increased serum half-life. The Klotho extracellular domain may be derived from either the alpha or beta Klotho isoforms. Further, although the FGF component of the Klotho fusion polypeptide is described primarily with reference to fibroblast growth factor-19, fibroblast growth factor-21 and fibroblast growth factor-23, it is contemplated that any of the twenty-three known FGFs can be used in practicing the invention. The reader of the instant application may assume that each of every combination of alpha or beta extracellular domain with each human FGF protein or an active fragment thereof are individually and specifically contemplated.

According to the present invention, the extracellular domain of the Klotho protein can include one or both of the KL-D1 and KL-D2 domains of a Klotho protein. In some embodiments, the Klotho fusion polypeptide of the invention has at least two extracellular subdomains of a Klotho protein. For example, the at least two extracellular subdomains can be at least two KL-D1 domains in tandem repeats, at least two KL-D2 domains in tandem repeats, or at least one KL-D1 domain and at least one KL-D2 domain. In one embodiment, the fusion polypeptide of the invention comprises amino acids 28-292 of the full length alpha Klotho protein. In another embodiment, the fusion polypeptide of the invention comprises amino acids 52-997 of the full length beta Klotho protein.

According to the present invention, the components of a fusion polypeptide comprising (1) at least one extracellular subdomain of a Klotho protein, (2) a FGF or an active fragment thereof and (3) a modified Fc fragment having decreased affinity for Fc-gamma-receptor and/or increased serum half-life may be linked together covalently, for example, chemically linked or fused in frame by a peptide bond. They may also linked via a linker. Non-limiting examples of polypeptide linker are SEQ ID NOs:11, 12, 13, 14, 15, 16, 17, and 18. Such linkers may comprise at least one and up to about 30 repeats of SEQ ID NOs:11, 12, 13, 14, 15, 16, 17 and 18. In another non-limiting embodiment, the fusion comprises (2) a FGF or an active fragment thereof and (3) a modified Fc fragment. The various components of the fuion can be operatively linked in any order; the polypeptide (1) can be operatively linked to the N-terminus of the polypeptide for (2) or (3); the polypeptide for (2) can be operatively linked to the N-terminus of the polypeptide for (1) or (3); the polypeptide for (3) can be operatively linked to the N-terminus of the polypeptide for (1) or (2).

According to the present invention, the extracellular subdomain of a Klotho protein, the fibroblast growth factor and the (optional) modified Fc fragment having decreased affinity for Fc-gamma-receptor and/or increased serum half-life can be operatively linked to one another in a variety of orientations and manners. For example, the extracellular subdomain of the Klotho protein can be operatively linked to the N-terminus of the fibroblast growth factor or alternatively the fibroblast growth factor can be operatively linked to the N-terminus of an extracellular subdomain of the Klotho protein.

In one embodiment, the present invention provides a fusion polypeptide comprising a sKlotho of a Klotho protein and a linker. In another embodiment, the present invention provides a fusion polypeptide comprising a sKlotho of the alpha Klotho protein and a linker. In another embodiment, the present invention provides a fusion polypeptide comprising a sKlotho of the beta Klotho protein and a linker. In yet another embodiment, the present invention provides a human FGF protein or an active fragment thereof (e.g., without signal peptide) and a linker. Pharmaceutical compositions comprising the fusion proteins of the invention and their uses for treating or preventing age-related conditions or metabolic disorders are also encompassed by the present invention. In some embodiments, the fusion protein further comprises a modified Fc fragment having decreased affinity for Fc-gamma-receptor and/or increased serum half-life.

In one embodiment, the present invention provides a fusion polypeptide comprising a sKlotho of alpha Klotho protein with signal peptide fused (directly or indirectly via a linker) to FGF-23. In another embodiment, the present invention provides a fusion polypeptide comprising a sKlotho of alpha Klotho protein without signal peptide fused (directly or indirectly via a linker) to FGF-23. In another embodiment, the present invention provides sKlotho of alpha Klotho protein with signal peptide fused (directly or indirectly via a linker) to FGF-23 without signal peptide. In another embodiment, the present invention provides a fusion polypeptide comprising sKlotho of alpha Klotho protein without signal peptide fused (directly or indirectly via a linker) to FGF-23 without signal peptide. In some embodiments, the fusion protein further comprises a modified Fc fragment having decreased affinity for Fc-gamma-receptor and/or increased serum half-life.

In one embodiment, the present invention provides a fusion polypeptide comprising a sKlotho of alpha Klotho protein with signal peptide fused (directly or indirectly via a linker) to FGF-23 (R179Q) variant. In another embodiment, the present invention provides a fusion polypeptide comprising a sKlotho of alpha Klotho protein without signal peptide fused (directly or indirectly via a linker) to FGF-23 (R179Q) variant. In another embodiment, the present invention provides sKlotho of alpha Klotho protein with signal peptide fused (directly or indirectly via a linker) to FGF-23 (R179Q) variant without signal peptide. In another embodiment, the present invention provides a fusion polypeptide comprising sKlotho of alpha Klotho protein without signal peptide fused (directly or indirectly via a linker) to FGF-23 (R179Q) variant without signal peptide. In some embodiments, the fusion protein further comprises a modified Fc fragment having decreased affinity for Fc-gamma-receptor and/or increased serum half-life.

In one embodiment, the present invention provides a fusion polypeptide comprising (1) sKlotho of alpha Klotho protein with signal peptide; (2) a linker; and (3) FGF-23 (R179Q) variant without signal peptide. In another embodiment, the present invention provides a fusion polypeptide comprising (1) sKlotho of alpha Klotho protein without signal peptide; (2) a linker; and (3) FGF-23 (R179Q) variant without signal peptide. In some embodiments, the fusion polypeptides of the invention are glycosylated. In some embodiments, the fusion protein further comprises a modified Fc fragment having decreased affinity for Fc-gamma-receptor and/or increased serum half-life.

In one embodiment, the present invention provides a fusion polypeptide comprising (1) sKlotho of alpha Klotho protein with signal peptide (SEQ ID NO: 44 or SEQ ID NO:45); (2) a linker comprising SEQ ID NO:11; and (3) FGF-23 (R179Q) variant without signal peptide (SEQ ID NO: 43). In another embodiment, the present invention provides a fusion polypeptide comprising (1) sKlotho of alpha Klotho protein without signal peptide (SEQ ID NO:7); (2) a linker comprising SEQ ID NO:11; and (3) FGF-23 (R179Q) variant without signal peptide (SEQ ID NO: 43). In one embodiment, the present invention provides a fusion polypeptide comprising the amino acid sequence of SEQ ID NO:19, 20, 40, or 41. In some embodiments, the fusion polypeptides of the invention are glycosylated.

In one embodiment, the present invention provides a fusion polypeptide comprising sKlotho of alpha Klotho protein with signal peptide (SEQ ID NO:44 or SEQ ID NO:45); and a linker comprising SEQ ID NO:11. In another embodiment, the present invention provides a fusion polypeptide comprising sKlotho of alpha Klotho protein without signal peptide (SEQ ID NO:7); and a linker comprising SEQ ID NO:11. In some embodiments, the fusion polypeptides of the invention are glycosylated. In some embodiments, the fusion protein further comprises a modified Fc fragment having decreased affinity for Fc-gamma-receptor and/or increased serum half-life.

In one embodiment, the present invention provides a fusion polypeptide comprising a human FGF protein or an active fragment thereof (e.g., without the signal peptide); and a linker comprising SEQ ID NO:11. In some embodiments, the fusion polypeptides of the invention are glycosylated. In some embodiments, the fusion protein further comprises a modified Fc fragment having decreased affinity for Fc-gamma-receptor and/or increased serum half-life.

In one embodiment, the present invention provides a pharmaceutical composition (e.g., in an intra-muscular administering form) comprising (e.g., as a sole pharmaceutically active ingredient) a fusion polypeptide (e.g., glycosylated or non-glycosylated) that comprises (1) sKlotho of alpha Klotho protein with signal peptide (SEQ ID NO: 44 or SEQ ID NO:45); (2) a linker comprising SEQ ID NO:11; and (3) FGF-23 (R179Q) variant without signal peptide (SEQ ID NO: 43); and (4) optionally, a modified Fc fragment having decreased affinity for Fc-gamma-receptor and/or increased serum half-life; and uses of the pharmaceutical composition for treating and/or preventing age-related conditions, such as muscular atrophy. In another embodiment, the present invention provides a pharmaceutical composition (e.g., in an intra-muscular administering form) comprising (e.g., as a sole pharmaceutically active ingredient) a fusion polypeptide (e.g., glycosylated or non-glycosylated) that comprises (1) sKlotho of alpha Klotho protein without signal peptide (SEQ ID NO:7); (2) a linker comprising SEQ ID NO:11; and (3) FGF-23 (R179Q) variant without signal peptide (SEQ ID NO: 43); and (4) optionally, a modified Fc fragment having decreased affinity for Fc-gamma-receptor and/or increased serum half-life; and uses of the pharmaceutical composition for treating and/or preventing age-related conditions, such as muscular atrophy. In one embodiment, the present invention provides a pharmaceutical composition (e.g., in an intra-muscular administering form) comprising (e.g., as a sole pharmaceutically active ingredient) a fusion polypeptide (e.g., glycosylated or non-glycosylated) comprising the amino acid sequence of SEQ ID NO:19, 20, 40, or 41; and uses of the pharmaceutical composition for treating and/or preventing age-related conditions, such as muscular atrophy.

In one embodiment, the present invention provides a pharmaceutical composition (e.g., in all intra-muscular administering form) comprising (e.g., as a sole pharmaceutically active ingredient) a fusion polypeptide (e.g., glycosylated or non-glycosylated) that comprises sKlotho of alpha Klotho protein with signal peptide (SEQ ID NO:44 or SEQ ID NO:45); and a linker comprising SEQ ID NO:11; and uses of the pharmaceutical composition for treating and/or preventing age-related conditions, such as muscular atrophy. In another embodiment, the present invention provides a pharmaceutical composition (e.g., in an intra-muscular administering form) comprising (e.g., as a sole pharmaceutically active ingredient) a fusion polypeptide (e.g., glycosylated or non-glycosylated) comprising sKlotho of alpha Klotho protein without signal peptide (SEQ ID NO:7); and a linker comprising SEQ ID NO:11; and uses of the pharmaceutical composition for treating and/or preventing age-related conditions, such as muscular atrophy. In some embodiments, the fusion protein further comprises a modified Fc fragment.

In one embodiment, the present invention provides a pharmaceuticals composition comprising (e.g., as a sole pharmaceutically active ingredient) a fusion polypeptide (e.g., glycosylated or non-glycosylated) that comprises a human FGF protein or an active fragment thereof (e.g., without the signal peptide); and a linker comprising SEQ ID NO:11.

Pharmaceutical compositions comprising the fusion proteins of the invention and their uses for treating or preventing age-related conditions (e.g., muscle atrophy) or metabolic disorders (e.g., diabete) are also encompassed by the present invention.

In one embodiment, the present invention provides a fusion polypeptide that is at least 85%, at least 90%, at least 91%, at least 92%, at least 93%, at least 94%, at least 95%, at least 96%, at least 96%, at least 97%, at least 98%, at least 99% identical to SEQ ID NO: 19. In another embodiment, the present invention provides a fusion polypeptide that is at least 85%, at least 90%, at least 91%, at least 92%, at least 93%, at least 94%, at least 95%, at least 96%, at least 96%, at least 97%, at least 98%, at least 99% identical to SEQ ID NO: 20.

In one embodiment, the present invention provides a fusion polypeptide that is at least 85%, at least 90%, at least 91%, at least 92%, at least 93%, at least 94%, at least 95%, at least 96%, at least 96%, at least 97%, at least 98%, at least 99% identical to SEQ ID NO: 40. In another embodiment, the present invention provides a fusion polypeptide that is at least 85%, at least 90%, at least 91%, at least 92%, at least 93%, at least 94%, at least 95%, at least 96%, at least 96%, at least 97%, at least 98%, at least 99% identical to SEQ ID NO: 41.

In one embodiment, the present invention provides a fusion polypeptide that is at least 85%, at least 90%, at least 91%, at least 92%, at least 93%, at least 94%, at least 95%, at least 96%, at least 96%, at least 97%, at least 98%, at least 99% or 100% identical to SEQ ID NO: 46. In another embodiment, the present invention provides a fusion polypeptide that is at least 85%, at least 90%, at least 91%, at least 92%, at least 93%, at least 94%, at least 95%, at least 96%, at least 96%, at least 97%, at least 98%, at least 99% or 100% identical to SEQ ID NO: 47.

In another embodiment, the present invention provides a fusion polypeptide that is at least 85%, at least 90%, at least 91%, at least 92%, at least 93%, at least 94%, at least 95%, at least 96%, at least 96%, at least 97%, at least 98%, at least 99% or 100% identical to SEQ ID NO: 48. In another embodiment, the present invention provides a fusion polypeptide that is at least 85%, at least 90%, at least 91%, at least 92%, at least 93%, at least 94%, at least 95%, at least 96%, at least 96%, at least 97%, at least 98%, at least 99% or 100% identical to SEQ ID NO: 49.

In one embodiment, the present invention provides a fusion polypeptide that is at least 85%, at least 90%, at least 91%, at least 92%, at least 93%, at least 94%, at least 95%, at least 96%, at least 96%, at least 97%, at least 98%, at least 99% or 100% identical to SEQ ID NO: 50. In another embodiment, the present invention provides a fusion polypeptide that is at least 85%, at least 90%, at least 91%, at least 92%, at least 93%, at least 94%, at least 95%, at least 96%, at least 96%, at least 97%, at least 98%, at least 99% or 100% identical to SEQ ID NO: 51.

In one embodiment, the present invention provides a fusion polypeptide that is at least 85%, at least 90%, at least 91%, at least 92%, at least 93%, at least 94%, at least 95%, at least 96%, at least 96%, at least 97%, at least 98%, at least 99% or 100% identical to SEQ ID NO: 52. In another embodiment, the present invention provides a fusion polypeptide that is at least 85%, at least 90%, at least 91%, at least 92%, at least 93%, at least 94%, at least 95%, at least 96%, at least 96%, at least 97%, at least 98%, at least 99% or 100% identical to SEQ ID NO: 53.

In one embodiment, the present invention provides a fusion polypeptide comprising a sKlotho of beta Klotho protein with signal peptide fused (directly or indirectly via a linker) to FGF-19 or an active fragment thereof. In some embodiments, the fusion further comprises a modified Fc fragment having decreased affinity for Fc-gamma-receptor and/or increased serum half-life. In another embodiment, the present invention provides a fusion polypeptide comprising a sKlotho of beta Klotho protein without signal peptide fused (directly or indirectly via a linker) to FGF-19 or an active fragment thereof. In another embodiment, the present invention provides a fusion polypeptide comprising a sKlotho of beta Klotho protein with signal peptide fused (directly or indirectly via a linker) to FGF-21 or an active fragment thereof. In another embodiment, the present invention provides a fusion polypeptide comprising a sKlotho of beta Klotho protein without signal peptide fused (directly or indirectly via a linker) to FGF-21 or an active fragment thereof.

The invention provides nucleic acid sequences encoding any of the Klotho fusion polypeptides described herein and host cells containing the nucleic acids. In some embodiments, the fusion further comprises a modified Fc fragment having decreased affinity for Fc-gamma-receptor and/or increased serum half-life.

The invention also provides composition having any of the Klotho fusion polypeptides contemplated herein. The compositions of the invention can further include heparin. In some embodiments, the fusion further comprises a modified Fc fragment having decreased affinity for Fc-gamma-receptor and/or increased serum half-life.

The invention also provides a method for treating or preventing an age-related condition in an individual. An individual (e.g., human) is administered a therapeutically effective dose of a pharmaceutical composition containing a Klotho fusion polypeptide, having at least one extracellular subdomain of a Klotho protein (e.g., alpha Klotho protein) and a fibroblast growth factor or an active fragment thereof so as to treat or prevent the age-related condition. In some embodiments, the fusion further comprises a modified Fc fragment having decreased affinity for Fc-gamma-receptor and/or increased serum half-life. In particular, the invention provides a method of treating or preventing muscle wasting comprising administering to an individual (e.g., human) an therapeutically effective amount of a fusion polypeptide having at least one extracellular subdomain of an alpha Klotho protein and a fibroblast growth factor (or an active fragment thereof).

Additionally, the invention provides a method for treating or preventing a metabolic disorder in an individual. An individual is administered a therapeutically effective dose of a pharmaceutical composition containing a fusion polypeptide of the invention, having at least one extracellular subdomain of a Klotho protein and a fibroblast growth factor (or an active fragment thereof) so as to treat the metabolic disorder. In some embodiments, the fusion further comprises a modified Fc fragment having decreased affinity for Fc-gamma-receptor and/or increased serum half-life. In particular, a fusion polypeptide of the invention having at least one extracellular subdomain of a beta-Klotho protein and a fibroblast growth factor 21 is useful for treating a metabolic disorder.

Klotho-FGF23 fusion polypeptides of the invention can be used for treating or preventing hyperphosphatemia or calcinosis in an individual. In some embodiments, the fusion further comprises a modified Fc fragment having decreased affinity for Fc-gamma-receptor and/or increased serum half-life. A pharmacologically effective dose of a pharmaceutical composition containing the Klotho fusion polypeptide of the invention, having at least one extracellular subdomain of a Klotho protein and a fibroblast growth factor, is administered to treat or prevent hyperphosphatemia or calcinosis. In particular, a Klotho fusion polypeptide of the invention having at least one extracellular subdomain of an alpha Klotho protein and a fibroblast growth factor 23 is useful for treating hyperphosphatemia or calcinosis.

Klotho-FGF23 fusion polypeptides of the invention can be used for treating or preventing chronic renal disease or chronic renal failure in an individual. In some embodiments, the fusion further comprises a modified Fc fragment having decreased affinity for Fc-gamma-receptor and/or increased serum half-life. A therapeutically effective dose of a pharmaceutical composition containing the Klotho fusion polypeptide of the invention, having at least one extracellular subdomain of a Klotho protein (e.g., alpha Klotho protein) and a fibroblast growth factor, is administered to treat or prevent chronic renal disease or chronic renal failure.

Klotho-FGF23 fusion polypeptides of the invention can be used for treating or preventing cancer (e.g., breast cancer) in an individual. In some embodiments, the fusion further comprises a modified Fc fragment having decreased affinity for Fc-gamma-receptor and/or increased serum half-life. A therapeutically effective dose of a pharmaceutical composition containing the Klotho fusion polypeptide of the invention, having at least one extracellular subdomain of a Klotho protein (e.g., alpha Klotho protein) and a fibroblast growth factor, is administered to treat or prevent cancer or breast cancer.

The present invention provides fusion polypeptides comprising at least one extracellular subdomain of Klotho protein and a FGF or an active fragment thereof for use in medicine. In some embodiments, the fusion further comprises a modified Fc fragment having decreased affinity for Fc-gamma-receptor and/or increased serum half-life. In one embodiment, the present invention provides fusion polypeptides comprising at least one extracellular subdomain of Klotho protein and a FGF or an active fragment thereof for use in treating or preventing muscle atrophy. The present invention also provides a method of treating or preventing an age related condition (e.g., muscle atrophy) comprising administering to an individual in need thereof a therapeutically effective dose of a pharmaceutical composition comprising a soluble Klotho protein.

The invention also includes kits for treating or preventing an age-related disorder or metabolic disorder in an individual. The kit includes instructions for use and a purified Klotho fusion polypeptide having at least one extracellular subdomain of a Klotho protein and a fibroblast growth factor. In some embodiments, the fusion further comprises a modified Fc fragment having decreased affinity for Fc-gamma-receptor and/or increased serum half-life.

The invention also provides a kit for producing a Klotho fusion polypeptide of the invention. The kit of the invention includes instructions for use and a nucleic acid encoding a Klotho fusion polypeptide, having at least one extracellular subdomain of Klotho protein and a fibroblast growth factor. In some embodiments, the fusion further comprises a modified Fc fragment having decreased affinity for Fc-gamma-receptor and/or increased serum half-life.

In one embodiment of the invention, the fusion polypeptide comprises: (a) a polypeptide comprising a fibroblast growth factor; and (b) a modified Fc fragment having decreased affinity for Fc-gamma-receptor and/or increased serum half-life In one embodiment of the invention, the polypeptide of (a) and the polypeptide of (b) are connected by a polypeptide linker. The linker can be repeated 1 to 30 times, or more.

In one embodiment of the invention, the polypeptide linker comprises an amino acid sequence selected from the group consisting of: SEQ ID NO:11, SEQ ID NO:12, SEQ ID NO:13, SEQ ID NO:14, SEQ ID NO:15, SEQ ID NO:16, SEQ ID NO:17, and SEQ ID NO:18.

In one embodiment of the invention, the polypeptide of (a) is connected by a peptide bond to the N-terminus of said polypeptide linker, and the polypeptide of (b) is connected by a peptide bond to the C-terminus of said polypeptide linker.

In one embodiment of the invention, the fusion polypeptide further comprises a signal peptide.

In one embodiment of the invention, the signal peptide is the IgG signal peptide.

In one embodiment of the invention, the fibroblast growth factor is fibroblast growth factor-23 or a fibroblast growth factor-23 variant (R179Q).

In one embodiment of the invention, the fibroblast growth factor is fibroblast growth factor-19 or fibroblast growth factor-21.

In one embodiment of the invention, fusion polypeptide comprises an amino acid sequence which is 95% or more identical to the amino acid sequence of SEQ ID NO: 51, or SEQ ID NO: 53.

In one embodiment of the invention, fusion polypeptide comprises the amino acid sequence of SEQ ID NO:51, or SEQ ID NO:53.

In one embodiment of the invention, fusion polypeptide comprises FcLALA.

3. BRIEF DESCRIPTION OF THE DRAWINGS

Figure 1B:
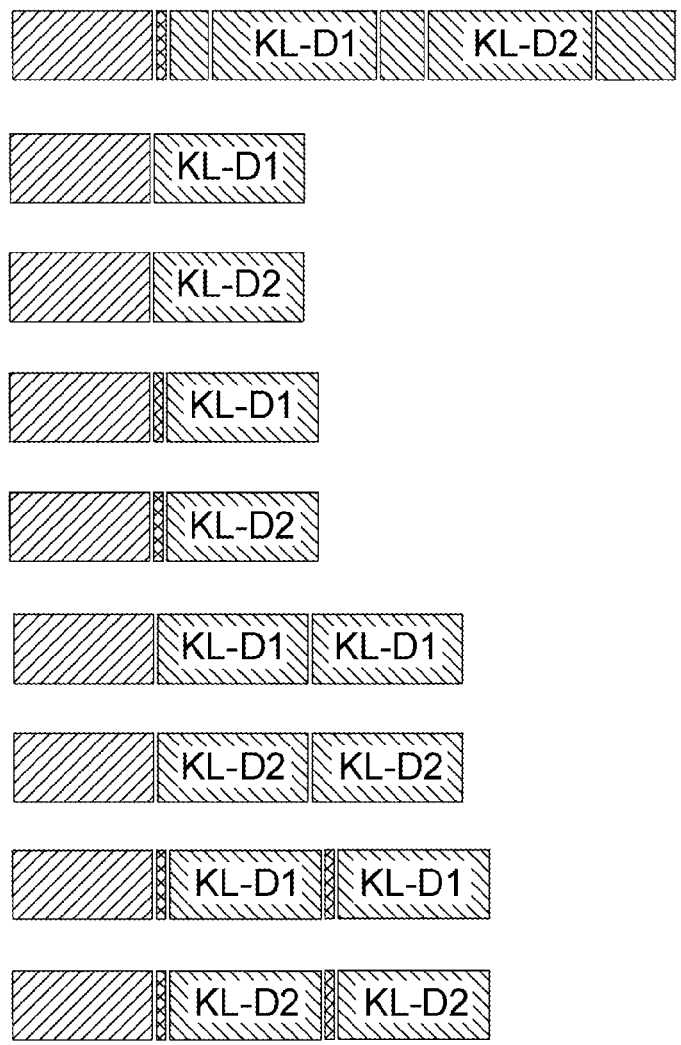

FIGS. 1A and 1B illustrate several different embodiments of the Klotho fusion polypeptides. The represented fusion polypeptides include one or more Klotho extracellular subdomains operatively linked to a fibroblast growth factor. Polypeptides containing one or more Klotho extracellular subdomains include, for example, an extracellular domain of Klotho (e.g., aa 1 to 982 of human Klotho), or an active fragment of Klotho.

Figure 2A:
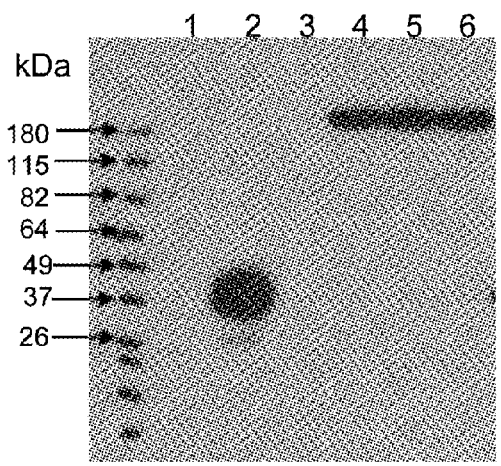
Figure 2B:
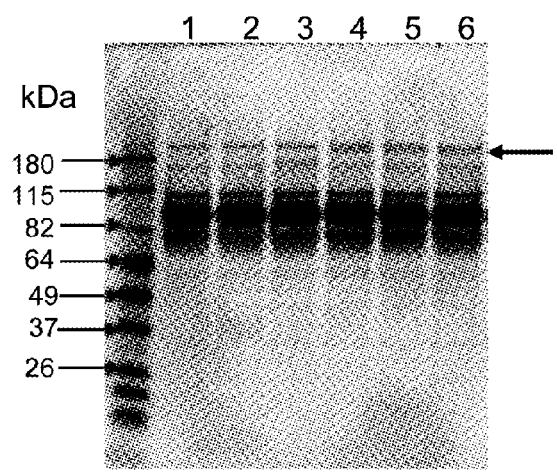
Figure 2C:
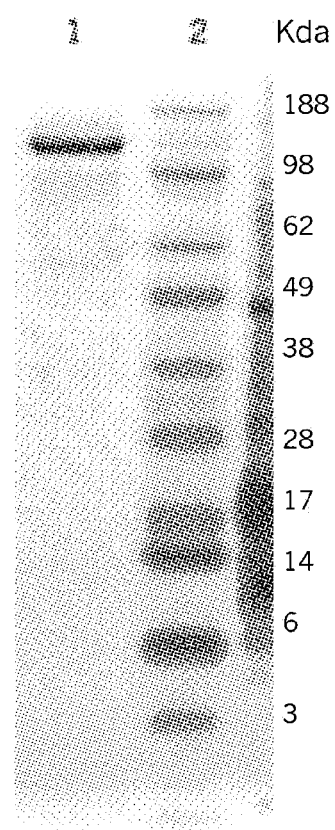

FIGS. 2A-2C depict protein expression of an sKlotho-FGF23 fusion protein. FIG. 2A shows that sKlotho-FGF23 fusion protein was detected in conditioned media by Western blotting with anti-FGF23 antibodies. FIG. 2B shows that sKlotho-FGF23 fusion protein was detected in conditioned media by SDS-PAGE and Coomassie blue staining FIG. 2C shows a highly purified sKlotho-FGF23-6×His fusion protein, analyzed by SDS-PAGE and Coomassie blue staining.

Figure 3:
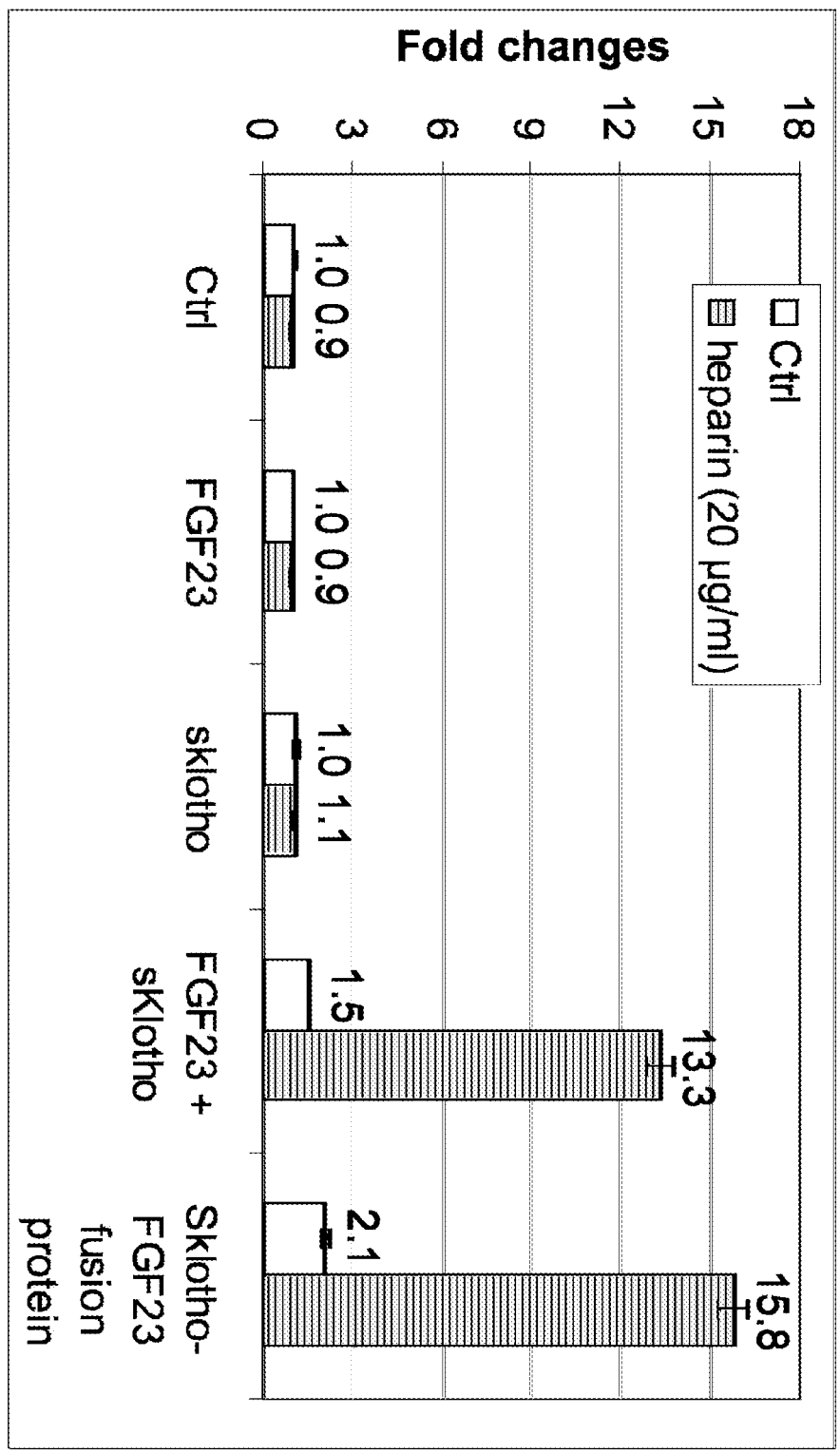

FIG. 3 illustrates the results of an Egr-1 luciferase assay comparing the activation level of Egr-1 in cells treated with conditioned media containing either a Klotho fusion polypeptide, a FGF23 polypeptide only, a soluble Klotho (sKlotho) polypeptide only, and a soluble Klotho polypeptide in combination with a FGF23 polypeptide in the absence or presence of heparin (20 µg/ml).

Figure 4A:
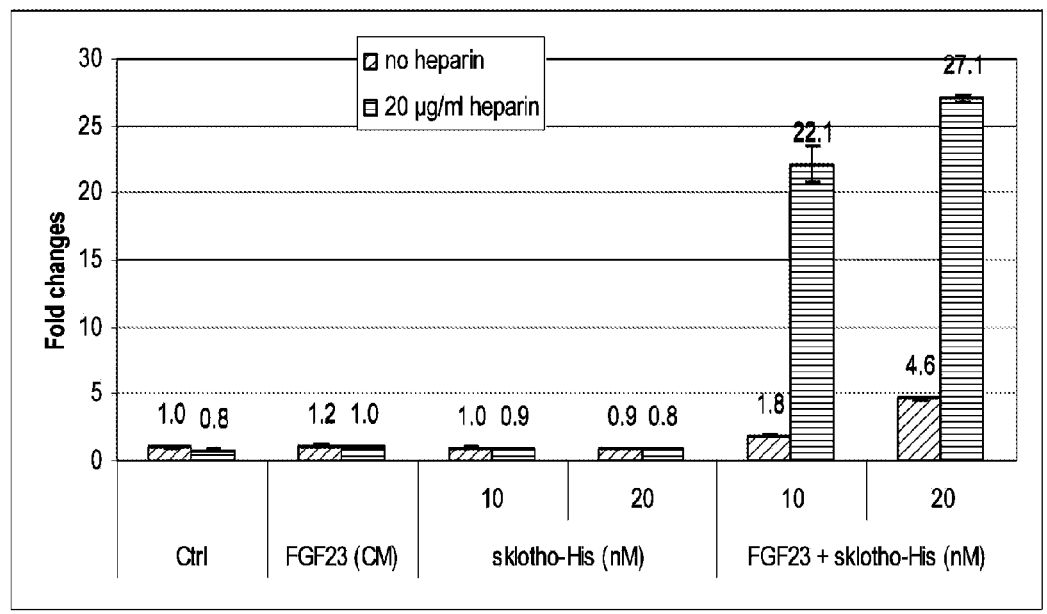
Figure 4B:
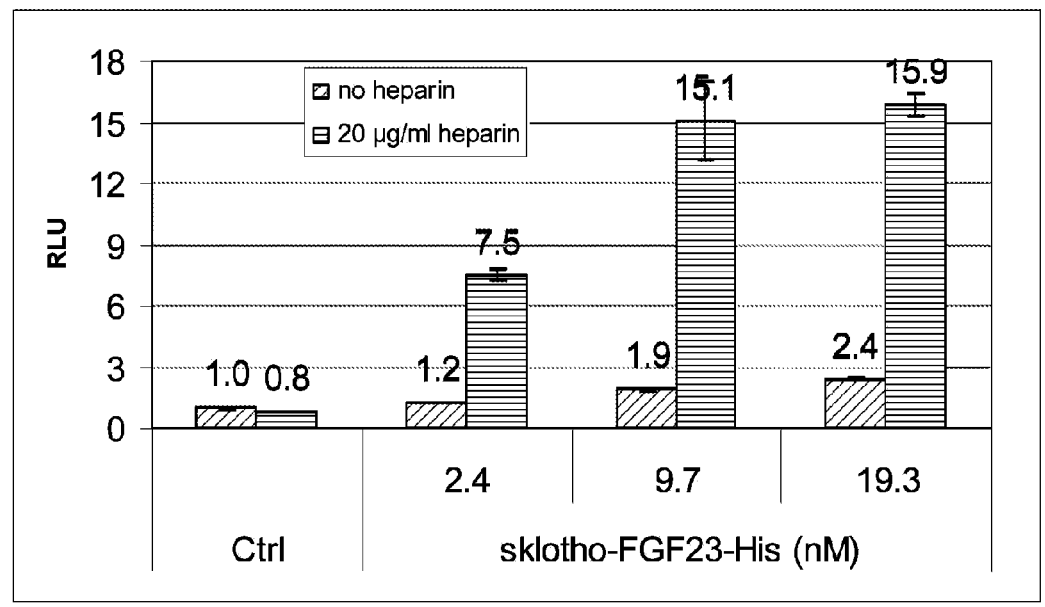

FIGS. 4A-4B depict the results of an Egr-1 luciferase assay comparing the activation level of Egr-1 in cells treated with purified Klotho fusion polypeptide, FGF23 polypeptide, or soluble Klotho polypeptide in the absence or presence of heparin. FIG. 4A shows the results of an experiment comparing the activation level of Egr-1 in cells treated with FGF23 alone, sKlotho-His (10 nM or 20 nM) and a combination of FGF23 and sKlotho-His (10 nM or 20 nM) in the absence or presence of heparin (20 µg/ml). FIG. 4B shows Egr-1 luciferase reporter activity in cells treated with sKlotho-FGF23-His fusion (0 nM, 0.6 nM, 1.21 nM, 2.41 nM, 4.83 nM, 9.65 nM, and 19.3 nM).

Figure 5A:
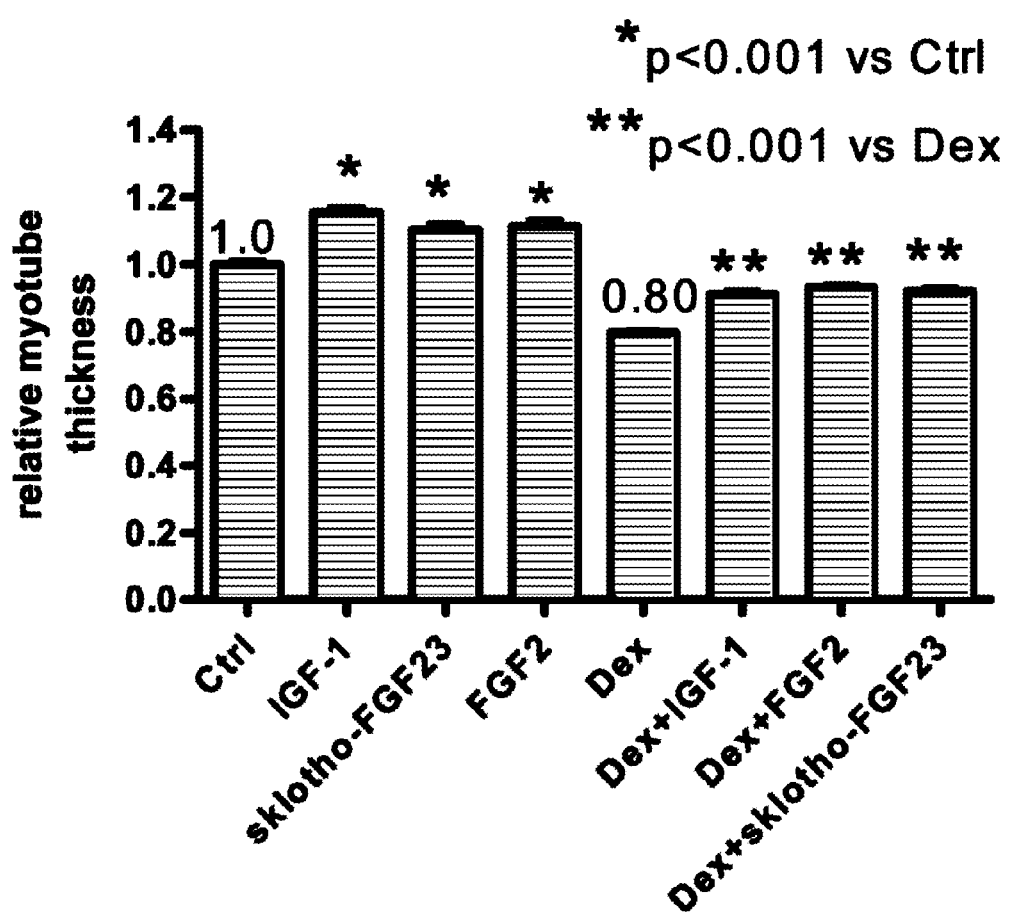
Figure 5B:
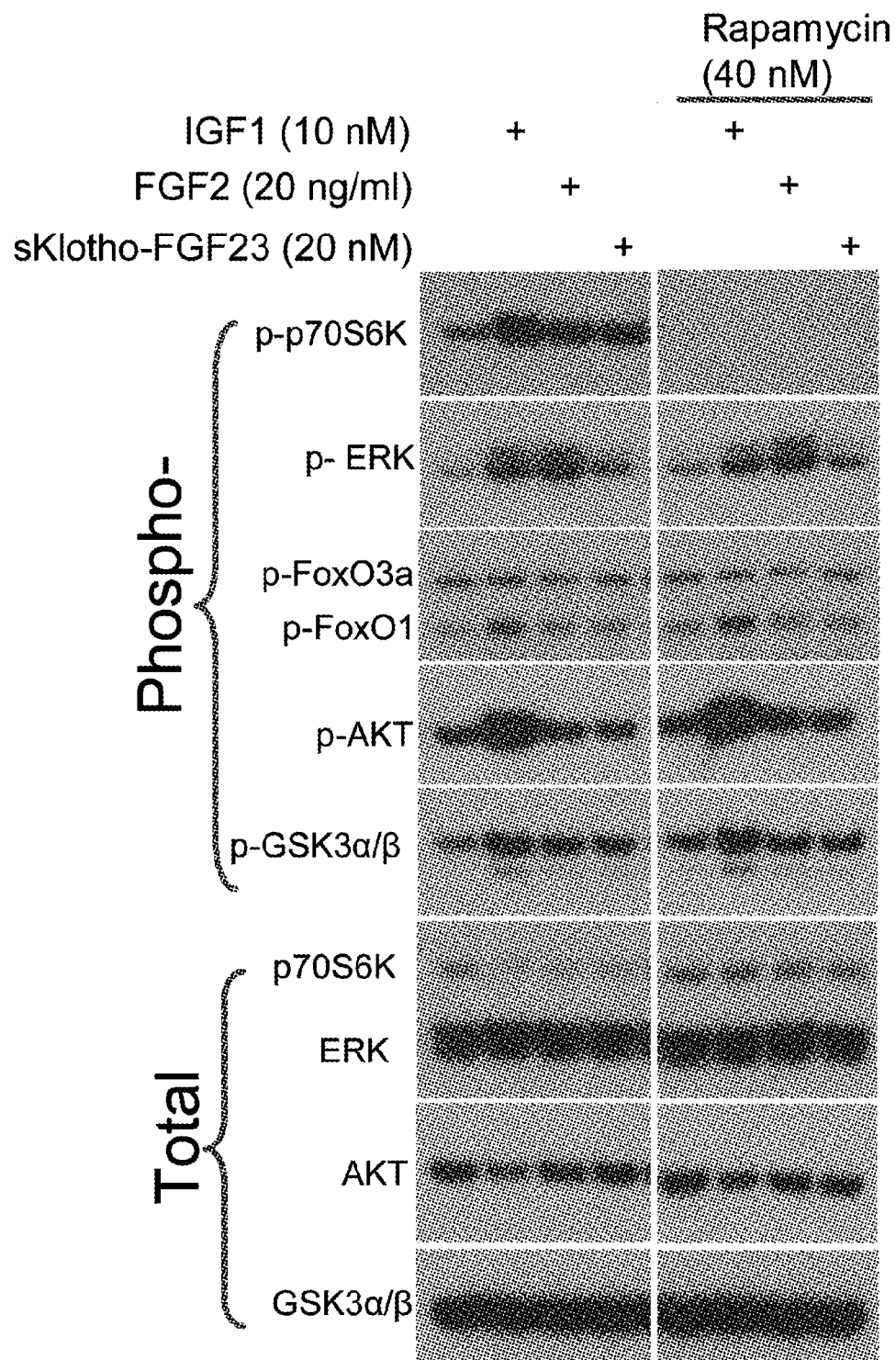

FIGS. 5A-5B illustrate the effect of treatment with a purified sKlotho fusion polypeptide on C2C12 muscle cells. FIG. 5A shows measurements of myotube diameter in C2C12 muscle cells treated with either IGF-1 (10 nM), FGF2 (20 ng/ml), or a purified Klotho fusion polypeptide (20 nM), in the absence or presence of dexamethasone (100 µM). FIG. 5B shows the phosphorylation of signaling pathway proteins in C2C12 muscle cells by IGF-1 (10 nM), FGF2 (20 ng/ml), or a purified Klotho fusion polypeptide (20 nM), in the absence or presence of rapamycin (40 nM).

4. DETAILED DESCRIPTION

The present invention is directed to methods, kits and compositions for preventing or treating age-related conditions and metabolic disorders. The fusion polypeptides of the invention include a Klotho protein or active fragment thereof. In some embodiments, the fusion polypeptides of the invention include a Klotho protein or an active fragment thereof operatively linked to a fibroblast growth factor polypeptide or active fragment thereof. In some embodiments, the fusion further comprises a modified Fc fragment with decreased ability to bind FcRn and/or increased stability in serum. In another embodiment, the fusion polypeptide comprises a FGF (e.g., FGF23) and a modified Fc fragment with decreased ability to bind FcRn and/or increased stability in serum.

The fusion proteins or sKlotho of the present invention are useful in the treatment and prevention of a variety of age-related conditions including sarcopenia, skin atrophy, muscle wasting, brain atrophy, atherosclerosis, arteriosclerosis, pulmonary emphysema, osteoporosis, osteoarthritis, immunologic incompetence, high blood pressure, dementia, Huntington's disease, Alzheimer's disease, cataracts, age-related macular degeneration, prostate cancer, stroke, diminished life expectancy, memory loss, wrinkles, impaired kidney function, and age-related hearing loss; and metabolic disorders including Type II Diabetes, Metabolic Syndrome, hyperglycemia, and obesity.

The present invention is based at least in part on the finding that despite the physical constraints (e.g., large size of both the Klotho and FGF polypeptides) the Klotho-FGF fusion polypeptides are highly effective in activating an FGF receptor. This finding is unexpected given that fusion of these two proteins would likely interfere with the heterodimerization and thus the activities of the proteins; e.g., the binding domains of the proteins may be perturbed by the fusion or the proteins may be mis-oriented spatially if put together in a "cis" formation.

The fusion polypeptides described herein are advantageous because they allow the administration of a single therapeutic protein that has enhanced activity compared to Klotho or FGF administered alone or together as separate polypeptides. The use of Klotho and FGF as a single fusion polypeptide rather than as two separate polypeptides (i.e., a Klotho polypeptide and a separate FGF polypeptide) is more effective at activating the FGF receptor.

Definitions

"Klotho polypeptide", "Klotho protein", or "Klotho" as used herein, includes active fragments, derivatives, mimetics, variants and chemically modified compounds or hybrids thereof of wild-type "Klotho". A Klotho active fragment has the ability to bind to an FGF polypeptide. Generally, a Klotho active polypeptide contains at least a Klotho subdomain (e.g., KL-D1 and KL-D2). Wild-type Klotho has the amino acid sequence as is found in nature. Exemplary Klotho polypeptides suitable for use with the present invention include alpha-Klotho (SEQ ID NO: 2) and beta-Klotho (SEQ ID NO: 4). Nucleotide and amino acid sequences of the alpha-Klotho and beta-Klotho are found in the GenBank database at Accession No. NM_004795; NP_004786 and NM_175737; NP 783864, respectively. Klotho polypeptides include those described in U.S. Pat. No. 6,579,850, the content of which is herein incorporated by reference in its entirety. The Klotho polypeptides include those from other species besides humans, including alpha-Klotho from mouse (NP_038851), rat (NP_112626), rabbit (NP_001075692) and beta-Klotho from mouse (NP_112457). Species predicted to have alpha-Klotho include chimpanzee (XP_522655), macaque (XP_001101127), horse (XP_001495662), cow (XP_001252500), platypus (XP_001510981), and chicken (XP_417105). Species predicted to have beta-Klotho include chimpanzee (XP 526550), macaque (XP_001091413), horse (XP_001495248), dog (XP 536257), rat (XP_001078178), platypus (XP_001512722), and chicken (XP 423224). The Klotho polypeptides have an amino acid sequence that is substantially identical to the amino acid sequence of SEQ ID NO: 2 or SEQ ID NO:4; i.e., at least 70%, 75%, 80%, 85%, 90%, 95%, 96%, 97%, 98%, 99% or more identical at the amino acid sequences of SEQ ID NO:2 or SEQ ID NO:4, or active fragment thereof.

"Fusion polypeptide" or "fusion protein", as used herein, shall mean a polypeptide comprising two or more different polypeptides or active fragments thereof that are not naturally present in the same polypeptide. In some embodiments, the two or more different polypeptides are operatively linked together covalently, e.g., chemically linked or fused in frame by a peptide bond. As used herein a "Klotho fusion polypeptide" is a fusion polypeptide which includes an amino acid sequence from a Klotho polypeptide or active fragment thereof. A fusion polypeptide can comprise, as non-limiting examples, Klotho (e.g., sKlotho), FGF (e.g., FG23), and (optionally) a modified Fc fragment (e.g., a modified Fc fragment with decreased binding affinity to FC-gamma-receptor and/or increased serum half— life). Examples of this type of fusion polypeptide are presented in SEQ ID NOs. 46 to 49. In another embodiment, the fusion proteins comprise FGF (e.g., FGF23) and a modified Fc (e.g., FcLALA). Fusion proteins comprising FGF23 and FcLALA are described in SEQ ID NOs. 50, 51, 52 and 53. FcLALA is a Fc fragment with a LALA mutation (L234A, L235A), which triggers ADCC with lowered efficiency, and binds and activates human complement weakly. Hessell et al. 2007 Nature 449:101-104.

"Fibroblast growth factor" and "FGF" are used interchangeably herein and shall refer to polypeptides that regulate cell proliferation, migration, differentiation, homeostasis, tissue repair and response to injury in an animal, including a human subject. FGFs have the ability to bind to a fibroblast growth factor receptor and regulate its activity, including autophosphorylation of FGFR, phosphorylation of FRS2 (FGF receptor substrate 2) and ERK1/2 (extracellular signal-regulated protein kinase 1/2), and activating Egr-1 (early growth response-1). The term "FGF" includes active fragments, derivatives, mimetics, variants and chemically modified compounds or hybrids thereof of wild-type "FGF", e.g., as known in the art and as described in U.S. Pat. No. 7,223,563 and U.S. Pat. No. 7,259,248, the contents of which are incorporated by reference in their entirety. Wild-type FGF has an amino acid sequence as is found in nature. Exemplary fibroblast growth factors suitable for use with the present invention include fibroblast growth factor-19 (FGF19; SEQ ID NO: 31), fibroblast growth factor-21 (FGF21; SEQ ID NO: 33), and fibroblast growth factor-23 (FGF23; SEQ ID NO: 35). The FGF polypeptides include those from other species besides humans, including murine FGFs. Generally, FGF polypeptides have an amino acid sequence that is substantially identical to the amino acid sequence of SEQ ID NO: 31, SEQ ID NO:33 or SEQ ID NO:35; i.e., having an amino acid sequence is which is at least 70%, 75%, 80%, 85%, 90%, 95%, 96%, 97%, 98%, 99% or more or 100% identical to the amino acid sequences of SEQ ID NO: 31 SEQ ID NO:33 or SEQ ID NO:35, or active fragments thereof. Additional non-limiting examples of FGF, particularly FGF23, are provided at aa 1002-1228 of SEQ ID NO:47; aa 1002-1228 of SEQ ID NO: 49; aa 1-251 of SEQ ID NO: 51, and aa 1-251 of SEQ ID NO:53; and sequences which are at least 70%, 75%, 80%, 85%, 90%, 95%, 96%, 97%, 98%, 99% or more or 100% identical to these sequences. Nucleotides encoding these sequences are provided in SEQ ID NOs: 46, 48, 50 and 52.

The term "FGF", includes active fragments of the full-length polypeptide. Active FGF fragments that are able to bind to their corresponding FGF receptors are known in the art and also contemplated for use in the present invention. One skilled in the art would appreciate, based on the sequences disclosed herein, that overlapping fragments of the FGFs can be generated using standard recombinant technology, for example, that described in Sambrook et al. (1989, Molecular Cloning: A Laboratory Manual, Cold Spring Harbor Laboratory Press, New York) and Ausubel et al. (1997, Current Protocols in Molecular Biology, Green & Wiley, New York). One skilled in the art would appreciate, based on the disclosure presented herein, that the biological activity of FGF fragments could be tested by methods well known in the art and described herein, including binding to the FGF receptor. Similarly, cell culture models which possess the necessary FGF signal transduction machinery (i.e. FGF receptor) may be transfected with FGF fragments and subsequently tested for alterations in FGF signaling, relative to wild type FGF.

FGFs are grouped into seven subfamilies based on the homology of the FGF core homology domain (approximately 120 amino acids long), which is flanked by N- and C-terminal sequences that are highly variable in both length and primary sequence, particularly among different FGF subfamilies (Goetz et al., Molecular and Cellular Biology, 2007, Vol. 27, 3417-3428). An FGF active polypeptide generally contains at least an FGF core homology domain. In some embodiments, an FGF active polypeptide may contain, in addition to an FGF core homology domain, flanking sequences which may confer additional specificity in binding FGF receptors. FGF19, FGF21, and FGF23 are grouped in the FGF19 subfamily because the core region of these ligands share high sequence identity relative to other FGFs (FGF19 v. FGF21: 38% identity; FGF19 v. FGF23: 36% identity). FGF19 subfamily members act analogously to signaling molecules of the endocrine system and regulate diverse physiological processes uncommon to classical FGFs (e.g., FGF19: energy and bile acid homeostasis; FGF21: glucose and lipid metabolism; and FGF 23: phosphate and vitamin D homeostasis).

"Fibroblast growth factor receptor" and "FGFR" as used herein refer to any one of FGFRs 1-4 known in the art, or splice variants thereof (e.g., FGFR1c). Exemplary fibroblast growth factor receptors suitable for use with the present invention include fibroblast growth factor receptor-19 (e.g., FGFR4-beta Klotho), fibroblast growth factor receptor-21 (e.g., FGFR1c-alpha Klotho), and fibroblast growth factor receptor-23 (e.g., FGFR1c-alpha Klotho, FGFR3-alpha Klotho, FGFR4-alpha Klotho).

"Extracellular domain", as used herein, refers to the fragment of a transmembrane protein existing outside of a cell (e.g., not including the intracellular or transmembrane region). The "extracellular domain of the Klotho protein", "soluble Klotho", or "sKlotho" (e.g., SEQ ID NO: 7; SEQ ID NO: 39), refers to an extracellular domain of the Klotho polypeptide that is capable of binding a fibroblast growth factor, and/or capable of enabling the binding of a fibroblast growth factor to a fibroblast growth factor receptor by binding to the fibroblast growth factor. The Klotho extracellular domain corresponds to amino acid residues 28-982 of the full length alpha Klotho sequence (SEQ ID NO: 2) and to amino acid residues 52-997 of the full length beta Klotho sequence (SEQ ID NO:4).

"Extracellular subdomain of Klotho protein" and "extracellular subdomain of Klotho protein" are used interchangeably herein and shall refer to a region in the extracellular domain of the Klotho polypeptide that is capable of binding a fibroblast growth factor, and/or is capable of enabling the binding of a fibroblast growth factor to a fibroblast growth factor receptor by binding to the fibroblast growth factor. In various embodiments, the fusion comprises a polypeptide comprising at least one extracellular subdomain of a Klotho protein; a polypeptide comprising a fibroblast growth factor; and, optionally, a modified Fc fragment having decreased affinity for Fc-gamma-receptor and/or increased serum half-life. The Klotho extracellular domain has two homologous subdomains that are repeated, i.e., KL-D1 (SEQ ID NO: 5) and KL-D2 (SEQ ID NO: 6). KL-D1 and KL-D2 correspond respectively to amino acid residues 58-506 and 517-953 of the full length alpha Klotho polypeptide (SEQ ID NO: 2) and respectively to amino acid residues 77-508 and 571-967 of the full length beta Klotho polypeptide (SEQ ID NO:4) and are suitable for use with the present invention. Generally, a polypeptide that contains at least one Klotho subdomain is a Klotho active polypeptide. The Klotho extracellular subdomain for use with the polypeptide of the invention may be an alpha Klotho or beta Klotho KL-D1 domain with an amino acid sequence that is substantially identical to the amino acid sequence of SEQ ID NO: 5 or SEQ ID NO: 37, respectively. Further, the Klotho KL-D1 domain may have an amino acid sequence that is at least 70%, 75%, 80%, 85%, 90%, 95%, 96%, 97%, 98%, 99% or more identical to the amino acid sequence of SEQ ID NO: 5 or SEQ ID NO: 37. The Klotho extracellular subdomain may also be an alpha or beta Klotho polypeptide KL-D2 domain that is substantially identical to the amino acid sequence of SEQ ID NO: 6 or SEQ ID NO: 38, respectively. In a further embodiment, the KL-D2 domain has an amino acid sequence that is at least at least 70%, 75%, 80%, 85%, 90%, 95%, 96%, 97%, 98%, 99% or more identical to the amino acid sequence of SEQ ID NO: 6 or SEQ ID NO: 38. In some embodiments, the fusion comprises at least two extracellular subdomains of the Klotho protein (e.g., KL-D1 and KL-D2; KL-D1 and KL-D1 in tandem repeats; KL-D2 and KL-D2 in tandem repeats, etc.).

"Modified Fc fragment", as used herein, shall mean an Fc fragment of an antibody comprising a modified sequence. The Fc fragment is a portion of an antibody comprising the CH2, CH3 and part of the hinge region. The modified Fc fragment can be derived from, for example, IgG1, IgG2, IgG3, or IgG4. FcLALA is a modified Fc fragment with a LALA mutation (L234A, L235A), which triggers ADCC with lowered efficiency, and binds and activates human complement weakly. Hessell et al. 2007 Nature 449:101-104. Additional modifications to the Fc fragment are described in, for example, U.S. Pat. No. 7,217,798. For example, in various modified Fc fragments: (a) amino acid residue 250 is glutamic acid and amino acid residue 428 is phenylalanine; or (b) amino acid residue 250 is glutamine and amino acid residue 428 is phenylalanine; or (c) amino acid residue 250 is glutamine and amino acid residue 428 is leucine. In some embodiments, amino acid residues 250 and 428 differ from the residues present in an unmodified Fc-fusion protein by amino acid residue 250 being glutamic acid or glutamine and amino acid residue 428 being leucine or phenylalanine, and wherein amino acid residues are numbered by the EU numbering system, as described in U.S. Pat. No. 7,217,798. In some embodiments, the modified Fc-fusion protein has a higher affinity for FcRn at pH 6.0 than at pH 8.0. Preferably, the modified Fc fragment has decreased affinity to FcRn and/or increased serum half-life. Non-limiting examples of modified Fc fragments include that at aa (amino acids) 1234-1459 of SEQ ID NO: 47; aa 1234 to 1450 of SEQ ID NO: 49; aa 257 to 482 of SEQ ID NO: 51; and aa 257 to 473 of SEQ ID NO: 53; and sequences which are at least 70%, 75%, 80%, 85%, 90%, 95%, 96%, 97%, 98%, 99% or more or 100% identical to these sequences. Nucleotides encoding these sequences are provided in SEQ ID NOs: 46, 48, 50 and 52.

"Signal peptide", as used herein, shall mean a peptide chain (3-60 amino acids long) that directs the post-translational transport of a protein to the endoplasmic reticulum and may be cleaved off. Exemplary signal peptides suitable for use with the present invention include the Klotho signal peptide (SEQ ID NO:19) and the IgG signal peptide (SEQ ID NO:20).

"Linker", as used herein, shall mean a functional group (e.g., chemical or polypeptide) that covalently attaches two or more polypeptides or nucleic acids so that they are connected with one another. As used herein, a "peptide linker" refers to one or more amino acids used to couple two proteins together (e.g., to couple the extracellular domain of Klotho and fibroblast growth factor-23). Peptide linkers suitable for use with the present invention include, but are not limited to, polypeptides with amino acid sequences represented by SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17 and SEQ ID NO:18. A polypeptide linker can comprise at least 1 and up to about 30 repeats of any of these amino acid sequences.

"Operatively linked", as used herein, shall mean the linking of two or more biomolecules so that the biological functions, activities, and/or structure associated with the biomolecules are at least retained. In reference to polypeptides, the term means that the linking of two or more polypeptides results in a fusion polypeptide that retains at least some of the respective individual activities of each polypeptide component. The two or more polypeptides may be linked directly or via a linker. In reference to nucleic acids, the term means that a first polynucleotide is positioned adjacent to a second polynucleotide that directs transcription of the first polynucleotide when appropriate molecules (e.g., transcriptional activator proteins) are bound to the second polynucleotide.

"Specifically binds", as used herein, shall refer to the ability of a first molecule to bind to a target molecule out of many, different types of molecules to which it may be exposed because of the ability of the first molecule to adopt a particular structure conducive to forming non-covalent interactions between itself and the other target molecule. The first molecule binds to the target forming a stable complex while there is substantially less recognition, contact, or complex formation of the first molecule with any other non-specific molecules.

"Polypeptide variant" or "protein variant", as used herein, refers to polypeptides in which one or more amino acids have been substituted by different amino acids from a reference sequence. It is well understood in the art that some amino acids may be substituted by others with broadly similar properties without changing the nature of the activity of the polypeptide (conservative substitutions) as described hereinafter. These terms also encompass polypeptides in which one or more amino acids have been added or deleted, or replaced with different amino acids, e.g., protein isoforms. An exemplary variant of fibroblast growth factor-23 suitable for use with the present invention is the fibroblast growth factor-23 variant (R179Q).

"Pharmaceutical composition", as used herein, shall mean a composition containing a compound (e.g., a fusion polypeptide of the invention) that may be administered to treat or prevent a disease or disorder in an individual.

"Individual" or "subject", as used herein, shall refer to a mammal, including, but not limited to, a human or non-human mammal, such as a bovine, equine, canine, ovine, or feline.

"Treat", as used herein, shall mean decrease, suppress, attenuate, diminish, arrest, or stabilize the development or progression of a disease. In the context of the invention, the administration of the polypeptides of the invention may be used to treat age-related conditions, including sarcopenia, skin atrophy, muscle wasting, brain atrophy, atherosclerosis, arteriosclerosis, pulmonary emphysema, osteoporosis, osteoarthritis, immunologic incompetence, high blood pressure, dementia, Huntington's disease, Alzheimer's disease, cataracts, age-related macular degeneration, prostate cancer, stroke, diminished life expectancy, memory loss, wrinkles, impaired kidney function, and age-related hearing loss; and metabolic disorders, including Type II Diabetes, Metabolic Syndrome, hyperglycemia, and obesity.

"Prevent", as used herein, shall refer to a decrease in the occurrence of a disorder or decrease in the risk of acquiring a disorder or its associated symptoms in a subject. In the context of the invention, the administration of the polypeptides of the invention may be used to prevent age-related conditions, including sarcopenia, skin atrophy, muscle wasting, brain atrophy, atherosclerosis, arteriosclerosis, pulmonary emphysema, osteoporosis, osteoarthritis, immunologic incompetence, high blood pressure, dementia, Huntington's disease, Alzheimer's disease, cataracts, age-related macular degeneration, prostate cancer, stroke, diminished life expectancy, memory loss, wrinkles, impaired kidney function, and age-related hearing loss; and metabolic disorders, including Type II Diabetes, Metabolic Syndrome, hyperglycemia, and obesity. The prevention may be complete, e.g., the total absence of an age-related condition or metabolic disorder. The prevention may also be partial, such that the likelihood of the occurrence of the age-related condition or metabolic disorder in a subject is less likely to occur than had the subject not received the present invention.

"Disease", as used herein, shall mean any condition or disorder that damages or interferes with the normal function of a cell, tissue, or organ.

"Age-related condition", as used herein, shall mean any disease or disorder whose incidence in a population or severity in an individual correlates with the progression of age. In one embodiment, the age-related condition is a disease or disorder whose incidence is at least 1.5 fold higher among human individuals greater than 60 years of age relative to human individuals between the ages of 30-40 and in a selected population of greater than 100,000 individuals. Age-related conditions relevant to the present invention include, but are not limited to, sarcopenia, skin atrophy, muscle wasting, brain atrophy, atherosclerosis, arteriosclerosis, pulmonary emphysema, osteoporosis, osteoarthritis, immunologic incompetence, high blood pressure, dementia, Huntington's disease, Alzheimer's disease, cataracts, age-related macular degeneration, prostate cancer, stroke, diminished life expectancy, memory loss, wrinkles, impaired kidney function, and age-related hearing loss.

"Metabolic disorder", as used herein, shall mean any disease or disorder that damages or interferes with normal function in a cell, tissue, or organ by affecting the production of energy in cells or the accumulation of toxins in a cell, tissue, organ, or individual. Metabolic disorders relevant to the present invention include, but are not limited to, Type II Diabetes, Metabolic Syndrome, hyperglycemia, and obesity.

An "effective dose" or "effective amount" is an amount sufficient to effect a beneficial or desired clinical result. In the context of the invention, it is an amount of a Klotho fusion polypeptide or sKlotho effective to produce the intended pharmacological, therapeutic or preventive result. A therapeutically effective dose results in the prevention or amelioration of the disorder or one or more symptoms of the disorder, (e.g., an age-related condition or metabolic disorder). Therapeutically effective doses will vary depending upon the subject and disease condition being treated, the weight and age of the subject, the severity of the disease condition, the manner of administration and the like which can be readily be determined by one of ordinary skill in the art.

"Klotho nucleic acid molecule", as used herein is a gene encoding a Klotho protein. An exemplary human Klotho gene is provided at GenBank Accession No. NM_004795 (SEQ ID NO:1). Additional non-limiting examples of Klotho are provided at aa 1-982 of SEQ ID NO:47 and aa 1-982 of SEQ ID NO: 49; and sequences which are at least 70%, 75%, 80%, 85%, 90%, 95%, 96%, 97%, 98%, 99% or more or 100% identical to these sequences.

"Fragment", as used herein, refers to a portion of a polypeptide or nucleic acid molecule. This portion contains, preferably, at least 10%, 20%, 30%, 40%, 50%, 60%, 70%, 80%, 90% or more of the entire length of the reference nucleic acid molecule or polypeptide. A fragment may contain 10, 20, 30, 40, 50, 60, 70, 80, 90, or 100, 200, 300, 400, 500, 600, 700, 800, 900, 1000 or up to 3000 nucleotides or amino acids.

The term "substantially identical" refers to a polypeptide or nucleic acid molecule exhibiting at least 50% identity to a reference amino acid sequence (for example, any one of the amino acid sequences described herein) or nucleic acid sequence (for example, any one of the nucleic acid sequences described herein). Preferably, such a sequence is at least 60%, 70%, 75%, 80% or 85%, 90%, 91%, 92%, 93%, 94%, 95%, 96%, 97%, 98%, 99% or more identical at the amino acid level or nucleic acid to the sequence used for comparison.

The present invention is directed to methods, kits and compositions for preventing or treating age-related conditions and metabolic disorders. In some embodiments, the invention provides a fusion polypeptide having at least one extracellular subdomain of a Klotho protein. In some embodiments, the fusion polypeptides further comprise a fibroblast growth factor or an active fragment thereof. In some embodiments, the fusion further comprises a modified Fc fragment having decreased affinity for Fc-gamma-receptor and/or increased serum half-life. In other embodiments, the fusion comprises an FGF (e.g., FGF19, FGF21, FGF23 or FGF23 variant R179Q) fused to a modified Fc (e.g., FcLALA). FcLALA is a Fc fragment with a LALA mutation (L234A, L235A), which triggers ADCC with lowered efficiency, and binds and activates human complement weakly. The Klotho extracellular domain may be derived from either the alpha or beta Klotho isoforms. Further, although the FGF component of the Klotho fusion polypeptide is described primarily with reference to fibroblast growth factor-19, fibroblast growth factor-21 and fibroblast growth factor-23, it is contemplated that any of the twenty-three known FGFs or an active fragment thereof can be used in practicing the invention.

The extracellular domain of the Klotho protein can include one or both of the KL-D1 and KL-D2 domains of a Klotho protein. In some embodiments, the Klotho fusion polypeptide has at least two extracellular subdomains of a Klotho protein. For example, the at least two extracellular subdomains can be at least two KL-D1 domains in tandem repeats, at least two KL-D2 domains in tandem repeats, or at least one KL-D1 domain and at least one KL-D2 domain.

The extracellular subdomain of a Klotho protein and the fibroblast growth factor (or an active fragment thereof) can be operatively linked to one another in a variety of orientations and manners. For example, the extracellular subdomain of the Klotho protein can be operatively linked to the N-terminus of the fibroblast growth factor or alternatively the fibroblast growth factor can be operatively linked to the N-terminus of the at least one extracellular subdomain of the Klotho protein.

The fusion polypeptide of the invention may include one or both of the Klotho extracellular domains, i.e., KL-D1 (SEQ ID NO: 5) and KL-D2 (SEQ ID NO: 6). KL-D1 and KL-D2 correspond respectively to amino acid residues 58-506 and 517-953 of the full length alpha Klotho polypeptide (SEQ ID NO: 2) and to amino acid residues 77-508 and 571-967 of the full length beta Klotho polypeptide (SEQ ID NO:4) and are suitable for use with the present invention. The Klotho fusion polypeptide may have a KL-D1 domain of an alpha Klotho polypeptide having an amino acid sequence that is substantially identical to the amino acid sequence of SEQ ID NO: 5 or of a beta Klotho polypeptide having an amino acid sequence that is substantially identical to the amino acid sequence of SEQ ID NO: 37. Specifically, the Klotho fusion polypeptide may have an amino acid sequence that is at least at least 70%, 75%, 80%, 85%, 90%, 95%, 96%, 97%, 98%, 99% or more identical to SEQ ID NO: 5 or SEQ ID NO: 37. The Klotho fusion polypeptide may have a KL-D2 domain of an alpha Klotho polypeptide with an amino acid sequence that is substantially identical to the amino acid sequence of SEQ ID NO: 6 or of a beta Klotho polypeptide having an amino acid sequence that is substantially identical to the amino acid sequence of SEQ ID NO: 38. Specifically, the Klotho fusion polypeptide may have an amino acid sequence that is at least at least 70%, 75%, 80%, 85%, 90%, 95%, 96%, 97%, 98%, 99% or more identical to SEQ ID NO: 6 or SEQ ID NO: 38, respectively.

In some embodiments, the Klotho fusion polypeptide of the invention is soluble and is capable of binding to an FGF receptor.

The Klotho fusion polypeptides of the invention can contain a polypeptide linker which connects the polypeptide having at least one extracellular subdomain of a Klotho protein and the fibroblast growth factor and the (optional) modified Fc fragment. Suitable linkers are well known in the art and generally contain several Gly and several Ser residues, e.g., $(Gly_4 Ser)_3$ (SEQ ID NO: 11), $Gly_4$ Ser polypeptide (SEQ ID NO: 12), Gly (SEQ ID NO: 13), Gly Gly (SEQ ID NO: 14), Gly Ser (SEQ ID NO: 15), $Gly_2$ Ser (SEQ ID NO: 16), Ala (SEQ ID NO: 17), and Ala Ala (SEQ ID NO: 18). In some embodiments, the linker will have at least 2 and up to about 30 repeats of an amino acid sequence represented by any one of SEQ ID NO:12, SEQ ID NO:13, SEQ ID NO:14, SEQ ID NO:15, SEQ ID NO:16, SEQ ID NO:17, or SEQ ID NO:18.

When a polypeptide linker is present in the Klotho fusion polypeptide of the invention, the polypeptide having at least one extracellular subdomain of a Klotho protein may be connected by a peptide bond to the N-terminus of the linker polypeptide with the FGF connected by a peptide bond to the C-terminus of the polypeptide linker. Alternatively, the FGF may be connected by a peptide bond to the N-terminus of the linker polypeptide with the polypeptide having at least one extracellular subdomain of Klotho connected by a peptide bond to the C-terminus of the polypeptide linker. A chemical linker can also be used to link the two polypeptides.

The Klotho fusion polypeptide of the invention may include a signal peptide. Exemplary signal peptides for use with the Klotho fusion polypeptide include, but are not limited to the Klotho signal peptide (SEQ ID NO: 8) and the IgG signal peptide (SEQ ID NO: 9).

In some embodiments, the invention provides a fusion between a FGF (e.g., FGF19, FGF21, FGF23, or FGF23 variant R179Q) and a modified Fc (e.g., FcLALA). The fusion can also optionally comprise linkers between the FGF and Fc portions. The fusion can also optionally comprise a signal peptide. In various embodiments, the invention encompasses nucleic acids encoding these fusion polypeptides, vectors comprising these nucleic acids, and host cells containing these nucleic acids.

4.1. Klotho and Fibroblast Growth Factor Polypeptides

The Klotho fusion polypeptides of the invention are expected to exhibit biological activities comparable to FGF in nature, such as binding to an FGF receptor and inducing the phosphorylation of an FGF receptor, FRS2 (FGF receptor substrate 2) and ERK1/2 (extracellular signal-regulated protein kinase 1/2) and activating Egr-1 (early growth response-1) gene. FGF is a secreted peptide growth factor that binds the FGF receptor. The amino acid and nucleic acid sequences of FGF are readily available to those of skill in the art. For example, exemplary nucleotide sequences for FGF19, FGF21, and FGF23 can be found in the GenBank database at Accession numbers: NM_005117, NM_019113, and NM_020638, respectively, and herein as SEQ ID NOs: 30, 32, and 34, respectively. Exemplary amino acid sequences for FGF19, FGF21, and FGF23 can be found in the GenBank database at Accession numbers: NP_005108, NP_061986, and NP_065689, respectively, and herein as SEQ ID NOs: 31, 35, and 35, respectively. Additionally, FGF may include one or more alterations which aid in the expression of the protein, e.g., the FGF23 (R179Q) variant (SEQ ID NO: 36).

The Klotho protein is a 130 kDa single pass type I transmembrane protein with an extracellular domain and a short cytoplasmic domain. The amino acid and nucleic acid sequences of Klotho are readily available to those of skill in the art. For example, exemplary nucleotide sequences for alpha-Klotho and beta-Klotho can be found in the GenBank database at Accession numbers: NM_004795 and NM_175737, respectively, and herein as SEQ ID NOs: 7 and 8, respectively. Exemplary amino acid sequences for alpha-Klotho and beta-Klotho can be found in the GenBank database at Accession numbers: NP_004786 and NP_783864, respectively, and herein as SEQ ID NOs: 2 and 4, respectively.

The Klotho fusion polypeptide of the invention can bind to a fibroblast growth factor receptor and has an alpha-Klotho or beta-Klotho extracellular domain operatively linked to either fibroblast growth factor-19 (SEQ ID NO: 31), fibroblast growth factor-21 (SEQ ID NO: 33), fibroblast growth factor- 23 (SEQ ID NO: 35), or variants thereof (which include fibroblast growth factor-23 variant (R179Q) (SEQ ID NO: 36)).

Specifically, the Klotho fusion polypeptide of the invention may include an alpha-Klotho (SEQ ID NO: 2) which is operatively coupled to fibroblast growth factor-23 (SEQ ID NO: 35) or fibroblast growth factor-23 variant (R179Q) (SEQ ID NO: 36). Additionally, the Klotho fusion polypeptide of the invention may have beta-Klotho (SEQ ID NO: 4), which is operatively coupled to fibroblast growth factor-19 (SEQ ID NO: 31). The Klotho fusion polypeptide of the invention may include a beta-Klotho (SEQ ID NO: 4), which is operatively coupled to fibroblast growth factor-21 (SEQ ID NO: 33).

The invention includes homologs of the various Klotho and FGF genes and proteins encoded by those genes. A "homolog," in reference to a gene refers to a nucleotide sequence that is substantially identical over at least part of the gene or to its complementary strand or a part thereof, provided that the nucleotide sequence encodes a protein that has substantially the same activity/function as the protein encoded by the gene which it is a homolog of. Homologs of the genes described herein can be identified by percent identity between amino acid or nucleotide sequences for putative homologs and the sequences for the genes or proteins encoded by them (e.g., nucleotide sequences for genes encoding Klotho and FGF or their complementary strands). Percent identity may be determined, for example, by visual inspection or by using various computer programs known in the art or as described herein. Sequence identity is typically measured using sequence analysis software (for example, Sequence Analysis Software Package of the Genetics Computer Group, University of Wisconsin Biotechnology Center, 1710 University Avenue, Madison, Wis. 53705, BLAST, BESTFIT, GAP, or PILEUP/PRETTYBOX programs). Such software matches identical or similar sequences by assigning degrees of homology to various substitutions, deletions, and/or other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine. In an exemplary approach to determining the degree of identity, a BLAST program may be used, with a probability score between $e^{-3}$ and $e^{-100}$ indicating a closely related sequence.

As used herein, the terms "homology" and "homologous" are not limited to designate proteins having a theoretical common genetic ancestor, but includes proteins which may be genetically unrelated that have, nonetheless, evolved to perform similar functions and/or have similar structures. Functional homology to the various proteins described herein also encompasses proteins that have an activity of the corresponding protein of which it is a homolog. For proteins to have functional homology, it is not required that they have significant identity in their amino acid sequences, but rather, proteins having functional homology are so defined by having similar or identical activities. For example, with respect to a Klotho molecule, the polypeptide should have the functional characteristics of binding to an FGF polypeptide and enable the binding of the FGF to an FGFR. With respect to an FGF molecule, the polypeptide should have the functional characteristics of binding to an FGFR and causing the activation of FGFR (e.g., phosphorylation). Assays for assessing FGF binding to the FGF receptor and/or activation of the FGF signaling pathway are known in the art and described herein (See Example 2). Assays for assessing Klotho activity are also known in the art and described herein (e.g., binding to a FGF polypeptide). Proteins with structural homology are defined as having analogous tertiary (or quaternary) structure and do not necessarily require amino acid identity or nucleic acid identity for the genes encoding them. In certain circumstances, structural homologs may include proteins which maintain structural homology only at the active site or binding site of the protein.

In addition to structural and functional homology, the present invention further encompasses proteins having amino acid identity to the various Klotho and FGF amino acid sequences described herein. To determine the percent identity/homology of two amino acid sequences, the sequences are aligned for optimal comparison purposes (e.g., gaps can be introduced in the amino acid sequence of one protein for optimal alignment with the amino acid sequence of another protein). The amino acid residues at corresponding amino acid positions are then compared. When a position in one sequence is occupied by the same amino acid residue as the corresponding position in the other, then the molecules are identical at that position. The percent identity between the two sequences is a function of the number of identical positions shared by the sequences (i.e., % identity=# of identical positions/total # of positions multiplied by 100).

The amino acid sequences of molecules of the invention described herein have all amino acid sequence which is at least about 60%, 70%, 80%, 90%, 95%, 96%, 97%, 98%, 99% or more identical or homologous to all amino acid sequence described herein.

The nucleic acid sequences of molecules of the invention described herein have a nucleotide sequence which hybridizes to or is at least about 60%, 70%, 80%, 90%, 95%, 96%, 97%, 98%, 99% or more identical or homologous to a nucleotide sequence described herein.

Nucleic acid molecules appropriate for use in the fusion polypeptides of the invention may have a Klotho or FGF nucleotide sequence which hybridizes under stringent conditions to the complement of a nucleic acid molecule encoding Klotho or FGF, respectively. As used herein, the term "hybridizes under stringent conditions" is intended to describe conditions for hybridization and washing under which nucleotide sequences at least about 70%, 80%, 85%, 90% or more homologous to each other typically remain hybridized to each other. Such stringent conditions are known to those skilled in the art and can be found in Ausubel et al. *Current Protocols in Molecular Biology*, Wiley Interscience, New York (2001), 6.3.1-6.3.6. A specific, non-limiting example of stringent hybridization conditions are hybridization in 6× sodium chloride/sodium citrate (SSC) at about 45° C., followed by one or more washes in 0.2×SSC, 0.1% SDS at 50-65° C.

4.2. Klotho-FGF Fusion Polypeptides of the Invention

In some embodiments of the invention, a Klotho fusion polypeptide has a polypeptide chain having a first polypeptide sequence of a Klotho polypeptide or an active fragment thereof and a second polypeptide sequence encoding FGF or an active fragment thereof. In some embodiments, the fusion further comprises a modified Fc fragment having decreased affinity for Fc-gamma-receptor and/or increased serum half-life.

The invention includes fusion polypeptides which are at least about 95% or more homologous to an amino acid sequence presented in SEQ ID NO:19-28. The amino acid sequence of SEQ ID NO: 19 encodes a Klotho fusion polypeptide having a Klotho extracellular domain N-terminally linked to the FGF23 (R179Q) variant (SEQ ID NO: 36). The amino acid sequence of SEQ ID NO: 20 encodes a Klotho fusion polypeptide having an IgG signal peptide N-terminally linked to a Klotho extracellular domain lacking a signal peptide N-terminally linked to the FGF23 (R179Q) variant. The amino acid sequence of SEQ ID NO: 21 encodes a Klotho fusion polypeptide having a KL-D1 extracellular subdomain N-terminally linked to the FGF23 (R179Q) variant. The amino acid sequence of SEQ ID NO: 22 encodes a Klotho fusion polypeptide having a KL-D2 extracellular subdomain N-terminally linked to the FGF23 (R179Q) variant. The amino acid sequence of SEQ ID NO: 23 encodes a Klotho fusion polypeptide having two KL-D1 extracellular subdomains N-terminally linked to the FGF23 (R179Q) variant. The amino acid sequence of SEQ ID NO: 24 encodes a Klotho fusion polypeptide having two KL-D2 extracellular subdomains N-terminally linked to the FGF23 (R179Q) variant. The amino acid sequence of SEQ ID NO: 25 encodes a Klotho fusion polypeptide having the FGF23 (R179Q) variant N-terminally linked to a Klotho extracellular domain. The amino acid sequence of SEQ ID NO: 26 encodes a Klotho fusion polypeptide having the FGF23 (R179Q) variant N-terminally linked to a KL-D1 extracellular subdomain. The amino acid sequence of SEQ ID NO: 27 encodes a Klotho fusion polypeptide having the FGF23 (R179Q) variant N-terminally linked to a KL-D2 extracellular subdomain. The amino acid sequence of SEQ ID NO: 28 encodes a Klotho fusion polypeptide having the FGF23 (R179Q) variant N-terminally linked to two KL-D1 extracellular subdomains. The amino acid sequence of SEQ ID NO: 29 encodes a Klotho fusion polypeptide having the FGF23 (R179Q) variant N-terminally linked to two KL-D2 extracellular subdomains. In some embodiments, the fusion further comprises a modified Fc fragment having decreased affinity for Fc-gamma-receptor and/or increased serum half-life.

The Klotho fusion polypeptide of the invention may include an amino acid sequence which is at least about 95% identical to the amino acid sequence set forth in SEQ ID NO:7. The amino acid sequence of SEQ ID NO: 7 encodes a Klotho extracellular domain lacking a signal peptide. In some embodiments, the fusion further comprises a modified Fc fragment having decreased affinity for Fc-gamma-receptor and/or increased serum half-life.

The subject fusion proteins are described herein and can be made using methods known in the art. For example, the fusion polypeptides of the invention may be constructed as described in U.S. Pat. No. 6,194,177. The use of Klotho polypeptides is described in U.S. Pat. No. 6,579,850. The use of FGF nucleic acid molecules is described in U.S. Pat. No. 7,223,563.

In some embodiments, a nucleic acid molecule encoding the Klotho is cloned by PCR and ligated, in frame, with a nucleic acid molecule encoding FGF. In some embodiments, the fusion further comprises a modified Fc fragment having decreased affinity for Fc-gamma-receptor and/or increased serum half-life. The nucleic acid encoding the fusion polypeptide is operatively linked to a promoter to allow for expression. The nucleic acid molecule encoding the fusion polypeptide is subsequently transfected into a host cell for expression. The sequence of the final construct can be confirmed by sequencing.

When preparing the fusion proteins of the present invention, a nucleic acid molecule encoding an extracellular subdomain of Klotho will be fused in frame to the nucleic acid molecule encoding FGF and the (optional) nucleic acid encoding the modified Fc fragment. Expression of the resulting nucleic acid molecule results in the extracellular subdomain of Klotho being fused N-terminal in relation to the FGF polypeptide. Fusions are also possible in which the extracellular subdomain of Klotho is fused C-terminal in relation to the FGF polypeptide. Methods for making fusion proteins are well known in the art.

The fusion polypeptides of the invention have at least two polypeptides that are covalently linked, in which one polypeptide comes from one protein sequence or domain, e.g., Klotho, and the other polypeptide comes from another protein sequence or domain, e.g., FGF. In some embodiments, the fusion further comprises a modified Fc fragment having decreased affinity for Fc-gamma-receptor and/or increased serum half-life. In another embodiment, the invention comprises a FGF fused to a modified Fc fragment. Klotho and/or FGF and/or the (optional) modified Fc fragment, of the fusion polypeptides of the invention, can be joined by methods well known to those of skill in the art. These methods include both chemical and recombinant means.

Nucleic acids encoding the domains to be incorporated into the fusion polypeptides of the invention can be obtained using routine techniques in the field of recombinant genetics. Basic texts disclosing the general methods of use in this invention include Sambrook and Russell, Molecular Cloning, A Laboratory Manual (3rd ed. 2001); Kriegler, Gene Transfer and Expression: A Laboratory Manual (1990); and Current Protocols in Molecular Biology (Ausubel et al., eds., 1994-1999). In nucleic acids encoding a Klotho fusion polypeptide of the invention, the nucleic acid sequence encoding alpha-Klotho or beta-Klotho, represented by SEQ ID NO: 1 and SEQ ID NO: 3, respectively, may be used. In nucleic acids encoding a Klotho fusion polypeptide, the nucleic acid sequence encoding FGF19, FGF21, or FGF23, represented by SEQ ID NO: 30, SEQ ID NO: 32 and SEQ ID NO: 34, respectively, may be used. Nucleic acid sequences of molecules of the invention described herein comprise a nucleotide sequence which hybridizes to or is at least about 60%, 70%, 80%, 90%, 95%, 96%, 97%, 98%, 99% or more identical or homologous to SEQ ID NO: 1, SEQ ID NO:3, SEQ ID NO: 30, SEQ ID NO: 32, or SEQ ID NO: 34.

Nucleic acid sequences that encode the various components of the fusion [Klotho, and/or FGF peptide and/or the (optional) modified Fc fragment] can be obtained using any of a variety of methods. For example, the nucleic acid sequences encoding the polypeptides may be cloned from cDNA and genomic DNA libraries by hybridization with probes, or isolated using amplification techniques with oligonucleotide primers. More commonly, amplification techniques are used to amplify and isolate the Klotho and FGF sequences using a DNA or RNA template (see, e.g., Dieffenfach & Dveksler, PCR Primers: A Laboratory Manual (1995)). Alternatively, overlapping oligonucleotides can be produced synthetically and joined to produce one or more of the domains. Nucleic acids encoding Klotho or FGF can also be isolated from expression libraries using antibodies as probes.

According to the present invention, the various components of the fusion [Klotho, and/or, FGF and/or the (optional) modified Fc fragment] can be linked either directly or via a covalent linker, including amino acid linkers, such as a polyglycine linker, or another type of chemical linker, including, carbohydrate linkers, lipid linkers, fatty acid linkers, polyether linkers, such as PEG, etc. (See for example, Hermanson, Bioconjugate techniques (1996)). The polypeptides forming the fusion/fusion polypeptide are typically linked C-terminus to N-terminus, although they can also be linked C-terminus to C-terminus, N-terminus to N-terminus, or N-terminus to C-terminus. One or more polypeptide domains may be inserted at an internal location within a fusion polypeptide of the invention. The polypeptides of the fusion protein can be in any order. The fusion polypeptides may be produced by covalently linking a chain of amino acids from one protein sequence, e.g., an extracellular subdomain of Klotho, to a chain of amino acids from another protein sequence, e.g., FGF, by preparing a recombinant polynucleotide contiguously encoding the fusion protein. The different chains of amino acids in a fusion protein may be directly spliced together or may be indirectly spliced together via a chemical linking group or an amino acid linking group. The amino acid linking group can be about 200 amino acids or more in length, or generally 1 to 100 amino acids. In some embodiments, proline residues are incorporated into the linker to prevent the formation of significant secondary structural elements by the linker. Linkers can often be flexible amino acid subsequences that are synthesized as part of a recombinant fusion protein. Such flexible linkers are known to persons of skill in the art.

According to the present invention, the amino acid sequences of the fusion [an extracellular subdomain of Klotho and/or the FGF and/or the (optional) modified Fc fragment] may be linked via a peptide linker. Exemplary peptide linkers are well known in the art and described herein. For example, peptide linkers generally include several Gly and several Ser residues, such as: $(Gly_4 Ser)_3$ (SEQ ID NO: 11), $Gly_4$ Ser polypeptide (SEQ ID NO: 12), Gly (SEQ ID NO: 13), Gly Gly (SEQ ID NO: 14), Gly Ser (SEQ ID NO: 15), $Gly_2$ Ser (SEQ ID NO: 16), Ala (SEQ ID NO: 17), and Ala Ala (SEQ ID NO: 18). Specifically, a peptide linker for use in a fusion protein of the invention may act as a flexible hinge.

The signal sequence of Klotho or FGF may be excluded prior to incorporation of Klotho into a fusion protein of the invention. The signal sequence for Klotho or FGF of the fusion protein may be included, e.g., the polypeptide represented by SEQ ID NO: 19. However, such sequences may also be omitted and replaced with the signal sequence of a different protein, e.g., the IgG signal sequence (SEQ ID NO: 9). Generally, the pharmaceutical compositions of the invention will contain the mature form of Klotho and FGF.

Generally, introns are excluded from either one or both the Klotho or the FGF moieties prior to incorporation into a fusion polypeptide.

The fusion polypeptides of the invention may include one or more polymers covalently attached to one or more reactive amino acid side chains. By way of example, not limitation, such polymers include polyethylene glycol (PEG), which can be attached to one or more free cysteine sulfhydryl residues, thereby blocking the formation of disulfide bonds and aggregation when the protein is exposed to oxidizing conditions. In addition, PEGylation of the fusion polypeptides of the invention is expected to provide such improved properties as increased half-life, solubility, and protease resistance. The fusion polypeptides of the invention may alternatively be modified by the covalent addition of polymers to free amino groups such as the lysine epsilon or the N-terminal amino group. Preferred cysteines and lysines for covalent modification will be those not involved in receptor binding, heparin binding, or in proper protein folding. It will be apparent to one skilled in the art that the methods for assaying the biochemical and/or biological activity of the fusion polypeptides may be employed in order to determine if modification of a particular amino acid residue affects the activity of the protein as desired. Other similar suitable modifications are contemplated and known in the art.

The invention is also directed to the expression of a fusion polypeptide that is at least about 95% or more homologous to an amino acid sequence presented in SEQ ID NO:19-28.

4.3. Expression of Fusion Polypeptides of the Invention

In order to express the fusion protein of the invention, DNA molecules obtained by any of the methods described herein or those that are known in the art, can be inserted into appropriate expression vectors by techniques well known in the art. For example, a double stranded cDNA can be cloned into a suitable vector by homopolymeric tailing or by restriction enzyme linking involving the use of synthetic DNA linkers or by blunt-ended ligation. DNA ligases are usually used to ligate the DNA molecules and undesirable joining can be avoided by treatment with alkaline phosphatase.

Therefore, the invention includes vectors (e.g., recombinant plasmids and bacteriophages) that include nucleic acid molecules (e.g., genes or recombinant nucleic acid molecules encoding genes) as described herein. The term "recombinant vector" includes a vector (e.g., plasmid, phage, phasmid, virus, cosmid, fosmid, or other purified nucleic acid vector) that has been altered, modified or engineered such that it contains greater, fewer or different nucleic acid sequences than those included in the native or natural nucleic acid molecule from which the recombinant vector was derived. For example, a recombinant vector may include a nucleotide sequence encoding a Klotho-FGF23 fusion operatively linked to regulatory sequences, e.g., promoter sequences, terminator sequences and/or artificial ribosome binding sites (RBSs), as defined herein. Recombinant vectors which allow for expression of the genes or nucleic acids included in them are referred to as "expression vectors."

For eukaryotic hosts, different transcriptional and translational regulatory sequences may be employed, depending on the nature of the host. They may be derived from viral sources, such as adenovirus, bovine papilloma virus, Simian virus or the like, where the regulatory signals are associated with a particular gene which has a high level of expression. Examples include, but are not limited to, the TK promoter of the Herpes virus, the SV40 early promoter, the yeast gal4 gene promoter, etc. Transcriptional initiation regulatory signals may be selected which allow for repression or activation, so that expression of the genes can be modulated.

In some of the molecules of the invention described herein, one or more DNA molecules having a nucleotide sequence encoding one or more polypeptide chains of a fusion polypeptide are operatively linked to one or more regulatory sequences, which are capable of integrating the desired DNA molecule into a host cell. Cells which have been stably transformed by the introduced DNA can be selected, for example, by introducing one or more markers which allow for selection of host cells which contain the expression vector. A selectable marker gene can either be linked directly to a nucleic acid sequence to be expressed, or be introduced into the same cell by co-transfection. Additional elements may also be needed for optimal synthesis of proteins described herein. It would be apparent to one of ordinary skill in the art which additional elements to use.

Factors of importance in selecting a particular plasmid or viral vector include, but are not limited to, the ease with which recipient cells that contain the vector are recognized and selected from those recipient cells which do not contain the vector; the number of copies of the vector which are desired in a particular host; and whether it is desirable to be able to "shuttle" the vector between host cells of different species.

Once the vector(s) is constructed to include a DNA sequence for expression, it may be introduced into an appropriate host cell by one or more of a variety of suitable methods that are known in the art, including but not limited to, for example, transformation, transfection, conjugation, protoplast fusion, electroporation, calcium phosphate-precipitation, direct microinjection, etc.

Host cells may either be prokaryotic or eukaryotic. Examples of eukaryotic host cells include, for example, mammalian cells, such as human, monkey, mouse, and Chinese hamster ovary (CHO) cells. Such cells facilitate post-translational modifications of proteins, including, for example, correct folding or glycosylation. Additionally, yeast cells can also be used to express fusion polypeptides of the invention. Like most mammalian cells, yeast cells also enable post-translational modifications of proteins, including, for example, glycosylation. A number of recombinant DNA strategies exist which utilize strong promoter sequences and high copy number plasmids that can be utilized for production of proteins in yeast. Yeast transcription and translation machinery can recognize leader sequences on cloned mammalian gene products, thereby enabling the secretion of peptides bearing leader sequences (i.e., pre-peptides). A particularly preferred method of high-yield production of the fusion polypeptides of the invention is through the use of dihydrofolate reductase (DHFR) amplification in DHFR-deficient CHO cells, by the use of successively increasing levels of methotrexate as described in U.S. Pat. No. 4,889,803. The polypeptide obtained may be in a glycosylated form.

After the introduction of one or more vector(s), host cells are usually grown in a selective medium, which selects for the growth of vector-containing cells. Purification of the recombinant proteins can be carried out by any of the methods known in the art or described herein, for example, any conventional procedures involving extraction, precipitation, chromatography and electrophoresis. A further purification procedure that may be used for purifying proteins is affinity chromatography using monoclonal antibodies which bind a target protein. Generally, crude preparations containing a recombinant protein are passed through a column on which a suitable monoclonal antibody is immobilized. The protein usually binds to the column via the specific antibody while the impurities pass through. After washing the column, the protein is eluted from the gel by changing pH or ionic strength, for example.

4.4. Assays for Assessing Fusion Polypeptide Activity

Assays described herein (See Example 2) and those known in the art can be used for detecting Klotho or FGF activity of the fusion polypeptides of the invention. Suitable activity assays include receptor binding assays, cellular proliferation assays and cell signaling assays. For example, a binding assay which may be used for determining whether a fusion polypeptide has Klotho or FGF activity includes, assaying the binding of a fusion polypeptide to an FGF receptor. FGF receptor binding assays include, but are not limited to, both competitive and non-competitive assay. For example, FGF receptor binding can be detected by contacting cells expressing an FGF receptor with a labeled FGF (for example, radioactive label) and increasing concentrations of an unlabeled Klotho-FGF fusion polypeptide. The two ligands that compete for binding to the same receptor are added to a reaction mixture containing the cell. The cells are subsequently washed and labeled FGF is measured. A decrease in the amount of the labeled FGF to its receptor in the presence of the unlabeled fusion polypeptide is indicative of binding of the Klotho-FGF fusion polypeptide to the receptor. Alternatively, the Klotho-FGF fusion polypeptide may be labeled and direct binding of the fusion polypeptide to the cell is detected.

Klotho or FGF activity can also be measured by determining whether the fusion polypeptide induces a cellular response. For example, in some embodiments, an assay for detecting the biological activity of a Klotho-FGF fusion polypeptide involves contacting cells which express an FGF receptor with a fusion polypeptide, assaying a cellular response such as, for example, cell proliferation or Egr-1 activation, myotube diameter in C2C12 cells, and comparing the cellular response in the presence and absence of the fusion polypeptide. An increase in the cellular response in the presence of the fusion polypeptide complex relative to the absence indicates that the fusion polypeptide has biological activity. Also, an increase in a downstream signaling event from the receptor can also be measured as indicia of biological activity (e.g., phosphorylation of FGFR, FRS2, ERK1/2, p70S6K etc.).

4.5 Pharmaceutical Compositions and Methods of Treatment

The invention also pertains to pharmaceutical compositions containing one or more fusion polypeptides of the invention and a pharmaceutically acceptable diluent or carrier. The pharmaceutical compositions can further include a pharmaceutically effective dose of heparin. Such pharmaceutical compositions may be included in a kit or container. Such kit or container may be packaged with instructions pertaining to the extended in vivo half-life or the in vitro shelf life of the fusion polypeptides. Optionally associated with such kit or container(s) can be a notice in the form prescribed by a governmental agency regulating the manufacture, use or sale of pharmaceuticals or biological products, which notice reflects approval by the agency of manufacture, use or sale for human administration. Such compositions may be used in methods of treating, preventing, or ameliorating a disease or a disease symptom (e.g., age-related condition or metabolic disorder) in a patient, preferably a mammal and most preferably a human, by administering the pharmaceutical composition to the patient.

In general, a therapeutically effective amount of a pharmaceutical composition of the invention is from about 0.0001 mg/kg to 0.001 mg/kg; 0.001 mg/kg to about 10 mg/kg body weight or from about 0.02 mg/kg to about 5 mg/kg body weight. Commonly, a therapeutically effective amount of a fusion polypeptide is from about 0.001 mg to about 0.01 mg, about 0.01 mg to about 100 mg, or from about 100 mg to about 1000 mg, for example. Preferably, a therapeutically effective amount of a fusion polypeptide is from about 0.001 mg/kg to 2 mg/kg.

The optimal pharmaceutical formulations for a fusion polypeptide can be determined by one or ordinary skilled in the art depending upon the route of administration and desired dosage. (See, for example, Remington's Pharmaceutical Sciences, 18th Ed. (1990), Mack Publishing Co., Easton, Pa., the entire disclosure of which is hereby incorporated by reference).

The fusion polypeptides of the invention may be administered as a pharmaceutical composition that may be in the form of a solid, liquid or gas (aerosol). Typical routes of administration may include, without limitation, oral, topical, parenteral, sublingual, rectal, vaginal, intradermal and intranasal. Parenteral administration includes subcutaneous injections, intravenous, intramuscular, intraperitoneal, intrapleural, intrasternal injection or infusion techniques. Preferably, the compositions are administered parenterally. More preferably, the compositions are administered intravenously. Pharmaceutical compositions of the invention can be formulated so as to allow a polypeptide of the invention to be bioavailable upon administration of the composition to a subject. Compositions can take the form of one or more dosage units, where, for example, a tablet can be a single dosage unit, and a container of a polypeptide of the invention in aerosol form can hold a plurality of dosage units.

Materials used in preparing the pharmaceutical compositions can be non-toxic in the amounts used. It will be evident to those of ordinary skill in the art that the optimal dosage of the active ingredient(s) in the pharmaceutical composition will depend on a variety of factors. Relevant factors include, without limitation, the type of subject (e.g., human), the overall health of the subject, the type of age-related condition or metabolic disorder the subject in need of treatment of, the use of the composition as part of a multi-drug regimen, the particular form of the polypeptide of the invention, the manner of administration, and the composition employed.

The pharmaceutically acceptable carrier or vehicle may be particulate, so that the compositions are, for example, in tablet or powder form. The carrier(s) can be liquid, with the compositions being, for example, an oral syrup or injectable liquid. In addition, the carrier(s) can be gaseous, so as to provide an aerosol composition useful in, e.g., inhalatory administration.

The term "carrier" refers to a diluent, adjuvant or excipient, with which a polypeptide of the invention is administered. Such pharmaceutical carriers can be liquids, such as water and oils, including those of petroleum, animal, vegetable or synthetic origin, such as peanut oil, soybean oil, mineral oil, sesame oil and the like. The carriers can be saline, gum acacia, gelatin, starch paste, talc, keratin, colloidal silica, urea, and the like. In addition, auxiliary, stabilizing, thickening, lubricating and coloring agents can be used. In one embodiment, when administered to a subject, the polypeptides of the invention and pharmaceutically acceptable carriers are sterile. Water is a preferred carrier when the polypeptide of the invention is administered intravenously. Saline solutions and aqueous dextrose and glycerol solutions can also be employed as liquid carriers, particularly for injectable solutions. Suitable pharmaceutical carriers also include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The present compositions, if desired, can also contain minor amounts of wetting or emulsifying agents, or pH buffering agents.

The composition may be intended for oral administration, and if so, the composition is preferably in solid or liquid form, where semi-solid, semi-liquid, suspension and gel forms are included within the forms considered herein as either solid or liquid.

As a solid composition for oral administration, the composition can be formulated into a powder, granule, compressed tablet, pill, capsule, chewing gum, wafer or the like form. Such a solid composition typically contains one or more inert diluents. In addition, one or more of the following can be present: binders such as ethyl cellulose, carboxymethylcellulose, microcrystalline cellulose, or gelatin; excipients such as starch, lactose or dextrins, disintegrating agents such as alginic acid, sodium alginate, Primogel, corn starch and the like; lubricants such as magnesium stearate or Sterotex; glidants such as colloidal silicon dioxide; sweetening agents such as sucrose or saccharin, a flavoring agent such as peppermint, methyl salicylate or orange flavoring, and a coloring agent.

When the pharmaceutical composition is in the form of a capsule, e.g., a gelatin capsule, it can contain, in addition to materials of the above type, a liquid carrier such as polyethylene glycol, cyclodextrin or a fatty oil.

The pharmaceutical composition can be in the form of a liquid, e.g., an elixir, syrup, solution, emulsion or suspension. The liquid can be useful for oral administration or for delivery by injection. When intended for oral administration, a composition can contain one or more of a sweetening agent, preservatives, dye/colorant and flavour enhancer. In a composition for administration by injection, one or more of a surfactant, preservative, wetting agent, dispersing agent, suspending agent, buffer, stabilizer and isotonic agent can also be included.

The liquid compositions of the invention, whether they are solutions, suspensions or other like form, can also include one or more of the following: sterile diluents such as water for injection, saline solution, preferably physiological saline, Ringer's solution, isotonic sodium chloride, fixed oils such as synthetic mono or digylcerides which can serve as the solvent or suspending medium, polyethylene glycols, glycerin, cyclodextrin, propylene glycol or other solvents; antibacterial agents such as benzyl alcohol or methyl paraben; antioxidants such as ascorbic acid or sodium bisulfate; chelating agents such as ethylenediaminetetraacetic acid; buffers such as acetates, citrates or phosphates and agents for the adjustment of tonicity such as sodium chloride or dextrose. A parenteral composition can be enclosed in an ampoule, a disposable syringe or a multiple-dose vial made of glass, plastic or other material. Physiological saline is a preferred adjuvant. An injectable composition is preferably sterile.

The pharmaceutical compositions contain an effective amount of a compound of the invention (e.g., fusion polypeptide) such that a suitable dosage will be obtained. The pharmaceutical compositions may contain the known effective amount of the compounds as currently prescribed for their respective disorders.

The route of administration of the polypeptide of the invention used in the prophylactic and/or therapeutic regimens which will be effective in the prevention, treatment, and/or management of a age-related condition or metabolic disorder can be based on the currently prescribed routes of administration for other therapeutics known in the art. The polypeptides of the invention can be administered by any convenient route, for example, by infusion or bolus injection, by absorption through epithelial or mucocutaneous linings (e.g., oral mucosa, rectal and intestinal mucosa, etc.). Administration can be systemic or local. Various delivery systems are known, e.g., microparticles, microcapsules, capsules, etc., and may be useful for administering a polypeptide of the invention. More than one polypeptides of the invention may be administered to a subject. Methods of administration may include, but are not limited to, oral administration and parenteral administration; parenteral administration including, but not limited to, intradermal, intramuscular, intraperitoneal, intravenous, subcutaneous, intranasal, epidural, sublingual, intranasal, intracerebral, intraventricular, intrathecal, intravaginal, transdermal, rectally, by inhalation, or topically to the ears, nose, eyes, or skin.

The polypeptides of the invention may be administered parenterally. Specifically, the polypeptides of the invention may be administered intravenously.

Pulmonary administration can also be employed, e.g., by use of an inhaler or nebulizer, and formulation with an aerosolizing agent, or via perfusion in a fluorocarbon or synthetic pulmonary surfactant. The polypeptides of the invention can also be formulated as a suppository, with traditional binders and carriers such as triglycerides.

The polypeptides of the invention can be delivered in a controlled release system. For example, a pump can be used (see Sefton, *CRC Crit. Ref Biomed. Eng.* 1987, 14, 201; Buchwald et al., Surgery 1980, 88: 507; Saudek et al., *N. Engl. J. Med.* 1989, 321: 574). Polymeric materials can also be used for controlled release of the polypeptides of the invention (see *Medical Applications of Controlled Release*, Langer and Wise (eds.), CRC Pres., Boca Raton, Fla., 1974; *Controlled Drug Bioavailability, Drug Product Design and Performance*, Smolen and Ball (eds.), Wiley, New York, 1984; Ranger and Peppas, *J. Macromol. Sci. Rev. Macromol. Chem.* 1983, 23, 61; see also Levy et al., *Science* 1985, 228, 190; During et al., *Ann. Neural.,* 1989, 25, 351; Howard et al., *J. Neurosurg.,* 1989, 71, 105). Specifically, a controlled-release system can be placed in proximity of the target of the polypeptides of the invention, e.g., the brain, thus requiring only a fraction of the systemic dose (see, e.g., Goodson, in *Medical Applications of Controlled Release*, supra, vol. 2, 1984, pp. 115-138). Other controlled-release systems discussed in the review by Langer (*Science* 1990, 249, 1527-1533) can be used.

Polymeric materials used to achieve controlled or sustained release of the polypeptides of the invention are disclosed, e.g., in U.S. Pat. No. 5,679,377; U.S. Pat. No. 5,916,597; U.S. Pat. No. 5,912,015; U.S. Pat. No. 5,989,463; U.S. Pat. No. 5,128,326; PCT Publication No. WO 99/15154; and PCT Publication No. WO 99/20253. Examples of polymers used in sustained release formulations include, but are not limited to, poly(2-hydroxy ethyl methacrylate), poly(methyl methacrylate), poly(acrylic acid), poly(ethylene-co-vinyl acetate), poly(methacrylic acid), polyglycolides (PLG), polyanhydrides, poly(N-vinyl pyrrolidone), poly(vinyl alcohol), polyacrylamide, poly(ethylene glycol), polylactides (PLA), poly(lactide-co-glycolides) (PLGA), and polyorthoesters. Preferably, the polymer used in a sustained release formulation is inert, free of leachable impurities, stable on storage, sterile, and biodegradable.

In general, a therapeutically effective amount of a pharmaceutical composition of the invention is from about 0.0001 mg/kg to 0.001 mg/kg; 0.001 mg/kg to about 10 mg/kg body weight or from about 0.02 mg/kg to about 5 mg/kg body weight.

In other embodiments, the prophylactic and/or therapeutic regimen involves administering to a patient one or more doses of an effective amount of a polypeptide of the invention, wherein the dose of an effective amount achieves a plasma level of at least 0.01 µg/mL to at least 400 µg/mL of the polypeptide of the invention.

A prophylactic and/or therapeutic regimen may involve administering to a patient a plurality of doses of an effective amount of a polypeptide of the invention, wherein the plurality of doses maintains a plasma level of at least 0.01 µg/mL, to 400 µg/mL of the polypeptide of the invention. The prophylactic and/or therapeutic regimen may be administered for at least 1 day, 1 month, 2 months, 3 months, 4 months, 5 months, 6 months, 7 months, 8 months or 9 months.

The prophylactic and/or therapeutic regimen may involve administration of a polypeptide of the invention in combination with one or more additional therapeutics. The recommended dosages of the one or more therapeutics currently used for the prevention, treatment, and/or management of an age-related condition or metabolic disorder can be obtained from any reference in the art including, but not limited to, Hardman et al., eds., *Goodman & Gilman's The Pharmacological Basis Of Basis Of Therapeutics,* 10th ed., McGraw-Hill, New York, 2001; *Physician's Desk Reference* (60$^{th}$ ed., 2006), which is incorporated herein by reference in its entirety.

The invention includes methods of treating disorders wherein agonistic activity of Klotho protein and FGF are desirable. Examples of such methods of the invention include, but are not limited to age-related condition or metabolic disorders.

The invention includes methods for treating or preventing an age-related condition in an individual. An individual in need of treatment is administered a pharmacologically effective dose of a pharmaceutical composition containing a Klotho fusion polypeptide, having at least one extracellular subdomain of a Klotho protein and a fibroblast growth factor and an (optional) modified Fc fragment, so as to treat or prevent the age-related condition. In some embodiments, the Klotho fusion polypeptide is co-administered with a pharmacologically effective dose of heparin. Age-related conditions include sarcopenia, skin atrophy, muscle wasting, brain atrophy, atherosclerosis, arteriosclerosis, pulmonary emphysema, osteoporosis, osteoarthritis, immunologic incompetence, high blood pressure, dementia, Huntington's disease, Alzheimer's disease, cataracts, age-related macular degeneration, prostate cancer, stroke, diminished life expectancy, memory loss, wrinkles, impaired kidney function, and age-related hearing loss. In some embodiments, the Klotho fusion polypeptide contains at least one extracellular domain of an alpha Klotho protein. In a particular embodiment, a Klotho fusion protein containing at least one extracellular domain of alpha Klotho protein and fibroblast growth factor 23 is administered to an individual in need of treatment for muscle wasting.

The invention is also directed to a method for treating or preventing a metabolic disorder in an individual. An individual in need of treatment is administered a pharmacologically effective dose of a pharmaceutical composition containing a Klotho fusion polypeptide, having at least one extracellular subdomain of a Klotho protein and a fibroblast growth factor so as to treat the metabolic disorder, and an (optional) modified Fc fragment having decreased binding to FcRn and/or increased serum half-life and/or stability. In some embodiments, the Klotho fusion polypeptide is co-administered with a pharmacologically effective dose of heparin. The method may be used in the treatment or prevention of Type II Diabetes, Metabolic Syndrome, hyperglycemia, and obesity. In a particular embodiment, a Klotho fusion protein containing at least one extracellular domain of a beta-Klotho protein and fibroblast growth factor 21 is administered to an individual in need of treatment for a metabolic disorder.

The invention also provides methods for treating or preventing hyperphosphatemia or calcinosis in an individual. An individual in need of treatment is administered a pharmacologically effective dose of a pharmaceutical composition containing a Klotho fusion polypeptide, having at least one extracellular subdomain of a Klotho protein, a fibroblast growth factor and an (optional) modified Fc fragment so as to treat hyperphosphatemia or calcinosis. In some embodiments, the Klotho fusion polypeptide is co-administered with a pharmacologically effective dose of heparin. In a particular embodiment, a Klotho fusion protein containing at least one extracellular domain of an alpha Klotho protein and fibroblast growth factor 23 and an (optional) modified Fc fragment is administered to all individual in need of treatment for a hyperphosphatemia or calcinosis.

The invention is also directed to a method for treating or preventing chronic renal disease or chronic renal failure in an individual. An individual in need of treatment is administered a pharmacologically effective dose of a pharmaceutical composition containing a Klotho fusion polypeptide, having at least one extracellular subdomain of a Klotho protein, a fibroblast growth factor and an (optional) modified Fc fragment so as to treat chronic renal disease or chronic renal failure. In some embodiments, the Klotho fusion polypeptide is co-administered with a pharmacologically effective dose of heparin. In some embodiments, a Klotho fusion protein containing at least one extracellular domain of an alpha Klotho protein is administered to an individual in need of treatment for chronic renal disease or chronic renal failure.

The invention also includes methods for treating or preventing cancer in an individual. An individual in need of treatment is administered a pharmacologically effective dose of a pharmaceutical composition containing a Klotho fusion polypeptide, having at least one extracellular subdomain of a Klotho protein, a fibroblast growth factor and all (optional) modified Fc fragment so as to treat cancer. The method may be used in the treatment or prevention of breast cancer. In some embodiments, the Klotho fusion polypeptide is co-administered with a pharmacologically effective dose of heparin. In some embodiments, a Klotho fusion protein containing at least one extracellular domain of all alpha Klotho protein is administered to an individual in need of treatment for cancer.

In methods of treating disorders by administering a pharmaceutical composition containing a Klotho fusion polypeptide, the Klotho fusion polypeptide and all (optional) modified Fc fragment has at least one extracellular subdomain of a Klotho protein and a fibroblast growth factor. In a particular embodiment, the Klotho fusion protein contains at least one extracellular domain of a beta Klotho protein and fibroblast growth factor 21.

In another embodiment, the fusion comprises a FGF (e.g., FGF19, FGF21, FGF23 or FGF23 variant) and a modified Fc fragment with decreased binding to FcRn and/or increased serum stability. This type of fusion can be used in various diseases, as described above, or used to treat or prevent any FGF-related disease known in the art. The fusion can be administered to all individual in need thereof.

The fusion polypeptide compositions can be administered according to any method of administration known to those of skill in the art and described herein. Preferred methods of administration include subcutaneous or intravenous. Other effective modes of administration are described herein.

4.6. Methods of Treatment and Assays for Assessing Efficacy

Methods of the invention which provide administering the fusion polypeptides described herein to an individual can be used to treat a variety of disorders including an age-related disorder or a metabolic disorder. Without being limited by any particular theory, fusion polypeptides may be used to treat disorders in which there is dysregulation of Klotho or FGF. Exemplary disorders include metabolic disorders and age-related disorders. For example, both FGF23 or Klotho knock-out mice display a variety of similar phenotypes including, low physical activity, growth retardation, muscle wasting, skin atrophy, atherosclerosis, short life spans, etc. (See Razzaque and Lanske, *J. of Endrocrinology*, 194:1-10 (2007), which is herein incorporated by reference).

In particular, fusion polypeptides of the invention are particularly useful in the treatment of aging-related disorders, including muscle wasting. Without being bound to theory, the ability of Klotho and FGF23 to control mineral (e.g., phosphate and calcium) and vitamin D homeostasis may be the means by which these proteins modulate aging and muscle atrophy.

On the other hand, fusion polypeptides of the invention may be used for treating a metabolic disorder. For example, beta-Klotho and FGF19 have been shown to control bile acid homeostasis by regulating cholesterol 7-α-hydroxylase (CYP7A1). A non-limiting example of bile homeostasis disorder is cholestasis. The beta-Klotho and FGF21 have been shown to induce lipolysis in adipocytes and, therefore, reduced fat storage and increased glucose uptake. Non-limiting examples of lipolysis/fat storage disorders are obesity and associated metabolic and cardiovascular diseases.

Based at least in part on the finding that FGF23 is able to stimulate excretion of phosphate in the urine and thereby reduce phosphate levels in the serum, Klotho-FGF23 fusion polypeptides of the invention can be used for treating or preventing hyperphosphatemia or calcinosis in an individual. For example, it has been shown that a homozygous missense mutation in Klotho resulting in a deficiency in Klotho in a patient can cause severe tumoral calcinosis and artery calcification (Ichikawa et al., *J. Clin. Invest.* 117:2684-2691 (2007), which is herein incorporated by reference). An individual is administered a pharmacologically effective dose of a pharmaceutical composition containing the Klotho fusion polypeptide, having at least one extracellular subdomain of a Klotho protein, a fibroblast growth factor and an (optional) modified Fc fragment so as to treat or prevent hyperphosphatemia or calcinosis. In particular, a Klotho fusion polypeptide containing at least one extracellular domain of an alpha Klotho protein, a fibroblast growth factor and an (optional) modified Fc fragment is useful for treating hyperphosphatemia or calcinosis.

Klotho fusion polypeptides of the invention can also be used for treating or preventing chronic renal disease or chronic renal failure in an individual. For example, it has been shown that Klotho expression is reduced in kidney of patients with chronic renal failure, compared to that in unaffected kidneys (Koh et al., *Biochem. Biophys. Res. Comm.* 280: 1015-1020 (2001), which is herein incorporated by reference). An individual is administered a pharmacologically effective dose of a pharmaceutical composition containing the Klotho fusion polypeptide, having at least one extracellular subdomain of a Klotho protein, a fibroblast growth factor and an (optional) modified Fc fragment so as to treat or prevent chronic renal disease or chronic renal failure. In particular, a Klotho fusion polypeptide containing at least one extracellular domain of an alpha Klotho protein is useful for treating chronic renal disease or chronic renal failure.

Klotho fusion polypeptides of the invention can also be used for treating or preventing cancer in an individual. For example, it has been shown that Klotho expression is reduced in breast cancer tissue, compared to normal breast cancer tissue (Wolf et al., *Oncogene* (2008) advance online publication, which is herein incorporated by reference). An individual is administered a pharmacologically effective dose of a pharmaceutical composition containing the Klotho fusion polypeptide, having at least one extracellular subdomain of a Klotho protein, a fibroblast growth factor and an (optional) modified Fc fragment so as to treat or prevent cancer or breast cancer. In particular, a Klotho fusion protein containing at least one extracellular domain of an alpha Klotho protein is useful for treating cancer or breast cancer.

Methods for evaluating the efficacy and/or determining the effective dose of a Klotho fusion polypeptide of the invention on an age-related disorder or metabolic disorder include organismal based assays, e.g., using a mammal (e.g., a mouse, rat, primate, or some other non-human), or other animal (e.g., *Xenopus*, zebrafish, or an invertebrate such as a fly or nematode). The Klotho fusion polypeptide can be administered to the organism once or as a regimen (regular or irregular). A parameter of the organism is then evaluated, e.g., an age-associated parameter. Klotho fusion polypeptides that are of interest result in a change in the parameter relative to a reference, e.g., a parameter of a control organism. Other parameters (e.g., related to toxicity, clearance, and pharmacokinetics) can also be evaluated.

The Klotho fusion polypeptide of the invention may be evaluated using an animal that has a particular disorder, e.g., a disorder described herein, e.g., an age-related disorder, a metabolic disorder. These disorders can also provide a sensitized system in which the test polypeptide's effects on physiology can be observed. Exemplary disorders include: denervation, disuse atrophy; metabolic disorders (e.g., disorder of obese and/or diabetic animals such as db/db mouse and ob/ob mouse); cerebral, liver ischemia; cisplatin/taxol/vincristine models; various tissue (xenograph) transplants; transgenic bone models; pain syndromes (include inflammatory and neuropathic disorders); Paraquat, genotoxic, and oxidative stress models; and tumor I models.

For measuring an age-related disorder, the animal model can be an animal that has an altered phenotype when calorically restricted. For example, F344 rats provide a useful assay system for evaluating a Klotho fusion polypeptide. When calorically restricted, F344 rats have a 0 to 10% incidence of nephropathy. However, when fed ad libitum, they have a 60 to 100% incidence of nephropathy.

To evaluate a Klotho fusion polypeptide of the invention, it is administered to the animal (e.g., an F344 rat or other suitable animal) and a parameter of the animal is evaluated, e.g., after a period of time. The animal can be fed ad libitum or normally (e.g., not under caloric restriction, although some parameters can be evaluated under such conditions). Typically, a cohort of such animals is used for the assay. Generally, a test polypeptide can be indicated as favorably altering lifespan regulation in the animal if the test polypeptide affects the parameter in the direction of the phenotype of a similar animal subject to caloric restriction. Such test polypeptides may cause at least some of the lifespan regulatory effects of caloric restriction, e.g., a subset of such effects, without having to deprive the organism of caloric intake.

The parameter to be tested may be an age-associated or disease associated parameter, e.g., a symptom of the disorder associated with the animal model. For example, the test polypeptide can be administered to a SH Rat, and blood pressure is monitored. A test polypeptide that is favorably indicated can cause an amelioration of the symptom relative to a similar reference animal not treated with the polypeptide. Other parameters relevant to a disorder or to aging can include: antioxidant levels (e.g. antioxidant enzyme levels or activity), stress resistance (e.g., paraquat resistance), core body temperature, glucose levels, insulin levels, thyroid-stimulating hormone levels, prolactin levels, and leutinizing hormone levels.

To measure the effectiveness of the polypeptides of the invention for treating an age-related disorder, an animal having decreased Klotho expression may be used, e.g., mouse with a mutant Klotho; See Kuroo, et al. Nature, 390; 45 (1997) and U.S. Pub. No. 2003/0119910, both of which are herein incorporated by reference in their entirety. For example, the test polypeptide is administered to the mutant mouse and age-related parameters are monitored. A test polypeptide that is favorably indicated can cause an amelioration of the symptom relative to a similar reference animal not treated with the polypeptide. A parameter relevant to a metabolic disorder or to aging can be assessed by measurement of body weight, examination on the acquisition of reproductive ability, measurement of blood sugar level, observation of life span, observation of skin, observation of motor functions such as walking, and the like. The assessment can also be made by measurement of thymus weight, observation of the size of calcified nodules formed on the inner surface of thoracic cavity, and the like. Further, quantitative determination of mRNA for the Klotho gene or Klotho protein is also useful for the assessment.

Still other in vivo models and organismal assays include evaluating an animal for a metabolic parameter, e.g., a parameter relevant to an insulin disorder, type II diabetes. Exemplary metabolic parameters include: glucose concentration, insulin concentration, and insulin sensitivity.

Another exemplary system features tumors, e.g., in an animal model. The tumors can be spontaneous or induced. For example, the tumors can be developed from cells that have a variety of genetic constitutions, e.g., they can be p53+ or p53−. It is also possible to use organisms that an autoimmune disorder, e.g., an NZB mouse, which is predisposed to SLE. To evaluate features of bone disease, it is possible, for example, to use an animal that has an ovariectomy as a model, e.g., for osteoporosis. Similarly, for joint disease, the model can be based on adjuvant arthritis (e.g., mice can be immunized with cartilage proteoglycans, high mobility group proteins, streptococcal cell wall material, or collagens); for kidney disease, kd/kd mice can be used. Animal models of cognition, particularly learning and memory are also available. Animal models of diabetes and its complications are also available, e.g., the streptozotocin model. Canine models can be used, for example, for evaluating stroke and ischemia.

In assessing whether a test polypeptide is capable of altering life span regulation, a number of age-associated parameters or biomarkers can be monitored or evaluated. Exemplary age associated parameters include: (i) lifespan of the cell or the organism; (ii) presence or abundance of a gene transcript or gene product in the cell or organism that has a biological age dependent expression pattern; (iii) resistance of the cell or organism to stress; (iv) one so or more metabolic parameters of the cell or organism (exemplary parameters include circulating insulin levels, blood glucose levels; fat content; core body temperature and so forth); (v) proliferative capacity of the cell or a set of cells present in the organism; and (vi) physical appearance or behavior of the cell or organism.

The term "average lifespan" refers to the average of the age of death of a cohort of organisms. In some cases, the "average lifespan" is assessed using a cohort of genetically identical organisms under controlled environmental conditions. Deaths due to mishap are discarded. Where average lifespan cannot be determined (e.g., for humans) under controlled environmental conditions, reliable statistical information (e.g., from actuarial tables) for a sufficiently large population can be used as the average lifespan.

Characterization of molecular differences between two such organisms, e.g., one reference organism and one organism treated with a Klotho fusion polypeptide can reveal a difference in the physiological state of the organisms. The reference organism and the treated organism are typically the same chronological age. The term "chronological age" as used herein refers to time elapsed since a preselected event, such as conception, a defined embryological or fetal stage, or, more preferably, birth. A variety of criteria can be used to determine whether organisms are of the "same" chronological age for the comparative analysis. Typically, the degree of accuracy required is a function of the average lifespan of a wildtype organism. For example, for the nematode *C. elegans*, for which the laboratory wildtype strain N2 lives an to average of about 16 days under some controlled conditions, organisms of the same age may have lived for the same number of days. For mice, organism of the same age may have lived for the same number of weeks or months; for primates or humans, the same number of years (or within 2, 3, or 5 years); and so forth. Generally, organisms of the same chronological age may have lived for an amount of time within 15, 10, 5, 3, 2 or 1% of the average lifespan of a wildtype organism of that species. Preferably, the organisms are adult organisms, e.g., the organisms have lived for at least an amount of time in which the average wildtype organism has matured to an age at which it is competent to reproduce.

The organismal screening assay can be performed before the organisms exhibit overt physical features of aging. For example, the organisms may be adults that have lived only 10, 30, 40, 50, 60, or 70% of the average lifespan of a wildtype organism of the same species. Age-associated changes in metabolism, immune competence, and chromosomal structure have been reported. Any of these changes can be evaluated, either in a test subject (e.g., for an organism based assay), or for a patient (e.g., prior, during or after treatment with a therapeutic described herein.

A marker associated with caloric restriction can also be evaluated in a subject organism of a screening assay (or a treated subject). Although these markers may not be age-associated, they may be indicative of a physiological state that is altered when the Klotho pathway is modulated. The marker can be an mRNA or protein whose abundance changes in calorically restricted animals. WO01/12851 and U.S. Pat. No. 6,406,853 describe exemplary markers. Cellular models derived from cells of an animal described herein or analogous to an animal model described herein can be used for a cell-based assay.

Models for evaluating the effect of a test polypeptide on muscle atrophy include: 1) rat medial gastrocnemius muscle mass loss resulting from denervation, e.g., by severing the right sciatic nerve at mid-thigh; 2) rat medial gastrocnemius muscle mass loss resulting from immobilization, e.g., by fixed the right ankle joint at 90 degrees of flexion; 3) rat medial gastrocnemius muscle mass loss resulting from hind limb suspension; (see, e.g., U.S. 2003-0129686); 4) skeletal muscle atrophy resulting from treatment with the cachectic cytokine, interleukin-1 (IL-1) (R. N. Cooney, S. R. Kimball, T. C. Vary, Shock 7, 1-16 (1997)); and 5) skeletal muscle atrophy resulting from treatment with the glucocorticoid, dexamethasone (A. L. Goldberg, *J. Biol. Chem.* 244, 3223-9 (1969).)

Exemplary animal models for AMD include: laser-induced mouse model simulating exudative (wet) macular degeneration Bora et al., *Proc. Natl. Acad. Sci.* USA., 100:2679-84 (2003); a transgenic mouse expressing a mutated form of cathepsin D resulting in features associated with the "geographic atrophy" form of AMD (Rakoczy et al., *Am. J. Pathol.*, 161:1515-24 (2002)); and a transgenic mouse over expressing VEGF in the retinal pigment epithelium resulting in CNV. Schwesinger et al., *Am. J. Pathol.* 158:1161-72 (2001).

Exemplary animal models of Parkinson's disease include primates rendered Parkinsonian by treatment with the dopaminergic neurotoxin 1-methyl-4 phenyl 1,2,3,6-tetrahydropyridine (MPTP) (see, e.g., U.S. Patent Publication No. 20030055231 and Wichmann et al., *Ann. N.Y. Acad. Sci.,* 991:199-213 (2003); 6-hydroxydopamine-lesioned rats (e.g., Lab. Anim. Sci., 49:363-71 (1999)); and transgenic invertebrate models (e.g., Lakso et al., *J. Neurochem.* 86:165-72 (2003) and Link, *Mech. Ageing Dev.,* 122:1639-49 (2001)).

Exemplary molecular models of Type II diabetes include: a transgenic mouse having defective Nkx-2.2 or Nkx-6.1; (U.S. Pat. No. 6,127,598); Zucker Diabetic Fatty fa/fa (ZDF) rat. (U.S. Pat. No. 6,569,832); and Rhesus monkeys, which spontaneously develop obesity and subsequently frequently progress to overt type 2 diabetes (Hotta et al., *Diabetes,* 50:1126-33 (2001); and a transgenic mouse with a dominant-negative IGF-I receptor (KR-IGF-IR) having Type 2 diabetes-like insulin resistance.

Exemplary animal and cellular models for neuropathy include: vincristine induced sensory-motor neuropathy in mice (U.S. Pat. No. 5,420,112) or rabbits (Ogawa et al., *Neurotoxicology,* 21:501-11 (2000)); a streptozotocin (STZ)-diabetic rat for study of autonomic neuropathy (Schmidt et al., *Am. J. Pathol.,* 163:21-8 (2003)); and a progressive motor neuropathy (pmn) mouse (Martin et al., *Genomics,* 75:9-16 (2001)).

Exemplary animal models of hyperphosphatemia or tumoral calcinosis include Klotho knockout mice and FGF23 knockout mice (Yoshida et al., *Endocrinology* 143:683-689 (2002)).

Exemplary animal models of chronic renal disease or chronic renal failure include COL4A3+/− mice (Beirowski et al., *J. Am. Soc. Nephrol.* 17:1986-1994 (2006)).

Exemplary animal models of cancer include the transplantation or implantation of cancer cells or tissue into nude mice, as is known in the art (Giovanella et al., *Adv. Cancer Res.* 44:69-120 (1985)). For example, animal models of breast cancer include nude mice transplanted or implanted with breast cancer cells or tissue (e.g., Yue et al., *Cancer Res.* 54:5092-5095 (1994); Glinsky et al., *Cancer Res.* 56:5319-5324 (1996); Visonneau *Am. J. Path.* 152:1299-1311 (1998)).

The compositions can be administered to a subject, e.g., an adult subject, particularly a healthy adult subject or a subject having an age-related disease. In the latter case, the method can include evaluating a subject, e.g., to characterize a symptom of an age-related disease or other disease marker, and thereby identifying a subject as having a neurodegenerative disease, e.g., Alzheimer's or an age-related disease or being pre-disposed to such a disease.

Skeletal Muscle Atrophy

Methods of the invention which provide administering the Klotho fusion polypeptide to an individual can be used to treat skeletal muscle atrophy. Muscle atrophy includes numerous neuromuscular, metabolic, immunological and neurological disorders and diseases as well as starvation, nutritional deficiency, metabolic stress, diabetes, aging, muscular dystrophy, or myopathy. Muscle atrophy occurs during the aging process. Muscle atrophy also results from reduced use or disuse of the muscle. Symptoms include a decline in skeletal muscle tissue mass. In human males, muscle mass declines by one-third between the ages of 50 and 80. Some molecular features of muscle atrophy include the upregulation of ubiquitin ligases, and the loss of myofibrillar proteins (Furuno et al., *J. Biol. Chem.*, 265:8550-8557, 1990). The breakdown of these proteins can be followed, e.g., by measuring 3-methyl-histidine production, which is a specific constituent of actin, and in certain muscles of myosin (Goodman, Biochem. J. 241: 121-12, 1987 and Lowell, et al., Metabolism, 35:1121-112, 1986; Stein and Schluter, *Am. J. Physiol. Endocrinol. Metab.* 272: E688-E696, 1997). Release of creatine kinase (a cell damage marker) (Jackson, et al., Neurology, 41: 101104, 1991) can also be indicative.

Non-Insulin-Dependent Diabetes

Methods of the invention which provide administering the Klotho fusion polypeptide to an individual can be used to treat Non-insulin-dependent Diabetes. Non-insulin-dependent Diabetes is also called "adult onset" diabetes and Type 2 diabetes. Type 2 diabetes also includes "non-obese type 2" and "obese type 2." Type II diabetes can be characterized by (1) reduced pancreatic-beta-islet-cell secretion of insulin such that less than necessary amounts of insulin are produced to keep blood glucose levels in balance and/or (2) "insulin resistance," wherein the body fails to respond normally to insulin. (U.S. Pat. No. 5,266,561 and U.S. Pat. No. 6,518, 069). For example, glucose-stimulated insulin levels typically fail to rise above 4.0 nmol/L. (U.S. Pat. No. 5,266,561). Exemplary symptoms of Type II diabetes include: hyperglycemia while fasting (U.S. Pat. No. 5,266,561); fatigue; excessive thirst; frequent urination; blurred vision; and an increased rate of infections. Molecular indications of Type II diabetes include islet amyloid deposition in the pancreases.

Neuropathy

Neuropathy can include a central and/or peripheral nerve dysfunction caused by systemic disease, hereditary condition or toxic agent affecting motor, sensory, sensorimotor or autonomic nerves. (see, e.g., US Patent Application No. 20030013771). Symptoms can vary depending upon the cause of the nerve damage and the particular types of nerves affected. For example, symptoms of motor neuropathy include clumsiness in performing physical tasks or as muscular weakness, exhaustion after minor exertion, difficulty in standing or walking and attenuation or absence of a neuromuscular reflex. (U.S. Patent Application No. 20030013771) symptoms of autonomic neuropathy include constipation, cardiac irregularities and attenuation of the postural hypotensive reflex. (U.S. Patent Application No. 20030013771), symptoms of sensory neuropathy include pain and numbness; tingling in the hands, legs or feet; and extreme sensitivity to touch, and symptoms of retinopathy include blurred vision, sudden loss of vision, black spots, and flashing lights.

Alzheimer's Disease

Methods of the invention which provide administering the Klotho fusion polypeptide to an individual can be used to treat Alzheimer's Disease (AD). Alzheimer's Disease is a complex neurodegenerative disease that results in the irreversible loss of neurons. It provides merely one example of a neurodegenerative disease that is also an age-related condition. Clinical hallmarks of Alzheimer's Disease include progressive impairment in memory, judgment, orientation to physical surroundings, and language. Neuropathological hallmarks of AD include region-specific neuronal loss, amyloid plaques, and neurofibrillary tangles. Amyloid plaques are extracellular plaques containing the amyloid peptide (also known as Ap, or Ap42), which is a cleavage product of the, 8-amyloid precursor protein (also known as APP). Neurofibrillary tangles are insoluble intracellular aggregates composed of filaments of the abnormally hyperphosphorylated microtubule-associated protein, taut Amyloid plaques and neurofibrillary tangles may contribute to secondary events that lead to neuronal loss by apoptosis (Clark and Karlawish, *Ann. Intern. Med.* 138(5): 400-410 (2003). For example, p-amyloid induces caspase-2-dependent apoptosis in cultured neurons (Troy et al. *J Neurosci.* 20(4):1386-1392). The deposition of plaques in viva may trigger apoptosis of proximal neurons in a similar manner.

A variety of criteria, including genetic, biochemical, physiological, and cognitive criteria, can be used to evaluate AD in a subject. Symptoms and diagnosis of AD are known to medical practitioners. Some exemplary symptoms and markers of AD are presented below. Information about these indications and other indications known to be associated with AD can be used as an "AD-related parameter." An AD related parameter can include qualitative or quantitative information. An example of quantitative information is a numerical value of one or more dimensions, e.g., a concentration of a protein or a tomographic map. Qualitative information can include an assessment, e.g., a physician's comments or a binary ("yes"/ "no") and so forth. An AD-related parameter includes information that indicates that the subject is not diagnosed with AD or does not have a particular indication of AD, e.g., a cognitive test result that is not typical of AD or a genetic APOE polymorphism not associated with AD.

Progressive cognitive impairment is a hallmark of AD. This impairment can present as decline in memory, judgment, decision making, orientation to physical surroundings, and language (Nussbaum and Ellis, *New Eng J. Med.* 348(14): 1356 35 1364 (2003)). Exclusion of other forms of dementia can assist in making a diagnosis of AD. Neuronal death leads to progressive cerebral atrophy in AD patients. Imaging techniques (e.g., magnetic resonance imaging, or computer assisted tomography) can be used to detect AD-associated lesions in the brain and/or brain atrophy.

AD patients may exhibit biochemical abnormalities that result from the pathology of the disease. For example, levels of tan protein in the cerebrospinal fluid is elevated in AD patients (Andreasen, N. et al. *Arch Neurol.* 58:349-350 (2001)).

Levels of amyloid beta 42 (A,B42) peptide can be reduced in CSF of AD patients. Levels of Ap42 can be increased in the plasma of AD patients (Ertekein-Taner, N., et al. *Science* 290:2303 2304 (2000)). Techniques to detect biochemical abnormalities in a sample from a subject include cellular, immunological, and other biological methods known in the art. For general guidance, see, e.g., techniques described in Sambrook & Russell, Molecular Cloning: A Laboratory Manual, 3r Edition, Cold Spring Harbor Laboratory, N.Y. (2001), Ausubel et al., Current Protocols in Molecular Biology (Greene Publishing Associates and Wiley Interscience, N.Y. (1989), (Harrow, E. and Lane, D. (1988) Antibodies: A Laboratory Manual, Cold Spring Harbor Laboratory Press, Cold Spring Harbor, N.Y.), and updated editions thereof.

For example, antibodies, other immunoglobulins, and other specific binding ligands can be used to detect a biomolecule, e.g., a protein or other antigen associated with AD. For example, one or more specific antibodies can be used to probe a sample. Various formats are possible, e.g., ELISAs, fluorescence-based assays, Western blots, and protein arrays. Methods of producing polypeptide arrays are described in the art, e.g., in De Wildt et al. (2000). *Nature Biotech.* 18, 989-994; Lucking et al. (1999). *Anal. Biochem.* 270, 103-111; Ge, H. (2000). *Nucleic Acids Res.* 28, e3, I-VII; MacBeath, G., and Schreiber, S. L. (2000). *Science* 289, 1760 to 1 763; and WO 99/5 1 773A1.

In one assay, a non-human animal model of AD (e.g., a mouse model) is used, e.g., to evaluate a polypeptide or a therapeutic regimen. For example, U.S. Pat. No. 6,509,515 describes one such model animal which is naturally able to be used with learning and memory tests. The animal expresses an amyloid precursor protein (APP) sequence at a level in brain tissues such that the animal develops a progressive necrologic disorder within a short period of time from birth, generally within a year from birth, preferably within 2 to 6 months, from birth. The APP protein sequence is introduced into the animal, or an ancestor of the animal, at an embryonic stage, preferably the one cell, or fertilized oocyte, stage, and generally not later than about the 8-cell stage. The zygote or embryo is then developed to term in a pseudo-pregnant as foster female. The amyloid precursor protein genes are introduced into an animal embryo so as to be chromosomally incorporated in a state which results in super endogenous expression of the amyloid precursor protein and the development of a progressive necrologic disease in the cortico-limbic areas of the brain, areas of the brain which are prominently affected in progressive necrologic disease states such as AD. The gliosis and clinical manifestations in affected transgenic animals model necrologic disease. The progressive aspects of the neurologic disease are characterized by diminished exploratory and/or locomotor behavior and diminished deoxyglucose uptake/utilization and hypertrophic gliosis in the cortico-limbic regions of the brain. Further, the changes that are seen are similar to those that are seen in some aging animals. Other animal models are also described in U.S. Pat. Nos. 5,387,742; 5,877,399; 6,358,752; and 6, 187,992.

Parkinson's Disease

Methods of the invention which provide administering the Klotho fusion polypeptide to an individual can be used to treat Parkinson's Disease. Parkinson's disease includes neurodegeneration of dopaminergic neurons in the substantia nigra resulting in the degeneration of the nigrostriatal dopamine system that regulates motor function. This pathology, in turn, leads to motor dysfunctions. (see, e.g., and Lotharius et al., *Nat. Rev. Neurosci.*, 3:932-42 (2002)). Exemplary motor symptoms include: akinesia, stooped posture, gait difficulty, postural instability, catalepsy, muscle rigidity, and tremor. Exemplary non-motor symptoms include: depression, lack of motivation, passivity, dementia and gastrointestinal dysfunction (see, e.g., Fahn, *Ann. N.Y. Acad. Sci.*, 991:1-14 (2003) and Pfeiffer, *Lancet Neural.*, 2:107-16 (2003)) Parkinson's has been observed in 0.5 to 1 percent of persons 65 to 69 years of age and 1 to 3 percent among persons 80 years of age and older. (see, e.g., Nussbaum et al., *N. Engl. J. Med.*, 348:1356-64 (2003)). Molecular markers of Parkinson's disease include reduction in aromatic L amino acid decarboxylase (AADC) (see, e.g., US App. No. 20020172664); and loss of dopamine content in the nigrostriatal neurons (see, e.g., Fahn, *Ann. N.Y. Acad. Sci.*, 991:1-14 (2003) and Lotharius et al., Nat. Rev. Neurosci., 3:932-42 (2002)). In some familial cases, PD is linked to mutations in single genes encoding alpha-synuclein and parkin (an E3 ubiquitin ligase) proteins. (e.g., Riess et al., J. Neurol. 250 Suppl 1:13 10 (2003) and Nussbaum et al., N. Engl. J. Med., 348:1356-64 (2003)). A missense mutation in a neuron-specific C-terminal ubiquitin hydrolase gene is also associated with Parkinson's. (e.g., Nussbaum et al., N. Engl. J. Med., 348:1356-64 (2003))

Huntington's Disease

Methods of the invention which provide administering the Klotho fusion polypeptide to an individual can be used to treat Huntington's Disease. Methods for evaluating the efficacy and/or determining the effective dose of a Klotho fusion polypeptide on Huntington's Disease include organismal based assays, e.g., using a mammal (e.g., a mouse, rat, primate, or some other non-human), or other animal (e.g., *Xenopus*, zebrafish, or an invertebrate such as a fly or nematode). A number of animal model system for Huntington's disease are available. See, e.g., Brouillet, Functional *Neurology* 15(4): 239-251 (2000); Ona et al. *Nature* 399: 263-267 (1999), Bates et al. *Hum Mol. Genet.* 6(10):1633-7 (1997); Hansson et al. *J. of Neurochemistry* 78: 694-703; and Rubinsztein, D. C., *Trends in Genetics*, Vol. 1S, No. 4, pp. 202-209 (a review on various animal and non-human models of HD).

An example of such an animal model is the transgenic mouse strain is the R6/2 line (Mangiarini et al. Cell 87: 493-506 (1996)). The R6/2 mice are transgenic Huntington's disease mice, which over-express exon 1 of the human HD gene (under the control of the endogenous promoter). The exon 1 of the R6/2 human HD gene has an expanded CAG/polyglutamine repeat lengths (150 CAG repeats on average). These mice develop a progressive, ultimately fatal neurological disease with many features of human Huntington's disease. Abnormal aggregates, constituted in part by the N terminal part of Huntingtin (encoded by HD exon 1), are observed in R6/2 mice, both 45 in the cytoplasm and nuclei of cells (Davies et al. *Cell* 90: 537-548 (1997)). For example, the human Huntingtin protein in the transgenic animal is encoded by a gene that includes at least 55 CAG repeats and more preferably about 150 CAG repeats. These transgenic animals can develop a Huntington's disease-like phenotype.

These transgenic mice are characterized by reduced weight gain, reduced lifespan and motor impairment characterized by abnormal gait, resting tremor, hindlimb clasping and hyperactivity from 8 to 10 weeks after birth (for example the R6/2 strain; see Mangiarini et al. *Cell* 87: 493-506 (1996)). The phenotype worsens progressively toward hypokinesia. The brains of these transgenic mice also demonstrate neurochemical and histological abnormalities, such as changes in neurotransmitter receptors (glutamate, dopaminergic), decreased concentration of N-acetylaspartate (a marker of neuronal integrity) and reduced striatum and brain size. Accordingly, evaluating can include assessing parameters related to neurotransmitter levels, neurotransmitter receptor levels, brain size and striatum size. In addition, abnormal aggregates containing the transgenic part of or full-length human Huntingtin protein are present in the brain tissue of these animals (e.g., the R6/2 transgenic mouse strain). See, e.g., Mangiarini et al. *Cell* 87: 493-506 (1996), Davies et al. *Cell* 90: 537-548 (1997), Brouillet, Functional Neurology 15(4): 239-251 (2000) and Cha et al. *Proc. Natl. Acad. Sci. USA* 95: 6480-6485 (1998).

To test the effect of the test polypeptide or known polypeptide described in the application in an animal model, different concentrations of test polypeptide are administered to the transgenic animal, for example by injecting the test polypeptide into circulation of the animal. A Huntington's disease-like symptom may be evaluated in the animal. The progression of the Huntington's disease-like symptoms, e.g., as described above for the mouse model, is then monitored to determine whether treatment with the test polypeptide results in reduction or delay of symptoms. In another assay, disaggregation of the Huntingtin protein aggregates in these animals is monitored. The animal can then be sacrificed and brain slices are obtained. The brain slices are then analyzed for the presence of aggregates containing the transgenic human Huntingtin protein, a portion thereof, or a fusion protein comprising human Huntingtin protein, or a portion thereof. This analysis can includes, for example, staining the slices of brain tissue with anti-Huntingtin antibody and adding a secondary antibody conjugated with FITC which recognizes the anti-Huntington's antibody (e.g., the anti-Huntingtin antibody is mouse anti-human antibody and the secondary antibody is specific for human antibody) and visualizing the protein aggregates by fluorescent microscopy.

A variety of methods are available to evaluate and/or monitor Huntington's disease. A variety of clinical symptoms and indicia for the disease are known. Huntington's disease causes a movement disorder, psychiatric difficulties and cognitive changes. The degree, age of onset, and manifestation of these symptoms can vary. The movement disorder can include quick, random, dance-like movements called chorea. Exemplary motor evaluations include: ocular pursuit, saccade initiation, saccade velocity, dysarthria, tongue protrusion, finger tap ability, pronate/supinate, a lo fist-hand-palm sequence, rigidity of arms, bradykinesia, maximal dystonia (trunk, upper and lower extremities), maximal chorea (e.g., trunk, face, upper and lower extremities), gait, tandem walking, and retropulsion. An exemplary treatment can cause a change in the Total Motor Score 4 (TMS-4), a subscale of the UHDRS, e.g., over a one-year period.

Cancer

Methods of the invention which provide administering the Klotho fusion polypeptide to an individual can be used to treat cancer. Cancer includes any disease that is caused by or results in inappropriately high levels of cell division, inappropriately low levels of apoptosis, or both. Examples of cancers include, without limitation, leukemias (e.g., acute leukemia, acute lymphocytic leukemia, acute myelocytic leukemia, acute myeloblastic leukemia, acute promyelocytic leukemia, acute myelomonocytic leukemia, acute monocytic leukemia, acute erythroleukemia, chronic leukemia, chronic myelocytic leukemia, chronic lymphocytic leukemia), polycythemia vera, lymphoma (Hodgkin's disease, non-Hodgkin's disease), Waldenstrom's macroglobulinemia, heavy chain disease, and solid tumors such as sarcomas and carcinomas (e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, nile duct carcinoma, choriocarcinoma, seminoma, embryonal carcinoma, Wilm's tumor, cervical cancer, uterine cancer, testicular cancer, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodenroglioma, schwannoma, meningioma, melanoma, neuroblastoma, and retinoblastoma). Lymphoproliferative disorders are also considered to be proliferative diseases.

All patents, patent applications, and published references cited herein are hereby incorporated by reference in their entirety. While this invention has been particularly shown and described with references to embodiments thereof, it will be understood by those skilled in the art that various changes in form and details may be made therein without departing from the scope of the invention encompassed by the appended claims.

5. EXAMPLES

Example 1

Expression and Purification of Klotho Fusion Polypeptides

Expression of the Klotho Fusion Polypeptide

The polypeptides of the invention were made by transiently transfecting HEK293T cells with an expression vector encoding a Klotho fusion polypeptide having the extracellular domain of alpha Klotho and the FGF23 (R179Q) variant. Conditioned media containing expressed polypeptides were generated by transient transfection of the respective expression plasmids for Klotho, FGF23, and the Klotho-FGF23 (R179Q) fusion protein. The transfections were performed in 6-well plates using Lipofectamine 2000 (Invitrogen, Cat #11668-019). Five hours after transfection, the transfection mix was replaced with 3 ml DMEM plus 1% FBS. Conditioned media were collected 72 hours after the addition of 3 ml DMEM plus 1% FBS. Samples of conditioned medium from various transiently transfected HEK293T cells were separated by SDS-polyacrylamide gel electrophoresis (SDS-PAGE) and analyzed by Western blot (FIG. 2A) or stained with Coomassie blue (FIG. 2B).

SDS-polyacrylamide gel electrophoresis was performed on various samples (lane 1, Control; lane 2, FGF23; lane 3, sKlotho; lanes 4-6, sKlotho-FGF23). Coomassie blue staining revealed the expression of a high, >180 kDa band (FIG. 2B, indicated by arrow on the right) that was not present in lanes 1-3, which contained samples that had not been transfected with the vector encoding the Klotho fusion polypeptide. The quality of the Klotho fusion polypeptide secreted into the media was evaluated by Western blot (FIG. 2A). An anti-FGF23 rat monoclonal IgG2A (R&D Systems, Cat# MAB26291) was used as the primary antibody to detect the Klotho fusion polypeptides by Western blot. The Western blot confirmed that the additional bands observed in the Coomassie stained gels were Klotho fusion polypeptides. The Western blot confirmed that the Klotho fusion polypeptides had the expected molecular weight for the Klotho fusion polypeptide. This analysis shows the expression of the Klotho-FGF23(R179Q) fusion protein.

Purification of the Klotho Fusion Polypeptide

The polypeptides of the invention were purified from conditioned media from a culture of HEK293T cells transiently transfected with an expression vector encoding a Klotho fusion polypeptide having the extracellular domain of alpha Klotho and the FGF23 R179Q variant. To generate conditioned medium, an expression vector encoding sKlotho-FGF23-6×His was transfected (500 μg DNA in 18 ml of OptiMEM 1 (GIBCO, Cat #11058) mixed with 18 ml of 2 μg/ml polyethlinimine (PEI) into HEK293 cells grown in suspension in expression medium (464 ml of HEK293T cells at $10^6$ cells/ml in Freestype 293 expression medium (GIBCO, Cat #12338)). After transfection, the culture was allowed to grow (120 hours; 37° C. in a 5% $CO_2$ incubator; shaking at 125 rpm). At the end of incubation, conditioned medium was harvested by centrifugation (1000 rpm for five minutes). The conditioned medium was then applied to a nickel-agarose column. The sKlotho-FGF23-6×His bound tightly to the column and was eluted with 50 mM imidazole. The resulting purified material was then dialyzed in PBS to remove imidazole. A sample of the purified sKlotho-FGF23-6×His was separated by SDS-PAGE (lane 1, purified sKlotho-FGF23-6× His; lane 2, molecular weight marker) and analyzed by staining with Coomassie blue (FIG. 2C). The stained SDS-PAGE gel confirmed that the purified sKlotho-FGF23-6×His had the expected molecular weight. The inability to detect bands corresponding to proteins other than full-length sKlotho-FGF23-6×His in the lane loaded with the purified material also showed that the sKlotho-FGF23-6×His was purified.

Example 2

In Vitro Assay Assessing the Activity of the Klotho Fusion Polypeptide

Egr-1-Luciferase

The biological activity of the expressed alpha Klotho fusion polypeptide was tested in Egr-1-luciferase reporter assays. Binding of the Klotho fusion polypeptide to the FGF23 receptor resulted in the downstream activation of Egr-1 and the expression of a luciferase reporter regulated by the Egr-1 promoter. The Egr-1-luciferase reporter gene was constructed based on that reported by Urakawa et al. (Nature, 2006, Vol. 444, 770-774). HEK293T cells seeded in 48-well poly-D-lysine plate were transfected with the Egr-1-luciferase reporter gene together with a transfection normalization reporter gene (Renilla luciferase). Five hours after transfection of the Egr-1 luciferase reporter gene, the transfection mix was replaced with 3 ml DMEM plus 1% FBS. Conditioned media were collected 72 hours after the addition of 3 ml DMEM plus 1% FBS. Five hours later, the transfection mix was replaced with a sample to be tested for activity. In initial experiments, 50% conditioned medium (alone or containing Klotho, FGF23, Klotho and FGF23, and the Klotho- FGF23(R179Q) fusion protein) and 50% DMEM with 1% FBS in the presence or absence of 20 µg/ml heparin (Sigma, Cat#H8537; dissolved in DMEM as 2 mg/ml stock) were tested in the Egr-1-luciferase reporter assays (FIG. 3). Further experiments used defined quantities of the purified polypeptides (FIGS. 4A and 4B). Cells were lysed 20 hours later in passive lysis buffer (Promega, Cat #E194A) and luciferase activities were determined using Dual-Glo Luciferase Assay System (Promega, Cat #E2940).

In initial experiments, Klotho fusion polypeptide activity was demonstrated in unfractionated conditioned medium. Using the Egr-1-luciferase reporter gene (FIG. 3) these experiments quantified the fold changes in the expression of the luciferase reporter. Conditioned medium containing a combination of FGF23 and the extracellular domain of Klotho protein activated Egr-1-luciferase, but conditioned medium containing only FGF23 or conditioned medium containing only the extracellular domain of Klotho, did not activate Egr-1-luciferase. Conditioned medium containing the fusion protein sKlotho-FGF23(R179Q) activated the Egr-1-luciferase reporter gene in contrast to conditioned media containing either FGF23 or Klotho alone. In these experiments, conditioned medium containing the fusion protein sKlotho-FGF23(R179Q) activated the Egr-1-luciferase reporter gene significantly better than conditioned medium containing a combination of FGF23 and Klotho. In the presence of heparin, the inductions by conditioned medium containing the fusion protein sKlotho-FGF23(R179Q) and the conditioned medium containing a combination of FGF23 and Klotho were significantly enhanced. Table 1 lists the relative expression of various FGF-Klotho fusion polypeptides in conditioned medium and the relative activity of the unfractionated conditioned medium corresponding to the various FGF-Klotho fusion polypeptides in Egr-1-luciferase reporter assays.

TABLE 1

Expression and Activities of sKlotho-FGF23 fusion variants

| | sKlotho-FGF23 fusion constructs | Expression | Activity in Egr-1-luc reporter gene |
| --- | --- | --- | --- |
| 1 | sKlotho-FGF23 | good | yes |
| 2 | IgG sp-sKlotho-FGF23 | good | yes |
| 3 | sKL-D1-FGF23 | good | no |
| 4 | sKL-D2-FGF23 | no | n.a. |
| 5 | s(KL-D1)2-FGF23 | good | no |
| 6 | sKL-D1/D2-FGF23 | no | n.a. |
| 7 | ssKlotho(ΔN-26)-FGF23 | poor | no* |
| 8 | sKLD1-D2(Δ692-965)-FGF23 | poor | no* |
| 9 | sKL-D1-D2(Δ507-798)-FGF23 | poor | no* |
| 10 | FGF23-sKlotho | poor | no* |

*lack of activity may be the result of low expression

Egr-1-luciferase reporter assays were also performed using defined quantities of proteins purified from the conditioned medium, using the purification procedure as described in Example 1. Consistent with previous results using unfractionated conditioned medium containing the expressed polypeptides, treatment with a combination of purified FGF23 and sKlotho resulted in luciferase reporter activity, but treatment with purified FGF23 alone did not (FIG. 4A). The luciferase reporter activity from the combination of purified FGF23 and sKlotho was further dependent on the dose of purified sKlotho, and the effect could be enhanced by the presence of heparin (20 µg/ml). An effect of the sKlotho-FGF23-6×His fusion polypeptide on luciferase activity could be detected at concentrations as low as about 1.21 nM (1.2 fold change) and at least up to about 19.3 nM (2.4 fold change) in Egr-1-luciferase reporter assays (FIG. 4B). The activity of the sKlotho-FGF23-6×His fusion polypeptide on luciferase activity was significantly enhanced in the presence of heparin (20 µg/ml). In the presence of heparin, the effect of the sKlotho-FGF23-6×His fusion polypeptide on luciferase activity could be detected at a concentration as low as about 0.6 nM (2.0 fold change). The result showed that purified sKlotho-FGF23-6×His dose-dependently induced the EGR-1-luc reporter gene, and that treatment with sKlotho-FGF23-6×His.

Example 3

In Vitro Assay Assessing the Effect of the Klotho Fusion Polypeptide on Muscle Cells The biological effect of the expressed Klotho fusion polypeptide was tested on C2C12 myoblasts. Treatment of C2C12 myoblasts with IGF-1, FGF2, or sKlotho-FGF23 resulted in myotube growth and phosphorylation of signaling proteins. C2C12 myoblasts were seeded at a density of 40,000 cells/well in 6-well poly-D-lysine and fibronectin coated plates in growth medium (3 parts DMEM and 1 part F12), 10% FBS, 1% Glut; 1% P/S; 1% Linolic acid; 0.1% ITS: [insulin (10 mg/ml), transferrin (5.5 mg/ml), and selenium (5 ng/ml)]. After myoblasts reached confluence (3 days), medium was changed into differentiation medium (DMED with 2% horse serum; 1% Glut; 1% P/S).

For the myotube diameter experiments, three days after confluent media was changed into differentiation medium, cells were treated with IGF-1 (10 nM), FGF2 (20 ng/ml) or sKlotho-FGF23 (20 nM) in the absence or presence of dexamethasone (100 µM) for 24 hours in differentiation medium. At the end of treatment, cells were fixed with glutaraldehyde (5% in PBS) and multiple fluorescent images were collected. Myotube diameter was measured using the Pipeline Pilot program to determine hypertrophy or atrophy.

For the signaling protein phosphorylation, experiments, three days after confluent media was changed into differentiation medium, cells were starved for four hours with DMEM without FBS and then treated with IGF-1 (10 nM), FGF2 (20 ng/ml) or sKlotho-FGF23 (20 nM) in the absence or presence of Rapamycin (40 nM) for 30 min. Cells were lysed in RIPA buffer in the presence of protease and phosphatase inhibitors. Western blot analysis was carried out and membranes were probed with different antibodies as indicated in the figure and developed on X-ray films, which were scanned.

The results of this study showed that sKlotho-FGF23 resulted in an increase in myotube diameter compared to the control and induced C2C12 myotube hypertrophy similar to results for IGF-1 and FGF2 (FIG. 4A). In addition, treatment with sKlotho-FGF23, IGF-1, and FGF2 could partially reverse myotube atrophy induced by dexamethasone, based on measurements of myotube diameter. No difference was observed between sKlotho-FGF23 and FGF2 on myotube morphology (measured by thickness of the myotubes) in the absence or presence of dexamethasone. The trophic effects of sKlotho-FGF23, IGF-1, and FGF2 were statistically significant.

Consistent with the effects on C2C12 myotubes, sKlotho-FGF23 fusion protein signaling led to the phosphorylation of p70S6K and ERK, but not AKT or FoxO, in C2C12 myotubes (FIG. 4B). The effect of sKlotho-FGF23 on signaling was similar to that of FGF2, but was distinct from that of IGF-1. The extent of ERK phosphorylation by sKlotho-FGF23 was observed to be less than that of IGF-1 or FGF2. The phosphorylation of p70S6K by sKlotho-FGF23 was rapamycin sensitive. In the experiments involving C2C12 cells, heparin was not required to activate signaling. These results show that a sKlotho-FGF23 fusion polypeptide activated signaling in C2C12 myotubes.

Example 4

Fusion Polypeptides Comprising sKlotho, FGF23 and FcLALA

Various fusion polypeptides are constructed using sKlotho, FGF23, and a modified Fc fragment of an antibody. These modified Fc molecules have altered (decreased) binding to FcRn and thus increased serum half-life. They also have modified bioavailability and alterered transport to mucosal surfaces and other targets in the body. In this example, the FGF23 and sKlotho are fused to FcLALA, which is described in U.S. Pat. No. 7,217,798 and Hessell et al. 2007 Nature 449:101-104, Intervening between the various components of these fusion polypeptides are linkers, as described in Lode et al. 1998 Proc. Natl. Acad. Sci. USA 95: 2475-2480. These fusions are inserted into constructs, e.g., pcDNA3.1 (Invitrogen, Carlsbad, Calif.), and expressed in HEK293 cells.

A. sKlotho-FGF23-FcLALA v1

A fusion is constructed which comprises: sKlotho, a linker, FGF23, another linker, and FcLALA. This embodiment, designated sKlotho-FGF23-FcLALA v1, is presented in SEQ ID NOs: 46 and 47, below.

The nucleotide sequence of sKlotho-FGF23-FcLALA v1 (wherein initiation ATG as 1) is presented as SEQ ID NO: 46.

The amino acid sequence of sKlotho-FGF23-FcLALA v1 is presented below as SEQ ID NO: 47.

In this sequence, the various components of the fusion are as follows: sKlotho: 1-982; Linked: 983-1001; FGF23: 1002-1228; Linker 2; 1229-1233; FcLALA: 1234-1459.

B. sKlotho-FGF23-FcLALA v2

A fusion is constructed which comprises: sKlotho, a linker, FGF23, another linker, and FcLALA. This embodiment is designated sKlotho-FGF23-FcLALA v2 and presented as SEQ ID NOs: 48 and 49, below.

The nucleotide sequence of sKlotho-FGF23-FcLALA v2 (wherein initiation ATG as 1) is presented as SEQ ID NO: 48.

The amino acid sequence of sKlotho-FGF23-FcLALA v2 is presented below as SEQ ID NO: 49.

In this sequence, the various components of the fusion are as follows:

sKlotho: (aa or amino acids) 1-982; Linker 1: 983-1001; FGF23: 1002-1228; Linker 2; 1229-1233; FcLALA: 1234-1450.

Other fusion polypeptides can be constructed by combining in various combinations the FGF, Klotho, modified Fc fragments, and (optionally) linker sequences, and variants and derivatives thereof, as described herein or known in the art.

Example 5

Fusion Polypeptides Comprising FGF23 and FcLALA

Various fusion polypeptides are constructed using FGF23, and a modified Fc fragment of an antibody, as described in U.S. Pat. No. 7,217,798. These modified Fc molecules have altered (decreased) binding to FcRn and thus increased serum half-life. They also have modified bioavailability and alterered transport to mucosal surfaces and other targets in the body. In this example, FGF23 is fused to FcLALA, Intervening between the various components of these fusion polypeptides are linkers, as described in Lode et al. 1998 Proc. Natl. Acad. Sci. USA 95: 2475-2480. These fusions are inserted constructs, e.g., pcDNA3.1 (Invitrogen, Carlsbad, Calif.), and expressed in HEK293 cells.

C. FGF23-FcLALA v1

A fusion is constructed which comprises: FGF23, a linker, and FcLALA. This construct is designated FGF23-FcLALA v1 and presented below as SEQ ID NOs: 50 and 51.

The nucleotide sequence of FGF23-FcLALA v1 (wherein initiation ATO as 1) is presented below as SEQ ID NO: 50.

The amino acid sequence of FGF23(R179Q)-FcLALAv1 is presented below as SEQ ID NO: 51.

In this sequence, the various components of the fusion are as follows:

FGF23: (aa) 1-251; Linker: 252-256; FcLALA: 257-482.

D. FGF23-FcLALA v2

A fusion is constructed which comprises: FGF23-FcLALA v2, which comprises FGF23 and FcLALA.

The nucleotide sequence of FGF23-FcLALA v2 (wherein initiation ATG as 1) is presented below as SEQ ID NO: 52.

The amino acid sequence of FGF23(R179Q)-FcLALAv2 is presented below as SEQ ID NO: 53.

In this sequence, the various components of the fusion are as follows:

FGF23: 1-251; Linker: 252-256; FcLALA: 257-473.

Other fusion polypeptides can be constructed by combining in various combinations the FGF sequences, modified Fc fragments, and (optionally) linkers, and variants and derivatives thereof, as described herein or known in the art.

What is claimed is:

1. A functionally active fusion polypeptide, wherein the sequence of the fusion polypeptide comprises the sequence of SEQ ID NO: 53.

2. A pharmaceutical composition comprising the fusion polypeptide of claim 1 and a pharmaceutically acceptable carrier.

3. A nucleic acid comprising a sequence that encodes a functionally active fusion polypeptide, wherein the sequence of the fusion polypeptide comprises the sequence of SEQ ID NO: 53.

4. A host cell containing the nucleic acid of claim 3.

5. A vector comprising the nucleic acid of claim 3.

6. A method for activating Egr-1 in an individual, comprising the step of:
administering to the individual a therapeutically effective dose of a pharmaceutical composition comprising a functionally active fusion polypeptide, wherein the sequence of the fusion polypeptide comprises the sequence of SEQ ID NO: 53.

7. The method of claim 6, wherein the individual is in need of a treatment for an age-related condition selected from the group consisting of sarcopenia, skin atrophy, muscle wasting, brain atrophy, atherosclerosis, arteriosclerosis, pulmonary emphysema, osteoporosis, osteoarthritis, immunologic incompetence, high blood pressure, dementia, Huntington's disease, Alzheimer's disease, cataracts, age-related macular degeneration, prostate cancer, stroke, diminished life expectancy, memory loss, wrinkles, impaired kidney function, and age-related hearing loss.

8. The method of claim 7, wherein the age-related condition is muscle wasting.

9. The method of claim 6 wherein the individual is in need of a treatment for a metabolic disorder selected from the group consisting of Type II Diabetes, Metabolic Syndrome, hyperglycemia, and obesity.

10. The method of claim 6, wherein the individual is in need of a treatment for hyperphosphatemia or calcinosis.

11. The method of claim 6, wherein the individual is in need of a treatment for chronic renal disease or chronic renal failure.

12. The method of claim 6, wherein the individual is in need of a treatment for cancer.

13. The method of claim 12, wherein the cancer is breast cancer.

14. The method of claim 6, wherein the individual is in need of a treatment for muscle atrophy.

15. A functionally active fusion polypeptide, wherein the sequence of the fusion polypeptide consists of the sequence of SEQ ID NO: 53.

16. A pharmaceutical composition comprising the fusion polypeptide of claim 15 and a pharmaceutically acceptable carrier.

17. A nucleic acid comprising a sequence that encodes a functionally active fusion polypeptide, wherein the sequence of the fusion polypeptide consists of the sequence of SEQ ID NO: 53.

18. The nucleic acid of claim 17, wherein the sequence of the nucleic acid is the sequence of SEQ ID NO: 52.

* * * * *